(12) United States Patent
Magnani et al.

(10) Patent No.: US 11,072,625 B2
(45) Date of Patent: Jul. 27, 2021

(54) HIGHLY POTENT MULTIMERIC E-SELECTIN ANTAGONISTS

(71) Applicant: GLYCOMIMETICS, INC., Rockville, MD (US)

(72) Inventors: John L. Magnani, Gaithersburg, MD (US); John M. Peterson, Slate Hill, NY (US); Myung-Gi Baek, Boyds, MD (US)

(73) Assignee: GLYCOMIMETICS, INC., Rockville, MD (US)

( * ) Notice: Subject to any disclaimer, the term of this patent is extended or adjusted under 35 U.S.C. 154(b) by 0 days.

(21) Appl. No.: 16/339,646

(22) PCT Filed: Oct. 6, 2017

(86) PCT No.: PCT/US2017/055648
§ 371 (c)(1),
(2) Date: Apr. 4, 2019

(87) PCT Pub. No.: WO2018/068010
PCT Pub. Date: Apr. 12, 2018

(65) Prior Publication Data
US 2019/0233458 A1 Aug. 1, 2019

Related U.S. Application Data

(60) Provisional application No. 62/405,792, filed on Oct. 7, 2016, provisional application No. 62/451,415, filed on Jan. 27, 2017.

(51) Int. Cl.
| | |
|---|---|
| C07H 7/04 | (2006.01) |
| C07H 7/06 | (2006.01) |
| C07H 15/26 | (2006.01) |
| A61K 47/60 | (2017.01) |
| C07H 15/207 | (2006.01) |
| A61P 35/04 | (2006.01) |
| A61P 1/04 | (2006.01) |

(52) U.S. Cl.
CPC ............ *C07H 7/06* (2013.01); *A61K 47/60* (2017.08); *A61P 1/04* (2018.01); *A61P 35/04* (2018.01); *C07H 7/04* (2013.01); *C07H 15/207* (2013.01); *C07H 15/26* (2013.01)

(58) Field of Classification Search
CPC ... C07H 7/06; C07H 7/04; A61P 35/04; A61P 1/04
USPC .......................................................... 514/32
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |
| 5,618,785 A | 4/1997 | Heavner et al. |
| 5,622,937 A | 4/1997 | Kogan et al. |
| 5,632,991 A | 5/1997 | Gimbrone, Jr. |
| 5,639,734 A | 6/1997 | Esko et al. |
| 5,646,123 A | 7/1997 | Ippolito et al. |

(Continued)

FOREIGN PATENT DOCUMENTS

| | | |
|---|---|---|
| DE | 2434953 | 2/1975 |
| EP | 319253 A2 | 6/1989 |

(Continued)

OTHER PUBLICATIONS

Abraham, W.M. et al., "Selectin Blockade Prevents Antigen-induced Late Bronchial Response and Airway Hyperresponsiveness in Allergic Sheep," Am J. Respir Crit Care Med. 159: 1205-1214, 1999.

(Continued)

*Primary Examiner* — Shaojia A Jiang
*Assistant Examiner* — Michael C Henry
(74) *Attorney, Agent, or Firm* — Finnegan, Henderson, Farabow, Garrett & Dunner, LLP

(57) ABSTRACT

Compounds, compositions, and methods for treatment and/or prevention of at least one disease, disorder, and/or condition by inhibiting binding of an E-selectin to an E-selectin ligand are disclosed. For example, highly potent multimeric E-selectin antagonist are desorbed and pharmaceutical compositions comprising at least one of the same.

35 Claims, 15 Drawing Sheets

(56) References Cited

U.S. PATENT DOCUMENTS

| | | | |
|---|---|---|---|
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |
| 5,658,880 A | 8/1997 | Dasgupta et al. |
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,856,300 A | 1/1999 | Rittershaus et al. |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,043,348 A | 3/2000 | Lawman et al. |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,372,712 B1 | 4/2002 | Briesewitz |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 10/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,125 B2 | 1/2005 | Bistrup et al. |
| 6,872,714 B1 | 3/2005 | Schols |
| 6,875,738 B1 | 4/2005 | Clark-Lewis et al. |
| 6,887,842 B1 | 5/2005 | Briesewitz |
| 6,921,531 B2 | 7/2005 | Briesewitz |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,390,784 B2 | 6/2008 | Briesowitz |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 | 4/2013 | Magnani |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 8,895,510 B2 | 11/2014 | Magnani |
| 8,921,328 B2 | 12/2014 | Ernst et al. |
| 9,109,002 B2 | 8/2015 | Magnani et al. |
| 9,254,322 B2 | 2/2016 | Levesque et al. |
| 9,486,497 B2 | 11/2016 | Levesque et al. |
| 9,534,009 B2 | 1/2017 | Magnani |
| 9,796,745 B2 | 10/2017 | Magnani et al. |
| 9,867,841 B2 | 1/2018 | Magnani |
| 2001/0046970 A1 | 11/2001 | Nagy et al. |
| 2001/0051370 A1 | 12/2001 | Bistrup et al. |
| 2002/0031508 A1 | 3/2002 | Wagner et al. |
| 2002/0040008 A1 | 4/2002 | Wagner et al. |
| 2002/0086356 A1 | 7/2002 | Tuschi et al. |
| 2002/0128225 A1 | 9/2002 | Liu et al. |
| 2002/0132220 A1 | 9/2002 | Berens et al. |
| 2002/0155429 A1 | 10/2002 | Allaway et al. |
| 2002/0164336 A1 | 11/2002 | Harrison et al. |
| 2002/0164748 A1 | 11/2002 | Bistrup et al. |
| 2002/0165178 A1 | 11/2002 | Schetter et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0036560 A1 | 2/2003 | Sonis et al. |
| 2003/0039683 A1 | 2/2003 | Cantrell et al. |
| 2003/0073632 A1 | 4/2003 | Ciaccia et al. |
| 2003/0211078 A1 | 11/2003 | Heavner |
| 2004/0067220 A1 | 4/2004 | Sykes |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0181987 A1 | 8/2005 | Blaszczyk-Thurin et al. |

(56) References Cited

U.S. PATENT DOCUMENTS

| | | |
|---|---|---|
| 2005/0187171 A1 | 8/2005 | Magnani et al. |
| 2005/0214283 A1 | 9/2005 | Sackstein et al. |
| 2006/0194745 A1 | 8/2006 | Magnani et al. |
| 2006/0217303 A1 | 9/2006 | Kriegler |
| 2006/0264451 A1 | 11/2006 | Shim et al. |
| 2006/0287253 A1 | 12/2006 | Kriegler et al. |
| 2007/0021378 A1 | 1/2007 | Varki et al. |
| 2007/0054870 A1 | 3/2007 | Magnani et al. |
| 2007/0054930 A1 | 3/2007 | Shim et al. |
| 2007/0213278 A1 | 9/2007 | Wong et al. |
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2008/0306098 A1 | 12/2008 | Mutz et al. |
| 2009/0036386 A1 | 2/2009 | Magnani et al. |
| 2009/0053198 A1 | 2/2009 | Sackstein |
| 2009/0054334 A1 | 2/2009 | Mutz et al. |
| 2009/0175792 A1 | 7/2009 | Magnani et al. |
| 2009/0176717 A1 | 7/2009 | Magnani |
| 2009/0253646 A1 | 10/2009 | Magnani |
| 2009/0312278 A1 | 12/2009 | Magnani et al. |
| 2010/0145032 A1 | 6/2010 | Laine et al. |
| 2010/0215575 A1 | 8/2010 | O'Neill et al. |
| 2010/0240773 A1 | 9/2010 | Korzekwa et al. |
| 2010/0292095 A1 | 11/2010 | Laukkanen et al. |
| 2010/0303766 A1 | 12/2010 | Miyaji et al. |
| 2010/0311105 A1 | 12/2010 | Lu et al. |
| 2011/0002881 A1 | 1/2011 | Levesque et al. |
| 2011/0020270 A1 | 1/2011 | Levesque et al. |
| 2011/0142856 A1 | 6/2011 | Kokubo et al. |
| 2011/0229409 A1 | 9/2011 | Ranganathan et al. |
| 2011/0245265 A1 | 10/2011 | Zuk et al. |
| 2011/0251148 A1 | 10/2011 | Magnani et al. |
| 2011/0257380 A1 | 10/2011 | Ernst et al. |
| 2012/0093782 A1 | 4/2012 | Grove et al. |
| 2012/0129712 A1 | 5/2012 | Satomaa et al. |
| 2012/0202762 A1 | 8/2012 | Magnani |
| 2012/0258043 A1 | 10/2012 | Ranganathan et al. |
| 2012/0329755 A1 | 12/2012 | Magnani et al. |
| 2013/0184229 A1 | 7/2013 | Magnani et al. |
| 2013/0261070 A1 | 10/2013 | Magnani et al. |
| 2013/0281646 A1 | 10/2013 | Korzekwa et al. |
| 2013/0331350 A1 | 12/2013 | Ernst et al. |
| 2014/0073594 A1 | 3/2014 | Magnani et al. |
| 2014/0178303 A1 | 6/2014 | Magnani et al. |
| 2015/0051164 A1 | 2/2015 | Magnani |
| 2015/0110808 A1 | 4/2015 | Magnani et al. |
| 2015/0284420 A1 | 10/2015 | Magnani et al. |
| 2016/0145290 A1 | 5/2016 | Magnani et al. |
| 2016/0184339 A1 | 6/2016 | Magnani |
| 2016/0193294 A1 | 7/2016 | Magnani et al. |
| 2016/0243145 A1 | 8/2016 | Magnani et al. |
| 2016/0289257 A1 | 10/2016 | Magnani et al. |
| 2016/0333043 A1 | 11/2016 | Magnani et al. |

FOREIGN PATENT DOCUMENTS

| | | |
|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/25043 | 11/1994 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 95/31210 | 11/1995 |
| WO | WO 96/20204 | 7/1996 |
| WO | WO 96/25418 | 8/1996 |
| WO | WO 96/26950 | 9/1996 |
| WO | WO 96/40942 | 12/1996 |
| WO | WO 97/01355 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 98/046771 | 10/1998 |
| WO | WO 99/42130 | 8/1999 |
| WO | WO 99/43353 | 9/1999 |
| WO | WO 99/43356 | 9/1999 |
| WO | WO 99/065712 | 12/1999 |
| WO | WO 00/02870 | 1/2000 |
| WO | WO 00/050032 | 8/2000 |
| WO | WO 00/066112 | 11/2000 |
| WO | WO 01/89564 | 11/2001 |
| WO | WO 02/22820 | 3/2002 |
| WO | WO 02/062810 | 8/2002 |
| WO | WO 03/032925 | 4/2003 |
| WO | WO 03/055876 | 7/2003 |
| WO | WO 03/088980 | 10/2003 |
| WO | WO 03/097658 | 11/2003 |
| WO | WO 04/004636 | 1/2004 |
| WO | WO 04/033663 | 4/2004 |
| WO | WO 04/058304 | 7/2004 |
| WO | WO 04/094619 | 11/2004 |
| WO | WO 05/016349 | 2/2005 |
| WO | WO 05/046597 | 5/2005 |
| WO | WO 05/051920 | 6/2005 |
| WO | WO 05/054264 | 6/2005 |
| WO | WO 05/058934 | 6/2005 |
| WO | WO 05/085219 | 9/2005 |
| WO | WO 05/116088 | 12/2005 |
| WO | WO 06/017180 | 2/2006 |
| WO | WO 06/022454 | 3/2006 |
| WO | WO 06/062946 | 6/2006 |
| WO | WO 06/074426 | 7/2006 |
| WO | WO 06/074428 | 7/2006 |
| WO | WO 06/089106 | 8/2006 |
| WO | WO 06/127906 | 11/2006 |
| WO | WO 07/021721 | 2/2007 |
| WO | WO 07/022089 | 2/2007 |
| WO | WO 07/022385 | 2/2007 |
| WO | WO 07/028050 | 3/2007 |
| WO | WO 07/033329 | 3/2007 |
| WO | WO 08/008852 | 1/2008 |
| WO | WO 08/008854 | 1/2008 |
| WO | WO 08/011094 | 1/2008 |
| WO | WO 08/060378 | 5/2008 |
| WO | WO 08/100453 | 8/2008 |
| WO | WO 08/109154 | 9/2008 |
| WO | WO 09/011889 | 1/2009 |
| WO | WO 09/073911 | 6/2009 |
| WO | WO 09/073916 | 6/2009 |
| WO | WO 09/126556 | 10/2009 |
| WO | WO 09/152245 | 12/2009 |
| WO | WO 10/126888 | 11/2010 |
| WO | WO 12/037034 | 3/2012 |
| WO | WO 12/045913 | 4/2012 |
| WO | WO 12/061662 | 5/2012 |
| WO | WO 12/151576 | 11/2012 |
| WO | WO 13/096926 | 6/2013 |
| WO | WO 14/070991 | 5/2014 |
| WO | WO 14/149837 | 9/2014 |
| WO | WO 15/048616 | 4/2015 |
| WO | WO 15/109049 | 7/2015 |
| WO | WO 16/089872 | 6/2016 |

(56) References Cited

FOREIGN PATENT DOCUMENTS

| WO | WO 16/164394 | 10/2016 |
|---|---|---|
| WO | WO 17/095904 | 6/2017 |

OTHER PUBLICATIONS

Acord, J. et al., "A rapid microplate method for quantifying inhibition of bacterial adhesion to eukaryotic cells," Journal of Microbiological Methods 60: 55-62, 2005.
Adams, E. W. et al., "Oligosaccharide and Glycoprotein Microarrays as Tools in HIV Glycobiology: Glycan-Dependent gp120/Protein Interactions," Chemistry & Biology 11:875-881, Jun. 2004.
Aggoune et al., "The Vascular Niche Is Involved in Regulating Leukemic Stem Cells in Murine Chronic Myelogenous Leukemia" Blood, 124(21):516, Dec. 6, 2014.
Aggouneet al., "The vascular niche is involved in regulating leukemic stem cells in murine chronic myelogenous leukemia," Proceedings of the 56$^{th}$ Annual Meeting of the American Society of Hematology, Abstract #516 Oral Presentation, Dec. 8, 2014, San Francisco, CA.
Alessandro et al., "Multiple Myeloma Cells Express Functional E-Selectin Ligands Which Can be Inhibited Both in vitro and in vivo Leading to Prolongation of Survival in a Murine Transplant Model," Blood, Dec. 6, 2014, XP055349837, 56$^{th}$ Annual Meeting of the American Society of Hematology, Dec. 6-9, 2014, San Francisco, CA.
Alessandro, et al., "Role of S128R polymorphism of E-selectin in colon metastasis formation," Int. J. Cancer, 121(3): 528-535 (2007).
Ali, M., et al., "Polymers bearing sLex-mimetics are superior inhibitors of E-selectin-dependent leukocyte rolling in vivo", The FASEB Journal 18(1), (2004), 152-154.
Alousi, A., et al., "Reduced-Intensity Conditioning Allogeneic Hematopoietic Stem Cell Transplantation", Clinical Advances in Hematoloav & Oncoloav. 5(7), (2007), 560-570.
Angelini et al., "E-Selectin Antagonist GMI-1271 Shows a Favorable Safety, PK and Bleeding Profile in Phase I Studies of Healthy Volunteers," Blood, 128(22), Abstract #3826, Dec. 6, 2014.
Angelini et al., "E-selectin Antagonist GMI-1271 Shows a Favorable Safety, PK and Bleeding Profile in Phase I Studies of Healthy Volunteers," Proceedings of the 56$^{th}$ Annual Meeting of the American Society of Hematology, Abstract #3826 Poster Presentation, Dec. 8, 2014, San Francisco, CA.
Arakaki, R. et al., "T134, a Small-Molecule CXCR4 Inhibitor, Has No Cross-Drug Resistance with AMD3100, a CXCR4 Antagonist with a Different Structure," Journal of Virology 73(2):1719-1723, Feb. 1999.
Aref et al., "L and E Selectins in Acute Myeloid Leukemia: Expression, Clinical Relevance and Relation to Patient Outcome," Hematology, 7(2), 83-87, 2002.
Arshad, S. et al., "Primary prevention of asthma and atopy during childhood by allergen avoidance in infacny: a randomised controlled study," Thorax., 58:489-493 (2003).
Arshad, S. et al., "Primary prevention of asthma and allergy," J. Allergy Clin. Immunol., 116: 3-14 (2005).
Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," Journal of Virology 82(13):6359-6368, Jul. 2008.
Azab et al., "P-selectin Glycoprotein Ligand Regulates the Interaction of Multiple Myeloma Cells with the Bone Marrow Microenvironment", Blood, 119(6),1468-1478, Nov. 16, 2011.
Azab et al., "Role of Selectins in the Pathogenesis of Multiple Myeloma", J Clin Oncol, 27(15s):Absrt 11103, 2009.
Azab et al, "Role of Selectins in the Pathogenesis of Multiple Myeloma", ASCO Annual Meeting 2009, Poster #11103, May 2009.
Baeckstrom et al., "Purification and Characterization of a Membrane-bound and a Secreted Mucin-type Glycoprotein Carrying the Carcinoma-associated Sialyl-Le.sup.a Epitope on Distinct Core Proteins," J. Biol. Chem. 266(32):21537-21547, 1991.
Banteli, R. et al., "Potent E-Selectin Antagonists," Helvetica Chimica Acta 83(11): 2893-2907, 2000.
Banteli et al., "Synthesis of sialyl lewisx mimics. Modifications of the 6-position of galactose," Bioorganic & Medicinal Chemistry Letters, 11(4): 459-462 (2001).
Barasch et al., "Palifermin for Management of Treatment-Induced Oral Mucositis in Cancer Patients", Biologics: Targets & Therapy, 3:111-116, 2009.
Barnes, P. et al., "How do corticosteroids work in asthma?" Ann. Intern. Med., 139: 359-370 (2003).
Barthel et al., "Targeting selectins and selectin ligands in inflammation and cancer," Expert Opinion Therapeutic Targets, 11(11), 1473-1491, 2007.
Bastin, R.. et al,"Salt Selection and Optimisation Procedures for Pharmaceutical New Chemical Entities" Organic Process Research & Development (2000), vol. 4, pp. 427-435.
Bedard et al., "Expert Opinion: Selectin Inhibitors: A Patent Review," Rights Link, 20(6):781-793, 2010.
Belcher, J.D. et al., "Activated monocytes in sickle cell disease: potential role in the activation of vascular endothelium and vaso-occlusion," Blood 96(7):2451-2459, Oct. 1, 2000.
Belcher, J.D. et al., "Inflammatory response in transgenic mouse models of human sickle cell anemia," Blood 96(11)Pt. 1 :600a, Abstract #2574, Nov. 16, 2000.
Bennett, C. F., et al., "Inhibition of Endothelial Cell Adhesion Molecule Expression with Antisense Oligonucleotides", Journal of Immunoloav. 152(7), (1994), 3530-3540.
Berg et al., "A Carbohydrate Domain Common to Both Sialyl Le.sup.a and Sialyl Le.sup.x Is Recognized by the Endothelial Cell Leukocyte Adhesion Molecule ELAM-1," J. Biol. Chem. 266(23):14869-14872, 1991.
Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.
Berger et al., "Adoptive transfer of effector CD8+ T cells derived from central memory cells establishes persistent T cell memory in primates." J. Clin. Invest. 118(1):294-305 (2008).
Bevilacqua, et al., "Endothelial-leukocyte adhesion molecules in human disease," Ann. Rev. Med., 45: 361-378 (1994).
Bhaskar, V. et al. "E-selectin Up-regulation Allows for Targeted Drug Delivery in Prostrate Cancer," Cancer Research, 63: 6387-6394 (Oct. 2003).
Bird et al., "Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978, and English Translation.
Bochner, B. et al., "Glycan array screening reveals a candidate ligand for Siglec-8," Journal of Biological Chemistry, 280(6): 4307-4312 (2005).
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour with Respect to the Enzyme Trehalase," European Journal of Biochemistry, 131:595-600, 1983.
Bogden, A. E., et al., "Amelioration of Chemotherapy-Induced Toxicity by Cotreatment with AcSDKP, a Tetrapeptide Inhibitor of Hematopoietic Stem Cell Proliferation", Annals New York Academy of Sciences. 628, (1991), 126-139.
Borsig et al., "Synergistic effects of L- and P-selectin in facilitating tumor metastasis can involve non-mucin ligands and implicate leukocytes ad enhancers of metastasis," Proceedings of the National Academy of Sciences, 99(4), 2193-2198, 2002.
Bowen et al., "Characterization of a Human Homologue of the Murine Peripheral Lymph Node Homing Receptor," Journal of Cell Biology, 109:421-427, 1989.

(56) References Cited

OTHER PUBLICATIONS

Bradford, G. B., et al., "Quiescence, cycling, and turnover in the primitive hematopoietic stem cell compartment", Experimental Hematoloav. 25, (1997), 445-453.
Brandley et al., "Carbohydrate Ligands of LEC Cell Adhesion Molecules," Cell, 63:861-863, 1990.
Breems et al., "Prognostic Index for Adult Patients With Acute Myeloid Leukemia in First Relapse," Journal of Clinical Oncology, 23(9(), 1969-1978, 2005.
Bridger, GJ et al. "Synthesis and Structure—Activity Relationships of Phenylenebis(methylene)—Linked Bis-Tetraazamacrocycles That Inhibit HIV Replication. Effects of Macrocyclic Ring Size and Substituents on the Aromatic Linker," J. Med. Chem., 38: 366-378 (1995).
Brodt et al., "Liver endothelial E-selectin mediates carcinoma cell adhesion and promotes liver metastasis," Int. J. Cancer, 71(4): 612-619 (1997).
Broquet et al., "Effect of Desipramine on a Glycoprotein Sialyltransferase Activity in C6 Cultured Glioma Cells," J. Neurochem., 54:388-394, 1990.
Burkhardt, K., et al., "The Significance of Adhesion Molecules in Nephrology", Artificial Oraans 20(5), (1996), 433-436.
Calarese, D. A. et al., "Antibody Domain Exchange is and Immunological Solution to Carbohydrate Cluster Recognition," Science 300:2065-2071, Jun. 2003.
Calarese, D. A. et al., "Dissection of the Carbohydrate Specificity of the Broadly Neutralizing Anti-HIV-1 Antibody 2G12," Proceedings of the National Academy of Sciences 102(38):13372-13377, Sep. 2005.
Cao, X. et al., "Defective Lymphoid Development in Mice Lacking Expression of the Common Cytokine Receptor Y Chain," Immunity, 2:223-238, Mar. 1995.
Ceder, O. et al., "On the Absolute Configuration of 3-Cyclohexene-l-carboxylic Acid," Acta Chemica Scandivavica, 24(8):2693-2698, 1970.
Chang et al., "Effects of Pan-Selectin Antagonist GMI-1070 on the Treatment of Vaso-Occlusion in Sickle Cell Mice", Blood, 112(11), Abstract #535, Nov. 2008.
Chang, J. et al. "GMI-1070, a novel pan-selectin antagonist, reverses acute vascular occlusions in sickle cell mice," Blood, 116(10): 1779-1786 (Sep. 2010).
Chase et al., "E-Selectin Ligands as Mechanosensitive Receptors on Neutrophils in Health and Disease", Annals of Biomedical Engineering, 40(4), pp. 849-899, Apr. 2012.
Chemical Abstracts (STN), Accession No. 1997:584307, Jul. 8, 1997.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML," Proceedings of the 54th Annual Meeting of the American Society of Hematology, Abstract #4092, Poster Presentation, Dec. 10, 2012, San Diego, CA.
Chien et al., "Adhesion of Acute Myeloid Leukemia Blasts to E-Selectin in the Vascular Niche Enhances Their Survival by Mechanisms Such as Wnt Activation", Blood, 122(21):61, Nov. 15, 2013.
Chien et al., "579 Novel Dual E-Selectin-CXCR4 Inhibitors Mobilize Human Acute Myeloid Leukemia (AML) Cells in the NODscid IL2Rγc-/- Xenograft and Confer Susceptibility to Cytarabine," Blood, 118(21) Abstract #579, Oral, Nov. 18, 2011.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", Blood, 120(21), Abstract #4092, Nov. 16, 2012.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", 2012 ASH Annual Meeting, Poster #54715, Dec. 10, 2012.
Chien et al., "Novel Dual E-Selectin-CXCR4 Inhibitors Mobilize Human Acute Myeloid Leukemia (AML) Cells in the NODscid IL2R{gamma}c-/- Xenograft and Confer Susceptibility to Cytarabine", Blood, 118(21), Abstract #579, Nov. 18, 2011.
Childs et al. ,"High-molecular-weight glycoproteins are the major carriers of the carbohydrate differentiation antigens I, I and SSEA-1 of mouse teratocarcinoma cells," Biochem. J., 215:491-503 (1983).
Choi, S. et al., "Synthetic Multivalent Molecules: Concepts and Biomedical Applications," Wiley-Interscience, p. xxi-xxvi, 1-17, 2004.
Christianson, S.W. et al.,"Enhanced Human CD4+ T Cell Engraftment in β2-Microglobulin-Deficient NOD-scid Mice," The Journal of Immunology, 158:3578-3586 (1997).
Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).
Collier, et al., "Membrane translocation by anthrax toxin," Molecular Aspects of Medicine, 30(6): 413-422 (Dec. 1, 2009).
Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).
Corson, Timothy W. et al., "Design and Applications of Bifunctional Small Molecules: Why Two Heads Are Better Than One," ACS Chemical Biology 3(11):677-692, Nov. 2008.
Cottler-Fox, M.H. et al., "Stem Cell Mobilization," Amer. Sci. Hematology, 419-437, (2003).
Crawford et al., "AMD070, a CXCR4 Chemokine Receptor Antagonist: Practical Large-Scale Laboratory Synthesis," Org. Process Res. Devel. 12:823-830, 2008.
Cumpstey, I. et al. "C2-Symmetrical Thiodigalactoside Bis-Benzamido Derivatives as High-Affinity Inhibitors of Galectin-3: Efficient Lectin Inhibition through Double Arginine—Arene Interactions," Angew Chem., 117:5240-5242 (2005).
Dagia, Nilesh et al., "G-CSF induces E-selecting ligand expression on human myeloid cells," Nature Medicine, 12(10): 1185-90, Oct. 1, 2006.
Daoudii, Jean-Michel et al., "New bicyclam-GalCer analogue conjugates: synthesis and in vitro anti-HIV activity," Bioorg. & Med. Chem. Letters 14:495-498, 2004.
Datta et al., "Isolation and purification of trehalose 6-mono- and 6,6'-di-corynomycolates from Cornyebacterium matruchotii. Structural characterization of .sup.1H NMR," Carbohydrate Research 245: 151-158, 1993.
De Castro et al., "Effects of GMI-1070, a Pan-Selectin Inhibitor, On Pain Intensity and Opioid Utilization in Sickle Cell Disease", Blood, 122(21):775, Nov. 15, 2013.
De Clercq, Erik, "The bicyclam AMD3100 story," Nat. Rev. Drug Disc. 2:581-587, Jul. 2003.
DeAngelo, "A Phase I/II Study of GMI-1271, a Novel ESelectin Antagonist, in Combination with Induction Chemotherapy in Relapsed/Refractory and Elderly Previously Untreated Acute Myeloid Leukemia; Results to Date," Blood, 128(22), Abstract #4049, Dec. 2, 2016.
Definition of allogenic. Medline Plus-Merriam-Webster Medical Dictionary (last accessed Jun. 3, 2013).
Definition of syngeneic. Medline Plus-Merriam-Webster Medical Dictionary (last accessed Jun. 3, 2013).
Definition of xenogeneic. Medline Plus-Merriam-Webster Medical Dictionary (last accessed Jun. 3, 2013).
Demain et al. "Natural products for cancer chemotherapy," Microbio. Biotechnol. 4(6): 687-699, 2011.
Devata et al., First in Human Phase 1 Single Dose Escalation Studies of the E-Selectin Antagonist GMI-1271 Show a Favorable Safety, Pharmacokinetic, and Biomarker Profile, Proceedings of the 57th Annual Meeting of the American Society of Hematology, Abstract #1004, Poster Presentation, Dec. 5, 2015, Orlando, FL.
Devata et al., "First in Human Phase 1 Single Dose Escalation Studies of the E-Selectin Antagonist GMI-1271 Show a Favorable Safety, Pharmacokinetic, and Biomarker Profile," Blood, 126(23), Abstract #1004, Dec. 3, 2015.
Devereux, J., et al., "A comprehensive set of sequence analysis programs for the VAX", Nucleic Acids Research 12(1), (1984), 387-395.

(56) References Cited

OTHER PUBLICATIONS

Devine, "Rapid Mobilization of CD34+ Cells Following Administration of the CXCR4 Antagonist AMD 3100 to Patients With Multiple Myeloma and Non-Hodgkin's Lymphoma," Journal of Clinical Oncology, 22(6): 1095-1102 (Feb. 23, 2004).
Deweerdt, "Animal models: Towards a myeloma mouse," Nature, 480 (7377): S38-39 (2011).
Diamandis et al., "Reflection on the Discovery of Carcinoembryonic Antigen, Prostate-Specific Antigen, and Cancer Antigens CA125 and CA19-9", Clin Chem, 59(1), Nov. 30, 2012.
Diaz-Ricart et al., "rPSGL-Ig" Drugs of the Future 27(4):346 (2002).
Dimasi et al., "Expression, crystallization and preliminary crystallographic analysis of the extracellular IgV-like domain of the human natural killer cell inhibitory receptor p75/AIRM1," Acta Crystallographica Section D, Biological Crystallography, 59(Pt 10), 1856-1858, 2003.
Dimasi et al., "Structure of the saccharide-binding domain of the human natural killer cell inhibitory receptor p75/AIR1. Erratum," Acta Crystallographica Section D, Biological Crystallography, 60(Pt 2), Erratta, 401-403, 2004.
Dittmar et al., "Adhesion Molecules and Chemokines: the Navigation System for Circulating Tumor (Stem) Cells to Metastasize in an Organ-Specific Manner," Clin. Exp. Metastasis 25:11-32, 2008.
Doranz et al., "Safe Use of the CSCR4 Inhibitor ALX40-4C in Humans," AIDS Research and Human Retroviruses 17(6):475-486, 2001.
Duijvestijn et al., "High Endothelial Differentiation in Human Lymphoid and Inflammatory Tissues Defined by Monoclonal Antibody HECA-452," Am. J. Path. 130:147-155, 1988.
Dupre et al., "Glycomimetic Selectin Inhibitors: (.alpha.-D-Mannopyranosyloxy)methylbiphenyls," Bioorganic & Medicinal Chemistry Letters 6(5): 569-572, 1996.
Dutta et al "E-selectin inhibition mitigates splenic HSC activation and myelopoiesis in hypercholesterolemic mice with myocardial infarction highlights" Arteriosclerosis, Thrombosis, and Vascular Biology 36(9):1802-08 (2016).
Dykewicz, "Summary of the Guidelines for Preventing Opportunistic Infections among Hematopoietic Stem Cell Transplant Recipients," Clin. Infectious Diseases, 33:139-144, Jul. 15, 2001.
Edgington, "How Sweet It Is: Selectin-Mediating Drugs," Biotechnology 10: 383-389, 1992.
Edwards, "Generally Applicable, Convenient Solid-Phase Synthesis and Receptor Affinities of Octreotide Analogs," J. Med. Chem. 37:3749-3757, 1994.
Egberink et al. "Bicyclams, Selective Antagonists of the Human Chemokine Receptor CXCR4, Potently Inhibit Feline Immunodeficiency Virus Replication," Journal of Virology, 73(8): 6346-6352 (1999).
Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al., "Specific Interaction between Le.sup.X and Le.sup.X Determinants. A Possible Basis for Cell Recognition in Preimplantation Embryos and in Embryonal Carcinoma Cells," J. Biol. Chem. 264(16):9476-9484, 1989.
Egger et al. "Nanomolar E-Selectin Antagonists with Prolonged Half-Lives by a Fragment-Based Approach," JACS, 135(26): 9820-9828 (Jul. 2013).
Embury et al., "The contribution of endothelial cell P-selectin to the microvascular flow of mouse sickle erythrocytes in vivo," Blood 104(10):3378-3385, Nov. 15, 2004.
English Abstract for DE 2434953, Feb. 6, 1975.
English Abstract for JP 9-176047, published Jul. 8, 1997.
English Abstract for JP 2002-520323, published Jul. 9, 2002/.
English Abstract for WO 96/20204, published Jul. 4, 1996.
English Translation of JP 06-0306092, dated Nov. 1, 1994.
English Translation of JP 2004-518704, dated Jun. 24, 2004.
Ernst et al., "Design and Synthesis of E-Selectin Antagonists," Chimia 55:268-274, 2001.
Ernst et al., "From carbohydrate leads to glycomimetic drugs," Nature Reviews 8:661-677, Aug. 2009.
Ernst, "Substrate and donor specificity of glycosyl transferases," Glycoconjugate Journal 16: 161-170, 1999.
Esposito et al., "Exploration of a Potent E-selectin Antagonist (GMI-1271) as a Potential Therapeutic for Treating Breast Cancer Metastasis to the Lung and Bone", AACR Annual Meeting 2014, Poster #4039, Apr. 8, 2014.
Esposito et al., "Exploration of a Potent E-selectin Antagonist (GMI-1271) as a Potential Therapeutic for Treating Breast Cancer Metastasis to the Lung and Bone", Cancer Res, Abstract #4039, Oct. 1, 2014.
Faber et al., "The Many Facets of SDF-1a, CXCR4 Agonists and Antagonists on Hematopoietic Progenitor Cells," J. Biomed. & Biotech. Article ID 26065:1-10, 2007.
Faderl et al., "Clofarabine Plus Cytarabine Compared With Cytarabine Alone in Older Patients With Relapsed or Refractory Acute Myelogenous Leukemia: Results From the Classic I Trial," Journal of Clinical Oncology, 30(20), 2492-2499, 2012.
Feletou, M. et al., "Endothelial dysfunction: a multifaceted disorder," Am. J. Physiol. Heart Circ. Physiol., 291: H985-H1002 (2006).
Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.
Fenderson et al., "The blood group I antigen defined by monoclonal antibody C6 is a marker of early mesoderm during murine embryogenesis," Differentiation 38:124-133, 1988.
Filser, C. et al., "Synthetic glycopeptides from the E-selectin ligand 1 with varied sialyl Lewis(x) structure as cell-adhesion inhibitors of E-selectin," Angewandte Chemie—International Edition, 46(12): 2108-2111 (2007).
Flanner et al., "Comparison of Predicted GMI-1070 Human Intravenous Pharmacokinetics from in silico PBPK and Allometric Scaling Models", AAPS Annual Meeting, Abstract, Nov. 2009.
Frenette, Paul S. et al., "Sulfated Glycans Induce Rapid Hematopoietic Progenitor Cell Mobilization: Evidence for Selectin-Dependent and Independent Mechanisms," Blood, 96:2460-2468, (2000).
Frison, N. et al., "Oligolysine-Based Oligosaccharide Clusters: Selective Recognition and Endocytosis by the Mannose Receptor and Dendritic Cell-Specific Intercellular Adhesion Molecule 3 (ICAM-3)-Grabbing Nonintegrin," The Journal of Biological Chemistry 278(26):23922-23929, Apr. 2003.
Fruehauf, S., et al., "Protection of hematopoietic stem cells from chemotherapy-induced toxicity by multidrug-resistance 1 gene transfer," Recent Results in Cancer Research, 144, Abstract Only), (1998), 1 pQ.
Fukushi et al., "Novel Fucolipids Accumulating in Human Adenocarcinoma," J. Biol. Chem. 259(16):10511-10517 (1984).
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al., "Endogenous Tumor Lectins: Overview and Perspectives," Anticancer Res. 6:573-578, 1986.
Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocyctes," Nature 304:30-34, 1983.
Garber, N. et al., "On the specificity of the D-galactose-binding lectin (PA-I) of Pseudomonas aeruginosa and its strong binding to hydrophobic derivatives of D-galactose and thiogalactose," Biochimica et Biophysica Acta, 1116:331-333 (1992).
Gelbrich, T. et al., "Preparation of 4-benzylsulfanyl[1,2,3,5]dithiadiazol-1-ylium chlorides: potential precursors to meso-ionic 1,2,3,5-dithiadiazolium-4-thiolate," Arkivoc, (vi): 224-223 (2002).

(56) References Cited

OTHER PUBLICATIONS

Ghobrial, Im, "Myeloma as a model for the process of metastasis: implications for therapy," 120(1): 20-30 (2012).
Gilboa-Gardner, N. et al., "A new mitogenic D-galactosephilic lectin isolated from seeds of the coral-tree *Erythrina corallodendron*. Comparison with *Glycine max* (soybean) and *Pseudomonas aeruginosa* lectins," Canadian Journal of Biochemistry, 59(5):315-320 (1981).
Goodman and Gillman's, "Pharmacological Basis of Therapeutics," 10th edition, p. 54 (2001).
Gooi et al., "Stage-specific embryonic antigen involves alpha 1-3 fucosylated type 2 blood group chains," Nature 292:156-158, 1981.
Gout, et al., "Selectins and selectin ligands in extravasation of cancer cells and organ selectivity of metastasis," Clin. Exp. Metastasis, 25(4): 335-344 (2008).
Gravina et al., "Abstract 428: Dual E-selectin and CXCR4 inhibition reduces tumor growth and increases the sensitivity to docetaxel in experimental bone metastases of prostate cancer," Cancer Research, 75(15 Supplemental), 428-429, Aug. 2, 2015.
Gravina et al., "Abstract 428: Dual E-selectin and CXCR4 inhibition reduces tumor growth and increases the sensitivity to docetaxel in experimental bone metastases of prostate cancer," Proceedings of the 106th Annual Meeting of the American Association for Cancer Research, Abstract #428, Apr. 18-22, 2015, Philadelphia, PA.
Griciuc et al., "Alzheimer's Disease Risk Gene CD33 Inhibits Microglial Uptake of Amyloid Beta," Neuron, 78(4), 631-643, May 22, 2013.
Guha et al., "Cod glycopeptide with picomolar affinity to galectin-3 suppresses T-cell apoptosis and prostate cancer metastasis," Proceedings of the National Academy of Science, 110(13), 5052-5057, 2013.
Hakomori, "Aberrant Glycosylation in Cancer Cell Membranes as Focused on Glycolipids: Overview and Perspectives," Cancer Res. 45:2405-2414, 1985.
Hakomori et al., "Novel Fucolipids Accumulating in Human Adenocarcinoma. I. Glycolipids With Di-or Trifucosylated Type 2 Chain," J. Biol. Chem. 259(7):4672-4680, 1984.
Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.
Halloran et al., "Ley/H: An endothelial-selective cytokine-inducible angiogenic mediator," Journal of Immunology, 164(9): 4868-4877 (May 1, 2000).
Hamamoto et al., "Inhibition of Dextram Sulphat Sodium (DSS)-induced Colitis in Mice by Intracolonically Administered Antibodies Against Adhesion Molecules (Endothelial Leucocyte Adhesion Molecule-1 (ELAM-1) or Intercellular Adhesion Molecule-1 (ICAM-1))", Clinical ExperimentalImmunoloqv, 117, (1999), 462-468.
Handa et al., "Selectin GMP-140 (CD62; PADGEM) Binds to Sialosyl-Le[a] and Sialosyl-Le[x], and Sulfated Glycans Modulate this Binding," Biochemical and Biophysical Research Communication 181(3):1223-1230, 1991.
Handschel et al., "Irradiation induces increase of adhesion molecules and accumulation of beta2-integrin-expressing cells in humans" International Journal of Radiation Oncology, Biology, Physics 45(2): 475-481 (1999).
Hansson et al., "Biosynthesis of the Cancer-associated Sialyl-Le.sup.a Antigen," Journal of Biological Chemistry 260(16):9388-9392, 1985.
Harlan, "Introduction-anti-adhesion therapy in sickle cell disease," Blood 95:365-367, 2000.
Hasegawa et al., "Synthesis of deoxy-L-fucose-containing sialyl Lewis X ganglioside analogues," Carbohydrate Research 257: 67-80, 1994.
Hasegawa et al., "Synthesis of sialyl Lewis X ganglioside analogues containing modified L-fucose residues," Carbohydrate Research 274: 165-181, 1995.

Hayashi et al., "Increased Level of Soluble E-Selectin in the Serum from Patients with Idiopathic Pulmonary Fibrosis," Inflammation, 28(1), 1-5, 2004.
Hebbar et al., "E-selectin gene S128R polymorphism is associated with poor prognosis in patients with stage II or III colorectal cancer," European Journal of Cancer, 45, 1871-1876, 2009.
Hebbel, P.R., "Blockade of Adhesion of Sickle Cells to Endothelium by Monoclonal Antibodies," The New England Journal of Medicine 342:1910-1912, Jun. 22, 2000.
Hendrix, C.W. et al., "Pharmacokinetics and Safety of AMD-3100, a Novel Antagonist of the CXCR-4 Chemokine Receptor, in Human Volunteers," Antimicrobial Agents and Chemotherapy 44(6):1667-1673, Jun. 2000.
Hickey et al., "Leukocyte-Endothelial Cell Interactions Are enhanced in Dermal Postcapillary Venules of MRL/fas[lpr] (Luplus-Prone) Mice: Roles of P- and E-Selectin," The Journal of Immunology, 168, 4728-4736, 2002.
Hiddemann et al., "Management of Acute Myeloid Leukemia in Elderly Patients," Journal of Clinical Oncology, 17(11), 3569-3576, 1999.
Hilal et al., "Electronic structure of orotic acid I. Geometry, conformational preference and tautomerism:, Journal of Molecular Structure (Theochem)" 685 (2004) 35-42.
Hilgenbrink. et al., "Folate receptor-mediated drug targeting: from therapeutics to diagnostics," J. Pharm. Sci., 94(10): 2135-2146 (2005).
Holgate, St et al., "Epithelium dysfunction in asthma," Current Reviews of Allergy and Clinical Immunology, 120: 1233-1234 (2007).
Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.
Hong, P. W.-P. et al., "Identification of the Optimal DC-SIGN Binding Site on Human Immunodeficiency Virus Type 1 gp120," Journal of Virology 18(15):8325-8336, Aug. 2007.
Horacek et al., "Multi-analytical evaluation of serum levels of cytokines and adhesion molecules in patients treated for acute myeloid leukemia using biochip array technology," Biomed Pap Med Fac Univ Palacky Olomouc, Czech Repub., 157(4), 277-279, Dec. 2013.
Horiya et al., "Recent strategies targeting HIV glycans in vaccine design," Nature Chemical Biology, 10, 990-999, 2014.
Huang et al., "Postischemic Cerebrovascular E-Selectin Expression Mediates Tissue Injury in Murine Stroke," Stroke, 31, 3047-3053, 2000.
Huse et al., "Generation of a Large Combinatorial Library of the Immunoglobulin Repertoire in Phage Lambda," Science 246:1275-1281, 1989.
Huwe, C. M. et al., "Design, Synthesis and Biological Evaluation of Aryl-substituted Sialyl Lewis X Mimetics Prepared Via Cross-metathesis of C-Fucopeptides," Biological & Medicinal Chemistry 7:773-788, 1999.
Hynes, R., "Integrins: A Family of Cell Surface Receptors," Cell 48:549-554, 1987.
Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.
International Search Report for PCT/US2017/055648 dated Jan. 2, 2018.
Inwald, D. P. et al, "Platelet and leucocyte activation in childhood sickle cell disease: association with nocturnal hypoxaemia," British Journal of Haematologyl 11:474-481, Nov. 2000.
Ishikawa, F. et al., "Chemotherapy-resistant human AML stem cells home to and engraft within the bone-marrow endosteal region," Nature Biotechnology 25(11):1315-1321, Nov. 2007.
Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.
Itai, S. et al., "Differentiation-dependent Expression of I and Sialyl I Antigens in the Developing Lung of Human Embryos and in Lung Cancers," Cancer Research 50: 7603-7611, 1990.

(56) References Cited

OTHER PUBLICATIONS

Jeffrey et al., "Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al., "Inhibition of Human Immunodeficiency Virus Type I Reverse Transcriptase by Suramin-related Compounds," The Journal of General Virology 68(8): 2183-2192, 1987.
Jentsch, TJ et al. "Ion Channels: Function Unravelled by Dysfunction," Nature Cell Biology, 6(11): 1039-1047 (Nov. 2004).
Jiang et al., "CD33 in Alzheimer's Disease," Molecular Neurobiology, 46, 529-535, 2014.
Jubeli et al., "E-selectin as a target for drug delivery and molecular imaging," Journal of controlled Release, 158, 194-206, 2012.
Juliusson et al., "Age and acute myeloid leukemia: real world data n decision to treat and outcomes from the Swedish Acute Leukemia Registry," Blood, 113, 4170-4187, 2009.
Kaila, N. et al., "β-C-Mannosides as Selectin Inhibitors," Journal of Medicinal Chemistry 45(8): 1563-1566, 2002.
Kaila, N. et al., "Design and synthesis of sialyl Lewis(x) mimics as E- and P-selectin inhibitors," Med Res Rev 22(6):566-601, Nov. 2002.
Kannagi, R. et al. "Carbohydrate-mediated cell adhesion in cancer metastasis and angiogenesis," Cancer Sci., 95(5): 377-384 (2004).
Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kannagi et al., "Stage-specific embryonic antigens (SSEA-3 and -4) are epitopes of a unique globo-series ganglioside isolated from human teratocarcinoma cells," Embo J. 2(12):2355-2361, 1983.
Kansas, G., "Selectins and Their Ligands: Current Concepts and Controversies," Blood, 88(9): 3259-3287 (1996).
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Katayama, Y., et al., "Cd 44 is a physiological E-selectin ligand on neutrophils", J. Exp. Med. 201(8), (2005), 1183-1189.
Katayama, Y. et al., "PSGL-1 Participates in E-Selectin-Mediated Progenitor Homing to Bone Marrow: Evidence for Cooperation Between E-Selectin Ligands and a4 Integrin," Blood, 102:2060-2067, (2003).
Kaul, D.K. et al., "Hypoxia/reoxygenation causes inflammatory response in transgenic sickle mice but not in normal mice," The Journal of Clinical Investigation 106(3):411-420, Aug. 2000.
Khatib, A.-M., et al., "Inhibition of Hepatic Endothelial E-Selectin Expression by C-raf antisense Oligonucleotides Blocks Colorectal Carcinoma Liver Metastasis", Cancer Research 62(19), (2002), 5393-5398.
Kiel, M. J., et al., "SLAM Family Receptors Distinguish Hematopoietic Stem and Progenitor Cells and Reveal Endothelial Niches for Stem Cells" Cell 121 (7) (2006}, 11 09-1121.
Kilgore et al., "Reducation of myocardial infarct size in vivo by carbohydrate-based glycomimetics" Journal of Pharmacology and Experimental Therapeutics, American Society for Pharmacology and Experimental Therapeutics, 284(1):427-435 (1998).
Kim et al., "Inhibition of the CXCR4/CXCL12 Chemokine Pathway Reduces the Development of Murine Pulmonary Metastases," Clin. Exp. Metastasis 25(3):201-211, 2008.
Kitagawa et al., "Characterization of Mucin-Type Oligosaccharides With the Sialyl-Le.sup.a Structure From Human Colorectal Adenocarcinoma Cells," Biochem. Biophys. Res. Commun. 178(3):1429-1436, 1991.
Kitagawa et al., "Immunoaffinity Isolation of a Sialyl-Le$^a$ Oligosaccharide from Human Milk," J. Biochem. 104:591-594, 1988.
Klyosov et al., "Galectins in Disease and Potential Therapeutic Approaches," In Galectins and Disease Implications for Targeted Therapeutics, American Chemical Society, Washington, DC, Chapter 1, pp. 3-43, 2012.

Kneuer et al: "Selectins—potential pharmacological targets?" Drug Discovery Today vol. 11, No. 21-22, pp. 1034-1040, Oct. 2006.
Ko, HL et al. "In Vitro and In Vivo Inhibition of Lectin Mediated Adhesion of Pseudomonas aeruginosa by Receptor Blocking Carbohydrates," Infection, 15(4): 21-24 (1987).
Kobayashi et al., "Cimetidine Inhibits Cancer Cell Adhesion to Endothelial Cells and Prevents Metastasis by Blocking E-selectin Expression," Cancer Research, 60, 3978-3984, 2000.
Koch, Alisa E et al., "Angiogenesis mediated by soluble forms of E-selectin and vascular cell adhesion molecule-1," Nature, 376(6540): 517-519 (1995).
Koenig et al., "Selectin Inhibition: Synthesis and Evaluation of Novel Sialylated, Sulfated and Fucosylated Oligosaccharides, Including the Major Capping Group of Glycam-1", Glycobiology, 7(1):79-93 (1997).
Kogan, T.P. et al., "Novel Synthetic Inhibitors of Selectin-Mediated Cell Adhesion: Synthesis of 1,6-Bis[3-(3-carboxymethylphenyl)-r-(2-.alpha.-.sub.D-monnopyranosyloxy)p-henyl]hexane (TBC1269)," J Med. Chem 41:1099-1111, 1998.
Kogan, T.P. et al., "Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38: 4976-4984, Dec. 22, 1995.
Kogan, T.P. et al., "Rational Design and Synthesis of Oligosaccharide Mimetics: Selectin Antagonists as Cell Adhesion Inhibitors," Abstracts of Papers, 210.sup.th ACS National Meeting, American Chemical Society, Chicago, IL, Aug. 20-24, 1995, MEDI-18.
Kohler et al., "Continuous cultures of fused cells secreting antibody of predefined specificity," Nature 256:495-497, 1975.
Kohler et al., "Derivation of specific antibody-producing tissue culture and tumor lines by cell fusion," Eur. J. Immunol. 6:511-519, 1976.
Kojima et al., "Specific Interaction between Gangliotriaosylceramide (G.sub.g3) and Sialosyllactosylceramide (G.sub.M3) as a Basis for Specific Cellular Recognition between Lymphoma and Melanoma Cells," J. Biol. Chem. 264(34):20159-20162, 1989.
Kolb et al., "Development of Tool for the Design of Selectin Antagonists," Chem. Eur. J. 3(10):1571-1578, 1997.
Kolb et al., "Recent progress in the glycodrug area," Pure & Applied Chemistry 69(9):1879-1884, 1997.
Komrokji et al., "The Colony-Stimulating Factors: Use to Prevent and Treat Neutropenia and Its Complications," Expert Opin.Biol. Ther., 4:1897-1910, (2004).
Koprowski et al., "Colorectal Carcinoma Antigens Detected by Hybridoma Antibodies," Somatic Cell Genetics 5(6):957-972, 1979.
Kulidjian et al., "Differential role of E-seletin and P-selectin in T lymphocyte migration to cutaneous inflammatory reactions induced by cytokines," International Immunology, 14(7), 751-760, 2002.
Kuuliala et al., "Circulating soluble E-selectin in early rheumatoid arthritis: a prospective five year study," Annals of Rheumatic Diseases, 61, 242-246, 2002.
Kuzuoka, "Antitumor activity of murine monoclonal antibody NCC-ST-421," Chem. Ab. 115:27344v, 1991.
Kwiatskowski et al., "Tautomerism and Electronic Structure of Biological Pyrimidines" Adv Het Chem 1975, pp. 199-335.
Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.
Kwong, P. D. et al., "Rational Design of Vaccines to Elicit Broadly Neutralizing Antibodies to HIV-1," Cold Spring Harbor Perspectives in Medicine 1-16, 2011.
Kyriakides et al., Surgery, 128(2):327-31, Aug. 2000.
Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.
Lanne, B. et al., "Binding of the galactose-specific Pseudomonas aeruginose lectin, PA-I, to glycosphingolipids and other glycoconjugates," Glycoconjugate Journal, 11:292-298 (1994).
Larsen et al., "PADGEM-Dependent Adhesion of Platelets to Monocytes and Neutrophils is Mediated by a Lineage-Specific Carbohydrate, LNF III (CD15)," Cell 63:467-474, 1990.

(56) References Cited

OTHER PUBLICATIONS

Lee et al., "A new method of sequencing linear oligosaccharides on gels using charged, fluorescent coniugates" Carbohydrate Research, vol. 214, 1991, pp. 155-168, XP000226749.

Lemoli et al., "Hematopoietic stem cell mobilization," Haematologica, 93 (3): 321-324 (2008).

Leppla, S H et al., "Anthrax Toxin Fusion Proteins for Intracellular Delivery of Macromolecules," Journal of Applied Microbiology., 87(2): p. 284 (Aug. 1, 1999).

Ley, K. et al., "Selectins in T-cell Recruitment to Non-Lymphoid Tissues and Sites of Inflammation," Nature Reviews, 4: 1-11 (May 2004).

Ley, K., "The role of selectins in inflammation and disease," Trends in Molecular Medicine, 9(6): 263-268 (Jun. 2003).

Li et al., "Hematopoietic-Derived Galectin-3 Causes Cellular and Systemic Insulin Resistance," Cell, 167, 973-984, 2016.

Li et al., "Increased CSF E-Selectin in Clinical Alzheimer's Disease without Altered CSF A$\beta_{42}$ and Tau," Journal of Alzheimer's Disease, 47, 883-887, 2015.

Li, B., et al., "Delaying Acute Graft-Versus-Host Disease in Mouse Bone Marrow Transplantation by Treating Donor Cells with Antibodies Directed at L-Selectin and a4 Integrin Prior to Infusion," Scand. J, I Immunol 59:464-468, 2004.

Liang et al., "Clinicopathological and prognostic significance of sialyl Lewis X overexpression in patients with cancer: a meta-analysis," Onco Targets and Therapy, 9, 3113-3125, 2016.

Lindenberg et al., "Carbohydrate binding properties of mouse embryos," J. Reprod. Fert. 89:431-439, 1990.

Lipartiti et al., "Monosialoganglioside GM1 Reduces NMDA Neurotoxicity in Neonatal Rat Brain," Experimental Neurology 113:301-305, 1991.

Liu et al., "Altering the Specificity of the Antibody Response to HIV gp120 with a Glycoconjugate Antigen," ACS Chemical Biology, 11, 1702-1709, 2016.

Liu et al., "Broadly Neutralizing Antibody-Guided Carbohydrate-Based HIV Vaccine Design: Challenges and Opportunities," ChemMedChem, 11, 357-362, 2016.

Llmer et al., "Cell surface galectin-3 defines a subset of chemoresistant gastrointestinal tumor-initiating cancer cells with heightened stem cell characteristics," Cell Death and Disease, 7, e2337, 1-9, 2016.

Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.

Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.

Lowe et al., "ELAM-1-Dependent Cell Adhesion to Vascular Endothelium Determined by a Transfected Human Fucosyltransferase cDNA," Cell 63:475-484, 1990.

Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870, May 2009.

Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.

Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.

Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.

Magnani et al., "Glycomimetic Drugs—A New Source of Therapeutic Opportunities," Discovery Medicine, 8(43), 247-252, 2009.

Magnani et al., "Pan-selectin Antagonist GMI-1070 affects Biomarkers of Adhesion, Activation and the Coagulation Cascade in Sickle Cell Adults at Steady State", Blood, 120, Abstract #87, Nov. 2012.

Magnani, "The Discovery, Biology, and Drug Development of Sialyl Le$^a$ and Sialyl Le$^{x}$", Archives of Biochemistry and Biophysics, 426:122-131, May 8, 2004.

Magnani, J., "Carbohydrate Sequences Detected by Murine Monoclonal Antibodies," Chemistry and Physics of Lipids 42:65-74, 1986.

Magnani, J., "Potent Glycomimetic Inhibitors of the Adhesion Molecule, PA-IIL, for the Bacterial Pathogen, Pseudomonas auroginosa," Glycobiology 13(11): 854, Abstract No. 104, Oct. 2003.

Maly, P., et al., "The a(1,3)Fucosyltransferase Fuc-TVII Controls Leukocyte Trafficking through an Essential Role in L-, E-, and P-selection Ligand Biosynthesis", Cell. 86(4), It 1996), 643-653.

Mann, AP et al., "Identification of Thioaptamer Ligand against E-Selectin: Potential Application for Inflamed Vasculature Targeting," PLoS ONE, 5(9): 1-11 (Sep. 2010).

Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.

Matsui, N. M. et al., "Heparin inhibits the flow adhesion of sickle red blood cells to Pselectin," Blood 100(10):3790-3796, Nov. 15, 2002.

Matsui, N. M. et al., "The Novel Adhesion of Erythrocytes to P-Selectin in Sickle Cell Disease," Blood 96(11) Pt. 1:600a, Abstract #2575, Nov. 16, 2000.

Matsui, N. M.et al., "P-selectin mediates the adhesion of sickle erythrocytes to the endothelium," Blood 98(6):1955-1962, Sep. 15, 2001.

Mauch, P., et al., "Hematopoietic Stem Cell Compartment: Acute and Late Effects of Radiation Therapy and Chemotherapy", Int. J. Radiation Oncology Bioi. Phys .. 31(5), 1995), 1319-1339.

McCavit et al., "An Analysis of the Pediatric Sub-Group From the Phase 2 Study of GMI-1070—A Novel Agent for the Vaso-Occlusive Crisis of Sickle Cell Anemia", Blood, 122(21):2206, Nov. 15, 2013.

McCavit et al., "An Analysis of the Pediatric Sub-Group From the Phase 2 Study of GMI-1070—A Novel Agent for the Vaso-Occlusive Crisis of Sickle Cell Anemia", ASH Annual Meeting 2013, Poster #56448, Dec. 8, 2013.

McEver et al., "Leukocyte trafficking mediated by selectin-carbohydrate interactions," J. Biol. Chem., 270 (19): 11025-11028 (1995).

McKenzie et al., "Low rhodamine 123 retention identifies long-term human hematopoietic stem cells with the Lin-CD34+CD38- population", Blood. 109, (2007), 543-545.

McLean et al., "Effects of a small molecule inhibitor of ICAM-1 and E-selectin expression on colonic inflammatory hyperalgesia and colitis" Digestive Disease 2003, Orlando FL, May 2003, abstract.

Menendez et al., "A Peptide Inhibitor of HIV-1 Neutralizing Antibody 2G12 is not a Structural Mimic of the Natural Carbohydrate Epitope on gp120," The FASEB Journal 22:1380-1382, May 2008.

Mimeault, et al., "Stem cells: a revolution in therapeutics-recent advances in stem cell biology and their therapeutic applications in regenerative medicine and cancer therapies," Clin. Pharmacol. Therapeutics, 82(3): 252-264 (2007).

Mitsiades, et al., "Preclinical studies in support of defibrotide for the treatment of multiple myeloma and other neoplasias," Clin. Cancer Res., 15 (4): 1210-1221 (2009).

Moore et al., "Evolution of an HIV Glycan-Dependent Broadly Neutralizing Antibody Epitope Through Immune Escape," Nature Medicine doi:10.1038/nm.2985 pp. 1-6, Oct. 2012.

Moore, "Waking Up HSCs: A new Role for E-Selectin," Nat. Med., 18:16131614, (2012).

Mosley et al., "Recent Patents Regarding the Discovery of Small Molecule CXCR4 Antagonists," Expert Opin. Ther. Patents 19(1):23-38, 2009.

Mulligan et al., "Role of Endothelial-Leukocyte Adhesion Molecule 1 (ELAM-1) in Neutrophil-mediated Lung Injury in Rats," J Clin Invest.,88(4):1396-406, Oct. 1991.

(56) References Cited

OTHER PUBLICATIONS

Mulligan et al., "Selection for animal cells that express the *Escherichia coli* gene coding for xanthine-gunine phosphoribosyltransferase," Proc. Natl. Acad. Sci. USA 78:2072-2076, 1981.

Myers et al., "E-Selectin Inhibitor GMI-1271 Works in Combination with Low-Molecular Weight Heparin to Decrease Venous Thrombosis and Bleeding Risk in a Mouse Model", Blood, 124(21):593, Dec. 6, 2014.

Myers et al., "Novel E-Selectin Antagonist GMI-1271 Decreases Venous Thrombosis without Increased Bleeding Potential in a Mouse Model", ASH Annual Meeting 2012, Poster #53444, Dec. 10, 2012.

Myers et al., "Pan-Selectin Antagonist, GMI-1070 Decreases Venous Thrombosis in a Mouse Model", Blood, 118, Abstract #3273, Nov. 2011.

Myers Jr. et al., "E-Selectin Inhibitor GMI-1271 Works in Combination with Low-Molecular Weight Heparin to Decrease Venous Thrombosis and Bleeding Risk in a Mouse Model," Proceedings of the 56$^{th}$ Annual Meeting of the American Society of Hematology, Abstract #593 Oral Presentation on Dec. 8, 2014, San Francisco, CA.

Myers Jr. et al., "Novel E-Selectin Antagonist GMI-1271 Decreases Venous Thrombosis without Increased Bleeding Potential in a Mouse Model," Blood, 120(21), Abstract #3422, Nov. 16, 2012.

Myers Jr. et al., "Novel E-Selectin Antagonist GMI-1271 Decreases Venous Thrombosis without Increased Bleeding Potential in a Mouse Model," Proceedings of the 54$^{th}$ Annual Meeting of the American Society of Hematology, Abstract #3422 Poster Presentation on Dec. 10, 2012, Atlanta, GA.

Nagel, R. L., "A Knockout of a Transgenic Mouse-Animal Models of Sickle Cell Anemia," The New England Journal of Medicine 339:194-195, Jul. 16, 1998.

Narita, T. et al., "Corticosteroids and medroxyprogesterone acetate inhibit the induction of breast cancer cells," Anticancer Research, 15(6B): 2523-2527 (1995)—Abstract.

Narumi, Tetsuo et al., "Synthesis and Biological Evaluation of Selective CXCR4 Antagonists Containing Alkene Dipeptide Isosteres," Organic & Biomolecular Chemistry, 8(3): 616-621(Feb. 7, 2010).

Natarajan, M.M. et al., "Adhesion of sickle red blood cells and damage to interleukinIbeta stimulated endothelial cells under flow in vitro," Blood 87:4845-4852, 1996.

Natoni et al., "E-Selectin Ligand Expression Increases with Progression of Myeloma and Induces Drug Resistance in a Murine Transplant Model, Which Is Overcome by the Glycomimetic E-Selectin Antagonist, GMI-1271," Blood, 126(23), Abstract #1805, Dec. 3, 2015.

Natoni et al., "E-Selectin Ligand Expression Increases with Progression of Myeloma and Induces Drug Resistance in a Murine Transplant Model, Which Is Overcome by the Glycomimetic E-Selectin Antagonist, GMI-1271," Proceedings of the 57$^{th}$ Annual Meeting of the American Society of Hematology, Abstract #1805 Poster Presentation on Dec. 5, 2015 in Orlando, FL.

Natoni et al., "Multiple Myeloma Cells Express Functional E-Selectin Ligands Which Can be Inhibited Both in-Vitro and in-Vivo Leading to Prolongation of Survival in a Murine Transplant Model", Blood, 124(21):4718, Dec. 6, 2014.

Natoni et al., Multiple Myeloma Cells Express Functional E-Selectin Ligands Which Can be Inhibited Both in vitro and in vivo Leading to Prolongation of Survival in a Murine Transplant Model, Proceedings of the 56$^{th}$ Annual Meeting of the American Society of Hematology, Abstract #4718 Poster Presentation on Dec. 8, 2014 in San Francisco, CA.

Newlaczyl et al., "Galectin-3—A jack-of-all-trades in cancer," Cancer Letters, 313, 123-128, 2011.

Nguyen, M et al., "Novel synthetic analogs 1-29 of sialyl Lewis X can inhibit angiogenesis in vitro and in vivo," Biochemical and Biophysical Research Communications, 228(3): 716-723 (Nov. 21, 1996).

Nicolaou et al., "Total Synthesis of the Tumor-Associated Le$^x$ Family of Glycosphingolipids," J. Amer. Chem. Soc. 112:3693-3695, 1990.

Noguchi, M. et al. "A minor E-selectin ligand, CD65, is critical for extravascular infiltration of acute myeloid leukemia cells," Leukemia Research, 25: 847-853 (2001).

Norman et al., "Sialyl Lewisx(sLex) and an sLex Mimetic, CGP69669A, Disrupt E-Selectin-Dependent Leukocyte Rolling In Vivo," Blood, 91(2):475-483 (Jan. 15, 1998).

Nudelman et al., "Novel Fucolipids of Human Adenocarcinoma: Disialosyl Lea Antigen (III.sup.4FucIII.sup.6NeuAcIV.sup.3NeuAcLc.sub.4) of Human Colonic Adenocarcinoma and the Monoclonal Antibody (FH7) Defining This Structure," J. Biol. Chem. 261:5487-5495,1986.

Nutku, E. et al., "Ligation of Siglec-8: a selective mechanism for induction of human eosinophil apoptosis," Blood, 101(12): 5014-5020 (2003).

Oancea et al., "Alleviation of Acute Drug-Induced Liver Injury Following Acetaminophen Overdose by Therapeutic Blockade of E-Selectin in Preclinical Mouse Model," Gastroenterology, 150(4), Supplement 1, S1029, Abstract #358, (no oral presentation available) New Orleans, LA, Apr. 2016.

Obermajer, N. et al., "Design, synthesis and activity evaluation of mannose-based DC-SIGN antagonists," Molecular Diversity 15:347-360, May 2011.

Orhlein, R., "Carbohydrates and Derivatives as Potential Drug Candidates with Emphasis on the Selectin and Linear-B Area," Mini Reviews in Medicinal Chemistry 1: 349-361, 2001.

Oxford Textbook of Oncology, vol. 1, published 1995 by Oxford University Press, pp. 447-453.

Palcic et al., "A Bisubstrate Analog Inhibitor for .alpha.(1.fwdarw.2)-Fucosyltransferase," J. Biol. Chem. 264:17174-17181, 1989.

Palcic et al., "Enzymic Synthesis of Oligosaccharides Terminating in the Tumor-Associated Sialyl-Lewis-a Determinant," Carbohydr. Res. 190:1-11, 1989.

Palcic et al., "Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.

Palma-Vargas, J.M. et al., "Small-Molecule Selectin Inhibitor Protects Against Liver Inflammatory Response After Ischemia and Reperfusion," J. Am. Coll. Surg. 185: 365-372, 1997.

Pamphilon et al., "Stem Cell Donation—What advice can be given to the donor?," Br. J. Haematol. 147(1):71-76, Oct. 2009, Author manuscript available at NIH Public access Aug. 1, 2012.

Patton, J. T. et al., "GMI-1070: a Small Glycomimetic, Pan-selectin Antagonist that Improves Blood Flow and Inhibits Blood Cell Adhesion in Sickle Mice," Abstract ID:ABSTY-5APYL-CA6TP-V2ET6, Sep. 2, 2005.

Payre, et al., "Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.

Payre, N. et al., "Chemoenzymatic Synthesis of a Modified Pentasaccharide as a Specific Substrate for a Sensitive Assay of a-Amylase by Fluorescence Quenching," Angew. Chem. Int. Ed. Engl. 34(11): 1239-1241 (1995).

Peacock et al., "Emergency Department Use of Galectin-3,"Critical Pathways in Cardiology, 13(2), 73-77, 2014.

Pejchal R. et al., "A Potent and Broad Neutralizing Antibody Recognizes and Penetrates the HIV Glycan Shield," Science 334:1097-1103, Nov. 2011.

Pelus, "Peripheral blood stem cell mobilization: new regimens, new cells, where do we stand," Curr. Opin. Hematol., 15(4): 285-292 (2008).

Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).

Pentelute, Brad L. et al., "Chemica 1 1-16 dissection of protein translocation through the anthrax toxin pore," Angewandte Chemie, 50(10): 2294-2296 (Mar. 1, 2011).

(56) References Cited

OTHER PUBLICATIONS

Perret, S. et al., "Structural basis for the interaction between human milk oligosaccharides and the bacterial lectin PA-IIL of Pseudomonas aeruginosa," Biochem. J. 389: 325-332, 2005. cited by other.
Pezeshkian et al., "Leukemia Mediated Endothelial Cell Activation Modulates Leukemia Cell Susceptibility to Chemotherapy through a Positive Feedback Loop Mechanism," PLOS One, 8(4), e60823, 2013.
Phillips et al., "ELAM-1 Mediates Cell Adhesion by Recognition of a Carbohydrate Ligand, Sialyl-Le.sup.x," Science 250:1130-1132, 1990.
Picker er al., "The Neutrophil Selectin LECAM-1 Presents Carbohydrate Ligands to the Vascular Selectins ELAM-1 and GMP-140," Cell 66:921-933, 1991.
Plasterk, R. H. A., et al., "The silence of the genes", Current Opinion in Genetics and Develooment 10 (2000), 562-567.
Price et al., "Breast Cancer Cells Metastasize to Bone through E-Selectin Positive Vascular Gateways", AACR Annual Meeting 2014, Poster #4831, Apr. 9, 2014.
Price et al., "Breast cancer cells metastasize to bone through E-selectin + vascular gateways," Cancer Research, 74(19 Supplement), 4831, Sep. 20, 2014.
Price et al., "Breast Cancer Cells Metastasize to Bone through E-Selectin Positive Vascular Gateways," Proceedings of the 105th Annual Meeting of the AACR, 4831, Apr. 5-9, 2014, San Diego, CA.
Price et al., "Metastatic breast cancer cell communication within a pro-dormancy bone marrow niche," Cancer Research, 75(15 Supplement), Abstract #3212, Aug. 2015.
Price et al., "Metastatic Breast Cancer Cell Communication Within a Pro-Dormancy Bone Marrow Niche," Proceedings of the 106th Annual Meeting of the American Association for Cancer Research, Abstract #3212, Apr. 18-22, 2015, Philadelphia, PA.
Prokazova et al., "Sialylated lactosylceramides. Possible inducers of non-specific immunosuppression and atherosclerotic lesions," European Journal of Biochemistry 172:1-6, 1988.
Purton et al., "Limiting Factors in Murine Hematopoietic Stem Cell Assays," Cell Stem Cell 1: 263-270, Sep. 2007.
Rapoport et al., "Ganglioside Binding Pattern of CD33-Related Siglecs," Bioorganic and Medicinal Chemistry Letters, 13(4), 675-678, Feb. 2003.
Rapoport, E. et al., "Probing Sialic Acid Binding Ig-Like Lectins (Siglecs) with Sulfated Oligosaccharides," Biochemistry (Moscow), 71(5): 496-504 (2006).
Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.
Ravandi et al., "Characteristics and outcome of patients with acute myeloid leukemia refractory to 1 cycle of high-dose cytarabine-based induction chemotherapy," Blood 116(26), 5818-5823, 2010.
Reina et al., "1,2-Mannobioside Mimic: Synthesis, DC-SIGN Interaction by NMR and Docking, and Antiviral Activity," ChemMedChem 2:1030-1036, 2007.
Rice et al., "An Inducible Endothelial Cell Surface Glycoprotein Mediates Melanoma Adhesion," Science 246:1303-1306, 1989.
Richert et al., "Inhibition of CXCR4 by Ctce-9908 Inhibits Breast Cancer Metastasis to Lung and Bone," Oncology Reports 21:761-767, 2009.
Roberge, J. Y., et al., "A Strategy for a Convergent Synthesis of N-Linked Glycopeptides on a Solid Support", Science 269(5221), (1995), 202-204.
Röllig et al., "Long-Term Prognosis of Acute Myeloid Leukemia According to the New Genetic Risk Classification of the European LeukemiaNet Recommendations: Evaluation of the Proposed Reporting System," Journal of Clinical Oncology, 29(20), 2758-2765, 2011.
Rood et al., "E-Selectin and Very Late Activation Antigen-r Mediate Adhesion of Hematopoietic Progenitor Cells to Bone Marrow Endothelium," Ann Hematol, 79:477-484, (2000).

Ruoslahti et al., "New Perspectives in Cell Adhesion: RGD and Integrins," Science 238:491-497, 1987.
Sackstein, "The Biology of CD44 and HCELL in Hematopoiesis: The 'Step 2-Bypass Pathway' and Other Emerging Perspectives", Current Opinion in Hematology, 18(4):239-248 (2011).
Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.
Salameh et al., "1H-1,2,3-Triazol-1-yl thiodigalactoside derivatives as high affinity galectin-3 inhibitors," Bioorganic & Medicinal Chemistry, 18, 5367-5378, 2010.
Sanz et al., "Roflumilast inhibits leukocyte-endothelial cell interactions, expression of adhesion molecules and microvascular permeability", British Journal of Pharmacology. 152(4), (2007), 481-492.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scanlan et al., "Exploiting the Defensive Sugars of HIV-1 for Drug and Vaccine Design," Nature 446:1038-1045, Apr. 2007.
Scanlan et al., "The Broadly Neutralizing Anti-Human Immunodeficiency Virus Type 1 Antibody 2G12 Recognizes a Cluster of α1-2 mannose Residues on the Outer Face of gp120," Journal of Virology 76:7306-7321, Jul. 2002.
Scharfman et al., "Pseudomonas aeruginosa binds to neoglycoconjugates bearing mucin carbohydrate determinants and predominantly to sialyl-Lewis x conjugates," Glycobiology 9(8): 757-764, 1999.
Scharfman et al., "Recognition of Lewis x Derivatives Present on Mucins by Flagellar Components of Pseudomonas aeruginosa," Infection and Immunity 69(9): 5243-5248, Sep. 2001.
Schief et al., "Challenges for Structure-Based HIV Vaccine Design," Current Opinion in HIV and AIDS 4:431-440, 2009.
Schwizer et al. "Pre-organization of the Core Structure of E-Selectin Antagonist," Chemistry—A European Journal, 18(5): 1342-1351 (Jan. 2012).
Shamay et al., "E-selectin binding peptide-polymer-drug conjugates and their selective cytotoxicity against vascular endothelial cells," Biomaterials, 30, 6460-6468, 2009.
Shan, M. et al., "HIV-1 gp120 Mannoses Induce Immunosuppressive Responses from Dendritic Cells," PLoS Pathogens 3(11):e169 1637-1650, Nov. 2007.
Sheen-Chen et al., "Serum levels of soluble E-selectin in women with breast cancer," British Journal of Surgery, 91, 1578-1581, 2004.
Shitara et al., "Application of Anti-Sialyl Le.sup.a Monoclonal antibody, KM231, for Immunotherapy of Cancer," Anticancer Res. 11:2003-2014, 1991.
Simanek et al. "Selectin-carbohydrate interactions: from natural ligands to designed mimics", Chemical Reviews vol. 98, No. 2, pp. 833-862, Jan. 1998.
Simon et al, "Effects of Selectin Antagonist GMI-1070 on the Activation State of Leukocytes in Sickle Cell Patients not in Crisis" ASH Annual Meeting 2010, Poster #32407, Dec. 6, 2010.
Simon et al., "Inhibition of E-Selectin Inflammatory Function by the Glycomimetic GMI-1070" Blood, 118, Abstract #851, Nov. 2011.
Simon et al., "Mightier than the sickle cell (editorial)", Blood, 116(10), 1633, Sep. 9, 2010.
Singh et al., "Evaluation of a CXCR4 Antagonist in a Xenograft Mouse Model of Inflammatory Breast Cancer," Clin. Exp. Metastasis 27:233-240, Mar. 2010.
Sipkins et al., "In Vivo Imaging of Specialized Bone Marrow Endothelial Microdomains for Tumor Engraftment," Nature Pub. Group GB 435 (7044):969-973, Jun. 2005.
Siuzdak et al., "Examination of the Sialyl Lewis X—Calcium Complex by Electrospray Mass Spectrometry," Bioorganic & Medicinal Chemistry Letters 4(24): 2863-2866, 1994.
Solovey et al., "Circulating Activated Endothelial Cells in Sickle Cell Anemia," The New England Journal of Medicine 337:1584-1590, Nov. 27, 1997.
Solovey et al. "Modulation of endothelial cell activation in sickle cell disease: a pilot study," Blood, 97(7): 1937-1941 (Apr. 2001).

(56) References Cited

OTHER PUBLICATIONS

Sprengard et al., "Synthesis and Biological Activity of Novel Sialyl-Lewis.sup.X Conjugates," Bioorganic & Medicinal Chemistry Letters 6(5): 509-514, 1996.
Stahn et al., Multivalent sialyl Lewis x ligands of definite structures as inhibitors of E-selectin mediated cell adhesion, Glycobiology, vol. 8, No. 4, 1998, pp. 311-319.
Stanley et al., "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23):11374-11381, 1988.
Steele et al., "#4503 A Small Molecule Glycomimetic Antagonist of E-selectin (GMI-1271) Prevents Pancreatic Tumor Metastasis and Offers Improved Efficacy of Chemotherapy," Proceedings of the 105$^{th}$ Annual Meeting of the American Association for Cancer Research, Abstract #4503, Apr. 5-9, 2014, San Diego, CA.
Steele et al., "425 A small molecule glycomimetic antagonist of E-selectin and CXCR4 (GMI-1359) prevents pancreatic tumor metastasis and offers improved chemotherapy" Cancer Research, Aug. 2015.
Steele et al., "425 A Small Molecule Glycomimetic Antagonist of E-selectin and CXCR4 (GMI-1359) Prevents Pancreatic Tumor Metastasis and Offers Improved Chemotherapy," Proceedings of the 106$^{th}$ Annual Meeting of the American Association for Cancer Research, Abstract #425, Apr. 18-22, 2015, Philadelphia, PA.
Steele et al., "A Small Molecule Glycomimetic Antagonist of E-selectin (GMI-1271) Prevents Pancreatic Tumor Metastasis and Offers Improved Efficacy of Chemotherapy", AACR Annual Meeting 2014, Poster #4503, Apr. 8, 2014.
Steele et al., "A Small Molecule Glycomimetic Antagonist of E-selectin (GMI-1271) Prevents Pancreatic Tumor Metastasis and Offers Improved Efficacy of Chemotherapy", Cancer Res, 74:Abstract 4503, Oct. 1, 2014.
Steele et al., "A small molecule glycomimetic antagonist of E-selectin and CXCR4 (GMI-1359) prevents pancreatic tumor metastasis and improves chemotherapy," Cancer Research, 75(15 Supplement), 425-426, Aug. 2, 2015.
Steele et al., "A small molecule glycomimetic antagonist of E-selectin and CXCR4 (GMI-1359) delays pancreatic tumor metastasis and significantly alters the pancreatic tumor microenvironment," Proceedings of the 107$^{th}$ Annual Meeting of the American Association for Cancer Research, Abstract #902, Apr. 16-20, 2016, New Orleans, LA.
Steele et al., "Abstract 4503: A small molecule glycomimetic antagonist of E-selectin (GMI-1271) prevents pancreatic tumor metastasis and offers a novel treatment for improved efficacy of chemotherapy," Cancer Research, 74(19 Supplement), Abstract #4503, Oct. 2014.
Stephens et al.,"The construction of highly efficient and versatile set of mammalian expression vectors," Nucleic Acids Research. 17:7110, 1989.
Stevenson et al., "Differential metastasis inhibition by clinically relevant levels of heparins," Clin. Cancer Res. 11(19): 7003-7011 (2005).
Streeter et al., "Immunohistologic and Functional Characterization of a Vascular Addressin Involved in Lymphocyte Homing into Peripheral Lymph Nodes," Journal of Cell Biology 107: 1853-1862, 1988.
Stroud et al. ,"Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439-8446, 1991.
Styles et al., GMI-1070, a Pan-Selectin Inhibitor: Safety and PK in a Phase 1/2 Study in Adults with Sickle Cell Disease, ASH Annual Meeting 2010, Poster #31824, Dec. 4, 2010.
Sudhoff et al., "Cutting Edge Communication: Circulating Endothelial Adhesion Molecules (sE-Selectin, sVCAM-1 and SICAM-1) During rHuG-CSF-Stimulated Stem Cell Mobilization," Jour. Hematother. & Stem Cell Res., 11:147-151 (2002).

Suzuma et al., "Contribution of E-Selectin to Cellular Infiltration during Endotoxin-Induced Uveitis," Invest. Ophthalmol. Vis. Sci., 39: 1620-1630 (1998).
Svenson et al., "Coupling of Acid Labile *Salmonella* Specific Oligosaccharides to Macromolecular Carriers," J. Immunol. Meth. 25:323-335, 1979.
Symon et al., "Selectins and their Counter receptors: a bitter sweet attraction," Thorax, 51: 1155-1157 (1996).
Tabarani et al., "Mannose Hyperbranched Dendritic Polymers Interact with Clustered Organization of DC-SGIN and Inhibit gp120 Binding," FEBS Letters 580:2402-2408, Mar. 2006.
Takada et al., "Adhesion of Human Cancer Cells to Vascular Endothelium Mediated by a Carbohydrate Antigen, Sialyl Lewis A$^1$," Biochem. Biophys. Res. Commun. 179(2):713-719, 1991.
Takahashi et al., "Design and Synthesis of a Water-Soluble Taxol Analogue : Taxol-Sialyl Conjugate," Bioorg. & Med. Chem. Letters 8:113-116, 1998.
Takeichi, "Cadherins: a molecular family essential for selective cell-cell adhesion and animal morphogenesis," Trends Genet. 3(8):213-217, 1987.
Tamamura. et al., "Identification of a New Class of Low Molecular Weight Antagonists against the Chemokine Receptor CXCR4 Having the Dipicolylamine-Zinc(II) Complex Structure" J. Med. Chem., 49: 3412-3415 (2006).
Tanaka et al., "Azamacrocyclic Metal Complexes as CXCR4 Antagonists," ChemMedChem, 6: 834-839 (2011).
Taniguchi et al., "Serum Levels of Galectin-3: Possible Association with Fibrosis, Aberrant Angiogenesis, and Immune Activation in Patients with Systemic Sclerosis," The Journal of Rheumatology, 39(3), 539-544, Mar. 2012.
Tedder et al., "The selectins: vascular adhesion molecules," FASEB J, 9(10): 866-73 (1995).
Tejler et al., "Fragment-based development of triazole-substituted O-galactosyl aldoximes with fragment-induced affinity and selectivity for galectin-3," Organic & Biomolecular Chemistry, 19(7), 3982-3992, 2009.
Tejler et al., "Synthesis of galactose-mimicking 1H-(1,2,3-triazol-1-yl)-mannosides as selective galectin-3 and 9N inhibitors," Carbohydrate Research, 342(12-13), 1869-1875, 2007.
Telen et al., "GMI 1070: Reduction in Time to Resolution of Vaso-Occlusive Crisis and Decreased Opioid Use in a Prospective, Randomized, Multi-Center Double Blind, Adaptive Phase 2 Study in Sickle Cell Disease" Blood, 122(21):776, Nov. 15, 2013.
Telen et al., "Randomized phase 2 study of GMI-1070 in SCD: reduction in time to resolution of vaso-occlusive events and decreased opioid use", Blood, 125(17):2656-2664, Apr. 23, 2015.
The Merck Manual of Diagnosis and Therapy, Seventeenth Edition, published 1999 by Merck Research Laboratories, pp. 397, 398, 948,949, 1916, 1979-1981.
Thoma G. et al., "A readily Available, Highly Potent E-Selectin Antagonist," Angew. Chem. Int. Ed. 40(19): 3644-3647, 2001.
Thoma, G et al., "Nanomolar E-selectin inhibitors: 700-fold potentiation of affinity by multivalent ligand presentation," Journal of the American Chemical Society, 123(41): 10113-10114 (Oct. 17, 2001).
Thoma, G. et al., "Preorganization of the Bioactive Conformation of Sialyl Lewis$^X$ Analogues Correlates with Their Affinity to E-Selectin," Angew. Chem. Int. Ed. 40(10): 1941-1945, 2001.
Thoma, G. et al., "Synthesis and biological evaluation of a potent E-selectin antagonist," J. Med. Chem. 42 (23): 4909-4913, Nov. 18, 1999.
Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.
Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.
Titz et al., "Is adamantine a suitable substituent to pre-organize the acid orientation in E-selectin antagonists?", Bioorganic & Medicinal Chemistry, 16 (2008), 1046-1056.
Titz et al., "Mimetics of Sialyl Lewis$^x$: The Pre-Organization of the Carboxylic Acid is Essential for Binding to Selectins", Chimia, 61:194-197, 2007.

(56) References Cited

OTHER PUBLICATIONS

Titz, A. et al., "Probing the carbohydrate recognition domain of E-selectin: The importance of the acid orientation in sLex mimetics," Bioorg. Med. Chem., 18(1): 19-27 (2010).
Todderund et al., "BMS-190394, a Selectin Inhbitor, Prevents Rat Cutaneous Inflammatory Reactions," J Pharmacal Exp Ther., 282(3):1298-304, Sep. 1997.
Toepfer et al., "Synthesis of Novel Mimetics of the Sialyl Lewis X Determinant," Tetrahedron Letters, vol. 36, No. 50, pp. 9161-9164, 1995.
Togel et al., "Administered mesenchymal stem cells protect against ischemic acute renal failure through differentiation-independent mechanisms," Am. J. Physical Renal Physiol., 289:F31-42, Jul. 2005.
Totani, K. et al., "Chemoenzymatic synthesis and application of glycopolymers containing multivalent sialyloligosaccharides with a poly(L-glutamic acid) backbone for inhibition of infection by influenza viruses," Glycobiology, 13(5): 315-326 (2003).
Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Turhan, et al., "Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," The American Journal of Pathology, 169(6): 1901-1909 (Dec. 2006).
Tyrrell, D. et al. "Structural requirements for the carbohydrate ligand of E-selectin," PNAS, 88: 10372-10376 (Nov. 1991).
Ueda et. al., "Structure-Activity Relationships of Cyclic Peptide-Based Chemokine Receptor CXCR4 Antagonists: Disclosing the Importance of Side-Chain and Backbone Functionalities," J. Med. Chem. 50:192-198, 2007.
Van Der Velde et al., "Galectin-3 and sST2 in prediction of left ventricular ejection fraction after myocardial infarction," Clinica Chimica Acta, 452, 50-57, Jan. 2016.
Venkataraman et al., "Reawakening Retrocyclins: Ancestral Human Defensins Active Against HIV-1," Plos Biology, 7(4): 720-729 (Apr. 2009).
Wai, "Blockade of Chemokine (C-X-C motif) Receptor 4 for the Inhibition of Hepatocellular Carcinoma Metastasis," A Thesis, in partial fulfillment of requirements for Ph.D. Degree at the Univ. of Hong Kong, Jun. 2008.
Waldmann et al., "Synthesis of 2-Acetamindo-2-Deoxyglucosylasparagine Glyco-Tripeptide and Pentapeptides by Selective C- and N-Terminal Elongation of the Peptide Chain," Carbohydrate Research 196: 75-93, 1990.
Walker et al., "Rapid Development of Glycan-Specific, Broad, and Potent Anti-HIV-1 gp120 Neutralizing Antibodies in an R5 SIV/HIV Chimeric Virus Infected Macaque," Proceedings of the National Academy of Sciences 108(50):20125-20129, Dec. 2011.
Walsh, "Novel Therapies for Asthma—Advances and Problems," Current Pharmaceutical Design, 11(23): 3027-3038 (2005).
Walz et al., "Recognition by ELAM-1 of the Sialyl-Le.sup.X Determinant on Myeloid and Tumor Cells," Science 250:1132-1135, 1990.
Wang et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.
Wang et al., "Effect of ginsenoside rg1 and rh1 on the expression of hla-dr, cd25, cd44, cd11c and e-selectin on dendritic cell," Zhongguo Mianyixue Zazhi, 23(1): 46-48 (2007)—Abstract.
Wang et al., "Galectin-3 promotes HIV-1 budding via association with Alix and Gag p6," Glycobiology, 24(11), 1022-1035, 2014.

Wang et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.
Ward et al., "Blocking of adhesion molecules in vivo as anti-inflammatory therapy," Immunology 1: 165-171, 1994.
Wesche et al., "Characterization of membrane translocation by anthrax protective antigen," Biochemistry, 37(45): 15737-15746 (Nov. 10, 1998).
Whisler et al., "Regulation of Lymphocyte Responses by Human Gangliosides. I. Characteristics of Inhibitory Effects and the Induction of Impaired Activation," Journal of Immunology 125(5):2106-2111, 1980.
Wicklein et al., "E- and P-Selectins Are Essential for Repopulation of Chronic Myelogenous and Chronic Eosinophilic Leukemias in a Scid Mouse Xenograft Model," PLOS One, 8(7), e70139, 2013.
Winkler et al., "Absence of E-selectin at vascular niche delays hematopoietic stem cell turn-over," Blood, 110(11):188A, Nov. 2007.
Winkler et al., "Absence or blockage of E-Selectin-Mediated Cell Adhesion Delays Hematopoietic Stem Cell", ASH Annual Meeting 2009, Abstract #564, Nov. 2009.
Winkler et al., "Absence or blockage of E-Selectin-Mediated Cell Adhesion Delays Hematopoietic Stem Cell", Blood, 114(22), Abstract #564, Dec. 7, 2009.
Winkler et al., "Adhesion of E-selectin promotes growth inhibition and apoptosis of human and murine hematopoietic progenitor cells independent of PSGL-1," Blood, 103(5):1685-92, Mar. 1, 2004.
Winkler et al., "Administration of E-selectin Antagonist GMI-1271 Improves Survival to High-Dose Chemotherapy by Alleviating Mucositis and Accelerating Neutrophil Recovery", Blood, 122(21):2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery", ASH Annual Meeting, Poster #63045, Dec. 8, 2013.
Winkler et al., "Administration of E-selectin Antagonist GMI-1271 Improves Survival After High-Dose Chemotherapy by Alleviating Mucositis and Accelerating Neutrophil Recovery," Blood, 122(21), Abstract #2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery," Proceedings of the 55th Annual Meeting of the American Society of Hematology, Abstract #2266, Poster Presentation on Dec. 9, 2013, New Orleans, LA.
Winkler et al., "Mobilisation of Reconstituting HSC Is Boosted by Synergy Between G-CSF and E-Selectin Antagonist GMI-1271", Blood, 124(21):317, Dec. 6, 2014.
Winkler et al., "Mobilisation of Reconstituting HSC Is Boosted by Synergy Between G-CSF and E-Selectin Antagonist GMI-1271," Blood, 124(21), Abstract #317, Dec. 6, 2014.
Winkler et al., "Mobilization of CD8[+] Central Memory T-Cells with Enhanced Reconstitution Potential in Mice by a Combination of G-CSF and GMI-1271-Mediated E-Selectin Blockade," Blood, 126(23), Abstract #512, Dec. 3, 2015.
Winkler et al., "Mobilization of CD8+ Central Memory T-Cells with Enhanced Reconstitution Potential in Mice by a Combination of G-CSF and GMI-1271-Mediated E-Selectin Blockade," Proceedings of the 57th Annual Meeting of the American Society of Hematology, Abstract #512, Oral Presentation, Dec. 7, 2015, Orlando, FL.
Winkler et al., "Vascular E-Selectin Protects leukemia Cells from Chemotherapy by Directly Activating Pro-Survival NF-Kb Signalling—Therapeutic Blockade of E-Selectin Dampens NF-Kb Activation," Blood, 128(22), Abstract #2823, Dec. 2, 2016.
Winkler et al., "Vascular Niche E-Selectin Protects Acute Myeloid Leukemia Stem Cells from Chemotherapy", Blood, 124(21):620, Dec. 6, 2014.
Winkler et al., "Vascular Niche E-Selectin Protects Acute Myeloid Leukaemia Stem Cells from Chemotherapy," Blood, 124(21), Abstract #620, Dec. 6, 2014.

(56) References Cited

OTHER PUBLICATIONS

Winkler et al., "Vascular Niche E-Selectin Regulates Hematopoietic Stem Cell Dormancy, Self Renewal and Chemoresistance", Nature Medicine, doi:10.1038/nm2969, Oct. 21, 2012.
Winkler et al., "Vascular niche E-selectin regulates hematopoietic stem cell dormancy, self renewal and chemoresistance," Nature Medicine, 18(11), 1651-1657, 2012.
Winkler et al., "Vascular niche E-selectin regulates hemopoietic stem cell dormancy, self-renewal and chemoresistance," Nature Medicine, 18(11), 1651-1657, Supplementary Figures and Table, 2012.
Winkler, "Mobilisation of reconstituting HSC is boosted by E-selectin antagonist GMI-1271," Proceedings of the 56$^{th}$ Annual Meeting of the American Society of Hematology, Abstract #317, Oral Presentation on Dec. 7, 2014, San Francisco, CA.
Winkler, "Vascular bone marrow niches protect AML Leukaemia stem cells from chemotherapy," Proceedings of the 56$^{th}$ Annual Meeting of the American Society of Hematology, Abstract #620, Oral Presentation on Dec. 8, 2014, San Francisco, CA.
Winnard, P. et al., "Real time non-invasive imaging of receptor-ligand interactions in vivo," J. Cell. Biochem., 90: 454-463 (2003).
Winzer, K. et al. "The Pseudomonas aeruginosa Lectins PA-IL and PA-IIL are Controlled by Quorom Sensing and by RpoS," J. Bacteriol. 182(22): 6401-6411 (2000).
Witz, "The involvement of selectins and their ligands in tumor-progression," Immunol. Lett., 104 (1-2): 89-93 (2006).
Wu et al., "Salivary Agglutinin Inhibits HIV Type 1 Infectivity through Interaction with Viral Glycoprotein 120," AIDS Research and Human Retroviruses, 19(30), 201-209, 2003.
Wu, B. et al. "Structures of the CXCR4 Chemokine GPCR with Small-Molecule and Cyclic Peptide Antagonists," Science, 330(6007): 1066-1071 (Nov. 2010).
Wun et al., "Pan-Selectin Antagonist Rivipansel (GMI-1070) Reduces Soluble E-Selectin Levels While Improving Clinical Outcomes in SCD Vaso-Occlusive Crisis" Blood, 124(21):2704, Dec. 6, 2014.
Xu, J. et al. "Molecular insights and therapeutic targets for diabetic endothelial dysfunction," Circulation, 120: 1266-1286 (2009).
Yamazaki, F. et al,. "Synthesis of an appropriately protected core glycotetraoside, a key intermediate for the synthesis of 'bisected' complex-type glycans of a glycoprotein," Carbohydrate Research 201: 15-30, 1990.
Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang et al., "3790 The Dual E-Selectin/CXCR4 Inhibitor, GMI-1359, Enhances Efficacy of Anti-Leukemia Chemotherapy in FLT3-ITD Mutated Acute Myeloid Leukemia," Blood, 126(23), Abstract #3790, Dec. 3, 2015.
Zhang et al., "The Dual E-selectin/CXCR4 Inhibitor, GMI-1359, Enhances Efficacy of Chemotherapy in FLT3-ITD-Mutated Acute Myeloid Leukemia," Proceedings of the 57$^{th}$ Annual Meeting of the American Society of Hematology, Abstract #3790, Poster Presentation, Dec. 7, 2015, Orlando, FL.
Zhang et al., "The E-selectin/CXCR4 Inhibitor GMI-1359 Effectively Mobilizes Bone Marrow Leukemia Cells and Enhances FLT3 Inhibitor Efficacy in a Murine AML Model," Proceedings of the 107$^{th}$ Annual Meeting of AACR, 3284, Apr. 16-20, 2016, New Orleans, LA.
Zhang, Z. et al. "CXCR4 but not CXCR7 is mainly implicated in ocular leukocyte trafficking during ovalbumin-induced acute uveitis," Experimental Eye Research, 89: 522-531 (2009).
Zhao T. et al. "Targeting human CD34+ hematopoietic stem cells with anti-CD45 x antimyosin light-chain bispecific antibody preserves cardiac function in myocardial infarction" Journal of Applied Physiology, 10(6):1793-1800 (2008).
Zheng, CX et al. "The prognostic value of preoperative serum levels of CEA, CA19-9 and CA72-4 in patients with colorectal cancer," World J. Gastroentero, 7(3): 431-434 (2001).
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of Et-Ra on expression of selectin on the surface of endothelial cell in mice with severe acute pancreatitis," Chongqing Yixue, 35(7): 624-626 (2006)—Abstract.
Zopf et al., "Affinity Purification of Antibodies Using Oligosaccharide-Phenethylamine Derivatives Coupled to Sepharose," Meth. Enzymol. 50:171-175, 1978.
Zuber et al., "Mouse models of human AML accurately predict chemotherapy response," Genes. Dev., 23 (7): 877-889 (2009).

Synthesis of Intermediate 7 a) i. TBTU, DIPEA, DMF, 0°C, ii. azetidine, 0°C to rt (44% compound 4, 36% compound 5); b) azetidine, DMF, 50°C (98%); c) ethylenediamine, 60°C (91%); d) Propargylic acid NHS ester, DIPEA, DMF, 0°C to rt (54%)

HIGHLY POTENT MULTIMERIC E-SELECTIN ANTAGONISTS

This application is a United States national stage application filed under 35 U.S.C. § 371 of International Patent Application No. PCT/US2017/055648 accorded an international filing date of Oct. 6, 2017; which claims the benefit under 35 U.S.C. § 119(e) to U.S. Provisional Application Nos. 62/405,792 filed Oct. 7, 2016 and 62/451,415 filed Jan. 27, 2017, all of which are incorporated by reference herein in their entirety.

Compounds, compositions, and methods for treating and/or preventing at least one disease, disorder, and/or condition associated with E-selectin activity including, for example, inflammatory diseases and cancers, are disclosed herein.

When a tissue is infected or damaged, the inflammatory process directs leukocytes and other immune system components to the site of infection or injury. Within this process, leukocytes play an important role in the engulfment and digestion of microorganisms. The recruitment of leukocytes to infected or damaged tissue is critical for mounting an effective immune defense.

Selectins are a group of structurally similar cell surface receptors important for mediating leukocyte binding to endothelial cells. These proteins are type I membrane proteins and are composed of an amino terminal lectin domain, an epidermal growth factor (EGF)-like domain, a variable number of complement receptor related repeats, a hydrophobic domain spanning region and a cytoplasmic domain. The binding interactions appear to be mediated by contact of the lectin domain of the selectins and various carbohydrate ligands.

There are three known selectins: E-selectin, P-selectin, and L-selectin. E-selectin is found on the surface of activated endothelial cells, which line the interior wall of capillaries. E-selectin binds to the carbohydrate sialyl-Lewis$^x$ (sLe$^x$), which is presented as a glycoprotein or glycolipid on the surface of certain leukocytes (monocytes and neutrophils) and helps these cells adhere to capillary walls in areas where surrounding tissue is infected or damaged; and E-selectin also binds to sialyl-Lewis$^a$ (sLe$^a$), which is expressed on many tumor cells. P-selectin is expressed on inflamed endothelium and platelets, and also recognizes sLe$^x$ and sLe$^a$, but also contains a second site that interacts with sulfated tyrosine. The expression of E-selectin and P-selectin is generally increased when the tissue adjacent to a capillary is infected or damaged. L-selectin is expressed on leukocytes. Selectin-mediated intercellular adhesion is an example of a selectin-mediated function.

Although selectin-mediated cell adhesion is required for fighting infection and destroying foreign material, there are situations in which such cell adhesion is undesirable or excessive, resulting in tissue damage instead of repair. For example, many pathologies (such as autoimmune and inflammatory diseases, shock and reperfusion injuries) involve abnormal adhesion of white blood cells. Such abnormal cell adhesion may also play a role in transplant and graft rejection. In addition, some circulating cancer cells appear to take advantage of the inflammatory mechanism to bind to activated endothelium. In such circumstances, modulation of selectin-mediated intercellular adhesion may be desirable.

Modulators of selectin-mediated function include the PSGL-1 protein (and smaller peptide fragments), fucoidan, glycyrrhizin (and derivatives), sulfated lactose derivatives, heparin and heparin fragments, sulfated hyaluronic acid, condroitin sulfate, sulfated dextran, sulfatides, and particular glycomimetic compounds (see, e.g., U.S. RE44,778). To date, all but the glycomimetics have shown to be unsuitable for drug development due to insufficient activity, toxicity, lack of specificity, poor ADME characteristics, and/or availability of material.

Accordingly, there is a need in the art for identifying inhibitors of selectin-mediated function, e.g., of selectin-dependent cell adhesion, and for the development of methods employing such compounds. The present disclosure may fulfill one or more of these needs and/or may provide other advantages.

Compounds, compositions, and methods for treating and/or preventing (i.e., reducing the likelihood of occurrence or reoccurrence) at least one disease, disorder, and/or condition in which inhibiting binding of E-selectin to one or more E-selectin ligands may play a role are disclosed.

Disclosed are highly potent multimeric E-selectin antagonists of Formula (I):

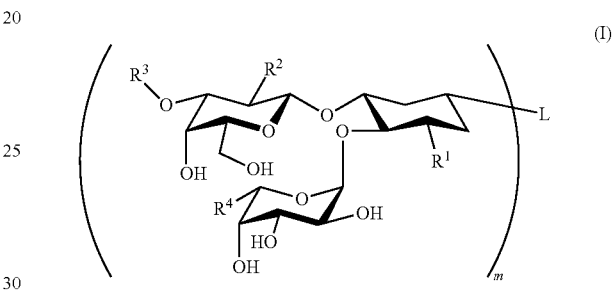

prodrugs of Formula (I), and pharmaceutically acceptable salts of any of the foregoing, wherein each $R^1$, $R^2$, $R^3$, and $R^4$ are defined herein.

As used herein, 'compound of Formula (I)' includes multimeric E-selectin antagonists of Formula (I), pharmaceutically acceptable salts of multimeric E-selectin antagonists of Formula (I), prodrugs of multimeric E-selectin antagonists of Formula (I), and pharmaceutically acceptable salts of prodrugs of multimeric E-selectin antagonists of Formula (I).

In some embodiments, pharmaceutical compositions comprising at least one compound of Formula (I) and optionally at least one additional pharmaceutically acceptable ingredient are presented.

In some embodiments, a method for treatment and/or prevention of at least one disease, disorder, and/or condition where inhibition of E-selectin mediated functions is useful is disclosed, the method comprising administering to a subject in need thereof an effective amount of at least one compound of Formula (I) or a pharmaceutical composition comprising at least one compound of Formula (I).

In the following description, certain specific details are set forth in order to provide a thorough understanding of various embodiments. However, one skilled in the art will understand that the disclosed embodiments may be practiced without these details. In other instances, well-known structures have not been shown or described in detail to avoid unnecessarily obscuring descriptions of the embodiments. These and other embodiments will become apparent upon reference to the following detailed description and attached drawings.

Figure 1:
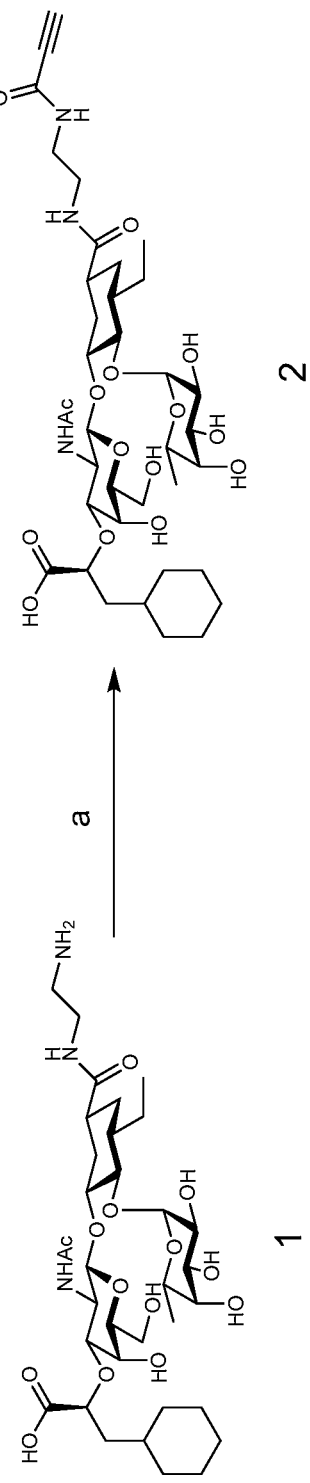
FIG. 1 is a diagram illustrating the synthesis of intermediate 2.
Figure 2:
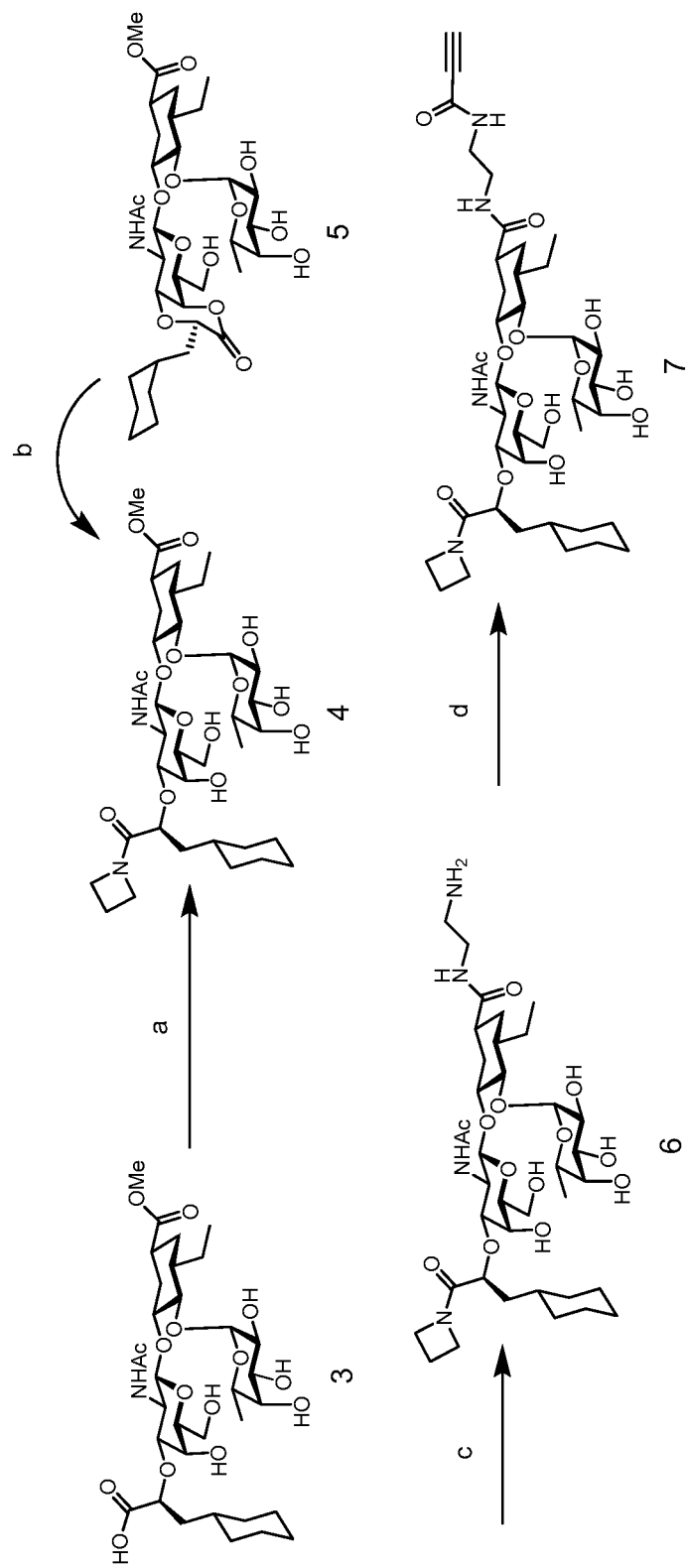
FIG. 2 is a diagram illustrating the synthesis of intermediate 7.
Figure 3:
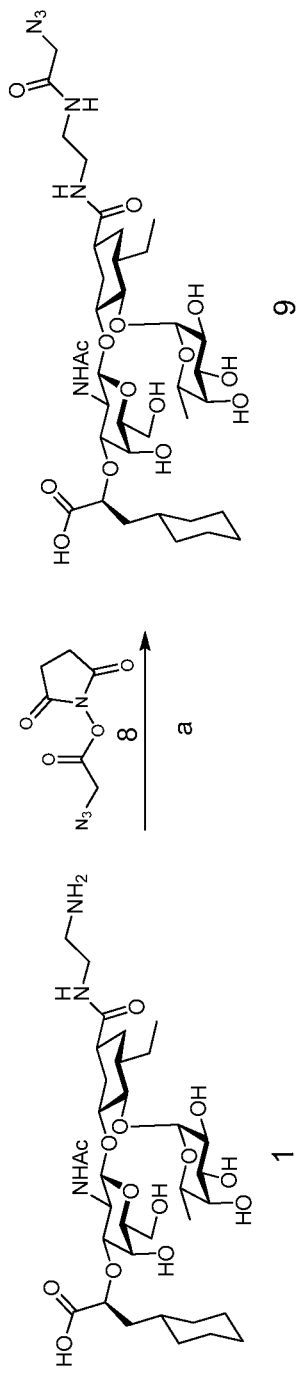
FIG. 3 is a diagram illustrating the synthesis of intermediate 9.
Figure 4:
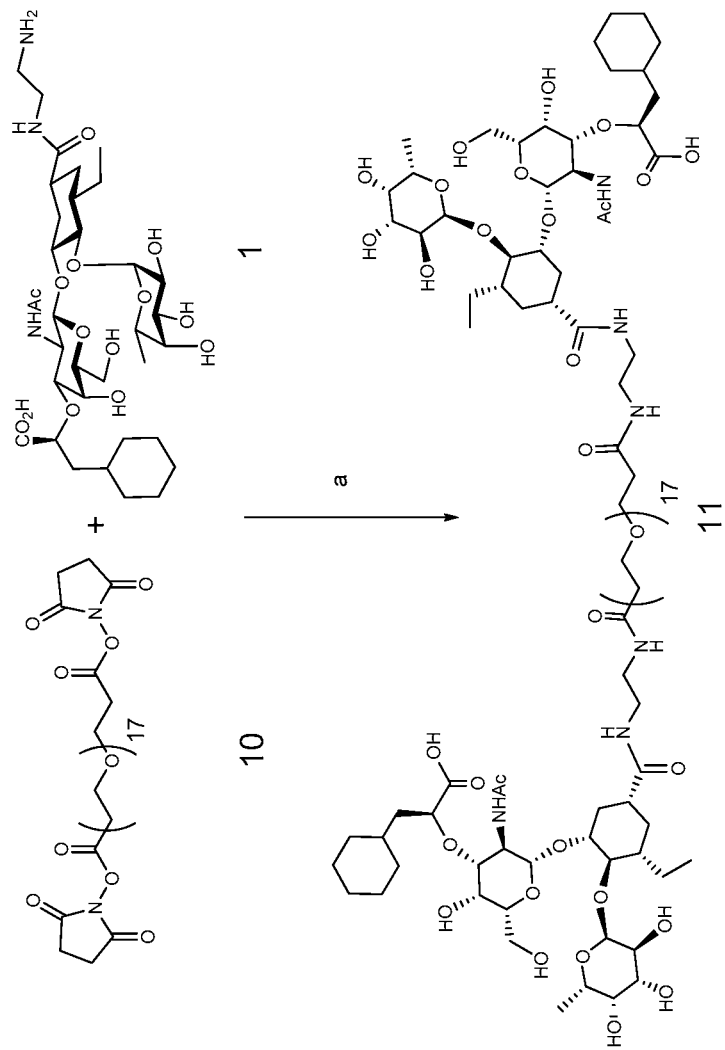
FIG. 4 is a diagram illustrating the synthesis of compound 11.
Figure 5:
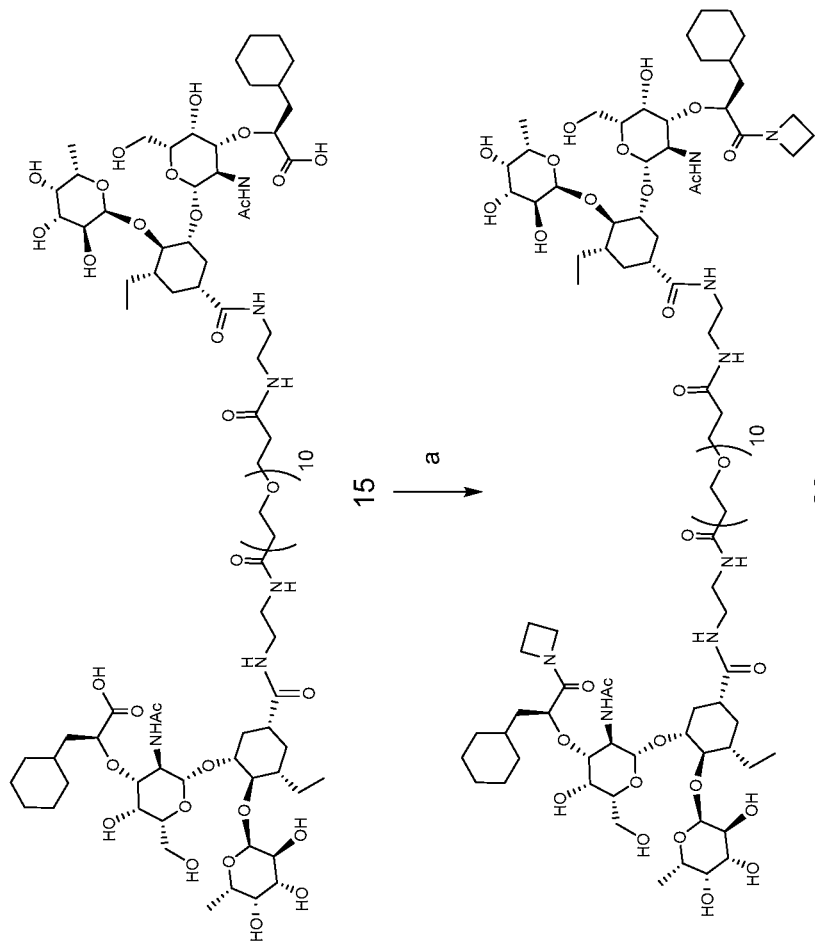
FIG. 5 is a diagram illustrating the synthesis of compound 20.
Figure 6:
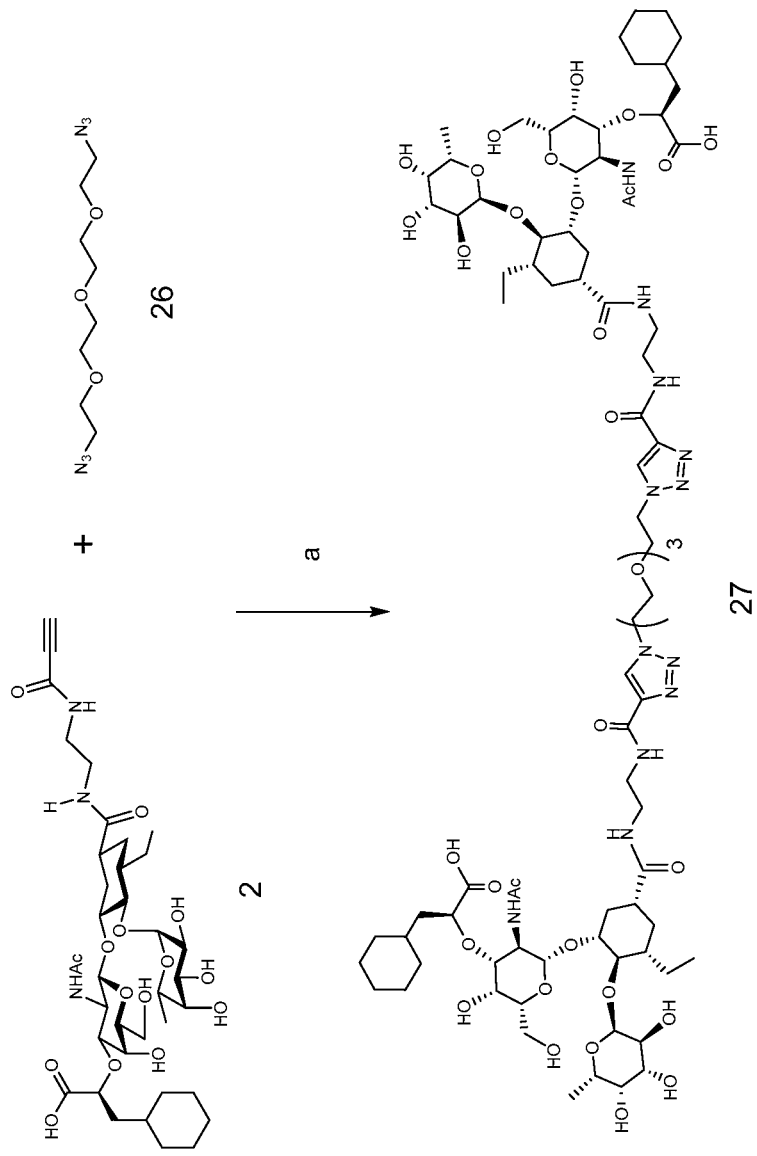
FIG. 6 is a diagram illustrating the synthesis of compound 27.
Figure 7:
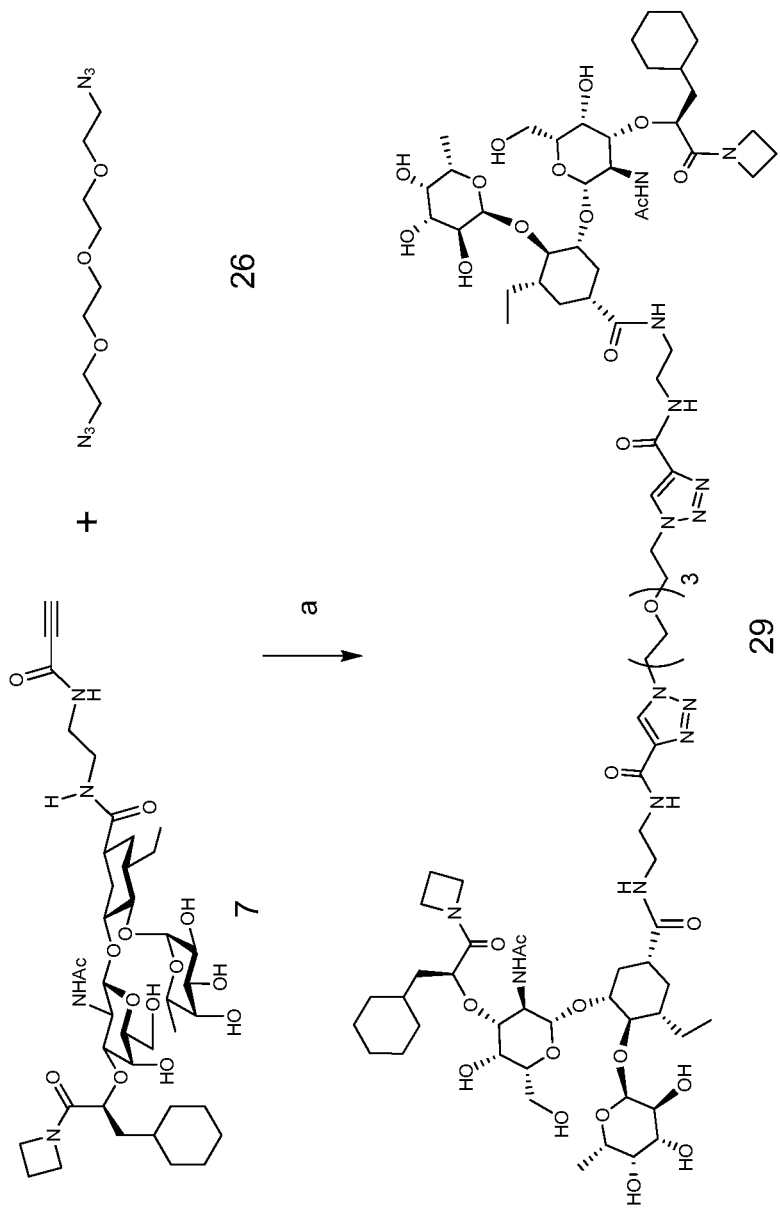
FIG. 7 is a diagram illustrating the synthesis of compound 29.
Figure 8:
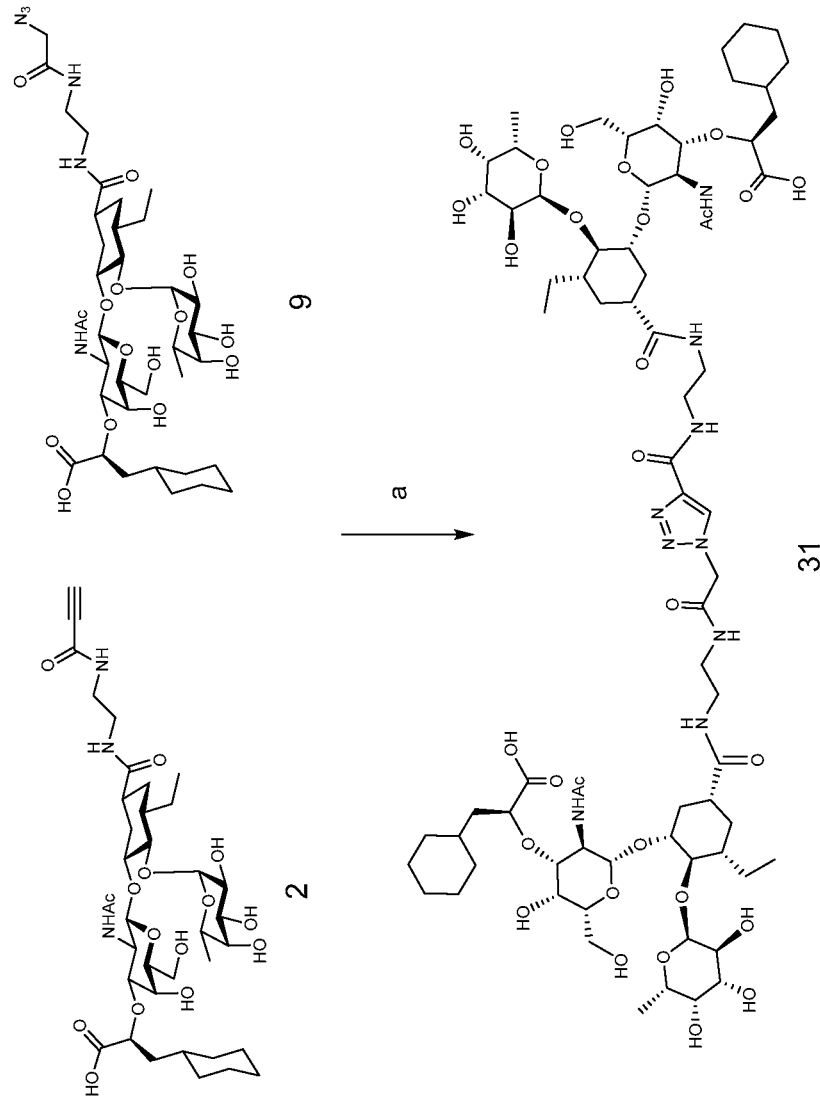
FIG. 8 is a diagram illustrating the synthesis of compound 31.
Figure 9A:
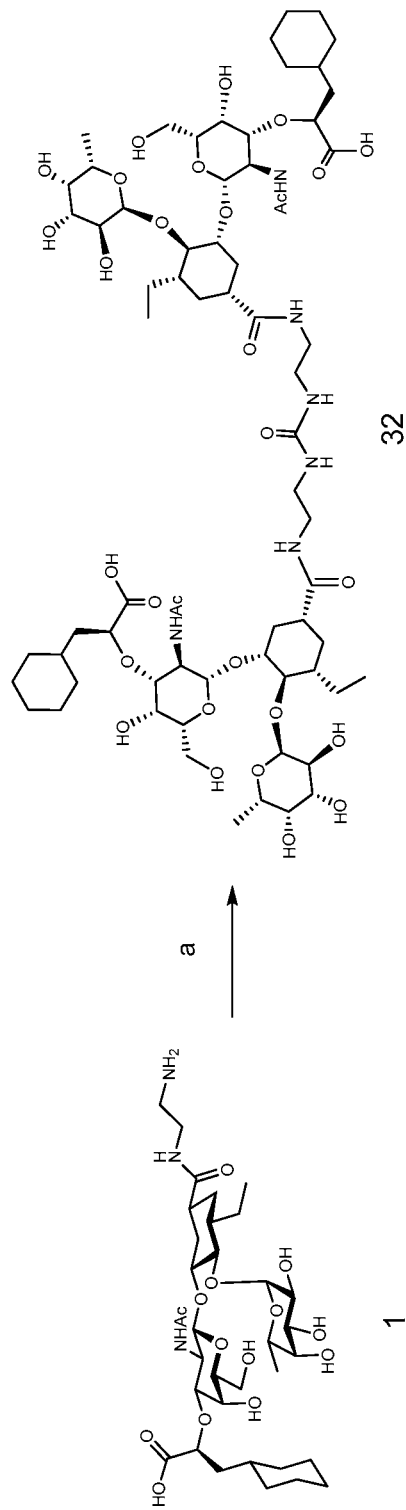
FIG. 9A is a diagram illustrating the synthesis of compound 32.
Figure 9B:
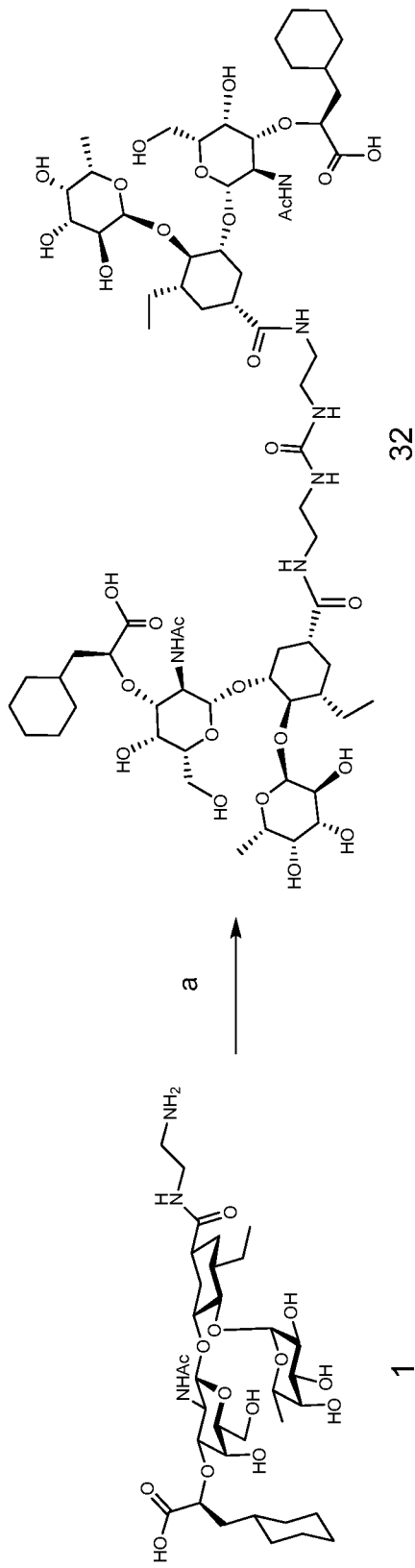
FIG. 9B is a diagram illustrating an alternative synthesis of compound 32.
Figure 10:
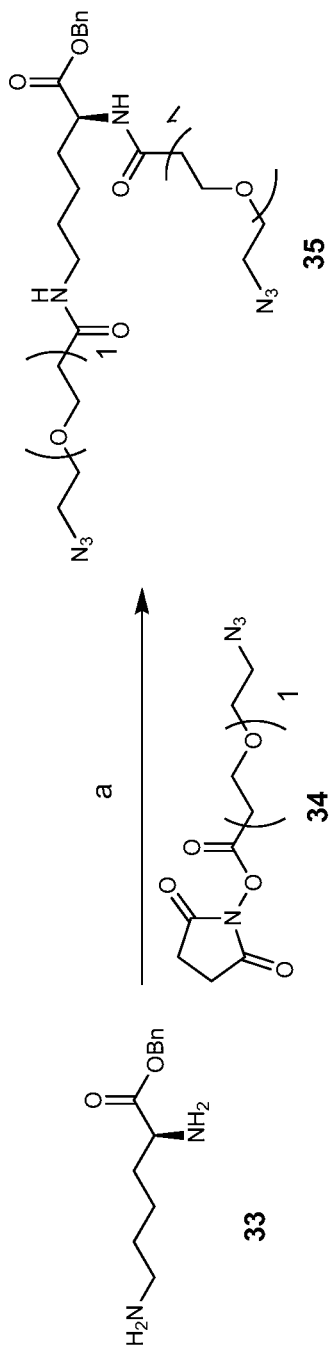
FIG. 10 is a diagram illustrating the synthesis of compound 35.
Figure 11:
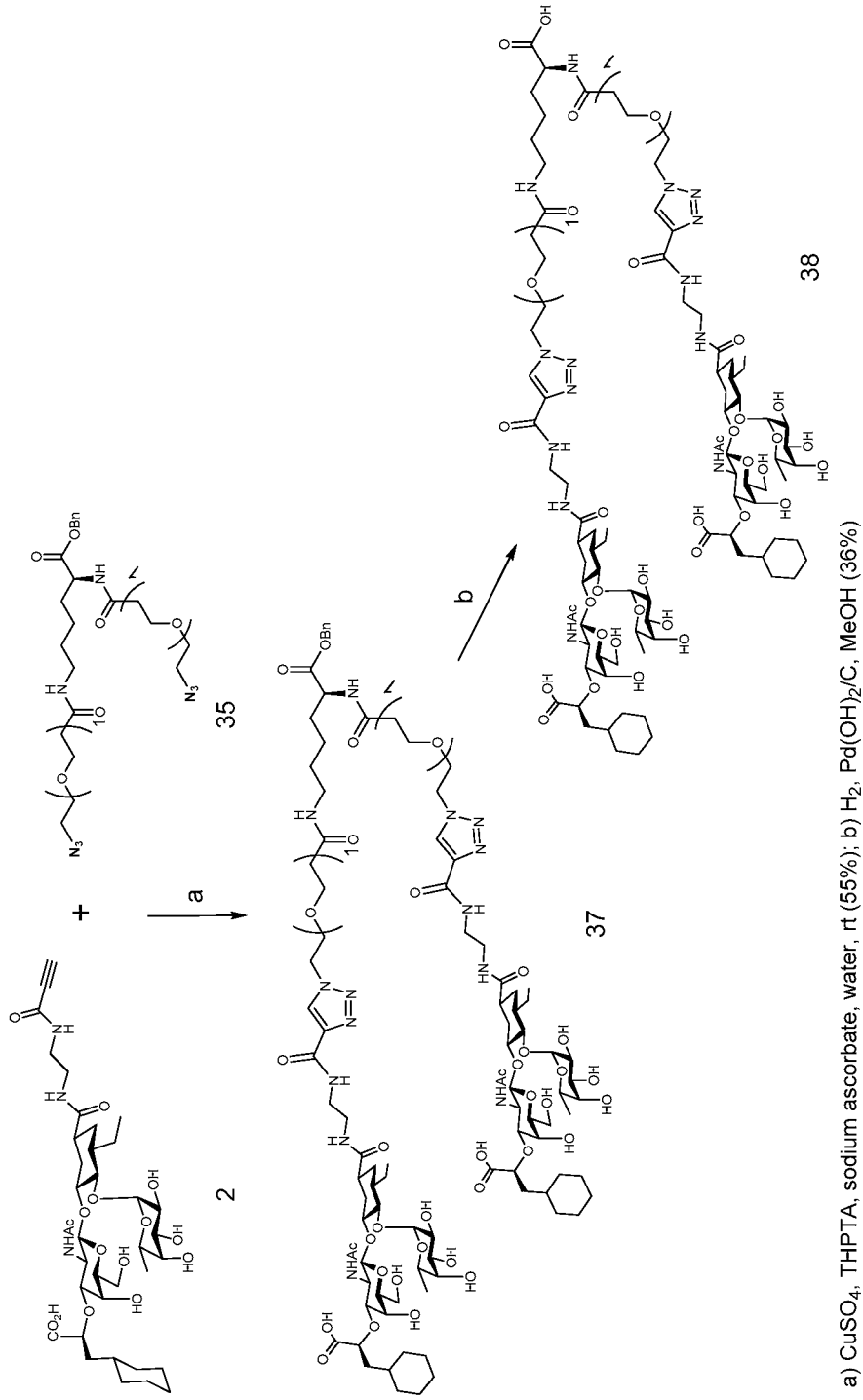
FIG. 11 is a diagram illustrating the synthesis of compound 38.
Figure 12:
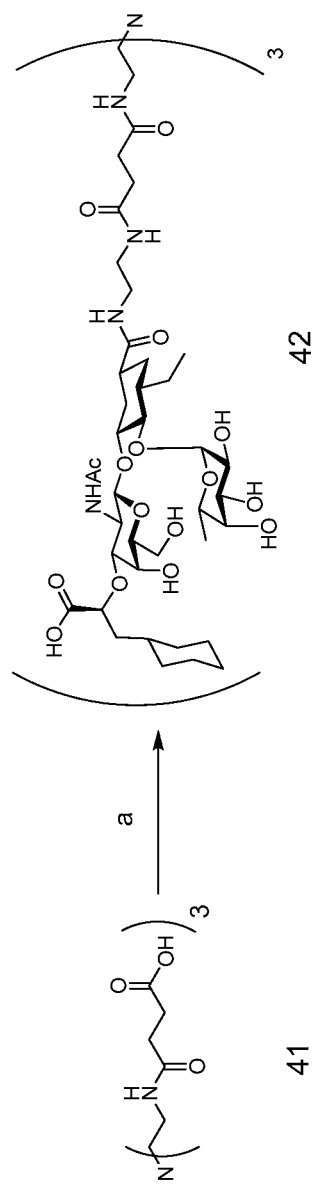
FIG. 12 is a diagram illustrating the synthesis of compound 42.
Figure 13:
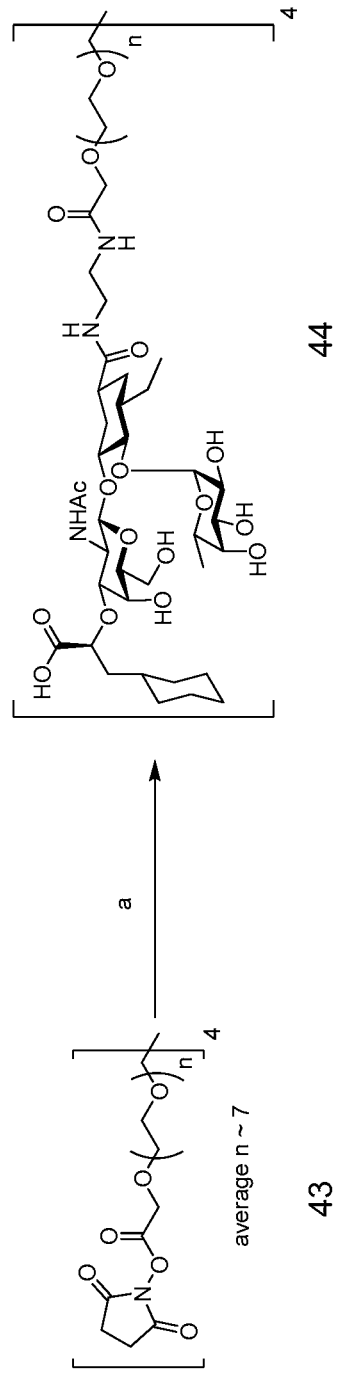
FIG. 13 is a diagram illustrating the synthesis of compound 44.
Figure 14:
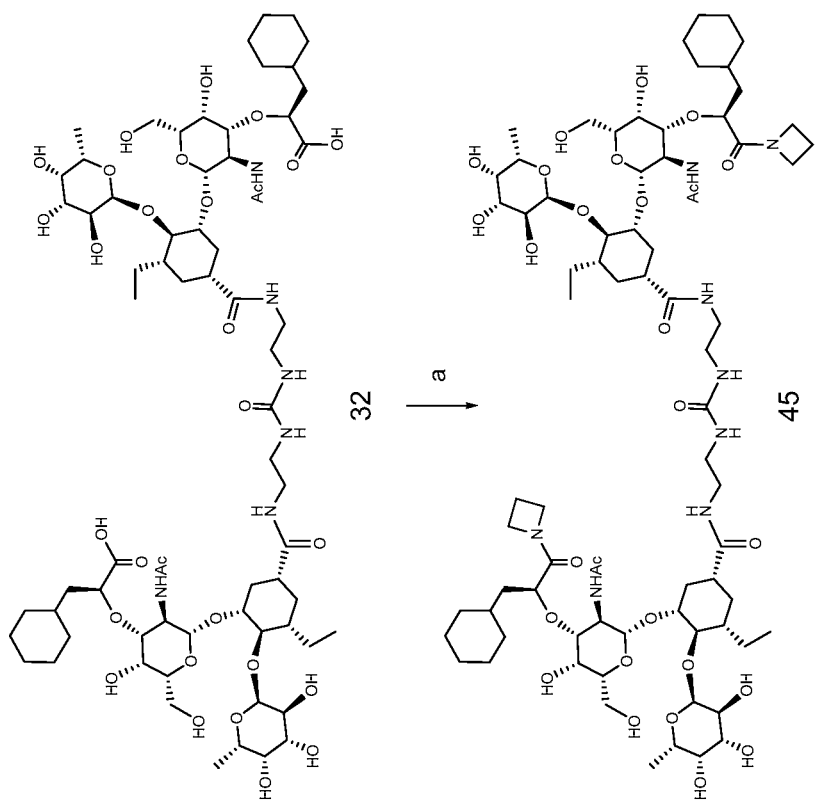
FIG. 14 is a diagram illustrating the synthesis of compound 45.

Disclosed herein are highly potent multimeric E-selectin antagonists, pharmaceutical compositions comprising the same, and methods for inhibiting E-selectin-mediated functions using the same. The compounds and compositions of the present disclosure may be useful for treating and/or preventing at least one disease, disorder, and/or condition that is treatable by inhibiting binding of E-selectin to one or more E-selectin ligands.

The compounds of the present disclosure have been found to be highly potent multimeric E-selectin antagonists, the potency being many times greater than the monomer. The compounds of the present disclosure may also have at least one improved physicochemical, pharmacological, and/or pharmacokinetic property.

In some embodiments, presented are highly potent multimeric E-selectin antagonists of Formula (I):

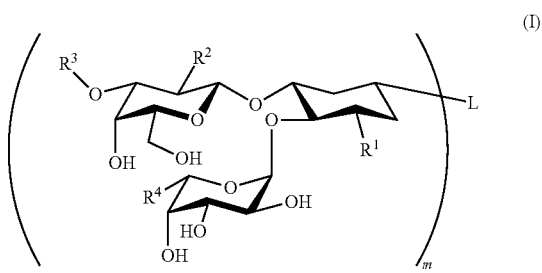

(I)

prodrugs of Formula (I), and pharmaceutically acceptable salts of any of the foregoing, wherein each $R^1$, which may be identical or different, is independently chosen from H, $C_{1-12}$ alkyl, $C_{2-12}$ alkenyl, $C_{2-12}$ alkynyl, and —NHC(=O)$R^5$ groups, wherein each $R^5$, which may be identical or different, is independently chosen from $C_{1-12}$ alkyl, $C_{2-12}$ alkenyl, $C_{2-12}$ alkynyl, $C_{6-18}$ aryl, and $C_{1-13}$ heteroaryl groups;

each $R^2$, which may be identical or different, is independently chosen from halo, —$OY^1$, —$NY^1Y^2$, —OC(=O)$Y^1$, —NHC(=O)$Y^1$, and —NHC(=O)$NY^1Y^2$ groups, wherein each $Y^1$ and each $Y^2$, which may be identical or different, are independently chosen from H, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{6-18}$ aryl, and $C_{1-13}$ heteroaryl groups, wherein $Y^1$ and $Y^2$ may join together along with the nitrogen atom to which they are attached to form a ring;

each $R^3$, which may be identical or different, is independently chosen from

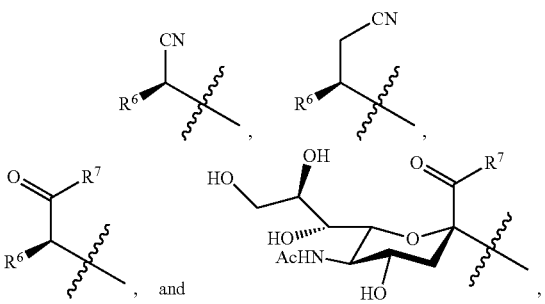

wherein each $R^6$, which may be identical or different, is independently chosen from H, $C_{1-12}$ alkyl and $C_{1-12}$ haloalkyl groups, and wherein each $R^7$, which may be identical or different, is independently chosen from $C_{1-8}$ alkyl, $C_{2-8}$ alkenyl, $C_{2-8}$ alkynyl, —$OY^3$, —NHOH, —NHOCH$_3$, —NHCN, and —$NY^3Y^4$ groups, wherein each $Y^3$ and each $Y^4$, which may be identical or different, are independently chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, wherein $Y^3$ and $Y^4$ may join together along with the nitrogen atom to which they are attached to form a ring;

each $R^4$, which may be identical or different, is independently chosen from —CN, $C_{1-4}$ alkyl, and $C_{1-4}$ haloalkyl groups;

m is chosen from integers ranging from 2 to 256; and

L is chosen from linker groups;

with the proviso that when m is 4, each $R^1$ and each $R^4$ is methyl, each $R^2$ is —OC(=O)Ph, and each $R^3$ is

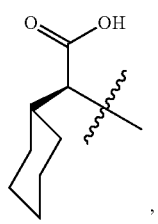 [SMILES: *[C@H](C(=O)O)C1CCCCC1]

then the linker groups are not chosen from

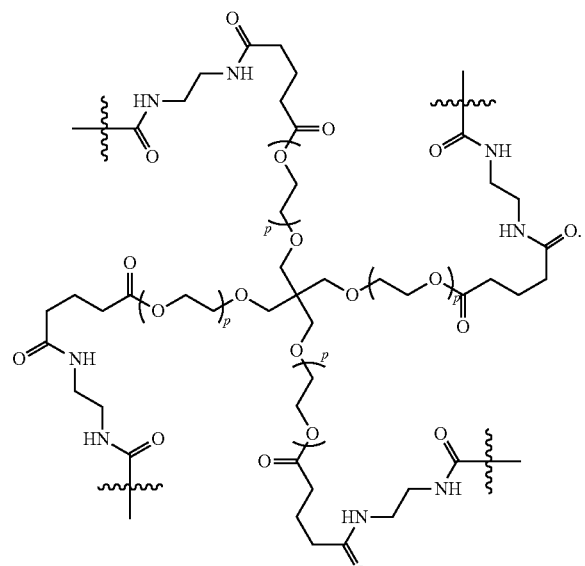

In some embodiments, at least one compound is chosen from compounds of Formula (I):

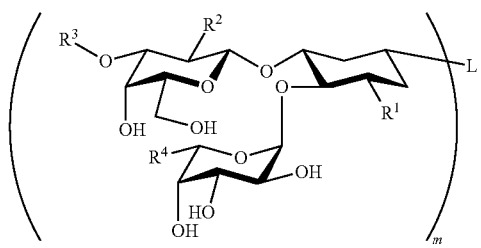

(I)

prodrugs of Formula (I), and pharmaceutically acceptable salts of any of the foregoing, wherein each $R^1$, which may be identical or different, is independently chosen from H, $C_{1-12}$ alkyl, $C_{2-12}$ alkenyl, $C_{2-12}$ alkynyl, and —NHC(=O)$R^5$ groups, wherein each $R^5$, which may be identical or different, is independently chosen from $C_{1-12}$ alkyl, $C_{2-12}$ alkenyl, $C_{2-12}$ alkynyl, $C_{6-18}$ aryl, and $C_{1-13}$ heteroaryl groups;

each $R^2$, which may be identical or different, is independently chosen from halo, —$OY^1$, —$NY^1Y^2$, —OC(=O)$Y^1$, —NHC(=O)$Y^1$, and —NHC(=O)$NY^1Y^2$ groups, wherein each $Y^1$ and each $Y^2$, which may be identical or different, are independently chosen from H, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{6-18}$ aryl, and $C_{1-13}$ heteroaryl groups, wherein $Y^1$ and $Y^2$ may join together along with the nitrogen atom to which they are attached to form a ring;

each $R^3$, which may be identical or different, is independently chosen from

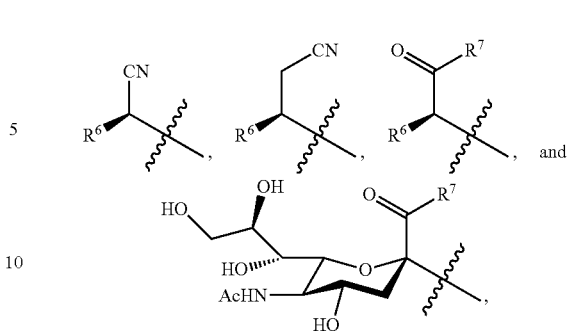

wherein each $R^6$, which may be identical or different, is independently chosen from H, $C_{1-12}$ alkyl and $C_{1-12}$ haloalkyl groups, and wherein each $R^7$, which may be identical or different, is independently chosen from $C_{1-8}$ alkyl, $C_{2-8}$ alkenyl, $C_{2-8}$ alkynyl, —$OY^3$, —NHOH, —NHOCH$_3$, —NHCN, and —$NY^3Y^4$ groups, wherein each $Y^3$ and each $Y^4$, which may be identical or different, are independently chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, wherein $Y^3$ and $Y^4$ may join together along with the nitrogen atom to which they are attached to form a ring;

each $R^4$, which may be identical or different, is independently chosen from —CN, $C_{1-4}$ alkyl, and $C_{1-4}$ haloalkyl groups;

m is chosen from integers ranging from 2 to 256; and

L is chosen from linker groups;

with the proviso that when m is 4, each $R^1$ and each $R^4$ is methyl, each $R^2$ is —OC(=O)Ph, and each $R^3$ is

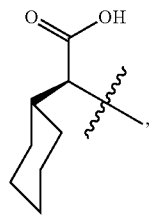 [SMILES: *[C@H](C(=O)O)C1CCCCC1]

then the linker groups are not chosen from

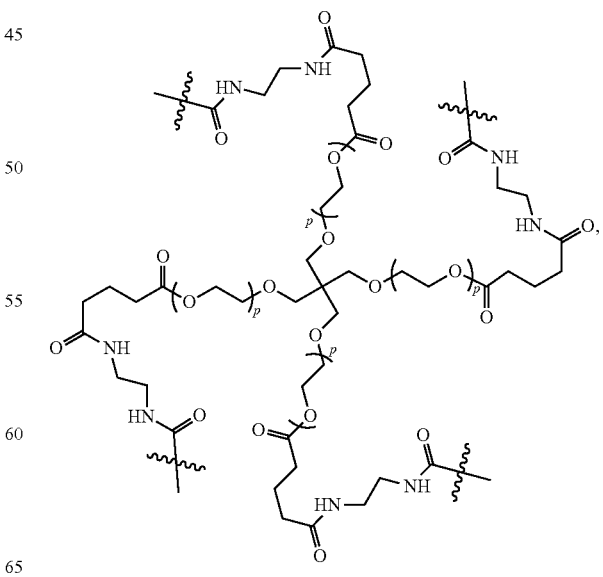

wherein p is chosen from integers ranging from 0 to 250.

In some embodiments, at least one $R^1$ is H. In some embodiments, at least one $R^1$ is chosen from $C_{1-12}$ alkyl groups. In some embodiments, at least one $R^1$ is chosen from $C_{1-6}$ alkyl groups. In some embodiments, at least one $R^1$ is methyl. In some embodiments, at least one $R^1$ is ethyl.

In some embodiments, each $R^1$ is H. In some embodiments, each $R^1$, which may be identical or different, is independently chosen from $C_{1-12}$ alkyl groups. In some embodiments, each $R^1$, which may be identical or different, is independently chosen from $C_{1-6}$ alkyl groups. In some embodiments, each $R^1$ is identical and chosen from $C_{1-6}$ alkyl groups. In some embodiments, each $R^1$ is methyl. In some embodiments, each $R^1$ is ethyl.

In some embodiments, at least one $R^1$ is chosen from —NHC(=O)$R^1$ groups. In some embodiments, each $R^1$ is chosen from —NHC(=O)R groups. In some embodiments, at least one $R^5$ is chosen from H, $C_{1-8}$ alkyl, $C_{6-18}$ aryl, and $C_{1-13}$ heteroaryl groups. In some embodiments, each $R^5$ is chosen from H, $C_{1-8}$ alkyl, $C_{6-18}$ aryl, and $C_{1-13}$ heteroaryl groups. In some embodiments, at least one $R^5$ is chosen from

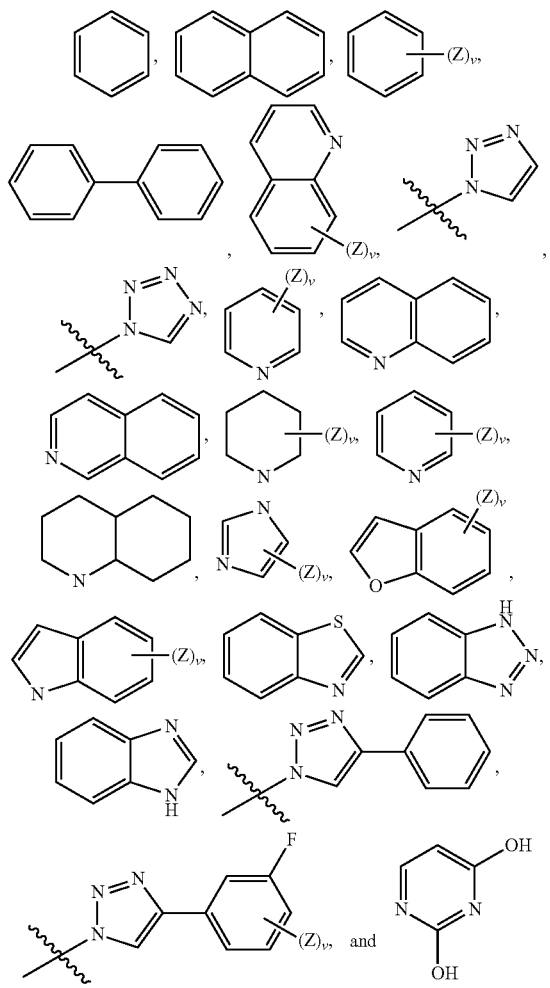

groups, wherein each Z is independently chosen from H, —OH, Cl, F, $N_3$, —$NH_2$, $C_{1-8}$ alkyl, $C_{2-8}$ alkenyl, $C_{2-8}$ alkynyl, $C_{6-14}$ aryl, —O$C_{1-8}$ alkyl, —O$C_{2-8}$ alkenyl, —O$C_{2-8}$ alkynyl, and —O$C_{6-14}$ aryl groups, wherein v is chosen from integers ranging from 0 to 3.

In some embodiments, at least one $R^2$ is chosen from halo groups. In some embodiments, at least one $R^2$ is fluoro. In some embodiments, at least one $R^2$ is chloro. In some embodiments, at least one $R^2$ is chosen from —O$Y^1$ groups. In some embodiments, at least one $R^2$ is —OH. In some embodiments, at least one $R^2$ is chosen from —N$Y^1Y^2$ groups. In some embodiments, at least one $R^2$ is chosen from —OC(=O)$Y^1$ groups. In some embodiments, at least one $R^2$ is chosen from —NHC(=O)$Y^1$ groups. In some embodiments, at least one $R^2$ is chosen from —NHC(=O)N$Y^1Y^2$ groups.

In some embodiments, each $R^2$, which may be identical or different, is independently chosen from halo groups. In some embodiments, each $R^2$ is fluoro. In some embodiments, each $R^2$ is chloro. In some embodiments, each $R^2$, which may be identical or different, is independently chosen from —O$Y^1$ groups. In some embodiments, each $R^2$ is —OH. In some embodiments, each $R^2$, which may be identical or different, is independently chosen from —N$Y^1Y^2$ groups. In some embodiments, each $R^2$, which may be identical or different, is independently chosen from —OC(=O)$Y^1$ groups. In some embodiments, each $R^2$, which may be identical or different, is independently chosen from —NHC(=O)$Y^1$ groups. In some embodiments, each $R^2$, which may be identical or different, is independently chosen from —NHC(=O)N$Y^1Y^2$ groups. In some embodiments, each $R^2$ is identical and chosen from —O$Y^1$ groups. In some embodiments, each $R^2$ is identical and chosen from —N$Y^1Y^2$ groups. In some embodiments, each $R^2$ is identical and chosen from —OC(=O)$Y^1$ groups. In some embodiments, each $R^2$ is identical and chosen from —NHC(=O)$Y^1$ groups. In some embodiments, each $R^2$ is identical and chosen from —NHC(=O)N$Y^1Y^2$ groups.

In some embodiments, at least one $Y^1$ and/or at least one $Y^1$ is chosen from H, $C_{1-12}$ alkyl, $C_{6-18}$ aryl, and $C_{1-13}$ heteroaryl groups. In some embodiments, at least one $Y^1$ and/or at least one $Y^2$ is H. In some embodiments, at least one $Y^1$ and/or at least one $Y^2$ is chosen from $C_{1-12}$ alkyl groups. In some embodiments, at least one $Y^1$ and/or at least one $Y^2$ is chosen from $C_{1-8}$ alkyl groups. In some embodiments, at least one $Y^1$ and/or at least one $Y^1$ is chosen from $C_{1-4}$ alkyl groups. In some embodiments, at least one $Y^1$ and/or at least one $Y^2$ is chosen from $C_{6-18}$ aryl groups. In some embodiments, at least one $Y^1$ and/or at least one $Y^2$ is chosen from $C_{6-12}$ aryl groups. In some embodiments, at least one $Y^1$ and/or at least one $Y^2$ is chosen from $C_{6-10}$ aryl groups. In some embodiments, at least one $Y^1$ and/or at least one $Y^2$ is chosen from $C_{1-13}$ heteroaryl groups. In some embodiments, at least one $Y^1$ and/or at least one $Y^2$ is chosen from $C_{1-9}$ heteroaryl groups. In some embodiments, at least one $Y^1$ and/or at least one $Y^2$ is chosen from $C_{1-5}$ heteroaryl groups. In some embodiments, at least one $Y^1$ and/or at least one $Y^2$ is chosen from $C_{1-3}$ heteroaryl groups.

In some embodiments, each $Y^1$, which may be identical or different, is independently chosen from H, $C_{1-12}$ alkyl, $C_{6-18}$ aryl, and $C_{1-13}$ heteroaryl groups. In some embodiments, each $Y^1$ is H. In some embodiments, each $Y^1$, which may be identical or different, is independently chosen from $C_{1-12}$ alkyl groups. In some embodiments, each $Y^1$, which may be identical or different, is independently chosen from $C_{1-8}$ alkyl groups. In some embodiments, each $Y^1$, which may be identical or different, is independently chosen from $C_{1-4}$ alkyl groups. In some embodiments, each $Y^1$, which may be identical or different, is independently chosen from $C_{6-18}$ aryl groups. In some embodiments, each $Y^1$, which may be identical or different, is independently chosen from $C_{6-12}$ aryl groups. In some embodiments, each $Y^1$, which may be identical or different, is independently chosen from $C_{6-10}$ aryl groups. In some embodiments, each $Y^1$, which may be identical or different, is independently chosen from $C_{1-13}$ heteroaryl groups. In some embodiments, each $Y^1$, which may be identical or different, is independently chosen from $C_{1-9}$ heteroaryl groups. In some embodiments, each $Y^1$, which may be identical or different, is independently chosen from $C_{1-5}$ heteroaryl groups. In some embodiments, each $Y^1$, which may be identical or different, is independently chosen from $C_{1-3}$ heteroaryl groups.

In some embodiments, each $Y^2$, which may be identical or different, is independently chosen from H, $C_{1-12}$ alkyl, $C_{6-18}$ aryl, and $C_{1-13}$ heteroaryl groups. In some embodiments, each $Y^2$ is H. In some embodiments, each $Y^2$, which may be identical or different, is independently chosen from $C_{1-12}$ alkyl groups. In some embodiments, each $Y^2$, which may be identical or different, is independently chosen from $C_{1-8}$ alkyl groups. In some embodiments, each $Y^2$, which may be identical or different, is independently chosen from $C_{1-4}$ alkyl groups. In some embodiments, each $Y^2$, which may be identical or different, is independently chosen from $C_{6-18}$ aryl groups. In some embodiments, each $Y^2$, which may be identical or different, is independently chosen from $C_{6-12}$ aryl groups. In some embodiments, each $Y^2$, which may be identical or different, is independently chosen from $C_{6-10}$ aryl groups. In some embodiments, each $Y^2$, which may be identical or different, is independently chosen from $C_{1-13}$ heteroaryl groups. In some embodiments, each $Y^2$, which may be identical or different, is independently chosen from $C_{1-9}$ heteroaryl groups. In some embodiments, each $Y^2$, which may be identical or different, is independently chosen from $C_{1-5}$ heteroaryl groups. In some embodiments, each $Y^2$, which may be identical or different, is independently chosen from $C_{1-3}$ heteroaryl groups.

In some embodiments, each $Y^1$ is identical and chosen from H, $C_{1-12}$ alkyl, $C_{6-18}$ aryl, and $C_{1-13}$ heteroaryl groups. In some embodiments, each $Y^1$ is identical and chosen from $C_{1-12}$ alkyl groups. In some embodiments, each $Y^1$ is identical and chosen from $C_{1-8}$ alkyl groups. In some embodiments, each $Y^1$ is identical and chosen from $C_{1-4}$ alkyl groups. In some embodiments, each $Y^1$ is identical and chosen from $C_{6-18}$ aryl groups. In some embodiments, each $Y^1$ is identical and chosen from $C_{6-12}$ aryl groups. In some embodiments, each $Y^1$ is identical and chosen from $C_{6-10}$ aryl groups. In some embodiments, each $Y^1$ is identical and chosen from $C_{1-9}$ heteroaryl groups. In some embodiments, each $Y^1$ is identical and chosen from $C_{1-5}$ heteroaryl groups. In some embodiments, each $Y^1$ is identical and chosen from $C_{1-5}$ heteroaryl groups. In some embodiments, each $Y^1$ is identical and chosen from $C_{1-3}$ heteroaryl groups.

In some embodiments, each $Y^2$ is identical and chosen from H, $C_{1-12}$ alkyl, $C_{6-18}$ aryl, and $C_{1-13}$ heteroaryl groups. In some embodiments, each $Y^2$ is identical and chosen from $C_{1-12}$ alkyl groups. In some embodiments, each $Y^2$ is identical and chosen from $C_{1-8}$ alkyl groups. In some embodiments, each $Y^2$ is identical and chosen from $C_{1-4}$ alkyl groups. In some embodiments, each $Y^2$ is identical and chosen from $C_{6-18}$ aryl groups. In some embodiments, each $Y^2$ is identical and chosen from $C_{6-12}$ aryl groups. In some embodiments, each $Y^2$ is identical and chosen from $C_{6-10}$ aryl groups. In some embodiments, each $Y^2$ is identical and chosen from $C_{1-13}$ heteroaryl groups. In some embodiments, each $Y^2$ is identical and chosen from $C_{1-9}$ heteroaryl groups. In some embodiments, each $Y^2$ is identical and chosen from $C_{1-5}$ heteroaryl groups. In some embodiments, each $Y^2$ is identical and chosen from $C_{1-3}$ heteroaryl groups.

In some embodiments, at least one $Y^1$ is methyl. In some embodiments, at least one $Y^1$ is phenyl. In some embodiments, each $Y^1$ is methyl. In some embodiments, each $Y^1$ is phenyl. In some embodiments, at least one $Y^1$ is methyl and at least one $Y^2$ is H. In some embodiments, at least one $Y^1$ is phenyl and at least one $Y^2$ is H. In some embodiments, each $Y^1$ is methyl and each $Y^2$ is H. In some embodiments, each $Y^1$ is phenyl and each $Y^2$ is H.

In some embodiments, at least one $R^2$ is chosen from

In some embodiments, each $R^2$ is

In some embodiments, each $R^2$ is

In some embodiments, each $R^2$ is

In some embodiments, at least one $R^3$, which may be identical or different, is independently chosen from In some embodiments, at least one $R^3$, which may be identical or different, is independently chosen from In some embodiments, at least one $R^3$, which may be identical or different, is independently chosen from

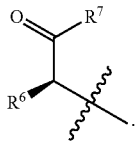

In some embodiments, at least one $R^3$ is

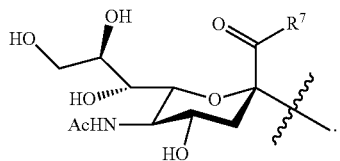

In some embodiments, each $R^3$, which may be identical or different, is independently chosen from

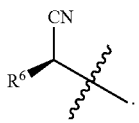

In some embodiments, each $R^3$, which may be identical or different, is independently chosen from

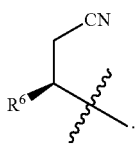

In some embodiments, each $R^3$, which may be identical or different, is independently chosen from

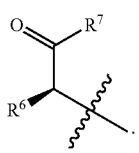

In some embodiments, each $R^3$ is

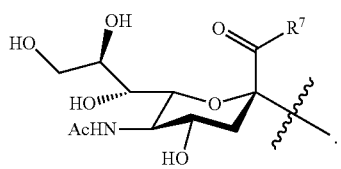

In some embodiments, each $R^3$ is identical and chosen from

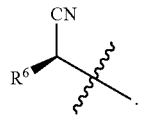

In some embodiments, each $R^3$ is identical and chosen from

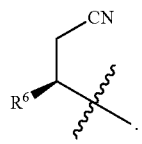

In some embodiments, each $R^3$ is identical and chosen from

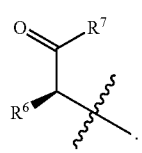

In some embodiments, each $R^6$, which may be identical or different, is independently chosen from $C_{1-12}$ alkyl and $C_{1-12}$ haloalkyl groups. In some embodiments, each $R^6$, which may be identical or different, is independently chosen from $C_{1-12}$ alkyl groups. In some embodiments, each $R^6$, which may be identical or different, is independently chosen from $C_{1-8}$ alkyl groups. In some embodiments, each $R^6$, which may be identical or different, is independently chosen from $C_{1-5}$ alkyl groups. In some embodiments, each $R^6$, which may be identical or different, is independently chosen from $C_{2-4}$ alkyl groups. In some embodiments, each $R^6$, which may be identical or different, is independently chosen from $C_{2-7}$ alkyl groups. In some embodiments, each $R^6$, which may be identical or different, is independently chosen from $C_{1-12}$ haloalkyl groups. In some embodiments, each $R^6$, which may be identical or different, is independently chosen from $C_{1-8}$ haloalkyl groups. In some embodiments, each $R^6$, which may be identical or different, is independently chosen from $C_{1-5}$ haloalkyl groups.

In some embodiments, each $R^6$ is identical and chosen from $C_{1-12}$ alkyl and $C_{1-12}$ haloalkyl groups. In some embodiments, each $R^6$ is identical and chosen from $C_{1-12}$ alkyl groups. In some embodiments, each $R^6$ is identical and chosen from $C_{1-8}$ alkyl groups. In some embodiments, each $R^6$ is identical and chosen from $C_{1-5}$ alkyl groups. In some embodiments, each $R^6$ is identical and chosen from $C_{2-4}$ alkyl groups. In some embodiments, each $R^6$ is identical and chosen from $C_{2-7}$ alkyl groups. In some embodiments, each $R^6$ is identical and chosen from $C_{1-12}$ haloalkyl groups. In some embodiments, each $R^6$ is identical and chosen from $C_{1-8}$ haloalkyl groups. In some embodiments, each $R^6$ is identical and chosen from $C_{1-5}$ haloalkyl groups.

In some embodiments, at least one $R^6$ is chosen from

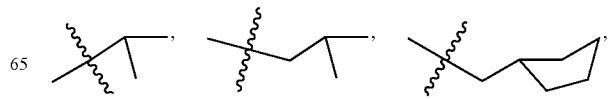

-continued

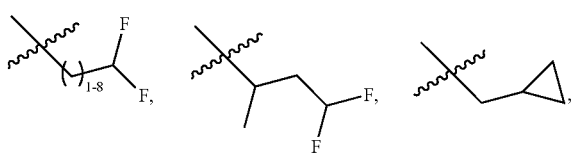

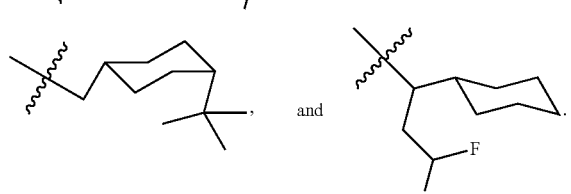

In some embodiments, at least one $R^6$ is

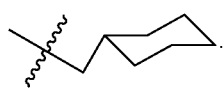 [SMILES: *CC1CCCCC1]

In some embodiments, at least one $R^6$ is

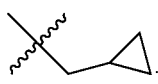 [SMILES: *CC1CC1]

In some embodiments, each $R^6$ is chosen from

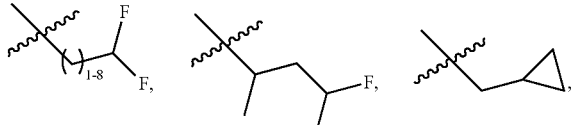

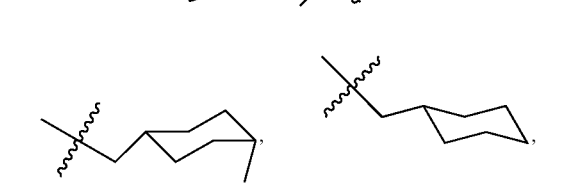

-continued

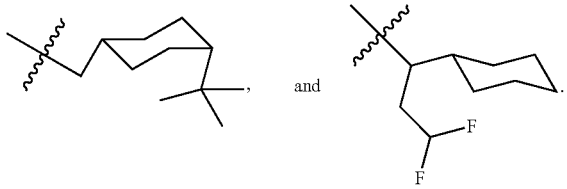

In some embodiments, each $R^6$ is

In some embodiments, each $R^6$ is

In some embodiments, at least one $R^7$ is —OH. In some embodiments, at least one $R^7$ is chosen from —NHY$^3$ groups. In some embodiments, at least one $R^7$ is chosen from —NY$^3$Y$^4$ groups. In some embodiments, each $R^7$, which may be identical or different, is independently chosen from —NHY$^3$ groups. In some embodiments, each $R^7$, which may be identical or different, is independently chosen from —NY$^3$Y$^4$ groups. In some embodiments, each $R^7$ is identical and chosen from —NHY$^3$ groups. In some embodiments, each $R^7$ is identical and chosen from —NY$^3$Y$^4$ groups. In some embodiments, each $R^7$ is —OH.

In some embodiments, at least one $Y^3$ and/or at least one $Y^4$ is chosen from $C_{1-8}$ alkyl and $C_{1-8}$ haloalkyl groups. In some embodiments, at least one $Y^3$ and/or at least one $Y^4$ is chosen from $C_{1-8}$ alkyl groups. In some embodiments, at least one $Y^3$ and/or at least one $Y^4$ is chosen from $C_{1-8}$ haloalkyl groups. In some embodiments, each $Y^3$ and/or each $Y^4$, which may be identical or different, are independently chosen from $C_{1-8}$ alkyl and $C_{1-8}$ haloalkyl groups. In some embodiments, each $Y^3$ and/or each $Y^4$, which may be identical or different, are independently chosen from $C_{1-8}$ alkyl groups. In some embodiments, each $Y^3$ and/or each $Y^4$, which may be identical or different, are independently chosen from $C_{1-8}$ haloalkyl groups.

In some embodiments, each $Y^3$ is identical and chosen from $C_{1-8}$ alkyl and $C_{1-8}$ haloalkyl groups. In some embodiments, each $Y^3$ is identical and chosen from $C_{1-8}$ alkyl groups. In some embodiments, each $Y^3$ is identical and chosen from $C_{1-8}$ haloalkyl groups.

In some embodiments, each $Y^4$ is identical and chosen from $C_{1-8}$ alkyl and $C_{1-8}$ haloalkyl groups. In some embodiments, each $Y^4$ is identical and chosen from $C_{1-8}$ alkyl groups. In some embodiments, each $Y^4$ is identical and chosen from $C_{1-8}$ haloalkyl groups.

In some embodiments, at least one $Y^3$ and/or at least one $Y^4$ is methyl. In some embodiments, at least one $Y^3$ and/or at least one $Y^4$ is ethyl. In some embodiments, at least one $Y^3$ and/or at least one $Y^4$ is H. In some embodiments, each $Y^3$ and/or each $Y^4$ is methyl. In some embodiments, each $Y^3$ and/or each $Y^4$ is ethyl. In some embodiments, each $Y^3$ and/or each $Y^4$ is H.

In some embodiments, at least one $Y^2$ and at least one $Y^3$ join together along with the nitrogen atom to which they are attached to form a ring. In some embodiments, each $Y^2$ and each $Y^3$ join together along with the nitrogen atom to which they are attached to form a ring.

In some embodiments, at least one $R^7$ is chosen from

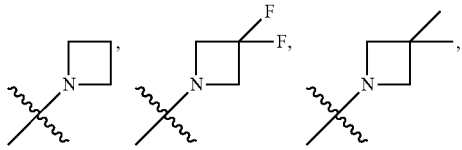

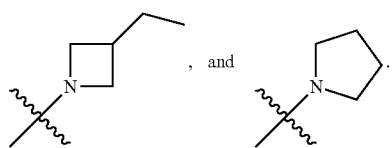

In some embodiments, each $R^7$ is

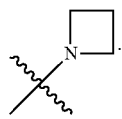

In some embodiments, each $R^7$ is

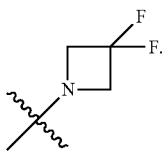 [SMILES: *N1CC(F)(F)C1]

In some embodiments, each $R^7$ is

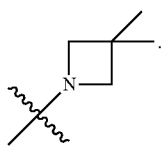 [SMILES: *N1CC(C)(C)C1]

In some embodiments, each $R^7$ is

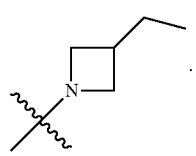 [SMILES: *N1CC(CC)C1]

In some embodiments, each $R^7$ is

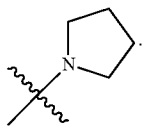

In some embodiments, at least one $R^4$ is chosen from halomethyl groups. In some embodiments, at least one $R^4$ is $CF_3$. In some embodiments, at least one $R^4$ is $CH_3$. In some embodiments, at least one $R^4$ is CN. In some embodiments, each $R^4$, which may be identical or different, is independently chosen from halomethyl groups. In some embodiments, each $R^4$ is identical and chosen from halomethyl groups. In some embodiments, each $R^4$ is $CF_3$. In some embodiments, each $R^4$ is $CH_3$. In some embodiments, each $R^4$ is CN.

In some embodiments, m is chosen from integers ranging from 2 to 128. In some embodiments, m is chosen from integers ranging from 2 to 64. In some embodiments, m is chosen from integers ranging from 2 to 32. In some embodiments, m is chosen from integers ranging from 2 to 16. In some embodiments, m is chosen from integers ranging from 2 to 8. In some embodiments, m is chosen from integers ranging from 2 to 4. In some embodiments, m is 4. In some embodiments, m is 3. In some embodiments, m is 2.

In some embodiments, linker groups may be chosen from groups comprising spacer groups, such spacer groups as, for example, $-(CH_2)_p-$ and $-O(CH_2)_9-$, wherein p is chosen from integers ranging from 1 to 250. Other non-limiting examples of spacer groups include carbonyl groups and carbonyl-containing groups such as, for example, amide groups. A non-limiting example of a spacer group is

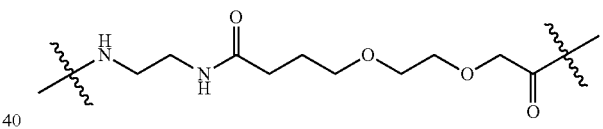

In some embodiments, the linker group is chosen from

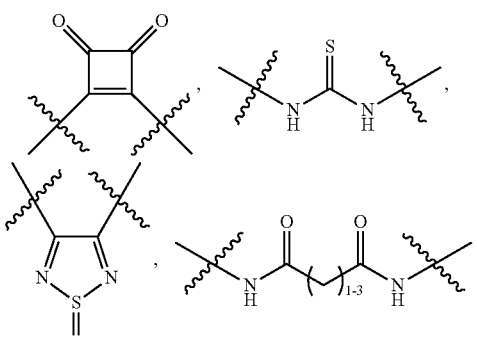

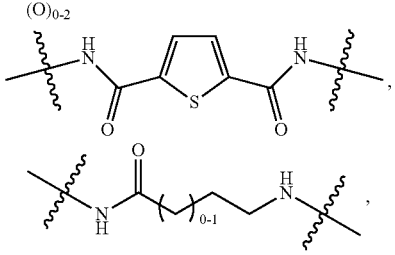

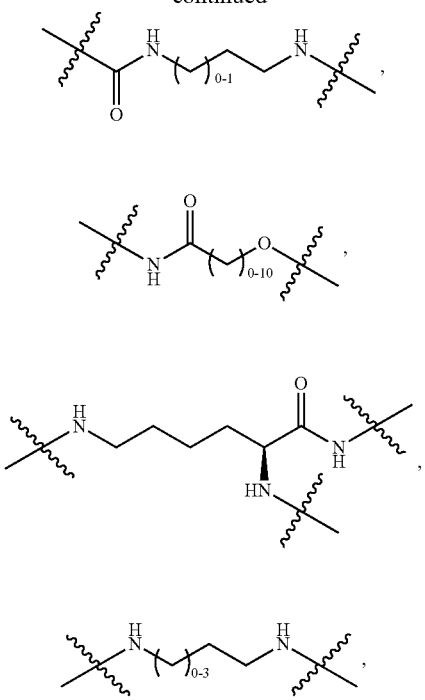

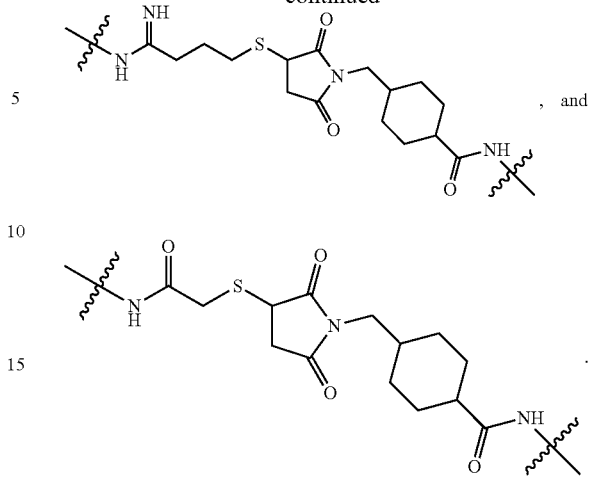

Other linker groups, such as, for example, polyethylene glycols (PEGs) and —C(=O)—NH—(CH$_2$)$_p$—C(=O)—NH—, wherein p is chosen from integers ranging from 1 to 250, will be familiar to those of ordinary skill in the art and/or those in possession of the present disclosure.

In some embodiments, the linker group is

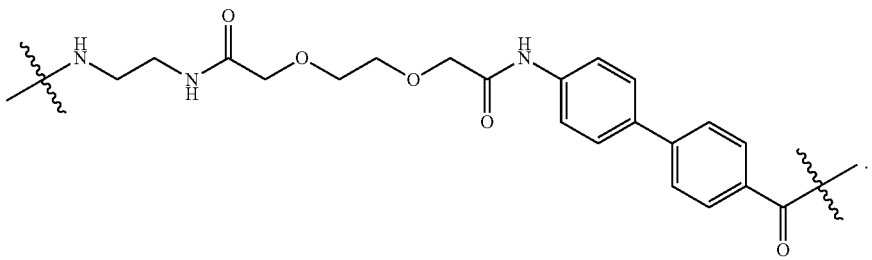 [SMILES: *NCCNC(=O)COCCOCC(=O)Nc1ccc(-c2ccc(C(*)=O)cc2)cc1]

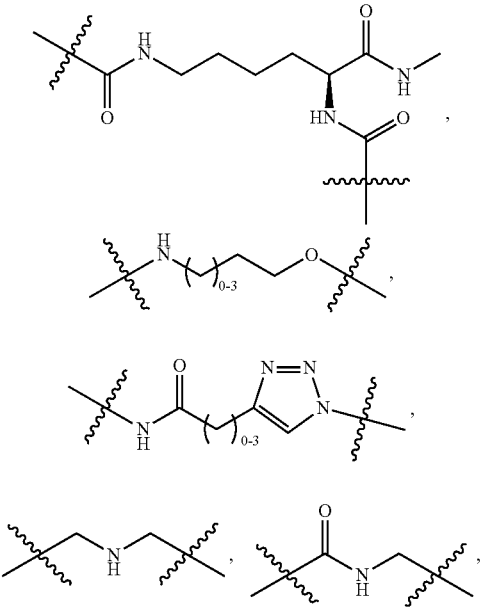

In some embodiments, the linker group is

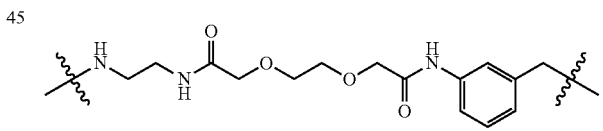

In some embodiments, the linker group is chosen from —C(=O)NH(CH$_2$)$_2$NH—, —CH$_2$NHCH$_2$—, and —C(=O)NHCH$_2$—. In some embodiments, the linker group is —C(=O)NH(CH$_2$)$_2$NH—.

In some embodiments, L is chosen from dendrimers. In some embodiments, L is chosen from polyamidoamine ("PAMAM") dendrimers. In some embodiments, L is chosen from PAMAM dendrimers comprising succinamic. In some embodiments, L is PAMAM G0 generating a tetramer. In some embodiments, L is PAMAM G1 generating an octamer. In some embodiments, L is PAMAM G2 generating a 16-mer. In some embodiments, L is PAMAM G3 generating a 32-mer. In some embodiments, L is PAMAM G4 generating a 64-mer. In some embodiments, L is PAMAM G5 generating a 128-mer.

In some embodiments, L is chosen from

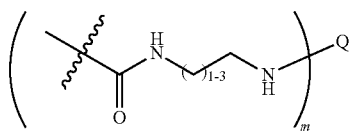

wherein Q is a chosen from

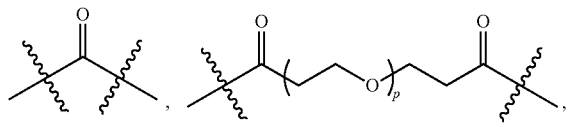

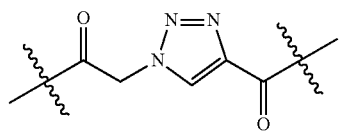

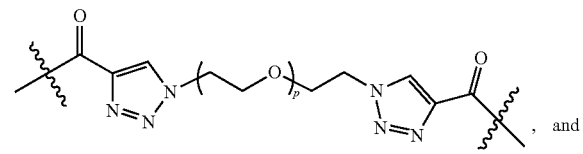

, and

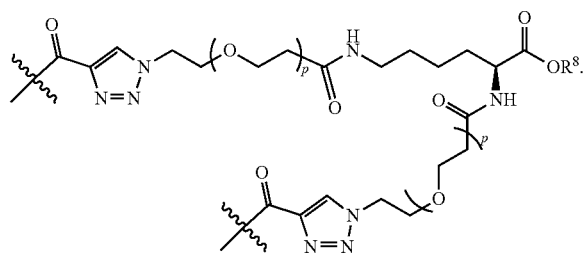

wherein $R^8$ is chosen from H, $C_{1-8}$ alkyl, $C_{6-18}$ aryl, $C_{7-19}$ arylalkyl, and $C_{1-13}$ heteroaryl groups and each p, which may be identical or different, is independently chosen from integers ranging from 0 to 250. In some embodiments, $R^8$ is chosen from $C_{1-8}$ alkyl. In some embodiments, $R^8$ is chosen from $C_{7-19}$ arylalkyl. In some embodiments, $R^8$ is H. In some embodiments, $R^8$ is benzyl.

In some embodiments, L is chosen from

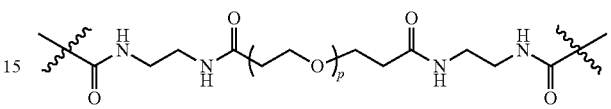

wherein p is chosen from integers ranging from 0 to 250.
In some embodiments, L is chosen from

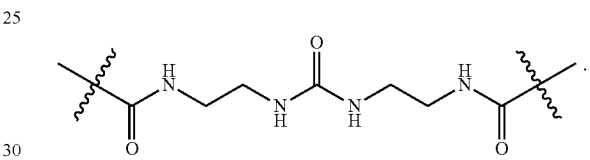

In some embodiments, L is chosen from

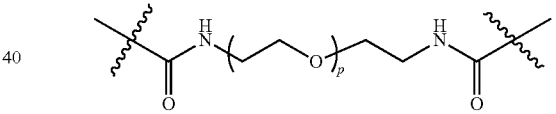

wherein p is chosen from integers ranging from 0 to 250.
In some embodiments, L is chosen from

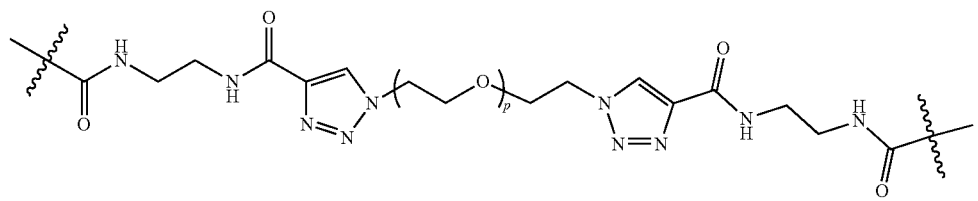

wherein p is chosen from integers ranging from 0 to 250.
In some embodiments, L is chosen from

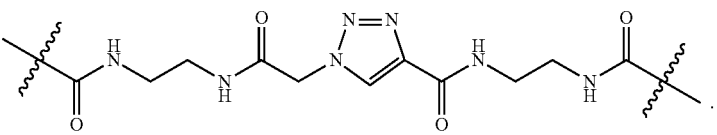 [SMILES: *C(=O)NCCNC(=O)Cn1cc(C(=O)NCCNC(*)=O)nn1]

In some embodiments, L is chosen from

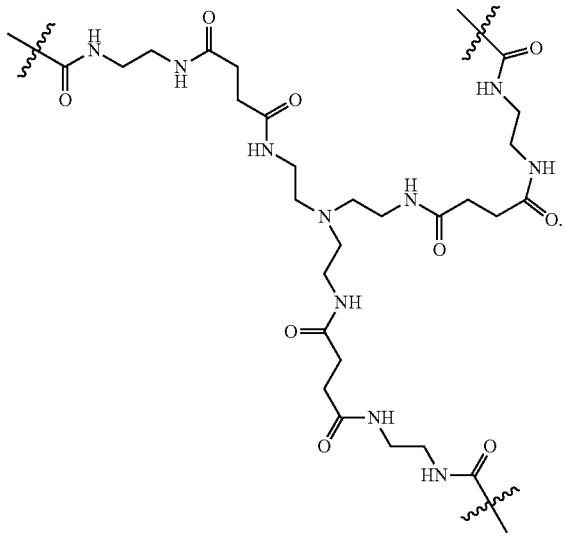 [SMILES: *C(=O)NCCNC(=O)CCC(=O)NCCN(CCNC(=O)CCC(=O)NCCNC(*)=O)CCNC(=O)CCC(=O)NCCNC(*)=O]

In some embodiments, L is chosen from

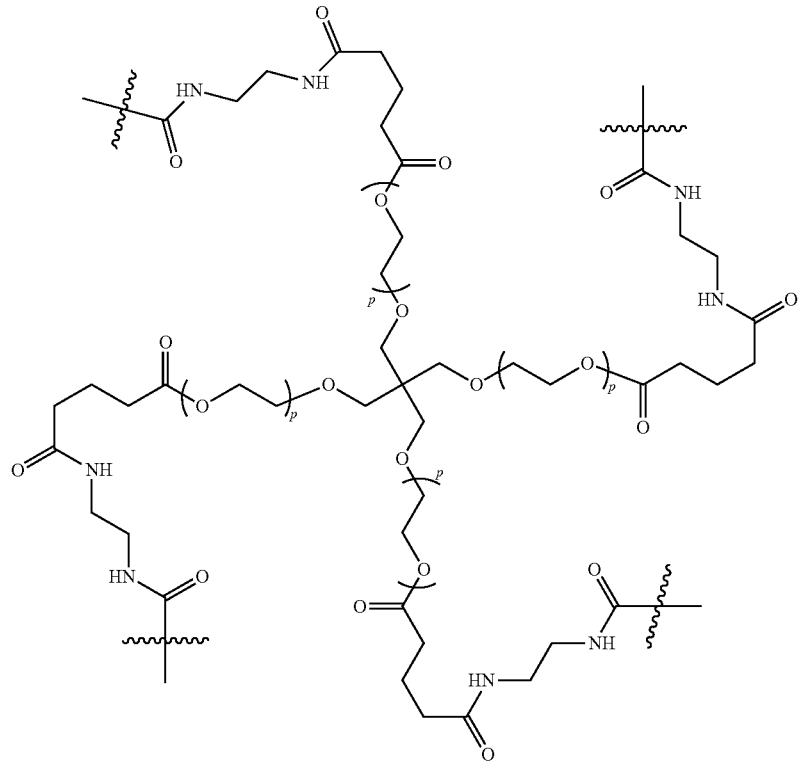

wherein p is chosen from integers ranging from 0 to 250.

In some embodiments, L is chosen from

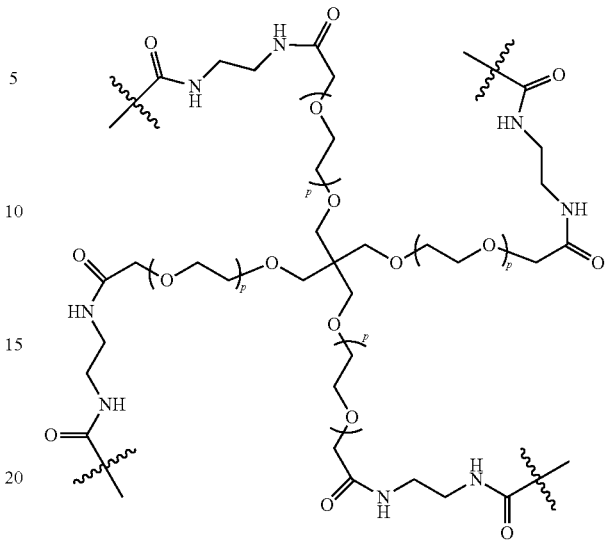

wherein p is chosen from integers ranging from 0 to 250. In some embodiments, p is chosen from integers ranging from 0 to 200. In some embodiments, p is chosen from integers ranging from 0 to 150. In some embodiments, p is chosen from integers ranging from 0 to 100. In some embodiments, p is chosen from integers ranging from 0 to 50. In some embodiments, p is chosen from integers ranging from 0 to 30. In some embodiments, p is chosen from integers ranging from 0 to 15. In some embodiments, p is chosen from integers ranging from 0 to 10. In some embodiments, p is chosen from integers ranging from 0 to 5. In some embodiments, p is 117. In some embodiments, p is 25. In some embodiments, p is 21. In some embodiments, p is 17. In some embodiments p is 13. In some embodiments, p is 10. In some embodiments, p is 8. In some embodiments, p is 6. In some embodiments, p is S. In some embodiments, p is 4. In some embodiments, p is 3. In some embodiments, p is 2. In some embodiments, p is 1. In some embodiments, p is 0.

In some embodiments, at least one compound is chosen from compounds of Formula (I), wherein said compound is symmetrical.

In some embodiments, at least one compound is chosen from compounds having the following Formula:

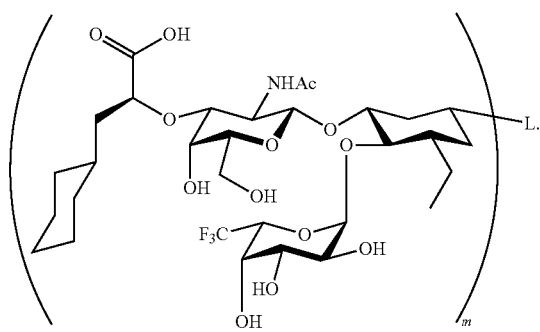

In some embodiments, at least one compound is chosen from compounds having the following Formula

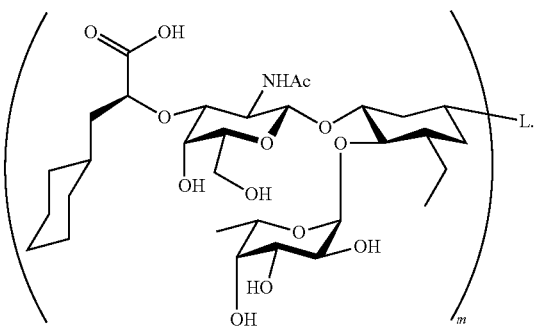

In some embodiments, at least one compound is chosen from compounds having the following Formula:

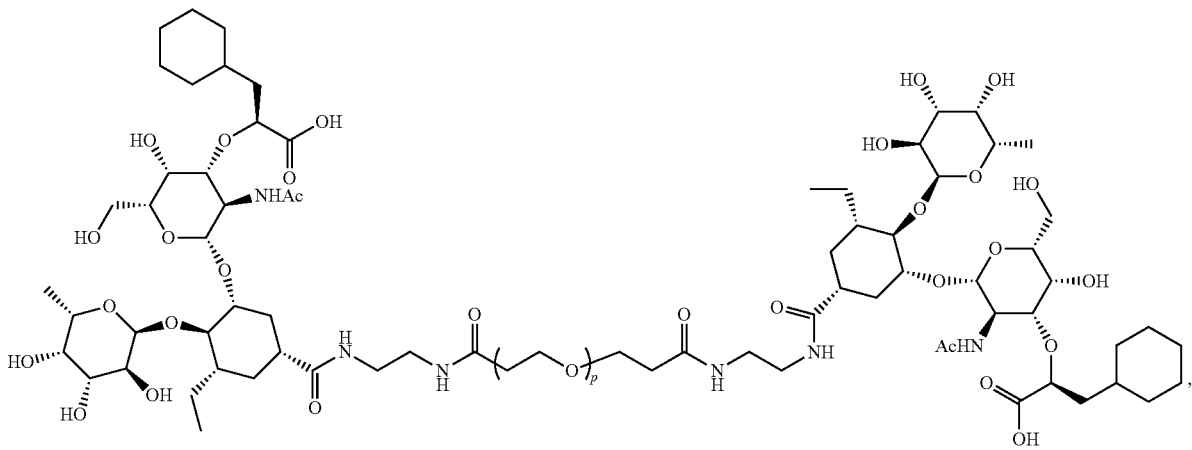

wherein p is chosen from integers ranging from 0 to 250. In some embodiments, p is chosen from integers ranging from 0 to 200. In some embodiments, p is chosen from integers ranging from 0 to 150. In some embodiments, p is chosen from integers ranging from 0 to 100. In some embodiments, p is chosen from integers ranging from 0 to 50. In some embodiments, p is chosen from integers ranging from 0 to 25. In some embodiments, p is chosen from integers ranging from 0 to 13. In some embodiments, p is chosen from integers ranging from 0 to 10.

In some embodiments, at least one compound is chosen from compounds having the following Formulae:

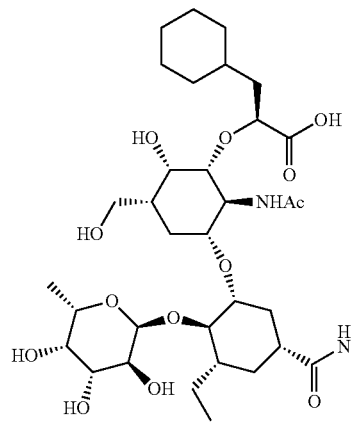
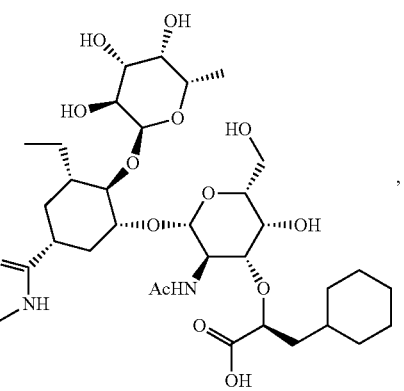
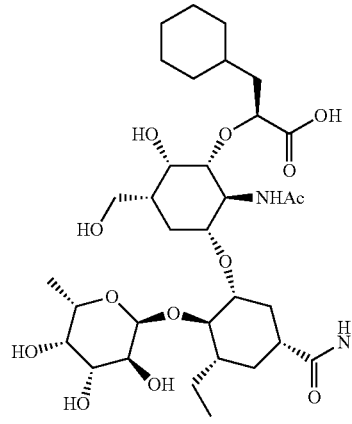
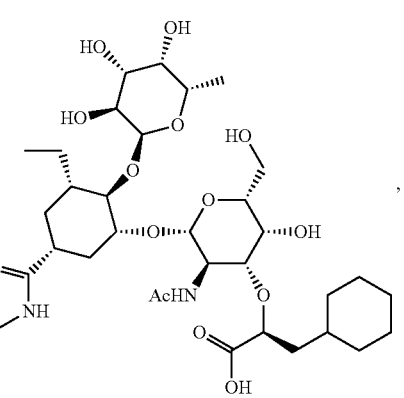
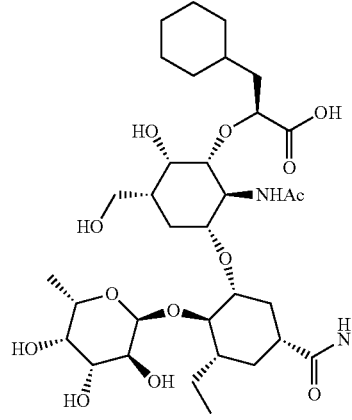
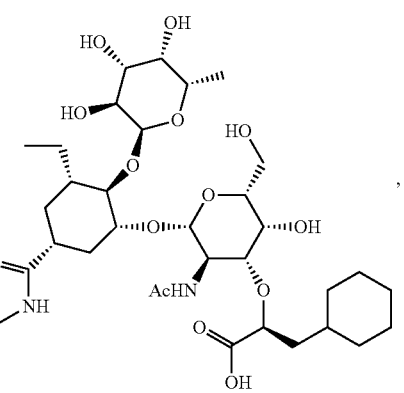
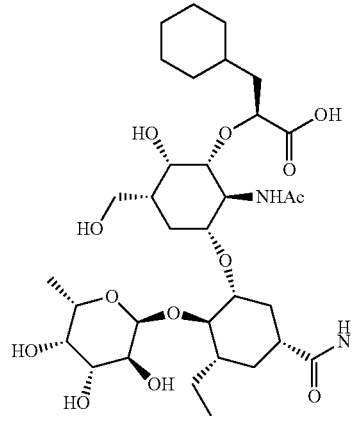
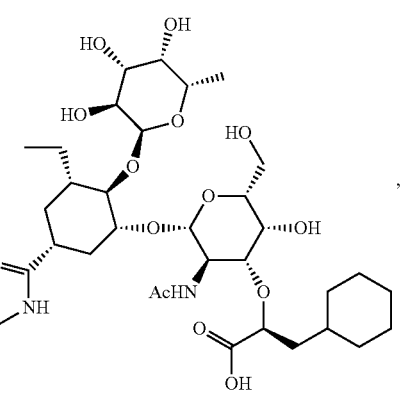

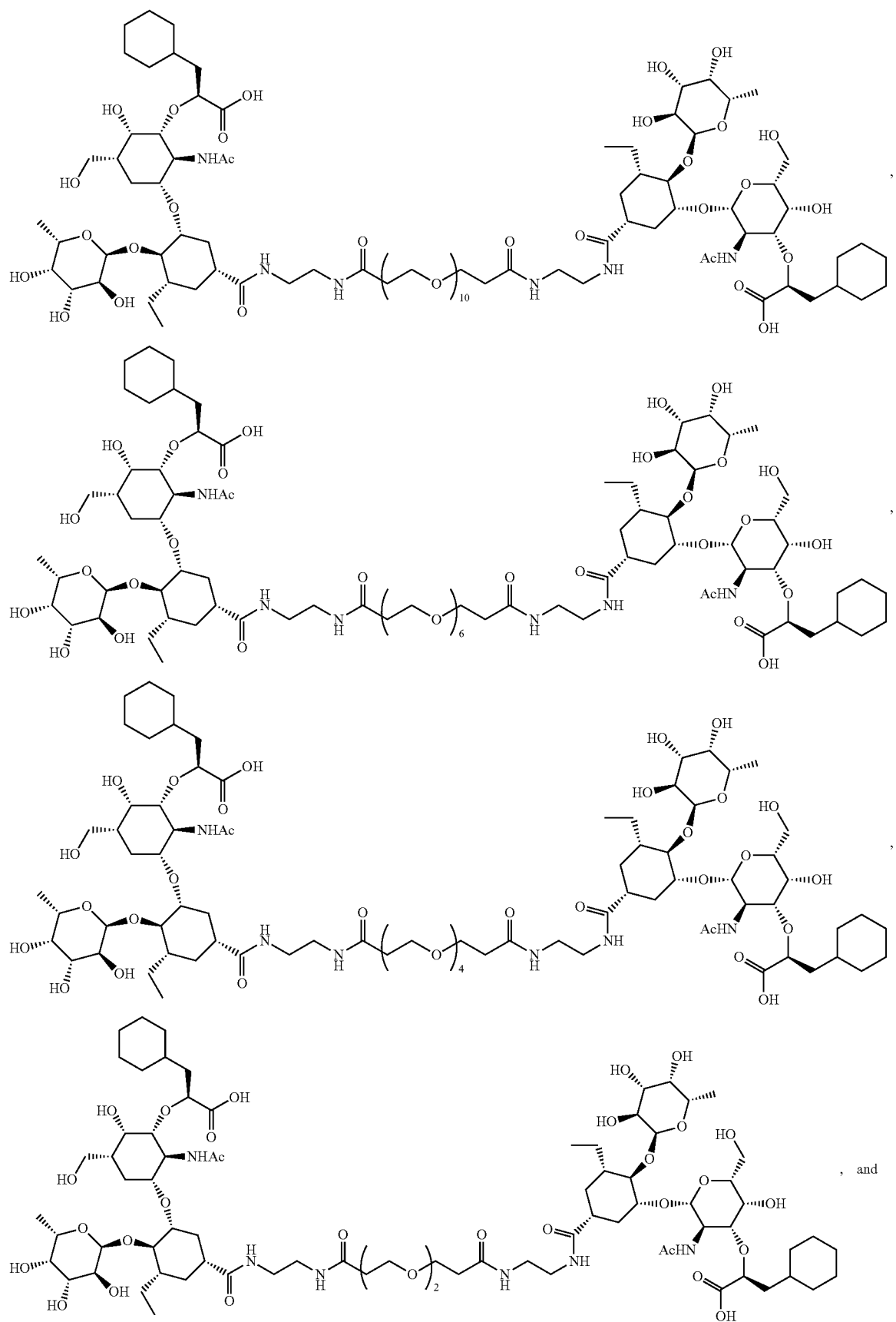

-continued

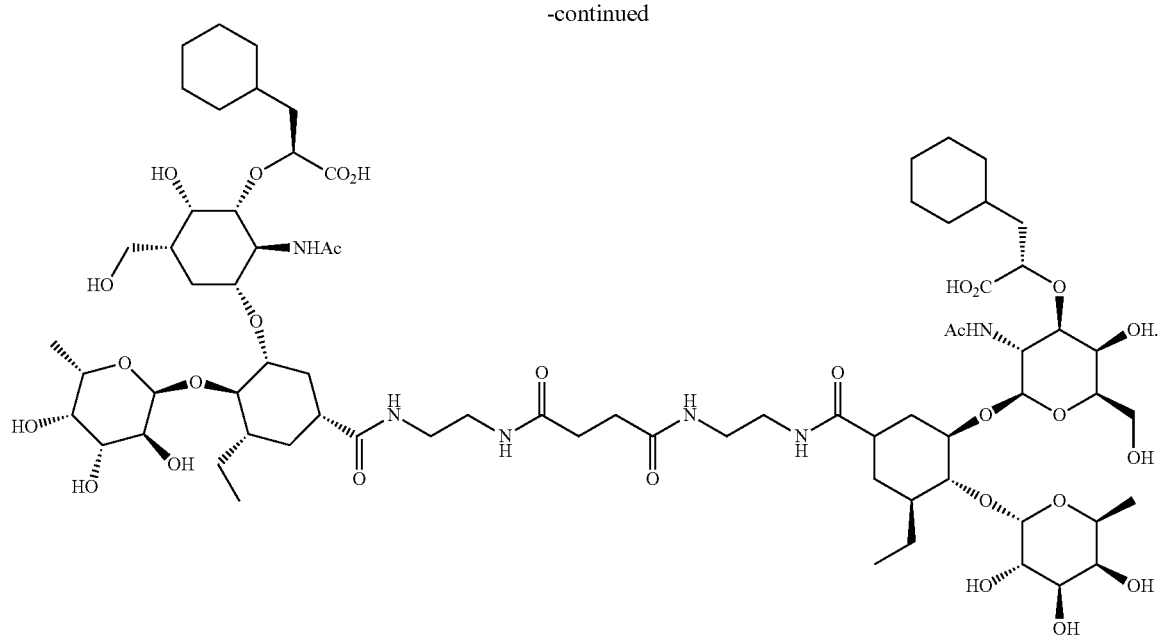

In some embodiments, at least one compound is chosen from compounds having the following Formula:

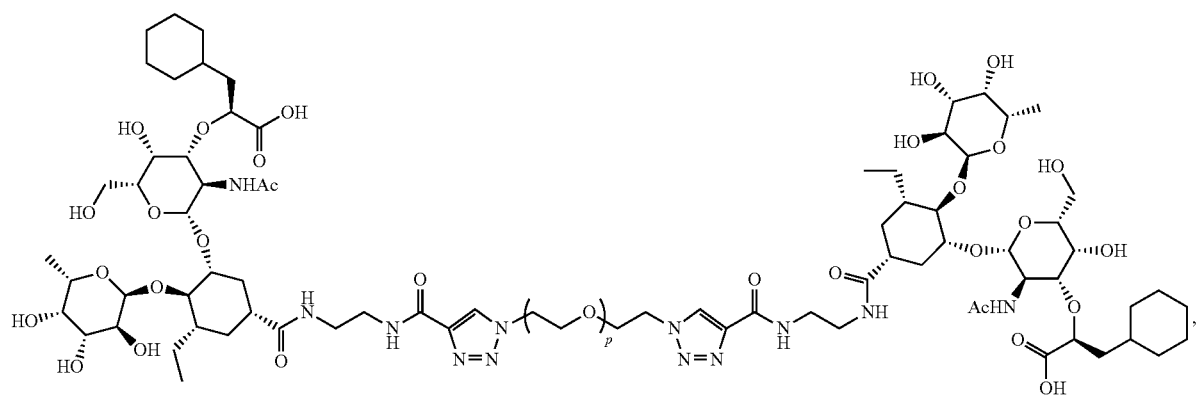

wherein p is chosen from integers ranging from 0 to 250. In some embodiments, p is chosen from integers ranging from 0 to 200. In some embodiments, p is chosen from integers ranging from 0 to 150. In some embodiments, p is chosen from integers ranging from 0 to 100. In some embodiments, p is chosen from integers ranging from 0 to 50. In some embodiments, p is chosen from integers ranging from 0 to 25. In some embodiments, p is chosen from integers ranging from 0 to 13. In some embodiments, p is chosen from integers ranging from 0 to 10. In some embodiments, p is chosen from integers ranging from 0 to 5.

In some embodiments, at least one compound is chosen from compounds having the following Formulae:

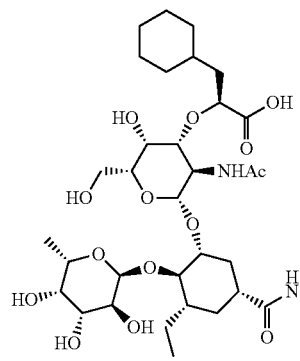
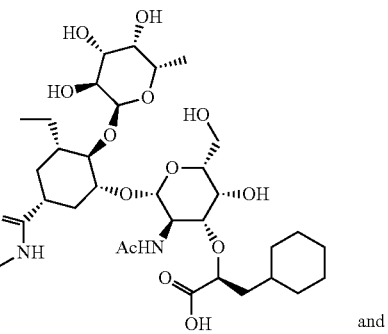

and

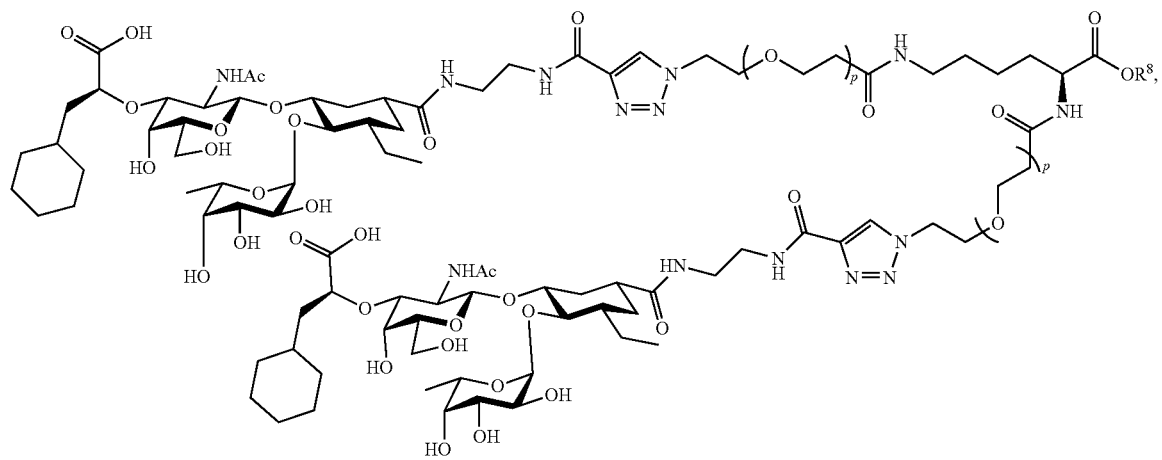
,

In some embodiments, at least one compound is chosen from compounds having the following Formula:

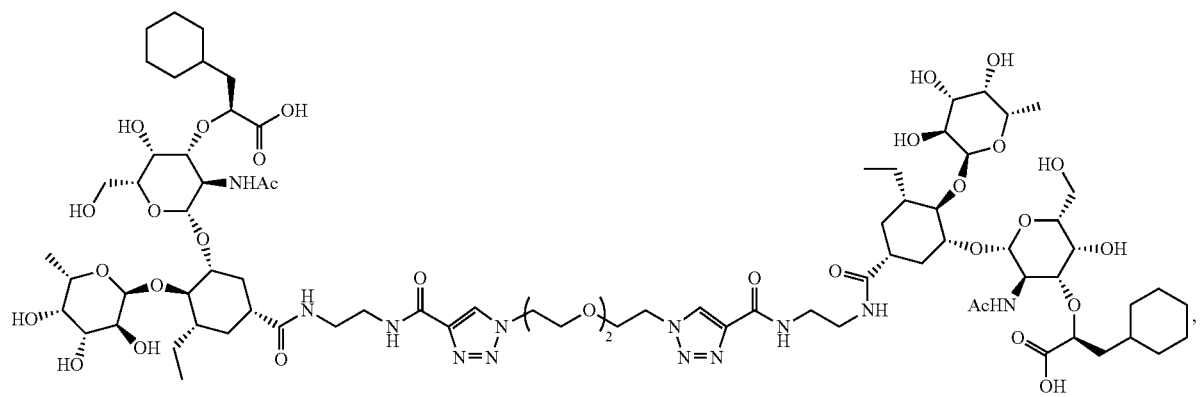

wherein $R^8$ is chosen from H, $C_{1-8}$ alkyl, $C_{6-18}$ aryl, $C_{7-19}$ arylalkyl, and $C_{1-13}$ heteroaryl groups and each p, which may be identical or different, is independently chosen from integers ranging from 0 to 250. In some embodiments, $R^8$ is chosen from H, $C_{1-8}$ alkyl, and $C_{7-19}$ arylalkyl groups. In some embodiments, $R^8$ is chosen from $C_{1-8}$ alkyl groups. In some embodiments, $R^8$ is chosen from $C_{7-19}$ arylalkyl groups. In some embodiments, $R^8$ is H. In some embodiments, $R^8$ is benzyl. In some embodiments, each p is identical and chosen from integers ranging from 0 to 250. In some embodiments, p is chosen from integers ranging from 0 to 200. In some embodiments, p is chosen from integers ranging from 0 to 150. In some embodiments, p is chosen from integers ranging from 0 to 100. In some embodiments, p is chosen from integers ranging from 0 to 50. In some embodiments, p is chosen from integers ranging from 0 to 25. In some embodiments, p is chosen from integers ranging from 0 to 13. In some embodiments, p is chosen from integers ranging from 0 to 10. In some embodiments, p is chosen from integers ranging from 0 to 5.

In some embodiments, at least one compound is chosen from compounds having the following Formulae:

33 34
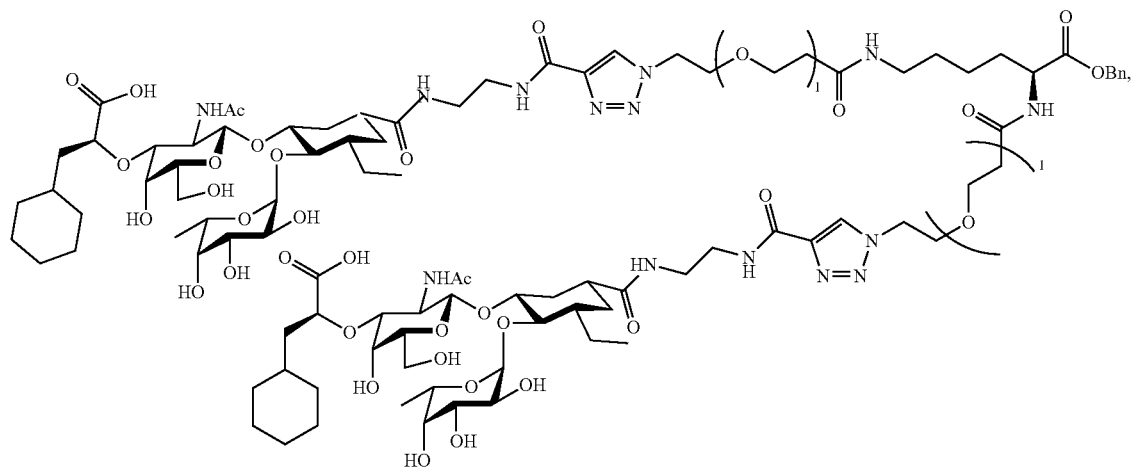
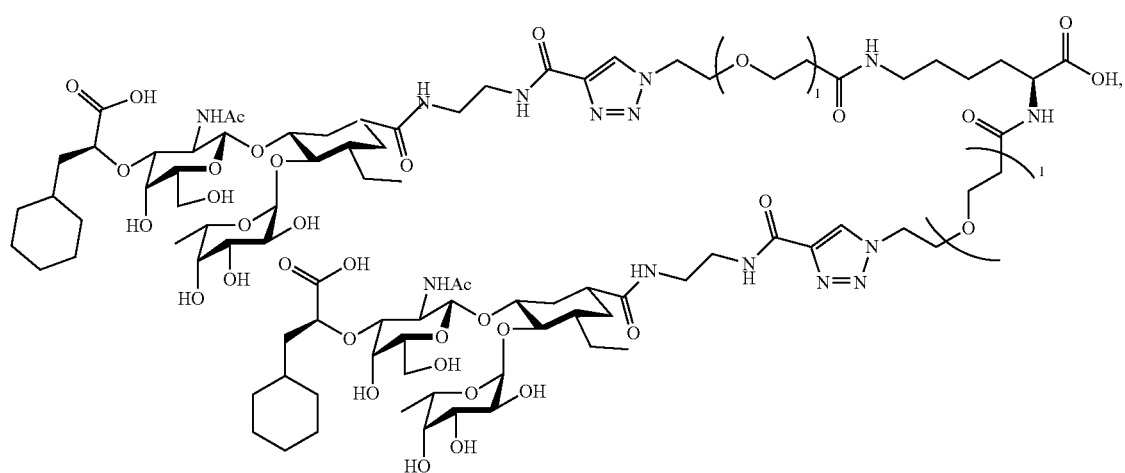
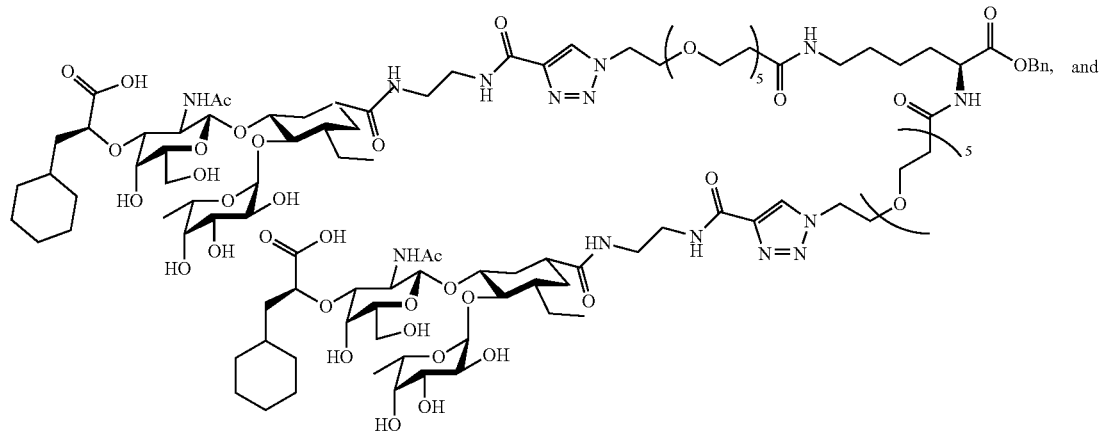
and

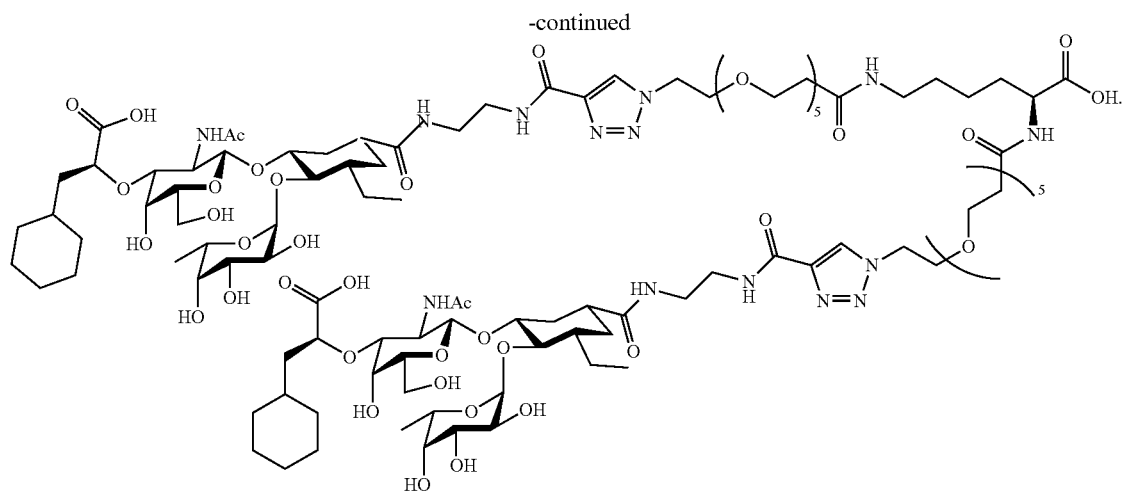
In some embodiments, at least one compound is chosen from compounds having the following Formula:
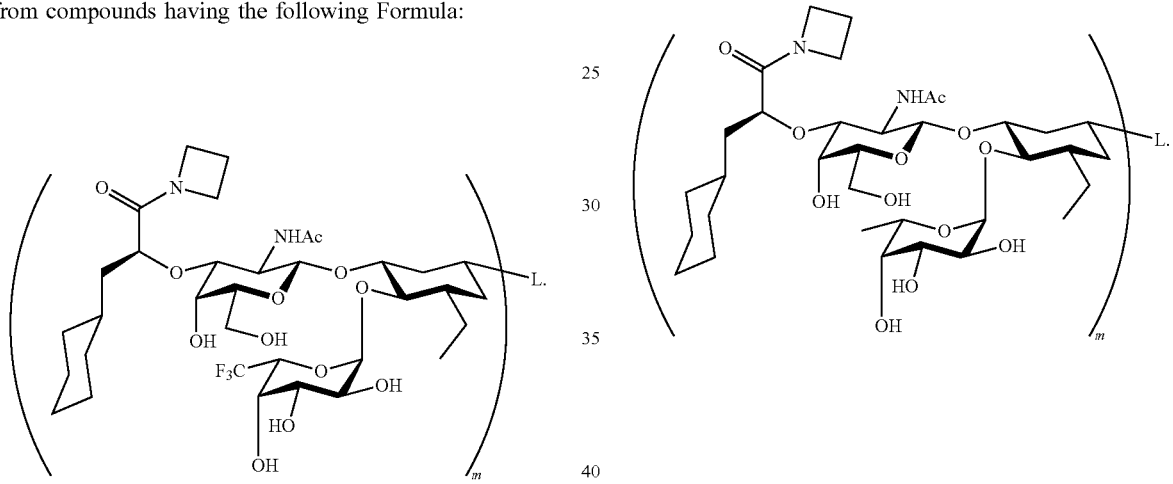
In some embodiments, at least one compound is chosen from compounds having the following Formula:
In some embodiments, at least one compound is chosen from compounds having the following Formula:
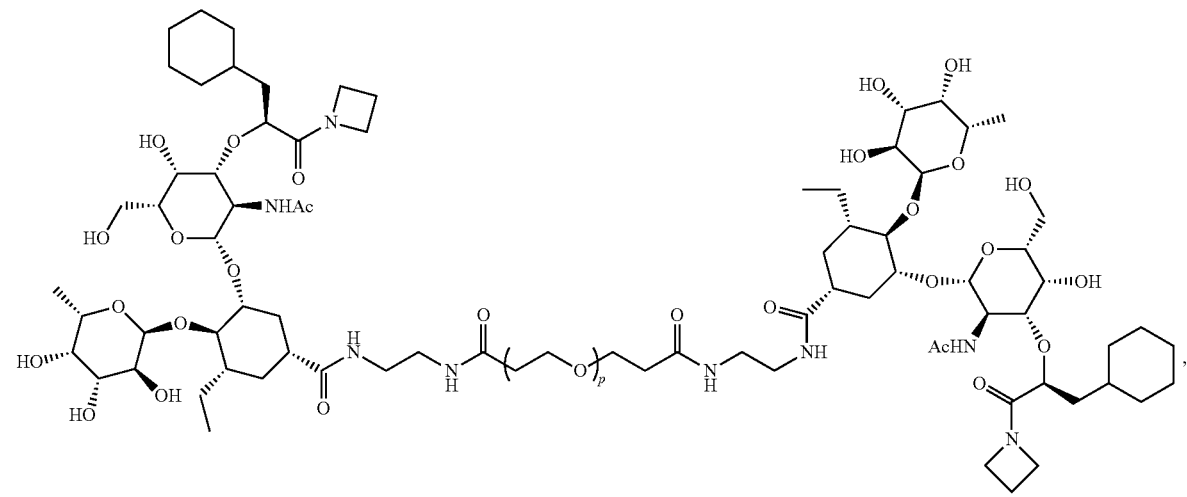

wherein p is chosen from integers ranging from 0 to 250. In some embodiments, p is chosen from integers ranging from 0 to 200. In some embodiments, p is chosen from integers ranging from 0 to 150. In some embodiments, p is chosen from integers ranging from 0 to 100. In some embodiments, p is chosen from integers ranging from 0 to 50. In some embodiments, p is chosen from integers ranging from 0 to 25. In some embodiments, p is chosen from integers ranging from 0 to 13. In some embodiments, p is chosen from integers ranging from 0 to 10.

In some embodiments, at least one compound is chosen from compounds having the following Formulae:

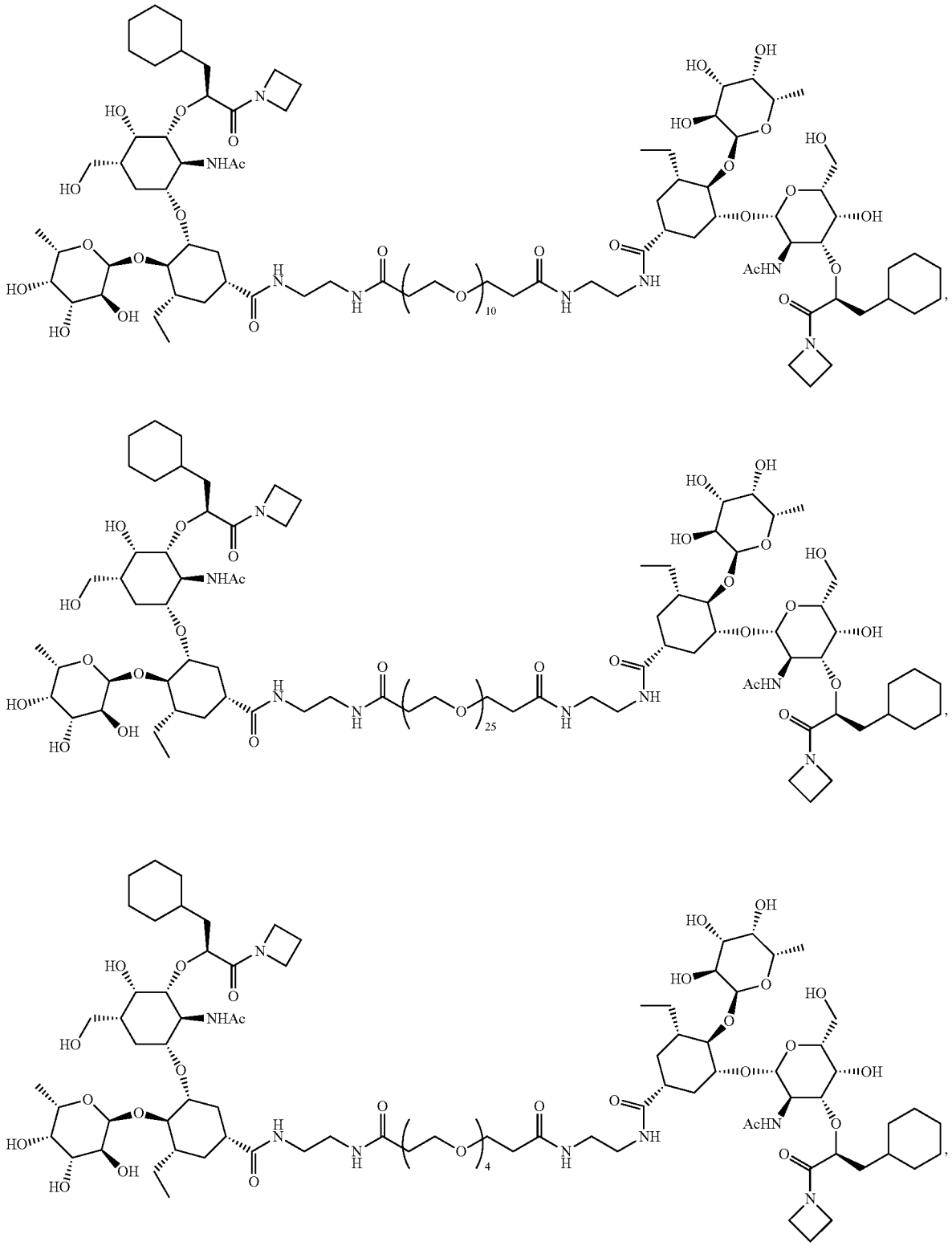

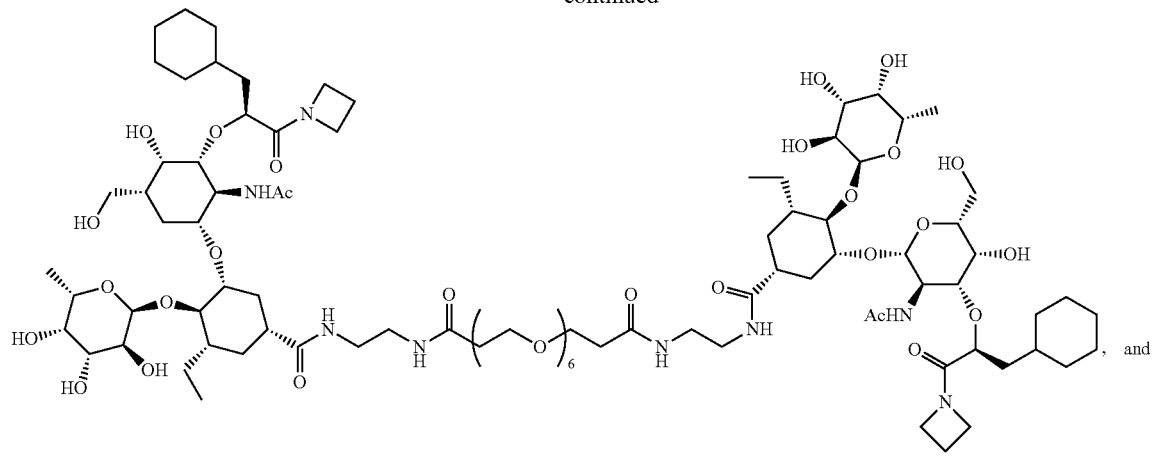

In some embodiments, at least one compound is chosen from compounds having the following Formula:

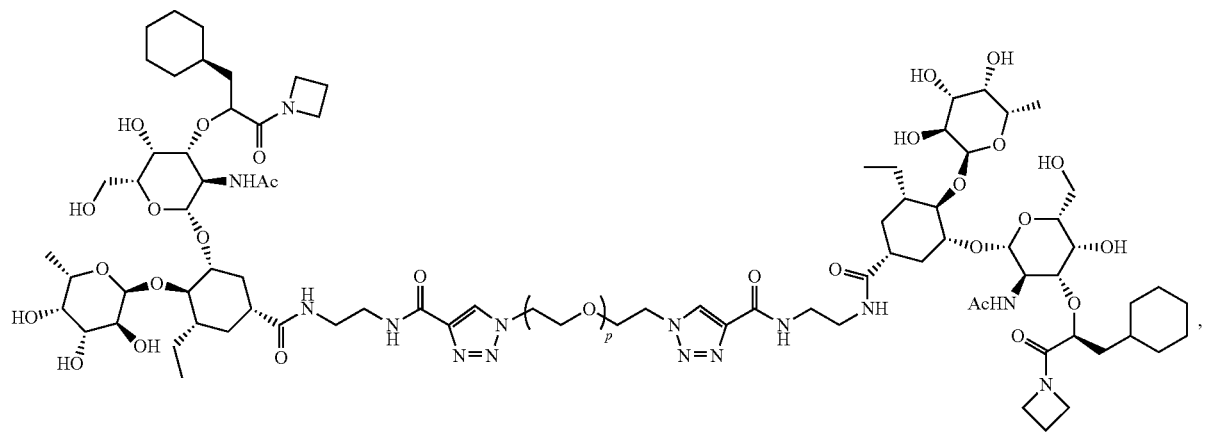

wherein p is chosen from integers ranging from 0 to 250. In some embodiments, p is chosen from integers ranging from 0 to 200. In some embodiments, p is chosen from integers ranging from 0 to 150. In some embodiments, p is chosen from integers ranging from 0 to 100. In some embodiments, p is chosen from integers ranging from 0 to 50. In some embodiments, p is chosen from integers ranging from 0 to 25. In some embodiments, p is chosen from integers ranging from 0 to 13. In some embodiments, p is chosen from integers ranging from 0 to 10.

In some embodiments, at least one compound is chosen from compounds having the following Formulae:

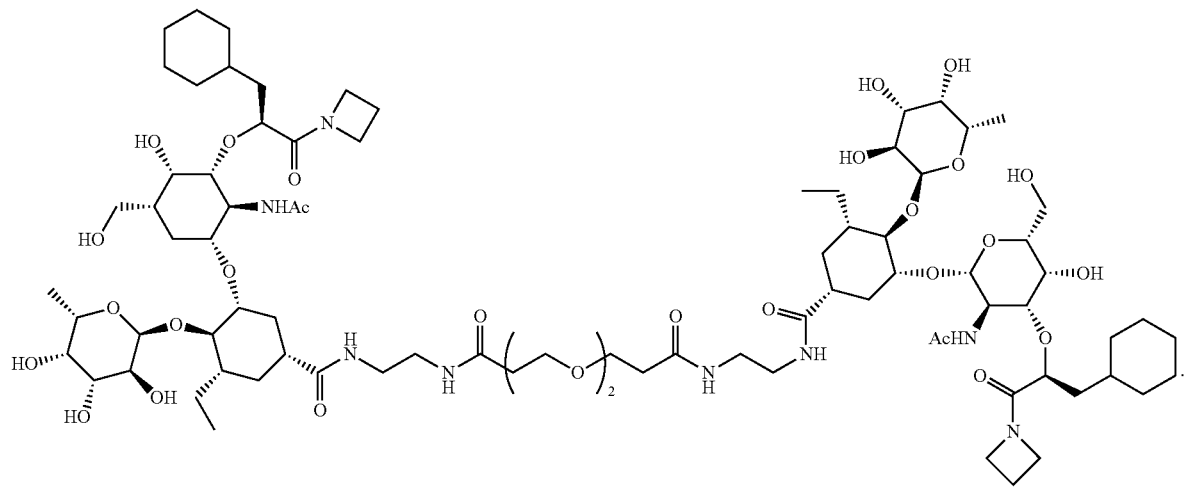

41
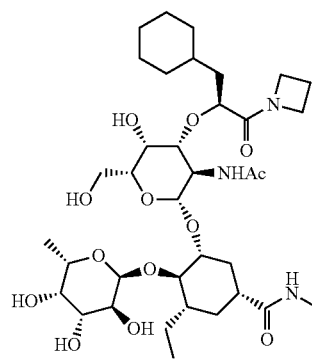 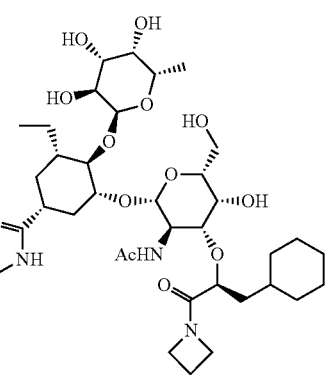
and
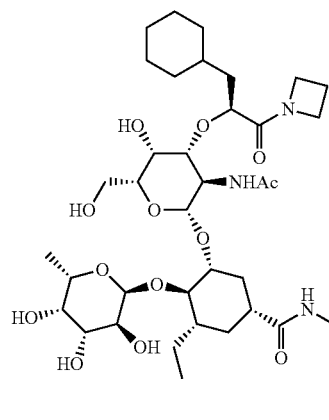 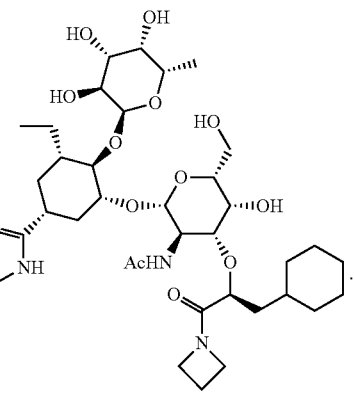
.
In some embodiments, at least one compound is chosen from compounds having the following Formula:
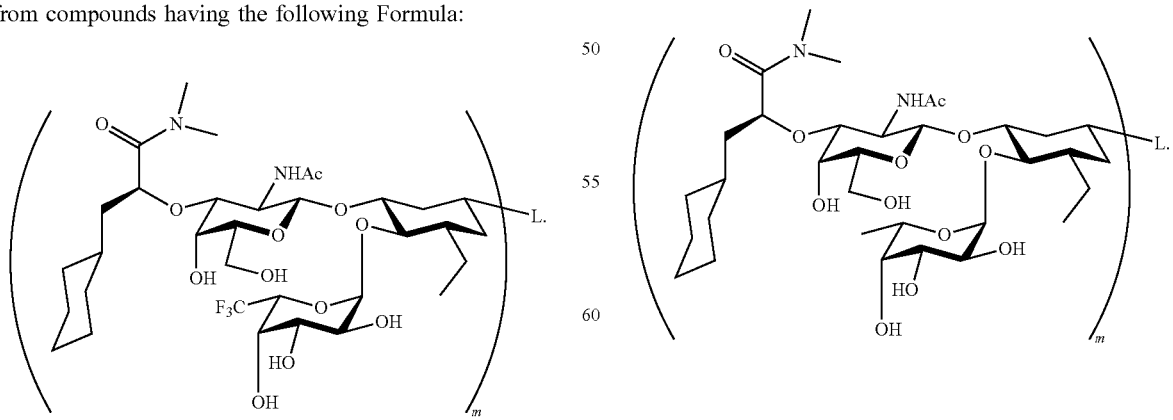
In some embodiments, at least one compound is chosen from compounds having the following Formula:
In some embodiments, at least one compound is chosen from compounds having the following Formula:

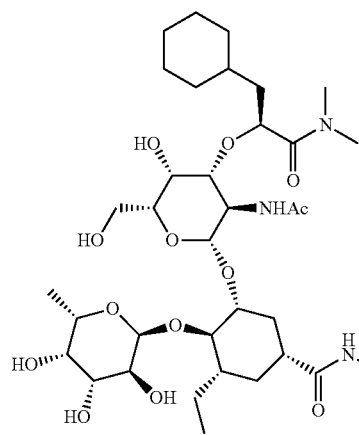
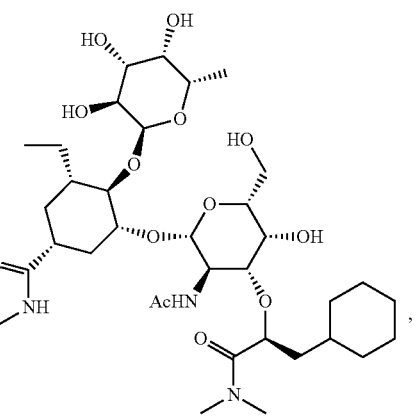

wherein p is chosen from integers ranging from 0 to 250. In some embodiments, p is chosen from integers ranging from 0 to 200. In some embodiments, p is chosen from integers ranging from 0 to 150. In some embodiments, p is chosen from integers ranging from 0 to 100. In some embodiments, p is chosen from integers ranging from 0 to 50. In some embodiments, p is chosen from integers ranging from 0 to 25. In some embodiments, p is chosen from integers ranging from 0 to 13. In some embodiments, p is chosen from integers ranging from 0 to 10.

In some embodiments, at least one compound is:

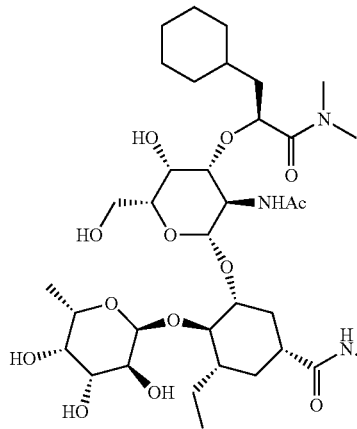
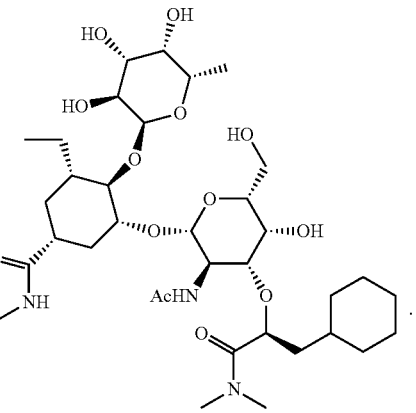

In some embodiments, at least one compound is chosen from compounds of the following Formulae:

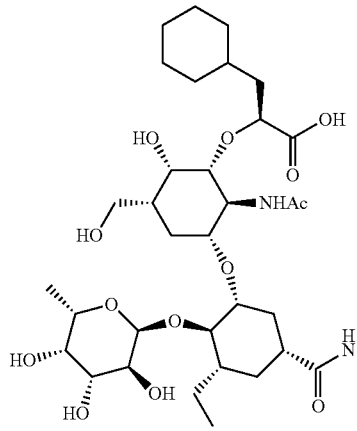
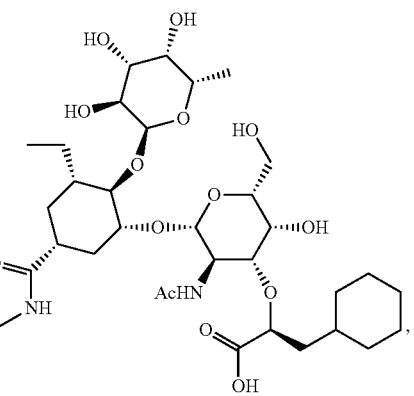

-continued
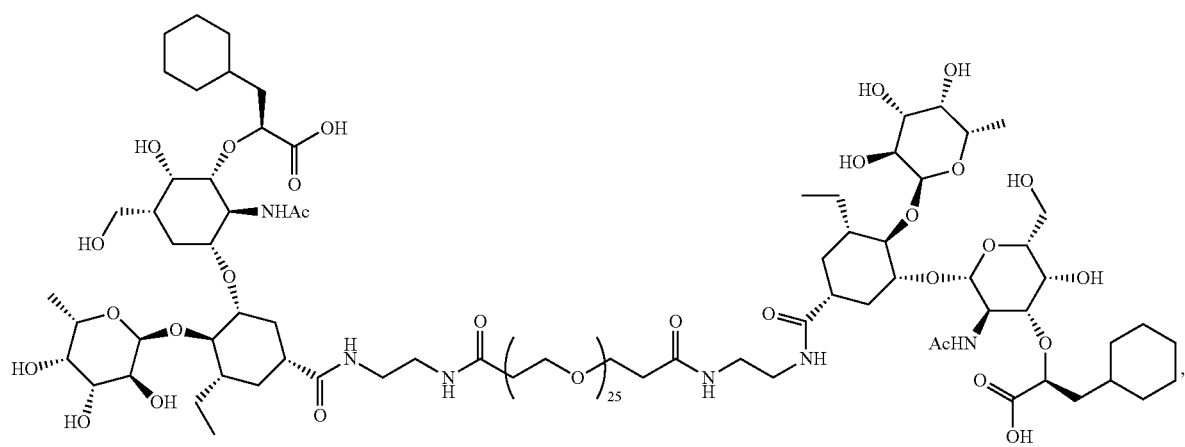
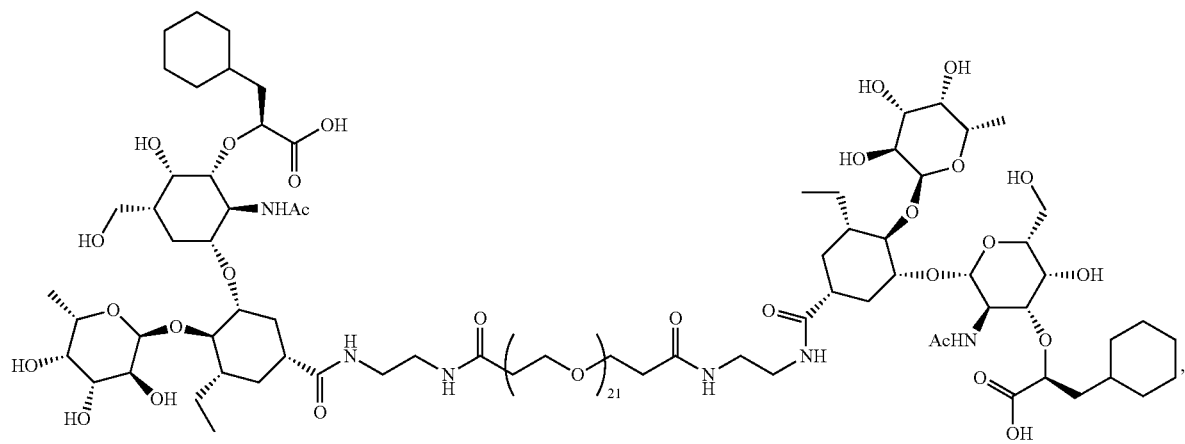
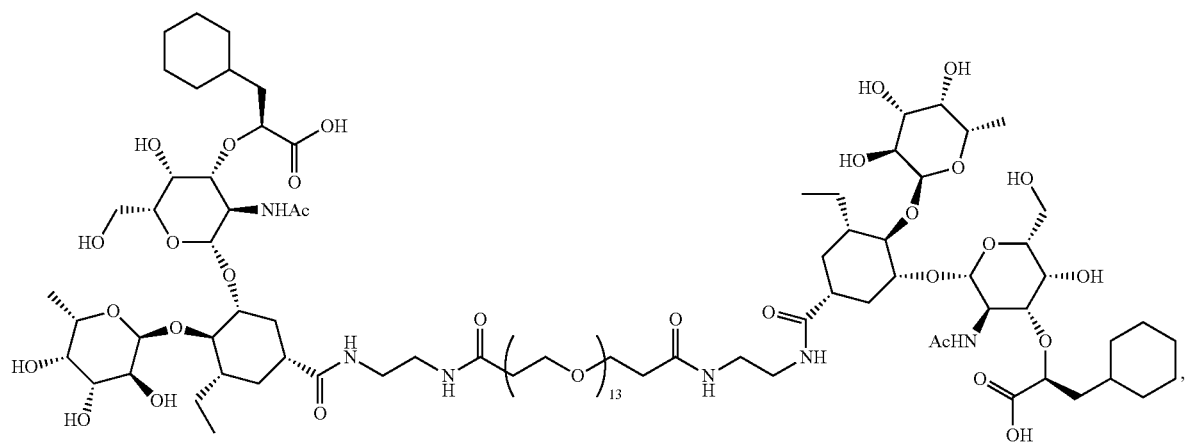

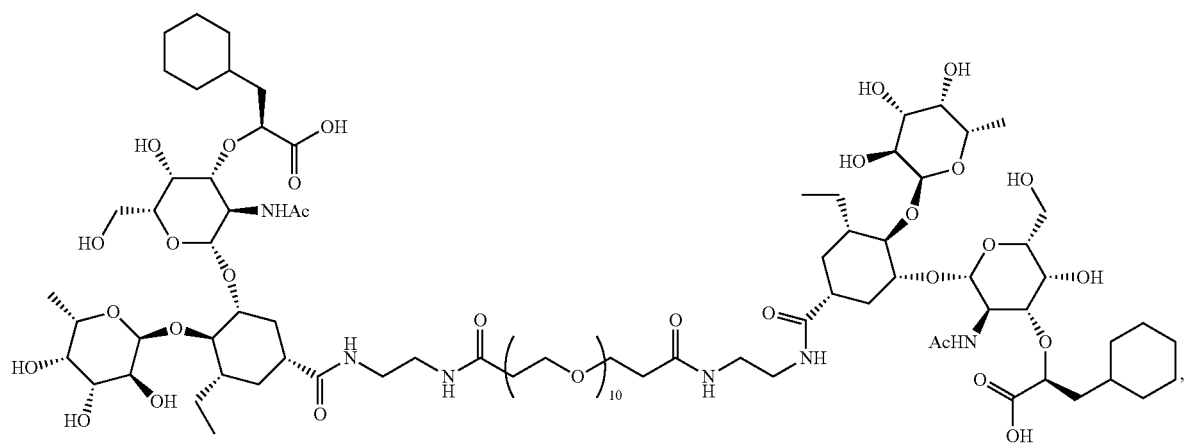
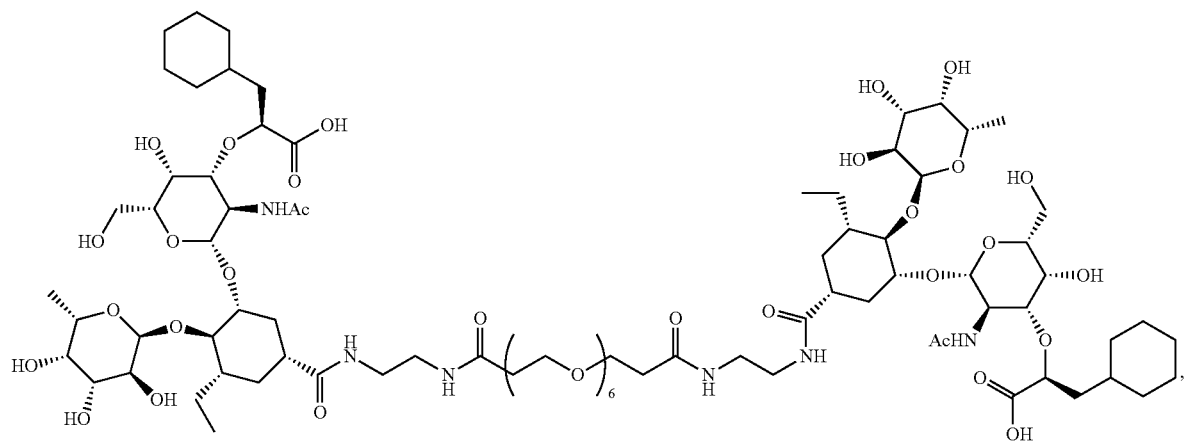
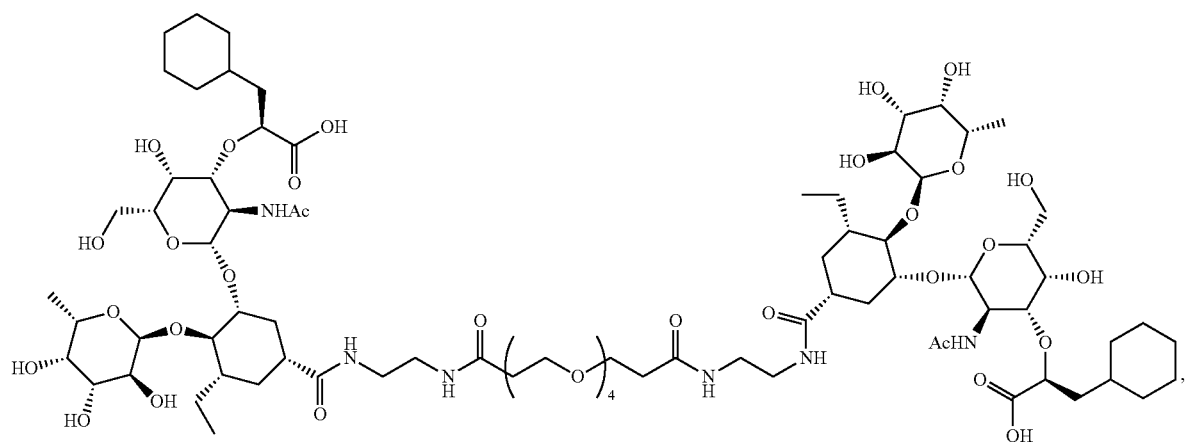

49
50
-continued
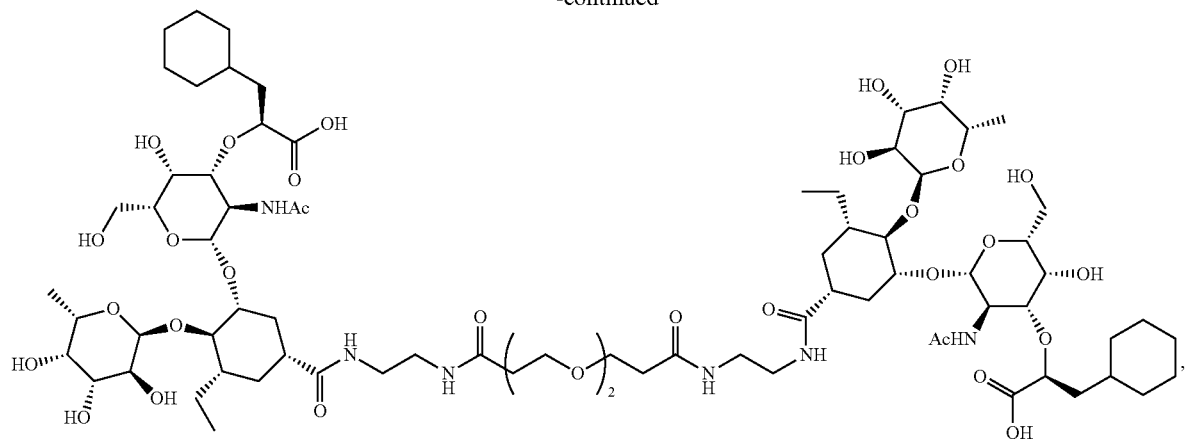
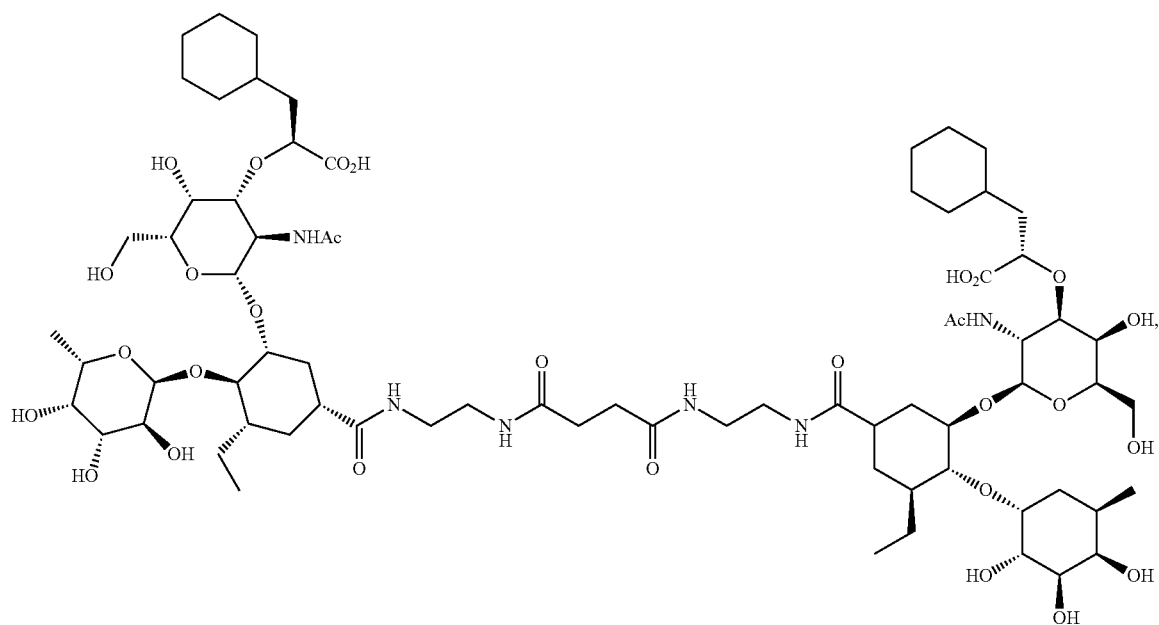
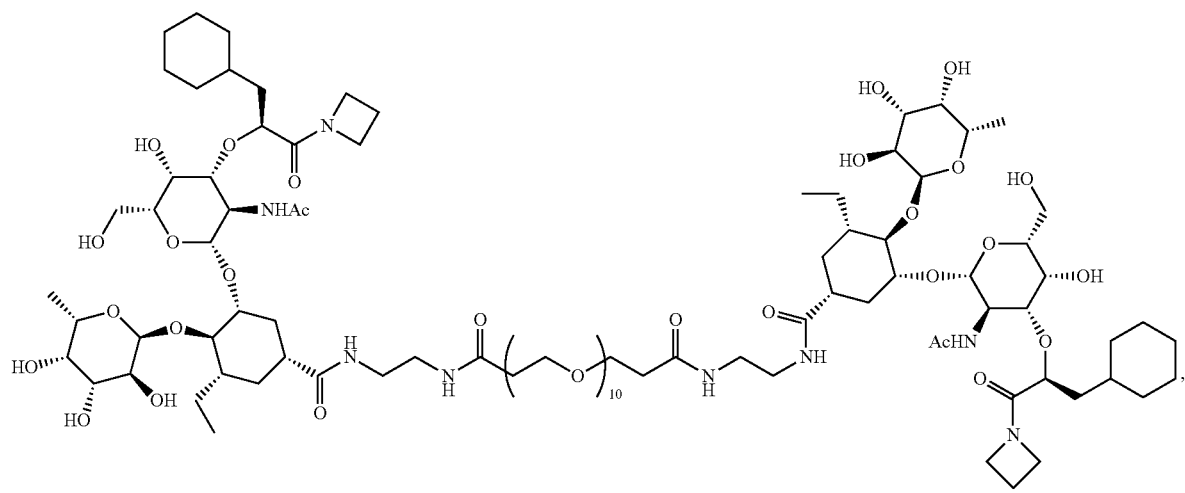

51
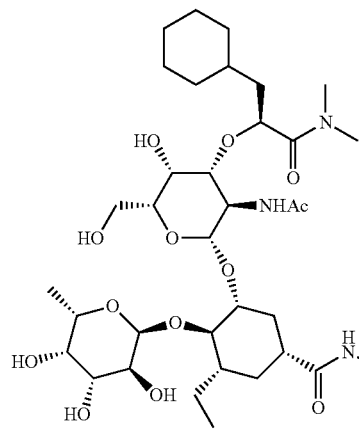
52
-continued
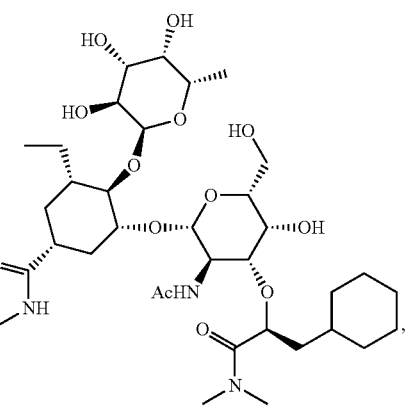
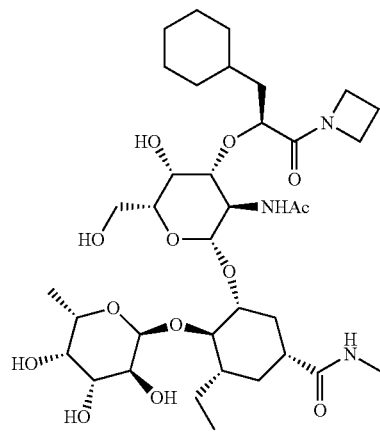
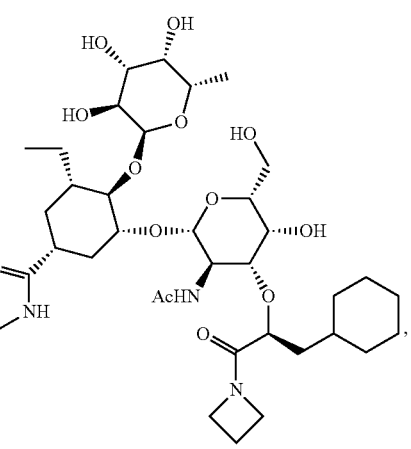
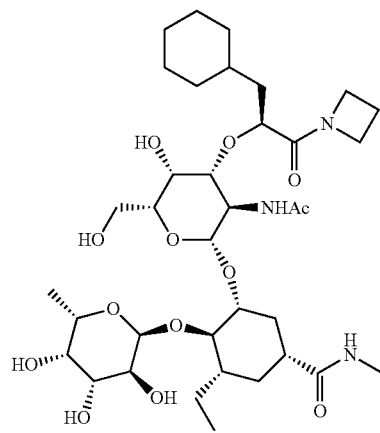
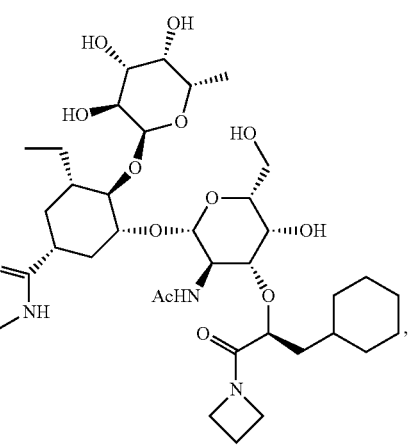

-continued
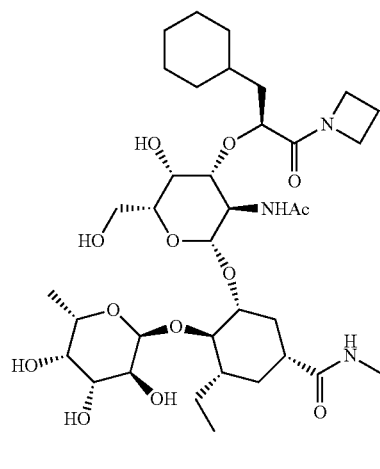 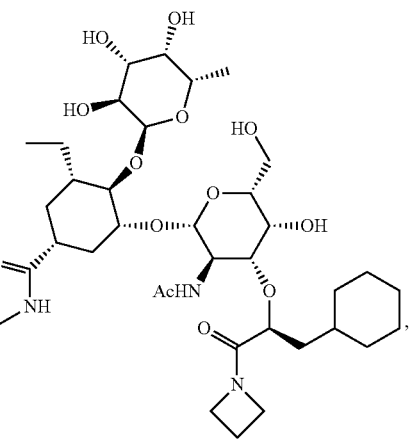
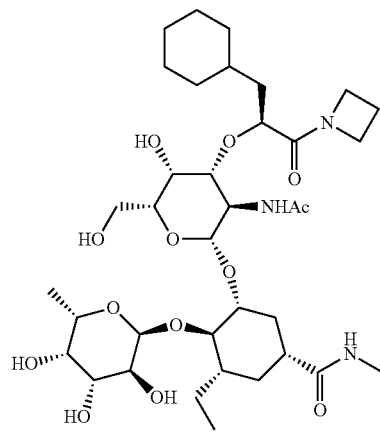 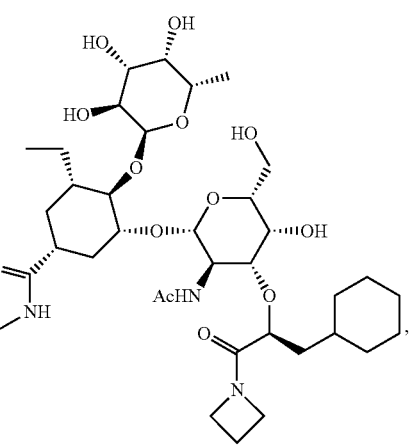
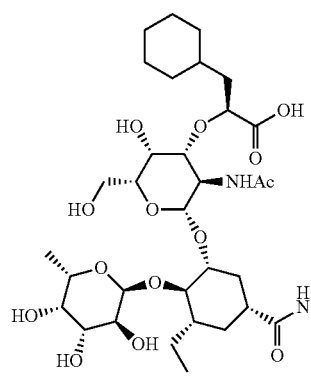 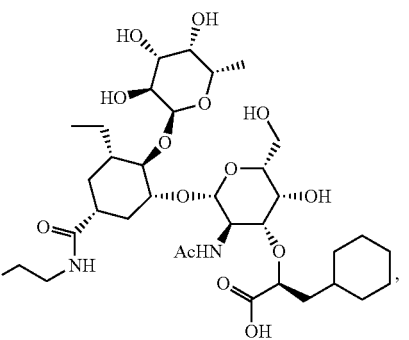
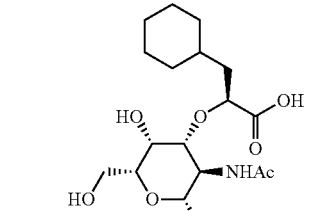 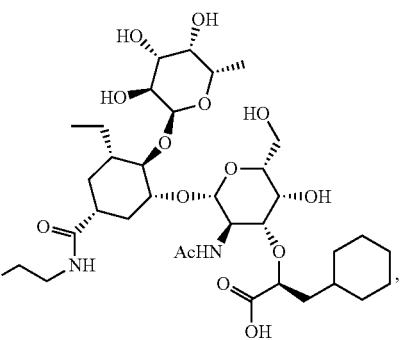
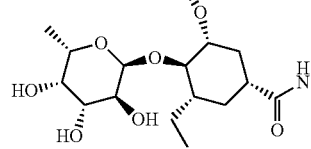

55
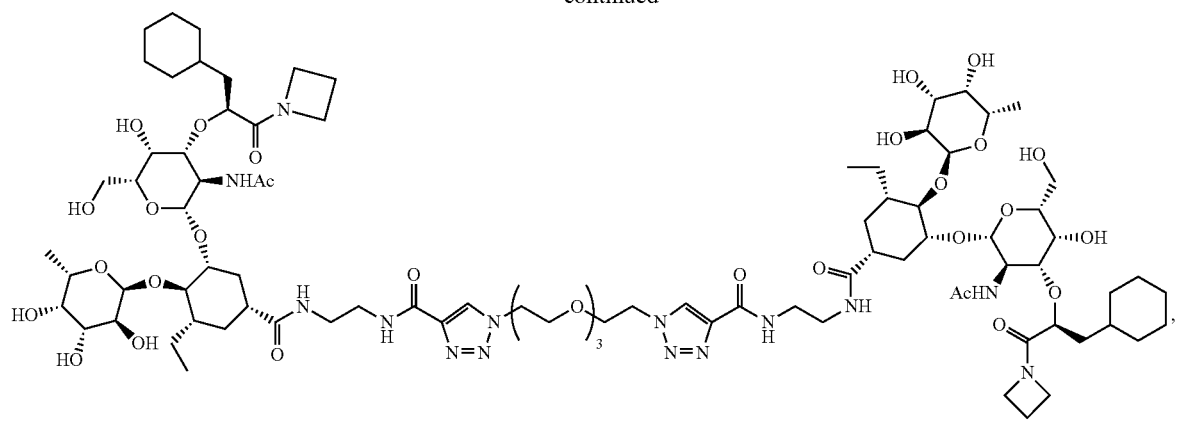
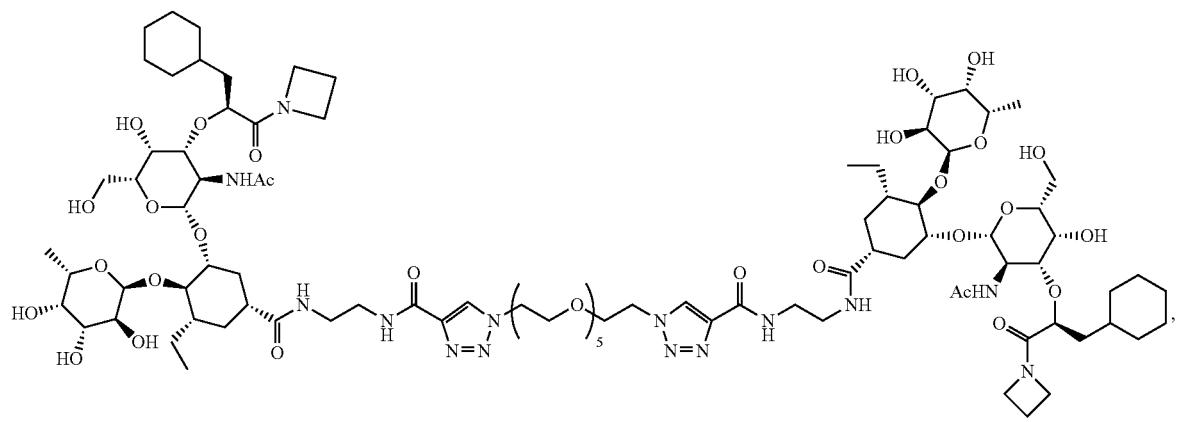
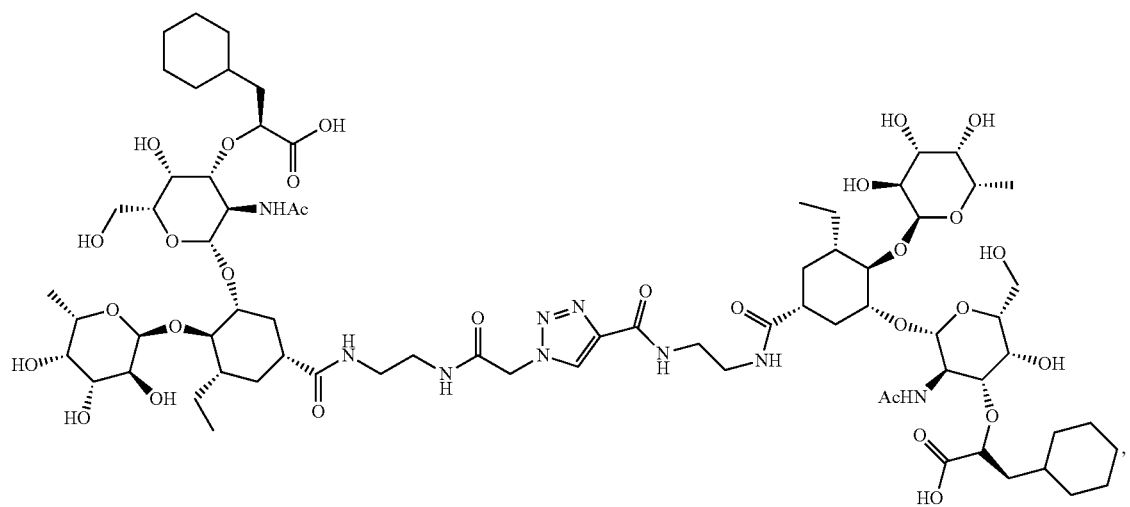

57
58
-continued
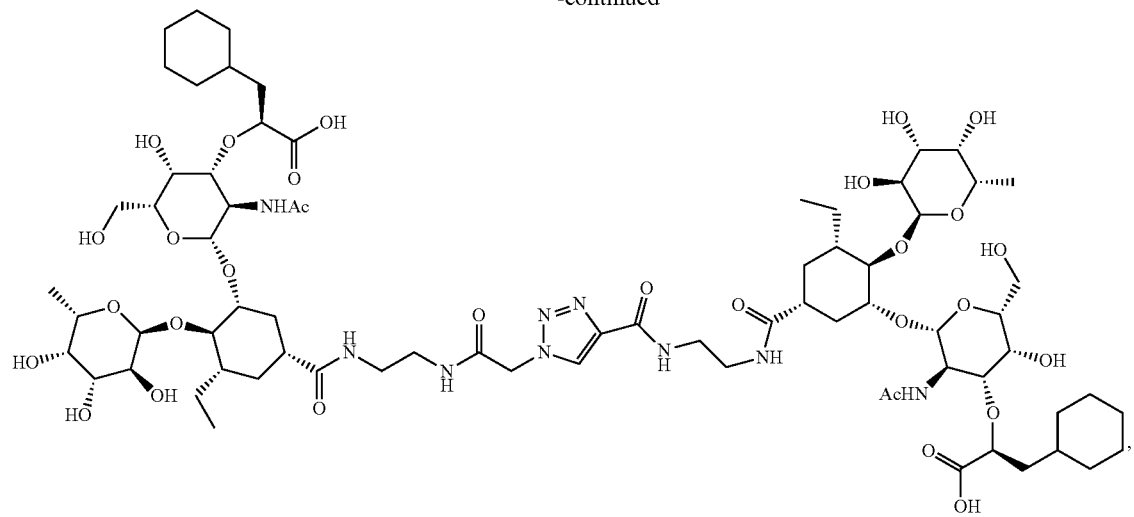
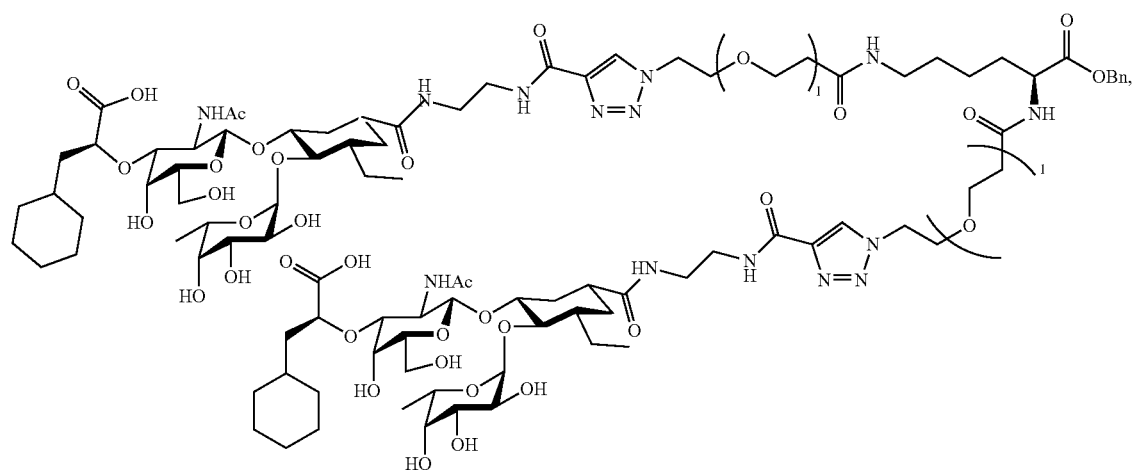
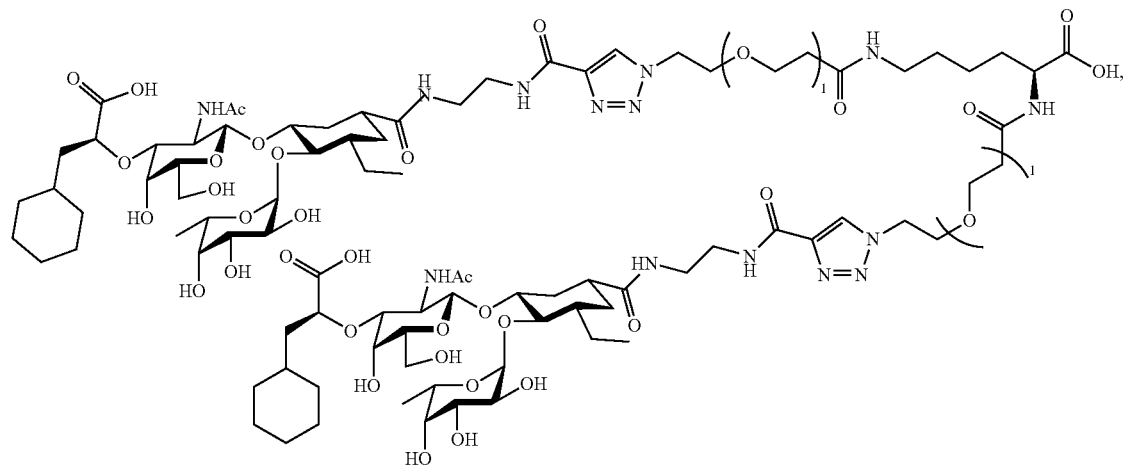

-continued
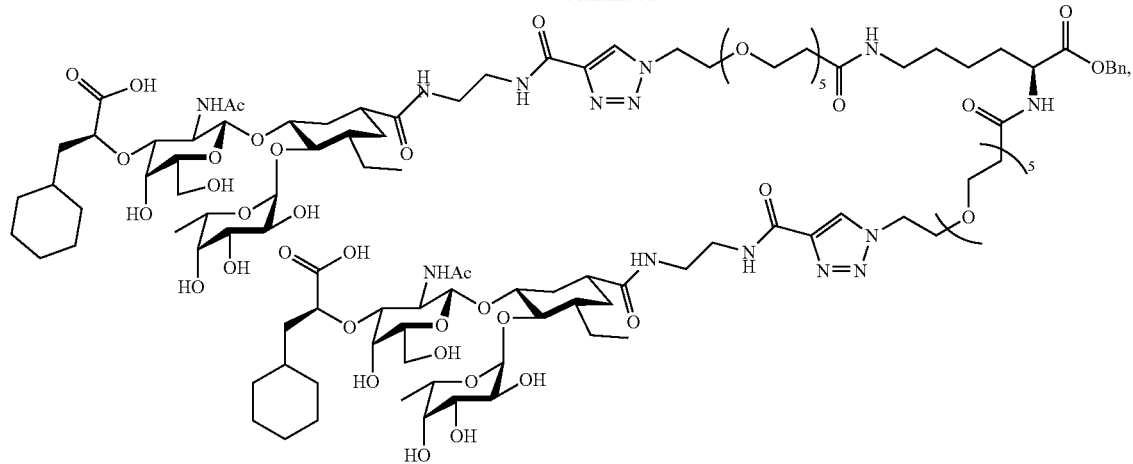
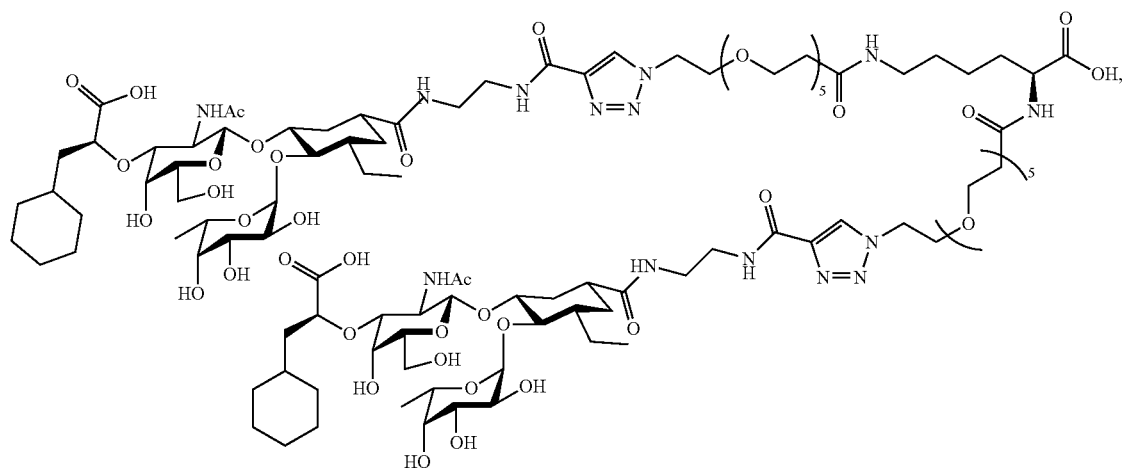
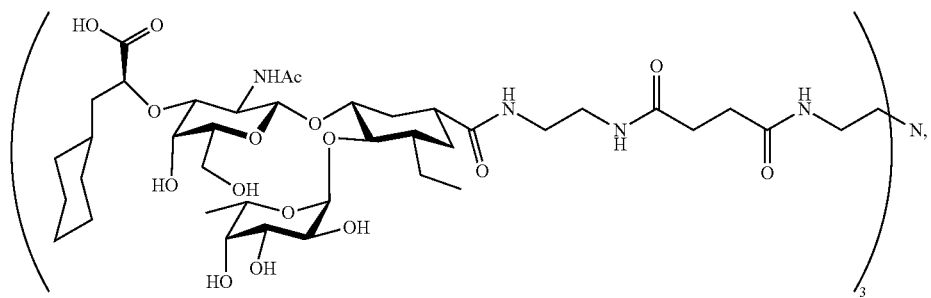
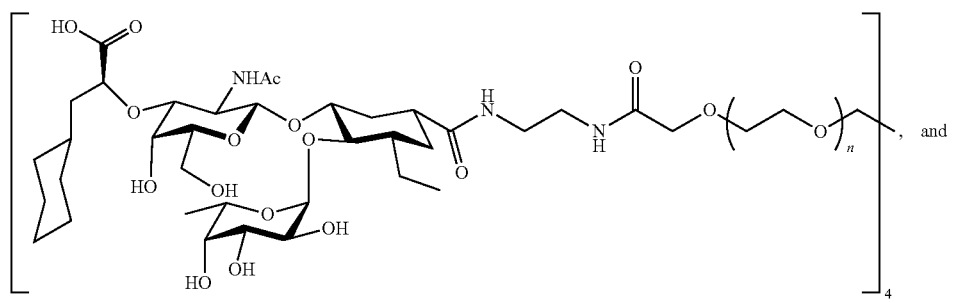

-continued

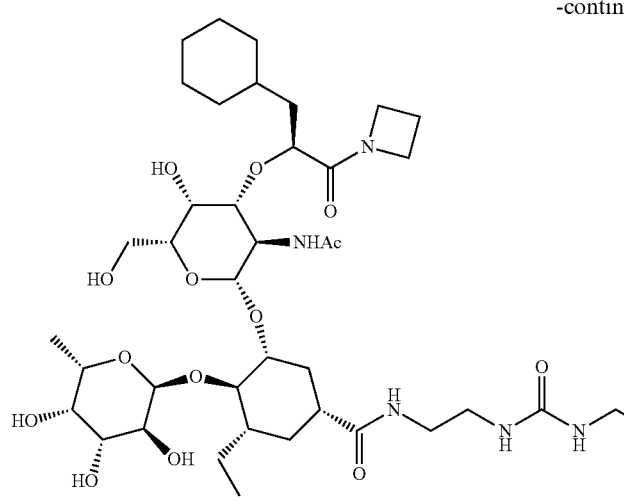
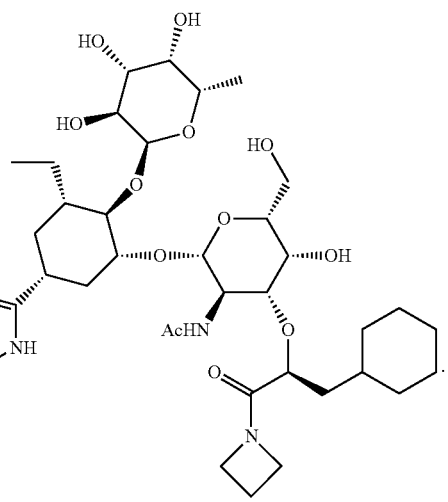

Also provided are pharmaceutical compositions comprising at least one compound of Formula (I). Such pharmaceutical compositions are described in greater detail herein. These compounds and compositions may be used in the methods described herein.

In some embodiments, a method for treating and/or preventing at least one disease, disorder, and/or condition where inhibition of E-selectin mediated functions may be useful is disclosed, the method comprising administering at least one compound of Formula (I) and/or a pharmaceutical composition comprising at least one compound of Formula (I).

In some embodiments, a method for treating and/or preventing at least one inflammatory disease, disorder, and/or condition in which the adhesion and/or migration of cells occurs in the disease, disorder, and/or condition is disclosed, the method comprising administering at least one compound of Formula (I) and/or a pharmaceutical composition comprising at least one compound of Formula (I).

In some embodiments, a method for inhibiting adhesion of a cancer cell that expresses a ligand of E-selectin to an endothelial cell expressing E-selectin on the cell surface of the endothelial cell is disclosed, the method comprising contacting the endothelial cell and at least one compound of Formula (I) and/or a pharmaceutical composition comprising at least one compound of Formula (I) such that the at least one compound of Formula (I) interacts with E-selectin on the endothelial cell, thereby inhibiting binding of the cancer cell to the endothelial cell. In some embodiments, the endothelial cell is present in the bone marrow.

In some embodiment, a method for treating and/or preventing a cancer is disclosed, the method comprising administering to a subject in need thereof an effective amount of at least one compound of Formula (I) and/or a pharmaceutical composition comprising at least one compound of Formula (I). In some embodiments, at least one compound of Formula (I) and/or pharmaceutical composition comprising at least one compound of Formula (I) may be administered in conjunction with (i.e., as an adjunct therapy, which is also called adjunctive therapy) chemotherapy and/or radiotherapy.

The chemotherapy and/or radiotherapy may be referred to as the primary anti-tumor or anti-cancer therapy that is being administered to the subject to treat the particular cancer. In some embodiments, a method for reducing (i.e., inhibiting, diminishing) chemosensitivity and/or radiosensitivity of hematopoietic stem cells (HSC) to the chemotherapeutic drug(s) and/or radiotherapy, respectively, is disclosed, the method comprising administering to a subject in need thereof an effective amount of at least one compound of Formula (I) and/or a pharmaceutical composition comprising at least one compound of Formula (I).

In some embodiments, a method for enhancing (i.e., promoting) survival of hematopoietic stem cells is provided, the method comprising administering to a subject in need thereof at least one compound of Formula (I) or a pharmaceutical composition comprising at least one compound of Formula (I).

In some embodiments, a method for decreasing the likelihood of occurrence of metastasis of cancer cells (also called tumor cells herein) in a subject who is in need thereof is disclosed, the method comprising administering an effective amount of at least one compound of Formula (I) and/or a pharmaceutical composition comprising at least one compound of Formula (I).

In some embodiments, a method for treatment and/or prevention of at least one cancer in which the cancer cells may leave the primary site is disclosed, the method comprising administering to a subject in need thereof an effective amount of at least one compound of Formula (I) and/or a pharmaceutical composition comprising at least one compound of Formula (I). A primary site may be, for example, solid tissue (e.g., breast or prostate) or the bloodstream.

In some embodiments, a method for treatment and/or prevention of at least one cancer in which it is desirable to mobilize cancer cells from a site into the bloodstream and/or retain the cancer cells in the bloodstream is disclosed, the method comprising administering to a subject in need thereof an effective amount of at least one compound of Formula (I) and/or a pharmaceutical composition comprising at least one compound of Formula (I).

In some embodiments, a method for decreasing the likelihood of occurrence of infiltration of cancer cells into bone marrow is disclosed, the method comprises administering to a subject in need thereof an effective amount of at least one compound of Formula (I) and/or a pharmaceutical composition comprising at least one compound of Formula (I).

In some embodiments, a method for releasing cells into circulating blood and enhancing retention of the cells in the blood is disclosed, the method comprising administering to a subject in need thereof an effective amount of at least one compound of Formula (I) and/or a pharmaceutical composition comprising at least one compound of Formula (I). In some embodiments, the method further includes collecting the released cells. In some embodiments, collecting the released cells utilizes apheresis. In some embodiments, the released cells are stem cells (e.g., bone marrow progenitor cells). In some embodiments, G-CSF is administered to the individual.

In some embodiments, a method for treating and/or preventing thrombosis is disclosed, the method comprising administering to a subject in need thereof an effective amount of at least one compound of Formula (I) and/or a pharmaceutical composition comprising at least one compound of Formula (I).

In some embodiments, a method for treating and/or preventing mucositis is disclosed, the method comprising administering to a subject in need thereof an effective amount of at least one compound of Formula (I) and/or a pharmaceutical composition comprising at least one compound of Formula (I).

In some embodiments, a compound of Formula (I) and/or a pharmaceutical composition comprising at least one compound of Formula (I) may be used for the preparation and/or manufacture of a medicament for use in treating and/or preventing at least one of the diseases, disorders, and/or conditions described herein.

Whenever a term in the specification is identified as a range (e.g., $C_{1-4}$ alkyl), the range independently discloses and includes each element of the range. As a non-limiting example, $C_{1-4}$ alkyl groups includes, independently, $C_1$ alkyl groups, $C_2$ alkyl groups, $C_3$ alkyl groups, and $C_4$ alkyl groups.

The term "at least one" refers to one or more, such as one, two, etc. For example, the term "at least one $C_{1-4}$ alkyl group" refers to one or more $C_{1-4}$ alkyl groups, such as one $C_{1-4}$ alkyl group, two $C_{1-4}$ alkyl groups, etc.

The term "alkyl" includes saturated straight, branched, and cyclic (also identified as cycloalkyl), primary, secondary, and tertiary hydrocarbon groups. Non-limiting examples of alkyl groups include methyl, ethyl, propyl, isopropyl, cyclopropyl, butyl, secbutyl, isobutyl, ter/butyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless stated otherwise specifically in the specification, an alkyl group may be optionally substituted.

The term "alkenyl" includes straight, branched, and cyclic hydrocarbon groups comprising at least one double bond. The double bond of an alkenyl group can be unconjugated or conjugated with another unsaturated group. Non-limiting examples of alkenyl groups include vinyl, allyl, butenyl, pentenyl, hexenyl, butadienyl, pentadienyl, hexadienyl, 2-ethylhexenyl, and cyclopent-1-en-1-yl. Unless stated otherwise specifically in the specification, an alkenyl group may be optionally substituted.

The term "alkynyl" includes straight and branched hydrocarbon groups comprising at least one triple bond. The triple bond of an alkynyl group can be unconjugated or conjugated with another unsaturated group. Non-limiting examples of alkynyl groups include ethynyl, propynyl, butynyl, pentynyl, and hexynyl. Unless stated otherwise specifically in the specification, an alkynyl group may be optionally substituted.

The term "aryl" includes hydrocarbon ring system groups comprising at least 6 carbon atoms and at least one aromatic ring. The aryl group may be a monocyclic, bicyclic, tricyclic or tetracyclic ring system, which may include fused or bridged ring systems. Non-limiting examples of aryl groups include aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted.

The term "E-selectin antagonist" includes inhibitors of E-selectin only, as well as inhibitors of E-selectin and either P-selectin or L-selectin, and inhibitors of E-selectin, P-selectin, and L-selectin.

The term "glycomimetic" includes any naturally occurring or non-naturally occurring carbohydrate compound in which at least one substituent has been replaced, or at least one ring has been modified (e.g., substitution of carbon for a ring oxygen), to yield a compound that is not fully carbohydrate.

The term "halo" or "halogen" includes fluoro, chloro, bromo, and iodo.

The term "haloalkyl" includes alkyl groups, as defined herein, substituted by at least one halogen, as defined herein. Non-limiting examples of haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl. A "fluoroalkyl" is a haloalkyl wherein at least one halogen is fluoro. Unless stated otherwise specifically in the specification, a haloalkyl group may be optionally substituted.

The term "haloalkenyl" includes alkenyl groups, as defined herein, substituted by at least one halogen, as defined herein. Non-limiting examples of haloalkenyl groups include fluoroethenyl, 1,2-difluoroethenyl, 3-bromo-2-fluoropropenyl, and 1,2-dibromoethenyl. A "fluoroalkenyl" is a haloalkenyl substituted with at least one fluoro group. Unless stated otherwise specifically in the specification, a haloalkenyl group may be optionally substituted.

The term "haloalkynyl" includes alkynyl groups, as defined herein, substituted by at least one halogen, as defined herein. Non-limiting examples include fluoroethynyl, 1,2-difluoroethynyl, 3-bromo-2-fluoropropynyl, and 1,2-dibromoethenyl. A "fluoroalkynyl" is a haloalkynyl wherein at least one halogen is fluoro. Unless stated otherwise specifically in the specification, a haloalkynyl group may be optionally substituted.

The term "heterocyclyl" or "heterocyclic ring" includes 3- to 24-membered saturated or partially unsaturated non-aromatic ring groups comprising 2 to 23 ring carbon atoms and 1 to 8 ring heteroatom(s) each independently chosen from N, O, and S. Unless stated otherwise specifically in the specification, the heterocyclyl groups may be monocyclic, bicyclic, tricyclic or tetracyclic ring systems, which may include fused or bridged ring systems, and may be partially or fully saturated; any nitrogen, carbon or sulfur atom(s) in the heterocyclyl group may be optionally oxidized; any nitrogen atom in the heterocyclyl group may be optionally quaternized; and the heterocyclyl group. Non-limiting examples of heterocyclic ring include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

The term "heteroaryl" includes 5- to 14-membered ring groups comprising 1 to 13 ring carbon atoms and 1 to 6 ring heteroatom(s) each independently chosen from N, O, and S. and at least one aromatic ring. Unless stated otherwise specifically in the specification, the heteroaryl group may be a monocyclic, bicyclic, tricyclic or tetracyclic ring system, which may include fused or bridged ring systems, and the nitrogen, carbon or sulfur atoms in the heteroaryl radical may be optionally oxidized; the nitrogen atom may be optionally quaternized. Non-limiting examples include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

The term "pharmaceutically acceptable salts" includes both acid and base addition salts. Non-limiting examples of pharmaceutically acceptable acid addition salts include chlorides, bromides, sulfates, nitrates, phosphates, sulfonates, methane sulfonates, formates, tartrates, maleates, citrates, benzoates, salicylates, and ascorbates. Non-limiting examples of pharmaceutically acceptable base addition salts include sodium, potassium, lithium, ammonium (substituted and unsubstituted), calcium, magnesium, iron, zinc, copper, manganese, and aluminum salts. Pharmaceutically acceptable salts may, for example, be obtained using standard procedures well known in the field of pharmaceuticals.

The term "prodrug" includes compounds that may be converted, for example, under physiological conditions or by solvolysis, to a biologically active compound described herein. Thus, the term "prodrug" includes metabolic precursors of compounds described herein that are pharmaceutically acceptable. A discussion of prodrugs can be found, for example, in Higuchi, T., et al., "Pro-drugs as Novel Delivery Systems." A.C.S. Symposium Series, Vol. 14, and in Bioreversible Carriers in Drug Design, ed. Edward B. Roche, American Pharmaceutical Association and Pergamon Press, 1987. The term "prodrug" also includes covalently bonded carriers that release the active compound(s) as described herein in vivo when such prodrug is administered to a subject. Non-limiting examples of prodrugs include ester and amide derivatives of hydroxy, carboxy, mercapto and amino functional groups in the compounds described herein.

The term "substituted" includes the situation where, in any of the above groups, at least one hydrogen atom is replaced by a non-hydrogen atom such as, for example, a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also includes the situation where, in any of the above groups, at least one hydrogen atom is replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles.

The present disclosure includes within its scope all the possible geometric isomers. e.g., Z and E isomers (cis and trans isomers), of the compounds as well as all the possible optical isomers, e.g., diastereomers and enantiomers, of the compounds. Furthermore, the present disclosure includes in its scope both the individual isomers and any mixtures thereof, e.g., racemic mixtures. The individual isomers may be obtained using the corresponding isomeric forms of the starting material or they may be separated after the preparation of the end compound according to conventional separation methods. For the separation of optical isomers, e.g., enantiomers, from the mixture thereof conventional resolution methods, e.g., fractional crystallization, may be used.

The present disclosure includes within its scope all possible tautomers. Furthermore, the present disclosure includes in its scope both the individual tautomers and any mixtures thereof.

Compounds of Formula (I) may be prepared according to the General Reaction Scheme shown in FIG. 1. It is understood that one of ordinary skill in the art may be able to make these compounds by similar methods or by combining other methods known to one of ordinary skill in the art. It is also understood that one of ordinary skill in the art would be able to make, in a similar manner as described in FIG. 1, other compounds of Formula (I) not specifically illustrated herein by using appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. and/or synthesized according to sources known to those of ordinary skill in the art (see, for example, Advanced Organic Chemistry: Reactions, Mechanisms, and Structure, 5th edition (Wiley, December 2000)) and/or prepared as described herein.

It will also be appreciated by those skilled in the art that in the processes described herein the functional groups of intermediate compounds may need to be protected by suitable protecting groups, even if not specifically described. Such functional groups include hydroxy, amino, mercapto, and carboxylic acid. Suitable protecting groups for hydroxy include but are not limited to trialkylsilyl or diarylalkylsilyl (for example, t-butyldimethylsilyl, I-butyldiphenylsilyl or trimethylsilyl), tetrahydropyranyl, benzyl, and the like. Suitable protecting groups for amino, amidino and guanidino include but are not limited to t-butoxycarbonyl, benzyloxycarbonyl, and the like. Suitable protecting groups for mercapto include but are not limited to —C(O)R" (where R" is alkyl, aryl or arylalkyl), p-methoxybenzyl, trityl and the like. Suitable protecting groups for carboxylic acid include but are not limited to alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Analogous reactants to those described herein may be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

Methods known to one of ordinary skill in the art may be identified through various reference books, articles, and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Biological activity of a compound described herein may be determined, for example, by performing at least one in vitro and/or in vivo study routinely practiced in the art and described herein or in the art. In vitro assays include without limitation binding assays, immunoassays, competitive binding assays, and cell based activity assays.

An inhibition assay may be used to screen for antagonists of E-selectin. For example, an assay may be performed to characterize the capability of a compound described herein to inhibit (i.e., reduce, block, decrease, or prevent in a statistically or biologically significant manner) interaction of E-selectin with $sLe^a$ or $sLe^x$. The inhibition assay may be a competitive binding assay, which allows the determination of $IC_{50}$ values. By way of example, E-selectin/Ig chimera may be immobilized onto a matrix (e.g., a multi-well plate, which may be made from a polymer, such as polystyrene; a test tube, and the like); a composition may be added to reduce nonspecific binding (e.g., a composition comprising non-fat dried milk or bovine serum albumin or other blocking buffer routinely used by a person skilled in the art); the immobilized E-selectin may be contacted with the candidate compound in the presence of $sLe^a$ comprising a reporter group under conditions and for a time sufficient to permit $sLe^a$ to bind to the immobilized E-selectin; the immobilized E-selectin may be washed; and the amount of $sLe^a$ bound to immobilized E-selectin may be detected. Variations of such steps can be readily and routinely accomplished by a person of ordinary skill in the art.

Conditions for a particular assay include temperature, buffers (including salts, cations, media), and other components that maintain the integrity of any cell used in the assay and the compound, which a person of ordinary skill in the art will be familiar and/or which can be readily determined. A person of ordinary skill in the art also readily appreciates that appropriate controls can be designed and included when performing the in vitro methods and in vivo methods described herein.

The source of a compound that is characterized by at least one assay and techniques described herein and in the art may be a biological sample that is obtained from a subject who has been treated with the compound. The cells that may be used in the assay may also be provided in a biological sample. A "biological sample" may include a sample from a subject, and may be a blood sample (from which serum or plasma may be prepared), a biopsy specimen, one or more body fluids (e.g., lung lavage, ascites, mucosal washings, synovial fluid, urine), bone marrow, lymph nodes, tissue explant, organ culture, or any other tissue or cell preparation from the subject or a biological source. A biological sample may further include a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In some embodiments, the subject or biological source may be a human or non-human animal, a primary cell culture (e.g., immune cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

As described herein, methods for characterizing E-selectin antagonists include animal model studies. Non-limiting examples of animal models for liquid cancers used in the art include multiple myeloma (see, e.g., DeWeerdt, Nature 480:S38-S39 (15 Dec. 2011) doi:10.1038/480S38a; Published online 14 Dec. 2011: Mitsiades et al., *Clin. Cancer Res.* 2009 15:1210021 (2009)); acute myeloid leukemia (AML) (Zuber et al., *Genes Dev.* 2009 Apr. 1; 23(7): 877-889). Animal models for acute lymphoblastic leukemia (ALL) have been used by persons of ordinary skill in the art for more than two decades. Numerous exemplary animal models for solid tumor cancers are routinely used and are well known to persons of ordinary skill in the art.

The compounds of the present disclosure and the pharmaceutical compositions comprising at least one of such compounds may be useful in methods for treating and/or preventing a disease or disorder that is treatable by inhibiting at least one activity of E-selectin (and/or inhibiting binding of E-selectin to a ligand, which in turn inhibits a biological activity). Focal adhesion of leukocytes to the endothelial lining of blood vessels is a characteristic step in certain vascular disease processes.

The compounds of the present disclosure and pharmaceutical compositions comprising at least one such compound may be useful in methods for treating and/or preventing at least one inflammatory disease. Inflammation comprises reaction of vascularized living tissue to injury. By way of example, although E-selectin-mediated cell adhesion is important to the body's anti-infective immune response, in other circumstances, E-selectin mediated cell adhesion may be undesirable or excessive, resulting in tissue damage instead of repair. For example, many pathologies (such as autoimmune and inflammatory diseases, shock and reperfusion injuries) involve abnormal adhesion of white blood cells. Therefore, inflammation affects blood vessels and adjacent tissues in response to an injury or abnormal stimulation by a physical, chemical, or biological agent. Examples of inflammatory diseases, disorders, or conditions include, without limitation, dermatitis, chronic eczema, psoriasis, multiple sclerosis, rheumatoid arthritis, systemic lupus erythematosus, graft versus host disease, sepsis, diabetes, atherosclerosis, Sjogren's syndrome, progressive systemic sclerosis, scleroderma, acute coronary syndrome, ischemic reperfusion, Crohn's disease, inflammatory bowel disease, endometriosis, glomerulonephritis, myasthenia gravis, idiopathic pulmonary fibrosis, asthma, allergic reaction, acute respiratory distress syndrome (ARDS) or other acute leukocyte-mediated lung injury, vasculitis, or inflammatory autoimmune myositis. Other diseases and disorders for which the glycomimetic compounds described herein may be useful for treating and/or preventing include hyperactive coronary circulation, microbial infection, cancer metastasis, thrombosis, wounds, burns, spinal cord damage, digestive tract mucous membrane disorders (e.g., gastritis, ulcers), osteoporosis, osteoarthritis, septic shock, traumatic shock, stroke, nephritis, atopic dermatitis, frostbite injury, adult dyspnoea syndrome, ulcerative colitis, diabetes and reperfusion injury following ischaemic episodes, prevention of restinosis associated with vascular stenting, and for undesirable angiogenesis, for example, angiogenesis associated with tumor growth.

As discussed in detail herein, a disease or disorder to be treated or prevented is a cancer and related metastasis and includes cancers that comprise solid tumor(s) and cancers that comprise liquid tumor(s). The compounds of the present disclosure and pharmaceutical compositions comprising at least one such compound may be useful in methods for preventing and/or treating cancer. In some embodiments, the at least one compound may be used for treating and/or preventing metastasis and/or for inhibiting (slowing, retarding, or preventing) metastasis of cancer cells.

In some embodiments, the compounds of present disclosure and pharmaceutical compositions comprising at least one such compound may be used for decreasing (i.e., reducing) the likelihood of occurrence of metastasis of cancer cells in an individual (i.e., subject, patient) who is in need thereof. The compounds of the present disclosure and compositions comprising at least one such compound may be used for decreasing (i.e., reducing) the likelihood of occurrence of infiltration of cancer cells into bone marrow in an individual who is in need thereof. The individuals (or subjects) in need of such treatments include subjects who have been diagnosed with a cancer, which includes cancers that comprise solid tumor(s) and cancers that comprise liquid tumor(s).

Non-limiting examples of cancers include colorectal cancer, liver cancer, gastric cancer, lung cancer, brain cancer, kidney cancer, bladder cancer, thyroid cancer, prostate cancer, ovarian cancer, cervical cancer, uterine cancer, endometrial cancer, melanoma, breast cancer, and pancreatic cancer. Liquid tumors can occur in the blood, bone marrow, the soft, sponge-like tissue in the center of most bones, and lymph nodes and include leukemia (e.g., AML, ALL, CLL, and CML), lymphoma, and myeloma (e.g., multiple myeloma). Lymphomas include Hodgkin lymphoma, which is marked by the presence of a type of cell called the Reed-Sternberg cell, and non-Hodgkin lymphomas, which includes a large, diverse group of cancers of immune system cells. Non-Hodgkin lymphomas can be further divided into cancers that have an indolent (slow-growing) course and those that have an aggressive (fast-growing) course, and which subtypes respond to treatment differently.

The compounds of the present disclosure and pharmaceutical compositions comprising at least one such compound may be administered as an adjunct therapy to chemotherapy and/or radiotherapy, which is/are being delivered to the subject as primary therapy for treating the cancer. The chemotherapy and/or radiotherapy that may be administered depend upon several factors including the type of cancer, location of the tumor(s), stage of the cancer, age and gender and general health status of the subject. A person of ordinary skill in the medical art can readily determine the appropriate chemotherapy regimen and/or radiotherapy regimen for the subject in need. The person of ordinary skill in the medical art can also determine, with the aid of preclinical and clinical studies, when the compound of the present disclosure or pharmaceutical composition comprising at least one such compound should be administered to the subject, that is whether the compound or composition is administered prior to, concurrent with, or subsequent to a cycle of the primary chemotherapy or radiation treatment.

Also provided herein is a method for inhibiting adhesion of a tumor cell that expresses a ligand of E-selectin to an endothelial cell expressing E-selectin on its cell surface, which method comprises contacting the endothelial cell with at least one compound of the present disclosure or pharmaceutical compositions comprising at least one such compound, thereby permitting the compound to interact with E-selectin on the endothelial cell surface and inhibiting binding of the tumor cell to the endothelial cell. Without wishing to be bound by theory, inhibiting adhesion of tumor cells to endothelial cells may reduce in a significant manner, the capability of the tumor cells to extravasate into other organs, blood vessels, lymph, or bone marrow and thereby reduce, decrease, or inhibit, or slow the progression of the cancer, including reducing, decreasing, inhibiting, or slowing metastasis.

As described herein, at least one of the compounds of the present disclosure or pharmaceutical compositions comprising at least one such compound may be administered in combination with at least one additional anti-cancer agent. Chemotherapy may comprise one or more chemotherapeutic agents. For example, chemotherapy agents, radiotherapeutic agents, inhibitors of phosphoinositide-3 kinase (PI3K), and inhibitors of VEGF may be used in combination with an E-selectin antagonist compound described herein. Non-limiting examples of inhibitors of PI3K include the compound named by Exelixis as "XL499." Non-limiting examples of VEGF inhibitors include the compound called "cabo" (previously known as XL184). Many other chemotherapeutics are small organic molecules. As understood by a person of ordinary skill in the art, chemotherapy may also refer to a combination of two or more chemotherapeutic molecules that are administered coordinately and which may be referred to as combination chemotherapy. Numerous chemotherapeutic drugs are used in the oncology art and include, for example, alkylating agents; antimetabolites; anthracyclines, plant alkaloids; and topoisomerase inhibitors.

The compounds of the present disclosure or pharmaceutical compositions comprising at least one such compound may function independently from the anti-cancer agent or may function in coordination with the anti-cancer agent, e.g., by enhancing effectiveness of the anti-cancer agent or vice versa. Accordingly, provided herein are methods for enhancing (i.e., enhancing, promoting, improving the likelihood of, enhancing in a statistically or biologically significant manner) and/or maintaining survival of hematopoietic stem cells (HSC) in a subject who is treated with and/or will be treated with a chemotherapeutic drug(s) and/or radioactive therapy, respectively, comprising administering at least one E-selectin antagonist glycomimetic compound as described herein. In some embodiments, the subject receives and/or will receive both chemotherapy and radiation therapy. Also, provided herein is a method for reducing (i.e., reducing, inhibiting, diminishing in a statistically or biologically significant manner) chemosensitivity and/or radiosensitivity of hematopoietic stem cells (HSC) to the chemotherapeutic drug(s) and/or radioactive therapy, respectively, in a subject. Because repeated cycles of chemotherapy and radiotherapy often diminish the ability of HSCs to recover and replenish bone marrow, the glycomimetic compounds described herein may be useful for subjects who will receive more than one cycle, such as at least two, three, four or more cycles, of chemotherapy and/or radiotherapy. HSCs reside in the bone marrow and generate the cells that are needed to replenish the immune system and the blood. Anatomically, bone marrow comprises a vascular niche that is adjacent to bone endothelial sinuses (see, e.g., Kiel et al., *Cell* 121: 1109-21 (2005); Sugiyama et al., *Immunity* 25:977-88 (2006); Mender-Ferrer et al., *Nature* 466:829-34 (2010); Butler et al., *Cell Stem Cell* 6:251-64 (2010)). A recent study describes that E-selectin promotes HSC proliferation and is an important component of the vascular niche (see, e.g., Winkler et al., *Nature Medicine* published online 21 Oct. 2012; doi:10.1038/nm.2969). Deletion or inhibition of E-selectin enhanced HSC survival in mice that were treated with chemotherapeutic agents or radiotherapy and accelerated blood neutrophil recovery (see, e.g., Winkler et al., supra).

In addition, the administration of at least one compound of the present disclosure or pharmaceutical composition comprising at least one such compounds may be in conjunction with one or more other therapies, e.g., for reducing toxicities of therapy. For example, at least one palliative agent to counteract (at least in part) a side effect of a therapy (e.g., anti-cancer therapy) may be administered. Agents (chemical or biological) that promote recovery, or counteract side effects of administration of antibiotics or corticosteroids, are examples of such palliative agents. At least one E-selectin antagonist described herein may be administered before, after, or concurrently with administration of at least one additional anti-cancer agent or at least one palliative agent to reduce a side effect of therapy. When administration is concurrent, the combination may be administered from a single container or two (or more) separate containers.

Cancer cells (also called herein tumor cells) that may be prevented (i.e., inhibited, slowed) from metastasizing, from adhering to an endothelial cell, or from infiltrating bone marrow include cells of solid tumors and liquid tumors (including hematological malignancies). Examples of solid tumors are described herein and include colorectal cancer, liver cancer, gastric cancer, lung cancer, brain cancer, kidney cancer, bladder cancer, thyroid cancer, prostate cancer, ovarian cancer, cervical cancer, uterine cancer, endometrial cancer, melanoma, breast cancer, and pancreatic cancer. Liquid tumors occur in the blood, bone marrow, and lymph nodes and include leukemia (e.g., AML, ALL, CLL, and CML), lymphoma (e.g., Hodgkin lymphoma and non-Hodgkin lymphoma), and myeloma (e.g., multiple myeloma). As used herein, the term cancer cells include mature, progenitor, and cancer stem cells.

Bones are a common location for cancer to infiltrate once leaving the primary tumor location. Once cancer resides in bone, it is frequently a cause of pain to the individual. In addition, if the particular bone affected is a source for production of blood cells in the bone marrow, the individual may develop a variety of blood cell related disorders. Breast and prostate cancer are examples of solid tumors that migrate to bones. Acute myelogenous leukemia (AML) and multiple myeloma (MM) are examples of liquid tumors that migrate to bones. Cancer cells that migrate to bone will typically migrate to the endosteal region of the bone marrow. Once cancer cells have infiltrated into the marrow, the cells become quiescent and are protected from chemotherapy. The compounds of the present disclosure block infiltration of disseminated cancer cells into bone marrow. A variety of individuals may benefit from treatment with the compounds. Examples of such individuals include individuals with a cancer type having a propensity to migrate to bone where the tumor is still localized or the tumor is disseminated but not yet infiltrated bone, or where individuals with such a cancer type are in remission.

The cancer patient population most likely to respond to treatment using the E-selectin antagonist agents (e.g., compounds of Formula (I)) described herein can be identified based on the mechanism of action of E-selectin. That is, patients may be selected that express a highly active E-selectin as determined by the genetic polymorphism for E-selectin of S128R (Alessandro et al., *Int. J. Cancer* 121:528-535, 2007). In addition, patients for treatment by the compounds described herein may also selected based on elevated expression of the E-selectin binding ligands (sialyl Le$^a$ and sialyl Le$^x$) as determined by antibodies directed against cancer-associated antigens CA-19-9 (Zheng et al., *World J. Gastroenterol.* 7:431-434, 2001) and CD65. In addition, antibodies HECA-452 and FH-6 which recognize similar carbohydrate ligands of E-selectin may also be used in a diagnostic assay to select the cancer patient population most likely to respond to this treatment.

The compounds of the present disclosure and pharmaceutical compositions comprising at least one such compound may be useful in methods for treating and/or preventing thrombosis. As described herein methods are provided for inhibiting formation of a thrombus or inhibiting the rate at which a thrombus is formed. These methods may therefore be used for preventing thrombosis (i.e., reducing or decreasing the likelihood of occurrence of a thrombus in a statistically or clinically significant manner).

Thrombus formation may occur in infants, children, teenagers and adults. An individual may have a hereditary predisposition to thrombosis. Thrombosis may be initiated, for example, due to a medical condition (such as cancer or pregnancy), a medical procedure (such as surgery) or an environmental condition (such as prolonged immobility). Other individuals at risk for thrombus formation include those who have previously presented with a thrombus.

The compounds of the present disclosure and pharmaceutical compositions comprising at least one such compound may be useful in methods for treating individuals undergoing thrombosis or who are at risk of a thrombotic event occurring. Such individuals may or may not have a risk of bleeding. In some embodiments, the individual has a risk of bleeding. In some embodiments, the thrombosis is a venous thromboembolism (VTE). VTE causes deep vein thrombosis and pulmonary embolism. Low molecular weight (LMW) heparin is the current mainstay therapy for the prevention and treatment of VTE. In many circumstances, however, the use of LMW heparin is contraindicated. LMW heparin is a known anti-coagulant and delays clotting over four times longer than control bleeding times. Patients undergoing surgery, patients with thrombocytopenia, patients with a history of stroke, and many cancer patients should avoid administration of heparin due to the risk of bleeding. By contract, administration of the E-selectin antagonist compounds of Formula (I) significantly reduces the time to clotting than occurs when LMW heparin is administered, and thus provide a significant improvement in reducing bleeding time compared with LMW heparin. Accordingly, the compounds and pharmaceutical compositions described herein may not only be useful for treating a patient for whom the risk of bleeding is not significant, but also may be useful in when the risk of bleeding is significant and the use of anti-thrombosis agents with anti-coagulant properties (such as LMW heparin) is contraindicated.

The compounds of the present disclosure and pharmaceutical compositions comprising at least one such compound may be administered in combination with at least one additional anti-thrombosis agent. The compounds of the present disclosure and pharmaceutical compositions comprising at least one such compound may function independently from the anti-thrombosis agent or may function in coordination with the at least one anti-thrombosis agent. In addition, the administration of one or more of the compounds or compositions may be in conjunction with one or more other therapies, e.g., for reducing toxicities of therapy. For example, at least one palliative agent to counteract (at least in part) a side effect of therapy may be administered. Agents (chemical or biological) that promote recovery and/or counteract side effects of administration of antibiotics or corticosteroids are examples of such palliative agents. The compounds of the present disclosure and pharmaceutical composition comprising at least one such compound may be administered before, after, or concurrently with administration of at least one additional anti-thrombosis agent or at least one palliative agent to reduce a side effect of therapy. Where administration is concurrent, the combination may be administered from a single container or two (or more) separate containers.

The compounds of the present disclosure and pharmaceutical compositions comprising at least one such compound may be useful in methods for preventing and/or treating mucositis. In some embodiments, at least one compound of Formula (I) or a pharmaceutical composition comprising at least one compound of Formula (I) may be used in methods described herein for decreasing the likelihood of occurrence of mucositis in a subject who is in need thereof by administering the compound or composition to the subject. In some embodiments, the mucositis is chosen from oral mucositis, esophageal mucositis, and gastrointestinal mucositis. In some embodiments, the mucositis is alimentary mucositis.

It is believed that approximately half of all cancer patients undergoing therapy suffer some degree of mucositis. Mucositis is believed to occur, for example, in virtually all patients treated with radiation therapy for head and neck tumors, all patients receiving radiation along the GI tract, and approximately 40% of those subjected to radiation therapy and/or chemotherapy for tumors in other locations (e.g., leukemias or lymphomas). It is also is believed to be highly prevalent in patients treated with high dose chemotherapy and/or irradiation for the purpose of myeloablation, such as in preparation for stem cell or bone marrow transplantation. The compounds of the present disclosure and pharmaceutical compositions comprising at least one such compound may be useful in methods for treating and/or preventing mucositis in a subject afflicted with cancer. In some embodiments, the subject is afflicted with a cancer chosen from head and neck cancer, breast cancer, lung cancer, ovarian cancer, prostate cancer, lymphatic cancer, leukemic cancer, and/or gastrointestinal cancer. In some embodiments, the mucositis is associated with radiation therapy and/or chemotherapy. In some embodiments, the chemotherapy comprises administering a therapeutically effective amount of at least one compound chosen from platinum, cisplatin, carboplatin, oxaliplatin, mechlorethamine, cyclophosphamide, chlorambucil, azathioprine, mercaptopurine, vincristine, vinblastine, vinorelbine, vindesine, etoposide, teniposide, paclitaxel, docetaxel, irinotecan, topotecan, amsacrine, etoposide, etoposide phosphate, teniposide, 5-flurouracil (5-FU), leucovorin, methotrexate, gemcitabine, taxane, leucovorin, mitomycin C, tegafur-uracil, idarubicin, fludarabine, mitoxantrone, ifosfamide and doxorubicin.

In some embodiments, the method further comprises administering a therapeutically effective amount of at least one MMP inhibitor, inflammatory cytokine inhibitor, mast cell inhibitor, NSAID, NO inhibitor, or antimicrobial compound.

In some embodiments, the method further comprises administering a therapeutically effective amount of velafermin and/or palifermin.

The compounds of the present disclosure and pharmaceutical compositions comprising at least one such compound may be useful in methods for mobilizing cells from the bone marrow to the peripheral vasculature and tissues. As discussed herein, in some embodiments, the compounds and compositions are useful for mobilizing hematopoietic cells, including hematopoietic stem cells and hematopoietic progenitor cells. In some embodiments, the compounds act as mobilizing agents of normal blood cell types. In some embodiments, the agents are used in methods for mobilizing mature white blood cells (which may also be called leukocytes herein), such as granulocytes (e.g., neutrophils, eosinophils, basophils), lymphocytes, and monocytes from the bone marrow or other immune cell compartments such as the spleen and liver. Methods are also provided for using the compounds of the present disclosure and pharmaceutical compositions comprising at least one such compound in methods for mobilizing tumor cells from the bone marrow. The tumor cells may be malignant cells (e.g., tumor cells that are metastatic cancer cells, or highly invasive tumor cells) in cancers. These tumor cells may be of hematopoietic origin or may be malignant cells of another origin residing in the bone.

In some embodiments, the methods using the E-selectin antagonists described herein are useful for mobilizing hematopoietic cells, such as hematopoietic stem cells and progenitor cells and leukocytes (including granulocytes such as neutrophils), which are collected (i.e., harvested, obtained) from the subject receiving the E-selectin antagonist and at a later time are administered back into the same subject (autologous donor) or administered to a different subject (allogeneic donor). Hematopoietic stem cell replacement and hematopoietic stem cell transplantation have been successfully used for treating a number of diseases (including cancers) as described herein and in the an. By way of example, stem cell replacement therapy or transplantation follows myeloablation of a subject, such as occurs with administration of high dose chemotherapy and/or radiotherapy. Desirably, an allogeneic donor shares sufficient HLA antigens with the recipient/subject to minimize the risk of host versus graft disease in the recipient (i.e., the subject receiving the hematopoietic stem cell transplant). Obtaining the hematopoietic cells from the donor subject (autologous or allogeneic) is performed by apheresis or leukapheresis. HLA typing of a potential donor and the recipient and apheresis or leukapheresis are methods routinely practiced in the clinical art.

By way of non-limiting example, autologous or allogenic hematopoietic stem cells and progenitors cells may be used for treating a recipient subject who has certain cancers, such as Hodgkin lymphoma, non-Hodgkin lymphoma, or multiple myeloma. Allogeneic hematopoietic stem cells and progenitors cells may be used, for example, for treating a recipient subject who has acute leukemias (e.g., AML, ALL); chronic lymphocytic leukemia (CLL); amegakaryocytosis/congenital thrombocytopenia; aplastic anemia/refractory anemia; familial erythrophagocytic lymphohistiocytosis; myelodysplastic syndrome/other myelodysplastic disorders; osteopetrosis; paroxysmal nocturnal hemoglobinuria; and Wiskott-aldrich syndrome, for example. Exemplary uses for autologous hematopoietic stem cells and progenitors cells include treating a recipient subject who has amyloidosis; germ cell tumors (e.g., testicular cancer); or a solid tumor. Allogeneic hematopoietic stem cell transplants have also been investigated for use in treating solid tumors (see, e.g., Ueno et al., *Blood* 102:3829-36 (2003)).

In some embodiments of the methods described herein, the subject is not a donor of peripheral hematopoietic cells but has a disease, disorder, or condition for which mobilization of hematopoietic cells in the subject will provide clinical benefit. Stated another way, while this clinical situation is similar to autologous hematopoietic cell replacement, the mobilized hematopoeitic cells are not removed and given back to the same subject at a later time as occurs, for example, with a subject who receives myeloablation therapy. Accordingly, methods are provided for mobilizing hematopoietic cells, such as hematopoietic stem cells and progenitor cells and leukocytes (including granulocytes, such as neutrophils), by administering at least once compound of Formula (I). Mobilizing hematopoietic stem cells and progenitor cells may be useful for treating an inflammatory condition or for tissue repair or wound healing. See, e.g., Mimeault et al., *Clin. Pharmacol. Therapeutics* 82:252-64 (2007).

In some embodiments, the methods described herein are useful for mobilizing hematopoietic leukocytes (white blood cells) in a subject, which methods may be used in treating diseases, disorders, and conditions for which an increase in white blood cells, such as neutrophils, eosinophils, lymphocytes, monocytes, basophils, will provide clinical benefit. For example, for cancer patients, the compounds of Formula (I) are beneficial for stimulating neutrophil production to compensate for hematopoietic deficits resulting from chemotherapy or radiation therapy. Other diseases, disorders, and conditions to be treated include infectious diseases and related conditions, such as sepsis. When the subject to whom at least one compound of Formula (I) is administered is a donor, neutrophils may be collected for administration to a recipient subject who has reduced hematopoietic function, reduced immune function, reduced neutrophil count, reduced neutrophil mobilization, severe chronic neutropenia, leucopenia, thrombocytopenia, anemia, and acquired immune deficiency syndrome. Mobilization of mature white blood cells may be useful in subjects to improve or to enhance tissue repair, and to minimize or prevent vascular injury and tissue damage, for example following liver transplantation, myocardial infarction or limb ischemia. See, e.g., Pelus, *Curr. Opin. Hematol.* 15:285-92 (2008); Lemoli et al., *Haematologica* 93:321-24 (2008).

The compound of Formula (I) may be used in combination with one or more other agents that mobilize hematopoietic cells. Such agents include, for example, G-CSF: AMD3100 or other CXCR4 antagonists; GRO-β (CXCL2) and an N-terminal 4-amino truncated form (SB-251353); IL-8SDF-1α peptide analogs, CTCE-0021 and CTCE-0214; and the SDF1 analog, Met-SDF-1β (see. e.g., Pelus, supra and references cited therein). In some embodiments, a compound of Formula (I) may be administered with other mobilizing agents used in the art, which may permit administration of a lower dose of GCSF or AMD3100, for example, than required in the absence of a compound of Formula (I). The appropriate therapeutic regimen for administering a compound of Formula (I) in combination with another mobilizing agent or agents can be readily determined by a person skilled in the clinical art.

The terms, "treat" and "treatment," include medical management of a disease, disorder, and/or condition of a subject (i.e., patient, individual) as would be understood by a person of ordinary skill in the art (see, e.g., Stedman's Medical Dictionary). In general, an appropriate dose and treatment regimen provide at least one of the compounds of the present disclosure in an amount sufficient to provide therapeutic and/or prophylactic benefit. For both therapeutic treatment and prophylactic or preventative measures, therapeutic and/or prophylactic benefit includes, for example, an improved clinical outcome, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated with the disease, condition, and/or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can include prolonging survival when compared to expected survival if a subject were not receiving treatment.

In some embodiments of the methods described herein, the subject is a human. In some embodiments of the methods described herein, the subject is a non-human animal. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of the compounds of the present disclosure in treating and/or preventing diseases, disorders, and/or conditions treatable by inhibiting an activity of E-selectin can readily be determined by a person of ordinary skill in the relevant art. Determining and adjusting an appropriate dosing regimen (e.g., adjusting the amount of compound per dose and/or number of doses and frequency of dosing) can also readily be performed by a person of ordinary skill in the relevant art. One or any combination of diagnostic methods, including physical examination, assessment and monitoring of clinical symptoms, and performance of analytical tests and methods described herein, may be used for monitoring the health status of the subject.

Also provided herein are pharmaceutical compositions comprising at least one compound of Formula (I). In some embodiments, the pharmaceutical composition further comprises at least one additional pharmaceutically acceptable ingredient.

In pharmaceutical dosage forms, any one or more of the compounds of the present disclosure may be administered in the form of a pharmaceutically acceptable derivative, such as a salt, and/or it or they may also be used alone and/or in appropriate association, as well as in combination, with other pharmaceutically active compounds.

An effective amount or therapeutically effective amount refers to an amount of at least one compound of the present disclosure or a pharmaceutical composition comprising at least one such compound that, when administered to a subject, either as a single dose or as part of a series of doses, is effective to produce at least one therapeutic effect. Optimal doses may generally be determined using experimental models and/or clinical trials. Design and execution of pre-clinical and clinical studies for each of the therapeutics (including when administered for prophylactic benefit) described herein are well within the skill of a person of ordinary skill in the relevant art. The optimal dose of a therapeutic may depend upon the body mass, weight, and/or blood volume of the subject. In general, the amount of at least one compound of Formula (I) as described herein, that is present in a dose, may range from about 0.01 µg to about 3000 µg per kg weight of the subject. The minimum dose that is sufficient to provide effective therapy may be used in some embodiments. Subjects may generally be monitored for therapeutic effectiveness using assays suitable for the disease, disorder and/or condition being treated or prevented, which assays will be familiar to those having ordinary skill in the art and are described herein. The level of a compound that is administered to a subject may be monitored by determining the level of the compound (or a metabolite of the compound) in a biological fluid, for example, in the blood, blood fraction (e.g. serum), and/or in the urine, and/or other biological sample from the subject. Any method practiced in the art to detect the compound, or metabolite thereof, may be used to measure the level of the compound during the course of a therapeutic regimen.

The dose of a compound described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease, disorder, and/or condition may be determined according to parameters understood by a person of ordinary skill in the medical art.

Pharmaceutical compositions may be administered in any manner appropriate to the disease, disorder, and/or condition to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively delivers an effective amount of the compound. Non-limiting examples of suitable administrative routes include topical, oral, nasal, intrathecal, enteral, buccal, sublingual, transdermal, rectal, vaginal, intraocular, subconjunctival, sublingual, and parenteral administration, including subcutaneous, intravenous, intramuscular, intrasternal, intracavernous, intrameatal, and intraurethral injection and/or infusion.

The pharmaceutical compositions described herein may, for example, be sterile aqueous or sterile non-aqueous solutions, suspensions, or emulsions, and may additionally comprise at least one pharmaceutically acceptable excipient (i.e., a non-toxic material that does not interfere with the activity of the active ingredient). Such compositions may, for example, be in the form of a solid, liquid, or gas (aerosol). Alternatively, the compositions described herein may, for example, be formulated as a lyophilizate, or compounds described herein may be encapsulated within liposomes using technology known in the art. The pharmaceutical compositions may further comprise at least one additional pharmaceutically acceptable ingredient, which may be biologically active or inactive. Non-limiting examples of such ingredients include buffers (e.g., neutral buffered saline or phosphate buffered saline), carbohydrates (e.g., glucose, mannose, sucrose or dextrans), mannitol, proteins, polypeptides, amino acids (e.g., glycine), antioxidants, chelating agents (e.g., EDTA and glutathione), stabilizers, dyes, flavoring agents, suspending agents, and preservatives.

Any suitable excipient or carrier known to those of ordinary skill in the art for use in compositions may be employed in the compositions described herein. Excipients for therapeutic use are well known, and are described, for example, in *Remington: The Science and Practice of Pharmacy* (Gennaro, 21$^{st}$ Ed. Mack Pub. Co., Easton, Pa. (2005)). In general, the type of excipient may be selected based on the mode of administration, as well as the chemical composition of the active ingredient(s). Compositions may be formulated for the particular mode of administration. For parenteral administration, pharmaceutical compositions may further comprise water, saline, alcohols, fats, waxes, and buffers. For oral administration, pharmaceutical compositions may further comprise at least one component chosen, for example, from any of the aforementioned ingredients, excipients and carriers, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose, and magnesium carbonate.

The pharmaceutical compositions (e.g., for oral administration or delivery by injection) may be in the form of a liquid. A liquid composition may include, for example, at least one the following: a sterile diluent such as water for injection, saline solution, including for example physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. In some embodiments, the pharmaceutical composition comprises physiological saline. In some embodiments, the pharmaceutical composition is an injectable composition, and in some embodiments, the injectable composition is sterile.

For oral formulations, at least one of the compounds of the present disclosure can be used alone or in combination with at least one additive appropriate to make tablets, powders, granules and/or capsules, for example, those chosen from conventional additives, disintegrators, lubricants, diluents, buffering agents, moistening agents, preservatives, coloring agents, and flavoring agents. The pharmaceutical compositions may be formulated to include at least one buffering agent, which may provide for protection of the active ingredient from low pH of the gastric environment and/or an enteric coating. A pharmaceutical composition may be formulated for oral delivery with at least one flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable; the formulation may provide a relatively constant level of active component release. The amount of active therapeutic contained within a sustained release formulation depends upon the site of implantation, the rate and expected duration of release, and the nature of the condition to be treated or prevented.

The pharmaceutical compositions described herein can be formulated as suppositories by mixing with a variety of bases such as emulsifying bases or water-soluble bases. The pharmaceutical compositions may be prepared as aerosol formulations to be administered via inhalation. The pharmaceutical compositions may be formulated into pressurized acceptable propellants such as dichlorodifluoromethane, propane, nitrogen and the like.

The compounds of the present disclosure and pharmaceutical compositions comprising these compounds may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press: Percutaneous Penetration Enhancers, eds. Smith et al. (CRC Press, 1995); Lennerãs et al., *J. Pharm. Pharmacol.* 54:499-508 (2002); Karande et al., *Pharm. Rev.* 19:655-60 (2002); Vaddi et al., *Int. J. Pharm.* 91:1639-51 (2002); Ventura et al., *J. Drug Target* 9:379-93 (2001); Shokri et al., *Int. J. Pharm.* 228 (1-2):99-107 (2001); Suzuki et al., *Biol. Pharm. Bull.* 24:698-700 (2001); Alberti et al., *J. Control Release* 71:319-27 (2001); Goldstein et al., *Urology* 57:301-5 (2001); Kiijavainen et al., *Eur. J. Pharm. Sci.* 10:97-102 (2000); and Tenjarla et al., *Int. J. Pharm.* 192: 147-58 (1999).

Kits comprising unit doses of at least one compound of the present disclosure, for example in oral or injectable doses, are provided. Such kits may include a container comprising the unit dose, an informational package insert describing the use and attendant benefits of the therapeutic in treating the pathological condition of interest, and/or optionally an appliance or device for delivery of the at least one compound of Formula (I) and/or pharmaceutical composition comprising the same.

EXAMPLES

Example 1: Compound 11

Compound 2:

A solution of 1-[(1-oxo-2-propynyl)oxy]-2,5-pyrrolidinedione (propargylic acid NHS ester) (57 mg, 0.34 mmole) in anhydrous DMF (1 mL) was added dropwise over 15 minutes to a slurry of compound 1 (0.19 g, 0.26 mmole) (preparation described in WO 2013096926) and DIPEA (0.1 mL) in anhydrous DMF (3 mL) at room temperature. The resulting solution was stirred for 1.5 hrs. The reaction mixture was concentrated under reduced pressure. The residue was separated by Combi-flash [EtOAc/(MeOH/water, 6/1, v/v), 9/1-3/7, v/v] to afford the desired compound as a light brown solid (0.14 g, 69%). MS: Calculated for $C_{37}H_{59}N_3O_{15}$=785.3, Found ES– positive m/z=808.3 (M+Na$^+$), ES-negative m/z=784.4 (M−1).

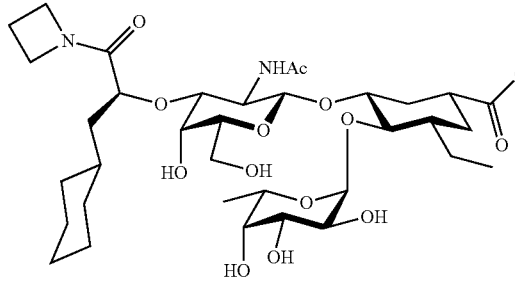

4

Compound 4:

To a solution of compound 3 (preparation described in WO 2013096926) (2.5 g, 3.54 mmole) and DIPEA (1.2 mL, 7.08 mmole) in anhydrous DMF (15 mL) was added TBTU (1.7 g, 5.31 mmole) at 0° C. and the solution was stirred for 20 min. Azetidine (0.85 mL, 35.4 mmole) was added and the resulting solution was stirred for 1 hr while the temperature was gradually increased to room temperature. After the reaction was completed, the solution was concentrated under reduced pressure. The reaction mixture was separated by Combi-flash (EtOAc/MeOH, 4/1-2/3, v/v) to give compound 4 (1.17 g, 1.57 mmole, 44%) and lactone side product compound 5 (0.88 g, 1.28 mmole, 36%).

Compound 4:

Compound 5 (0.88 g, 1.28 mmol) was dissolved in anhydrous DMF (5 mL). Azetidine (0.5 mL) was added, and then the resulting solution was stirred for 3 hrs at 50° C. The solution was concentrated and dried under high vacuum to give compound 4 (0.93 g, 1.25 mmole, 98%).

$^1$H NMR (400 MHz, Deuterium Oxide) δ 4.92 (d, J=4.0 Hz, 1H), 4.79 (q, J=7.3, 6.8 Hz, 1H), 4.43 (broad d, J=8.3 Hz, 1H), 4.24 (q, J=8.6 Hz, 1H), 4.15 (q, J=8.5 Hz, 1H), 4.01 (d, J=9.3 Hz, 1H), 3.99-3.80 (m, 3H), 3.76 (dd, J=10.6, 3.2 Hz, 1H), 3.73-3.51 (m, 8H), 3.42 (m, J=7.7, 4.4 Hz, 2H), 3.21 (t, J=9.7 Hz, 1H), 2.39 (broad t, J=12.7 Hz, 1H), 2.32-2.09 (m, 3H), 1.95 (s, 3H), 1.95 (m, 1H) 1.77 (m, 2H), 1.69-1.35 (m, 7H), 1.35-0.93 (m, 10H), 0.93-0.58 (m, 6H). MS: Calculated for $C_{36}H_{60}N_2O_{14}$=785.3, Found ES– positive m/z=767.3 (M+Na$^+$), ES-negative m/z=743.4 (M−1).

6

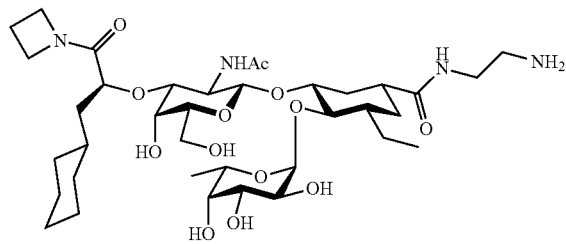

Compound 6:

A solution of compound 4 (0.93 g, 1.25 mmole) in ethylene diamine (10 mL) was stirred overnight at 60° C. The solution was concentrated under reduced pressure and the residue was directly purified by silica gel column chromatography (EtOAc/MeOH, 1/2, v/v) to give compound 6 as a light yellow gel (0.9 g, 1.16 mmole, 91%). MS: Calculated for $C_{37}H_{64}N_4O_{13}$=772.4, Found ES– positive m/z=773.4 (M+H$^+$).

7

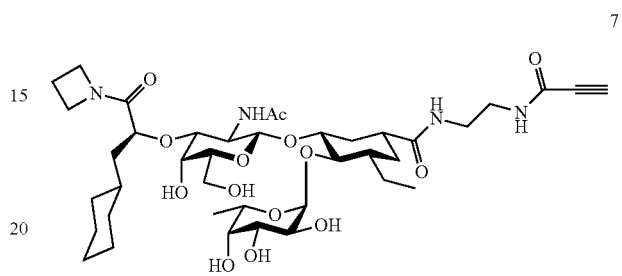

Compound 7:

A solution of compound 6 (0.22 g, 0.28 mmole) and 3 drops of DIPEA in anhydrous DMF (3 mL) was cooled to 0° C. Propargylic acid NHS ester (57 mg, 0.34 mmole) was slowly added. The resulting solution was stirred for 1 hr. The solution was concentrated under reduced pressure and the residue was directly purified by Combi-flash [EtOAc/(MeOH/water, 6/1, v/v), 1/9-2/8, v/v]. The product lyophilized to give compound 7 as an off-white solid (0.12 g, 0.15 mmole, 54%). MS: Calculated for $C_{40}H_{64}N_4O_{13}$=824.4, Found ES– positive m/z=847.3 (M+Na$^+$).

Compound 9:

To a slurry solution of compound 1 (0.12 g, 0.16 mmole) and DIPEA (0.1 mL) in anhydrous DMF (1 mL) was added a solution of azidoacetic acid-NHS ester (compound 8) (39 mg, 0.2 mmole) in anhydrous DMF (1 mL) dropwise over a 10 minute period at room temperature. The resulting solution was stirred for 3 hrs. The reaction mixture was concentrated under reduced pressure and the residue was purified by Combi-flash eluting with [EtOAc/(MeOH/water, 6/1, v/v), 9/1-2/8, v/v]. The product was collected then lyophilized to give compound 9 as a white solid (0.11 g, 0.13 mmole, 81%). MS: Calculated for $C_{37}H_{59}N_3O_{15}$=816.4, Found ES– positive m/z=838.7 (M+Na$^+$), ES– negative m/z=814.7 (M−H).

Compound 11:

A solution of PEG-17 Bis-NHS ester (compound 10) (0.2 g, 0.19 mmol) in DMSO (2 mL) was added to a solution of compound 1 (0.4 g, 0.56 mmole) and DIPEA (0.2 mL) in anhydrous DMSO (2 mL) dropwise over a 5 minute period at room temperature. The resulting solution was stirred overnight. The solution was dialyzed against distilled water for 3 days with dialysis tube MWCO 1000 while distilled water was changed every 12 hours. The solution in the tube was lyophilized overnight to give compound 11 as a white solid (0.32 g, 0.14 mmole, 77%).

11

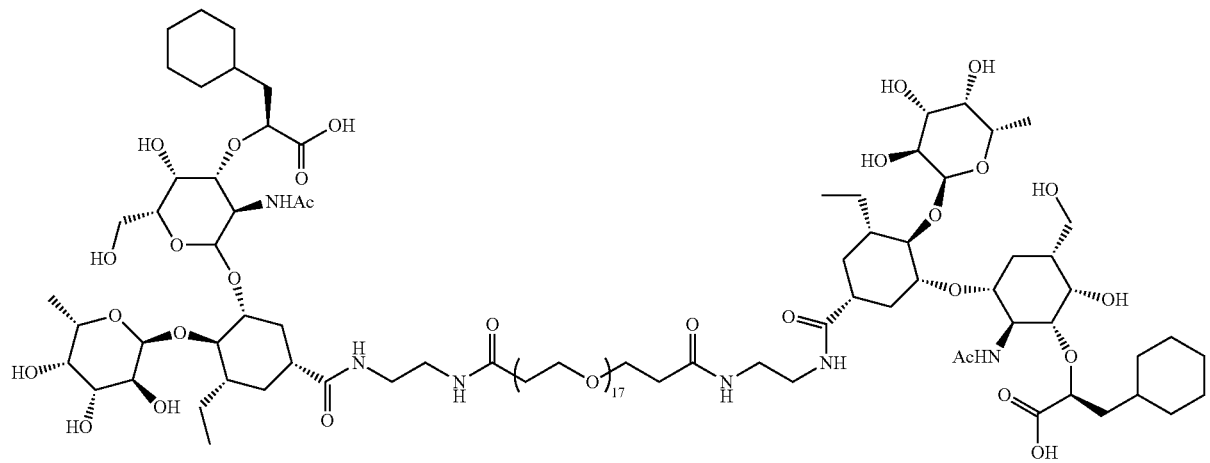

¹H NMR (400 MHz, Deuterium Oxide) δ 5.02 (d, J=3.9 Hz, 2H), 4.90 (q, J=6.7 Hz, 2H), 4.52 (broad d, J=8.4 Hz, 2H), 3.97 (broad t, 2H), 3.86-3.74 (m, 16H), 3.73-3.59 (m, 62H), 3.56 (t, J=5.8 Hz 2H), 3.44 (m, 2H), 3.34-3.26 (m, 10H), 2.50 (t, J=6.1 Hz 4H), 2.31 (broad t, 2H), 2.12 (m, 2H), 2.04 (s, 6H), 1.90-1.79 (m, 4H), 1.78-1.38 (m, 14H), 1.37-1.26 (m, 14H), 1.25-1.08 (m, 14H), 0.98-0.79 (m, 10H). MS: Calculated for $C_{106}H_{188}N_6O_{47}$=2297.2, Found MALDI-TOF m/z=2321, (M+Na⁺).

Example 2: Compound 12

Compound 12:

Prepared in an analogous manner from compound 1 and PEG-25 bis-NHS ester.

1H NMR (400 MHz, Deuterium Oxide) δ 5.03 (d, J=3.9 Hz, 2H), 4.91 (q, J=6.9 Hz, 2H), 4.53 (broad d, J=8.4 Hz, 2H), 3.98 (broad t, J=8.8 Hz 2H), 3.92-3.86 (m, 6H), 3.81-3.79 (m, 2H), 3.78-3.74 (m, 4H), 3.72-3.66 (m, 100H), 3.56 (t, J=5.7 Hz 2H), 3.52-3.40 (m, 2H), 3.37-3.25 (m, 10H), 2.53-2.49 (t, J=6.1 Hz 4H), 2.31 (m, 2H), 2.16-2.13 (m, 2H), 2.05 (s, 6H), 1.86-1.84 (m, 4H), 1.76-1.65 (m, 4H), 1.63-1.44 (m, 10H), 1.41-1.29 (m, 14H), 1.27-1.12 (m, 14H), 0.94-0.89 (m, 4H), 0.87-0.84 (t, J=7.2 Hz, 6H). MS: Calculated for $C_{122}H_{220}N_6O_{55}$=2649; Found MALDI-TOF m/z=2672 (M+Na⁺).

Example 3: Compound 13

Compound 13:

Prepared in an analogous manner from compound 1 and PEG-21 bis-NHS ester.

12

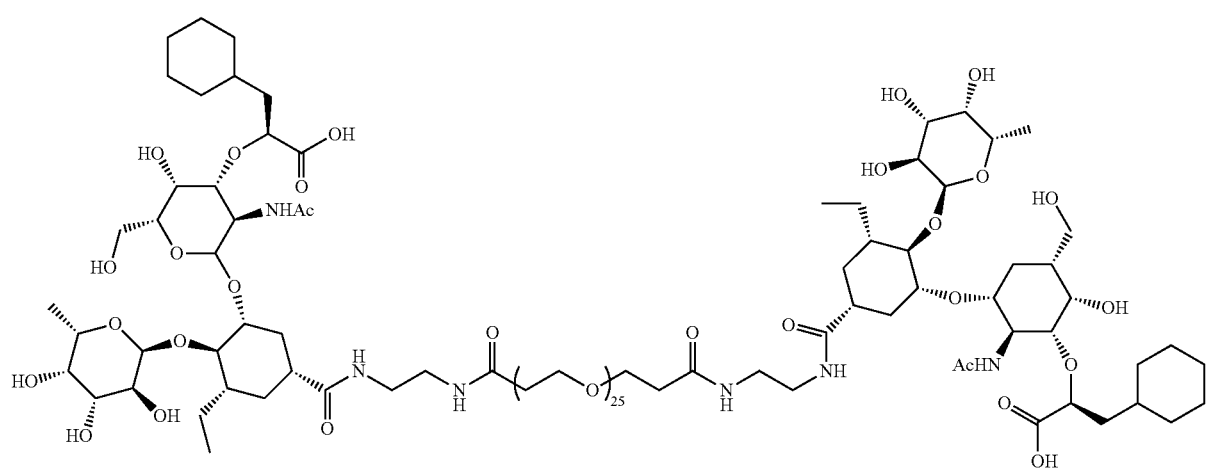

13

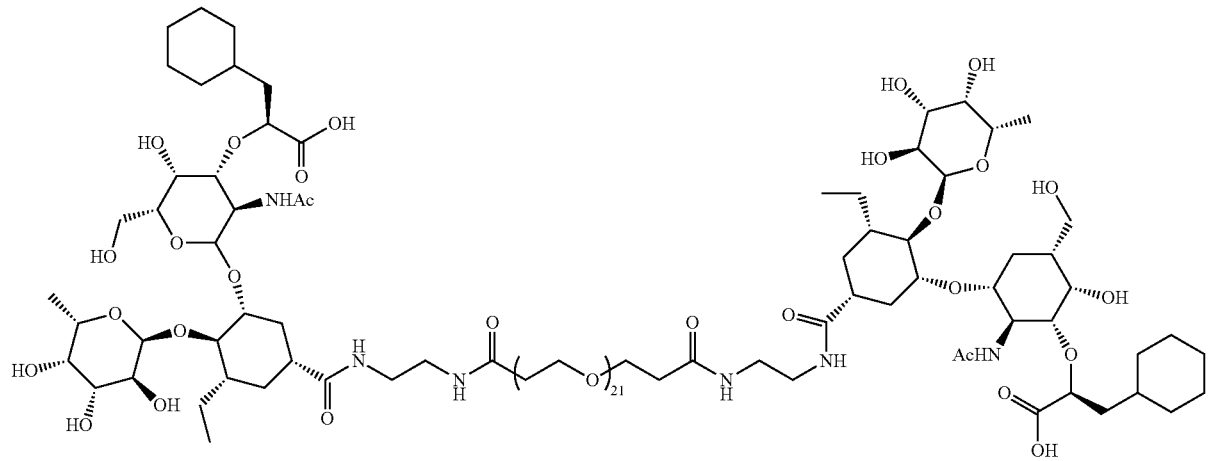

¹H NMR (400 MHz, Deuterium Oxide) δ 5.03 (d, J=3.9 Hz, 2H), 4.91 (q, J=6.7 Hz, 2H), 4.56 (broad d, J=8.4 Hz, 2H), 3.98 (broad t, 2H), 3.91-3.86 (m, 6H), 3.81-3.79 (m, 4H), 3.78-3.74 (m, 4H), 3.72 (m, 4H), 3.71-3.66 (m, 78H), 3.56 (t, J=5.8 Hz 2H), 3.47 (m, 2H), 3.35-3.27 (m, 10H), 2.53-2.49 (t, J=6.1 Hz 4H), 2.31 (broad t, 2H), 2.16-2.13 (m, 2H), 2.05 (s, 6H), 1.86-1.84 (m, 4H), 1.76-1.65 (m, 4H), 1.63-1.47 (m, 8H), 1.38-1.29 (m, 14H), 1.27-1.22 (m, 8H), 1.18-1.12 (m, 6H), 0.94-0.89 (m, 4H), 0.87-0.84 (t, J=7.2 Hz, 6H). MS: Calculated for $C_{114}H_{204}N_6O_{51}$=2473.3; Found MALDI-TOF m/z=2496 (M+Na⁺).

¹H NMR (400 MHz, Deuterium Oxide) δ 5.06 (d, J=4.1 Hz, 2H), 4.94 (q, J=6.6 Hz, 2H), 4.56 (broad d, J=8.4 Hz, 2H), 4.02 (Broad s, 2H), 3.94-3.90 (m, 6H), 3.84 (m, 2H), 3.80 (m, 4H), 3.76 (m, 6H), 3.72-3.70 (m, 50H), 3.59 (broad t, 2H), 3.49 (m, 2H), 3.38-3.33 (m, 10H), 2.54 (t, J=6.1 Hz 4H), 2.34 (broad t, 2H), 2.19-2.17 (m, 2H), 2.09 (s, 6H), 1.90-1.87 (m, 4H), 1.79-1.71 (m, 4H), 1.69-1.58 (m, 8H), 1.56 (m, 2H), 1.51 (m, 4H), 1.43-1.36 (m, 4H), 1.35-1.33 (m, 6H), 1.27-1.17 (m, 8H), 1.00-0.91 (m, 4H), 0.90-0.88 (t, J=7.4 Hz, 6H). MS: Calculated for $C_{98}H_{172}N_6O_{43}$=2121.1; Found MALDI-TOF m/z=2144 (M+Na⁺).

Example 4: Compound 14

Compound 14:
Prepared in an analogous manner from compound 1 and PEG-13 bis-NHS ester.

Example 5: Compound 15

Compound 15:
Prepared in an analogous manner from compound 1 and PEG-10 bis-NHS ester.

14

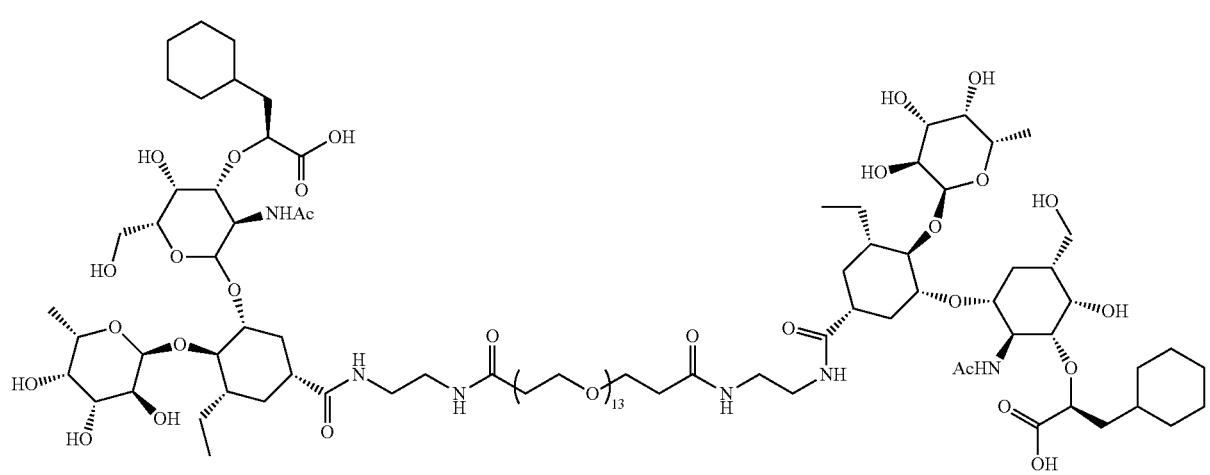

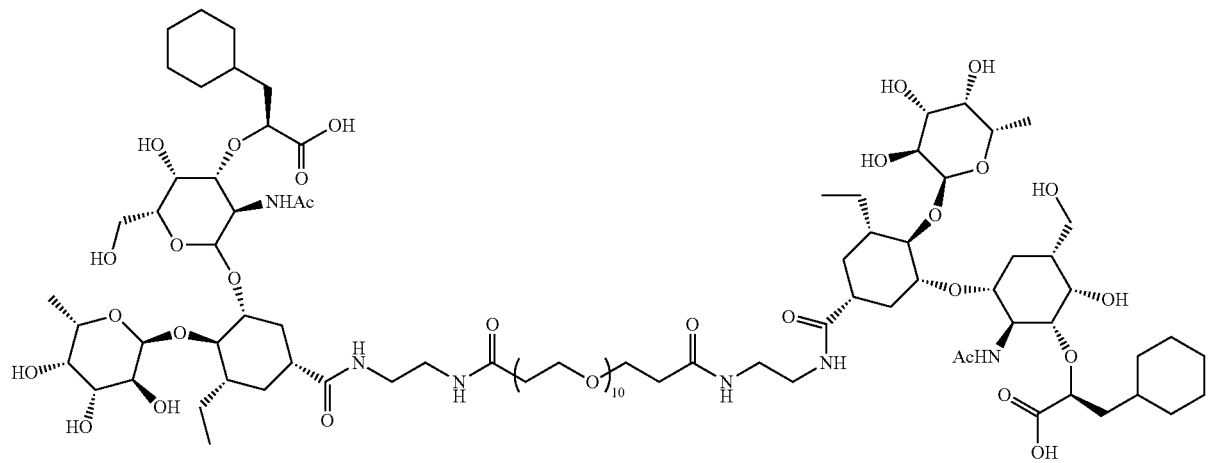

¹H NMR (400 MHz, Deuterium Oxide) δ 5.06 (d, J=4.0 Hz, 2H), 4.94 (q, J=6.7 Hz, 2H), 4.56 (broad d, J=8.4 Hz, 2H), 4.02 (broad s, 2H), 3.95-3.90 (m, 6H), 3.84 (m, 2H), 3.79 (m, 4H), 3.75 (m, 6H), 3.72 (m, 30H), 3.70 (broad s, 10H), 3.58 (broad t, J=5.6 Hz 2H), 3.51 (m, 2H), 3.38-3.35 (m, 6H), 3.34-3.31 (m, 4H), 2.54 (t, 4H), 2.34 (broad t, 2H), 2.19-2.17 (m, 2H), 2.09 (s, 6H), 1.90-1.87 (m, 4H), 1.79-1.66 (m, 4H), 1.63-1.55 (m, 8H), 1.53-1.49 (m, 2H), 1.41 (q, J=12.0 Hz, 4H), 1.37-1.32 (m, 8H), 1.27 (broad d, J=6.6 Hz, 6H), 1.24-1.17 (m, 8H), 0.98-0.93 (m, 4H), 0.90-0.88 (t, J=7.4 Hz, 6H). MS: Calculated for $C_{92}H_{180}N_6O_{40}$=1989.0; Found MALDI-TOF m/z=2013 (M+Na⁺).

Example 6: Compound 16

Compound 16:
Prepared in an analogous manner from compound 1 and PEG-9 bis-NHS ester.

¹H NMR (400 MHz, Deuterium Oxide) δ 7.82 (m, 2H), 6.83 (d, J=8.9 Hz, 2H), 4.91 (d, J=4.0 Hz, 2H), 4.79 (q, J=6.7 Hz, 2H), 4.39 (d, J=8.5 Hz, 2H), 3.96-3.83 (m, 4H), 3.81 (d, J=3.0 Hz, 2H), 3.79-3.71 (m, 4H), 3.71-3.47 (m, 34H), 3.47-3.31 (m, 4H), 3.31-3.07 (m, 10H), 2.39 (t, J=6.1 Hz, 4H), 2.19 (t, J=12.5 Hz, 2H), 2.03 (broad d, J=6.8 Hz, 2H), 1.93 (s, 6H), 1.73 (broad d, J=12.5 Hz, 4H), 1.68-1.34 (m, 16H), 1.34-1.15 (m, 4H), 1.15-0.91 (m, 14H), 0.91-0.65 (m, 10H). MS: Calculated for $C_{84}H_{144}N_6O_{36}$=1812.9; Found ES-Negative m/z:=1812.8 (M−1).

Example 7: Compound 17

Compound 17:
Prepared in an analogous manner from compound 1 and PEG-4 bis-NHS ester.

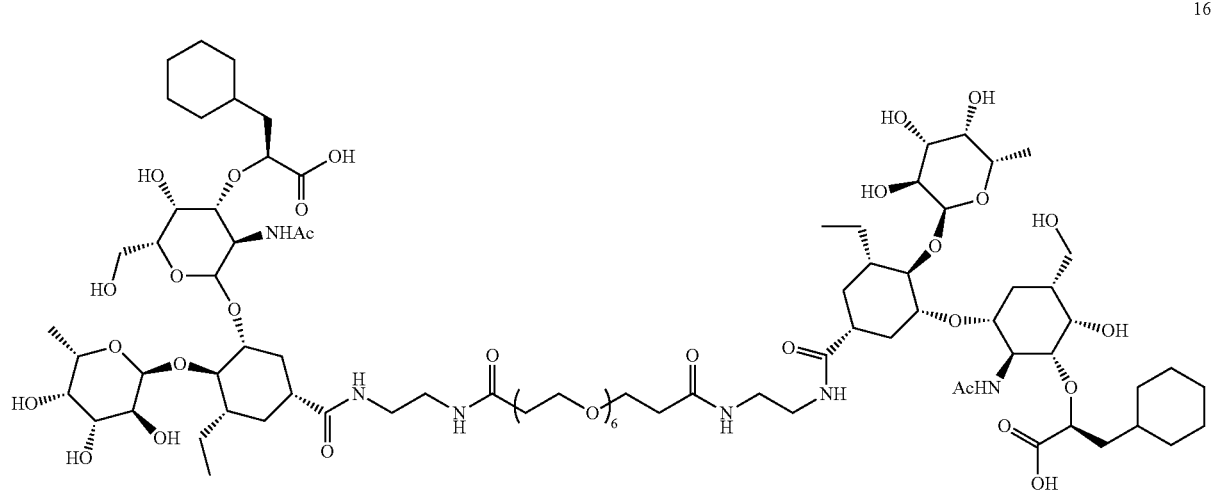

17

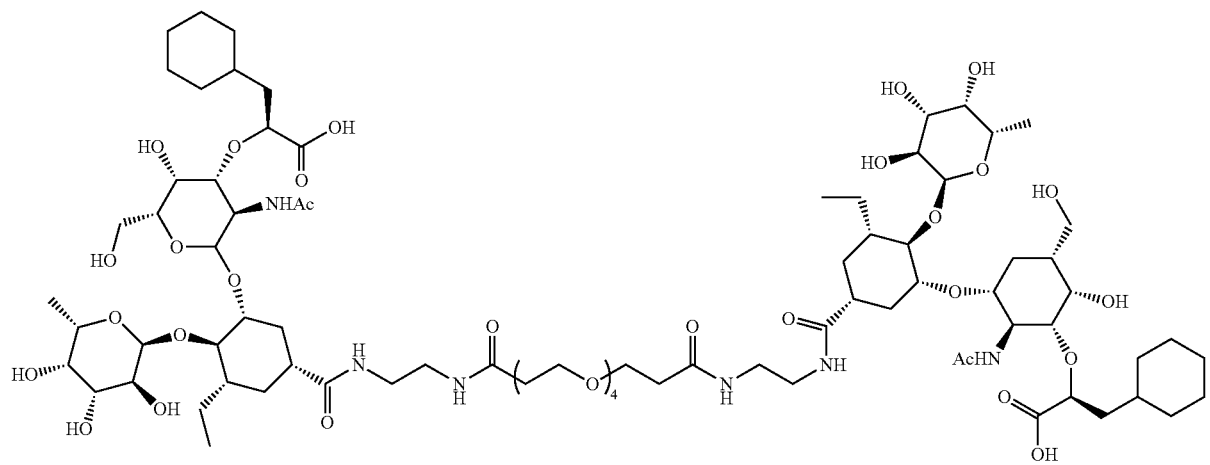

¹H NMR (400 MHz, Deuterium Oxide) δ 4.91 (d, J 4.0 Hz, 2H), 4.80 (q, J=6.7 Hz, 2H), 4.40 (broad d, J=8.4 Hz, 2H), 4.00-3.84 (m, 4H), 3.82 (d, J=3.0 Hz, 2H), 3.76 (dd, J=10.6, 3.2 Hz, 2H), 3.72-3.57 (m 12H), 3.55 (m, J=3.1 Hz, 14H), 3.42 (m, J=7.5, 4.5 Hz, 4H), 3.30-3.09 (m, 10H), 2.39 (t, J=6.1 Hz, 4H), 2.20 (broad t, J=12.6 Hz, 2H), 2.03 (m, J=6.5 Hz, 2H), 1.94 (s, 6H), 1.73 (broad d, J=12.5 Hz, 4H), 1.67-1.33 (m, 16H), 1.33-0.93 (m, 20H), 0.89-0.67 (m, 10H). MS: Calculated for $C_{80}H_{136}N_6O_{34}$=1724.9; Found ES-Negative m/z=1724.8 (M−1).

Example 8: Compound 18

Compound 18:
Prepared in an analogous manner from compound 1 and PEG-2 bis-NHS ester.

¹H NMR (400 MHz, Deuterium Oxide) δ 4.91 (d, J=4.0 Hz, 2H), 4.79 (q, J=6.7 Hz, 2H), 4.40 (broad d, J=8.5 Hz, 2H), 4.01-3.84 (m, 4H), 3.81 (d, J=3.0 Hz, 2H), 3.76 (dd, J=10.5, 3.2 Hz, 2H), 3.72-3.55 (m, 14H), 3.52 (s, 4H), 3.42 (m, J=6.0 Hz, 4H), 3.28-3.06 (m, 10H), 2.38 (1, J=6.1 Hz, 4H), 2.19 (broad t, J=12.7 Hz, 2H), 2.03 (m, J=6.5 Hz, 2H), 1.94 (s, 6H), 1.73 (m, J=12.5 Hz, 4H), 1.67-1.33 (m, 16H), 1.33-0.92 (m, 20H), 0.92-0.60 (m, 10H). MS: Calculated for $C_{76}H_{128}N_6O_{32}$=1636.8; Found ES-Negative m/z=1636.7 (M−1).

Example 9: Compound 19

Compound 19:
Prepared in an analogous manner from compound 1 and succinic acid bis-NHS ester.

18

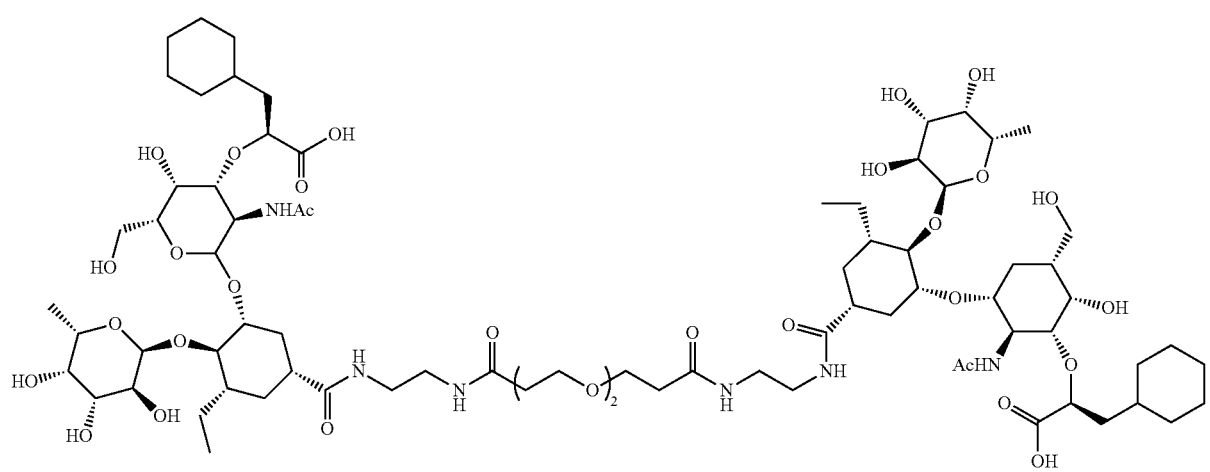

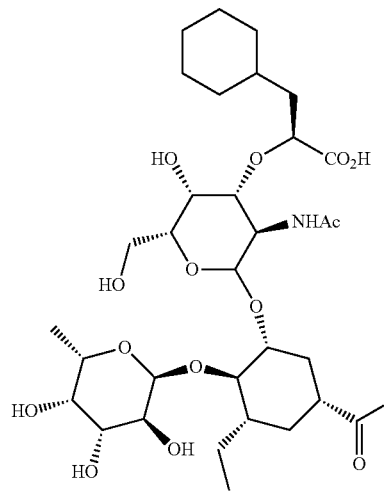

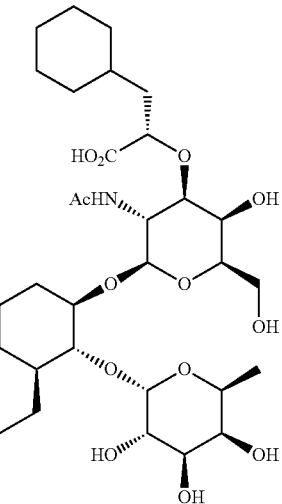

¹H NMR (400 MHz, Deuterium Oxide) δ 4.91 (d, J=4.0 Hz, 2H), 4.80 (q, J=6.8 Hz, 2H), 4.41 (broad d, J=8.6 Hz, 2H), 3.88 (m, 2H), 3.81-3.74 (m, 6H), 3.73-3.65 (m, 6H), 3.64-3.56 (m, 6H), 3.45 (broad t, 2H), 3.33 (broad d, J=9.9 Hz, 2H), 3.20 (m, J=11.4, 10.3 Hz, 10H), 2.39 (s, 4H), 2.19 (m, J=12.8 Hz, 2H), 2.02 (m, 2H), 1.94 (s, 6H), 1.84-1.69 (m, 4H), 1.51 (m, J=65.3, 30.1, 14.0 Hz, 14H), 1.26 (q, J=12.5 Hz, 6H), 1.09 (m, J=28.4, 8.7 Hz, 14H), 0.94-0.64 (m, 10H). MS: Calculated for $C_{72}H_{120}N_6O_{30}$=1548.8; Found ES-Negative m/z=1548.67 (M−1).

Example 10: Compound 20

Compound 20: A solution of compound 15 (12.4 mg, 6.23 μmole) and DIPEA (11 μL, 62.3 μmole) in anhydrous DMF (0.2 mL) was cooled to 0° C. and TBTU (12 mg, 37.8 μmole) was added. The resulting solution was stirred for 10 minute. Azetidine (8.4 μL, 124.6 μmole) was added and the resulting solution was stirred for 1 h at room temperature. The reaction mixture was concentrated under high vacuum and the residue was purified by HPLC. The product portion was collected and evaporated, re-dissolved in minimum amount of distilled water then lyophilized overnight to give compound 20 as a white solid (6.3 mg, 49%).

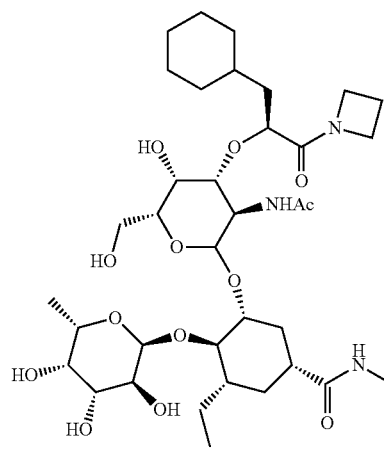

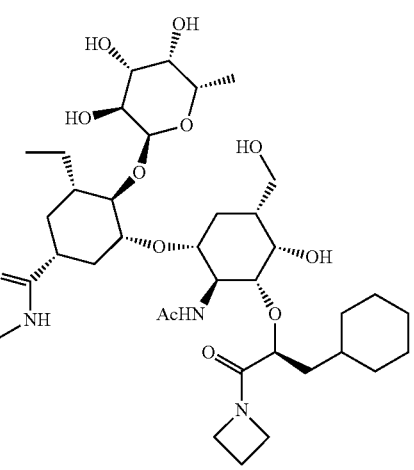

¹H NMR (400 MHz, Deuterium Oxide) δ 8.32 (s, 2H), 8.23 (d, J=9.5 Hz, 2H), 4.92 (broad d, 2H), 4.79 (q, J=6.7 Hz, 2H), 4.42 (m, 2H), 4.23 (q, J=7.8 Hz, 2H), 4.14 (q, J=7.8 Hz, 2H), 4.06-3.79 (m, 6H), 3.76 (dd, J=10.5 Hz, 2H), 3.66 (m, J=15.1, 13.8, 8.6 Hz, 8H), 3.57 (m, J=8.0 Hz, 46H), 3.41 (m, 41H), 3.21 (m, J=14.4, 12.2 Hz, 10H), 2.45-2.34 (t, 4H), 2.22 (m, J=12.9 Hz, 6H), 2.02 (m, 2H), 1.94 (s, 6H), 1.74 (broad d, J=12.2 Hz, 4H), 1.68-1.33 (m, 14H), 1.26 (m, J=11.1 Hz, 6H), 1.15-0.95 (m, 16H), 0.95-0.64 (m, 10H). MS: Calculated for $C_{98}H_{170}N_8O_{38}$=2067; Found ES-Negative m/z=1033.6 ((M−1)/2).

The following compounds were prepared in an analogous manner:

Example 11: Compound 21

Compound 21:

Prepared in an analogous manner from compound 15 and dimethylamine.

21

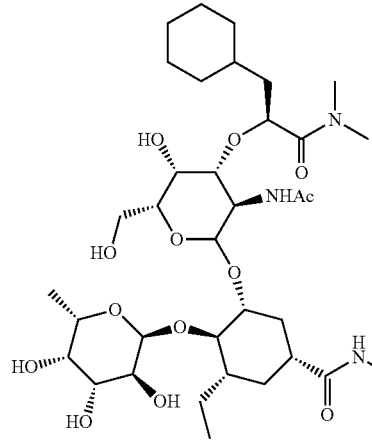
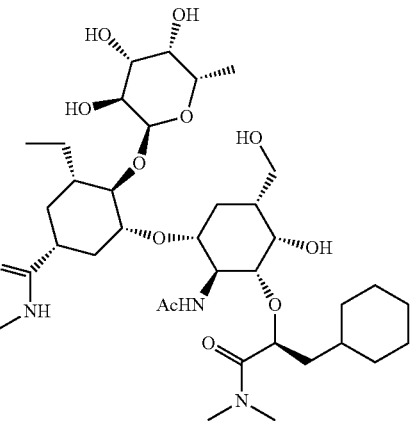

¹H NMR (400 MHz, Deuterium Oxide) δ 8.33 (s, 6H), 4.93 (broad s, 2H), 4.80 (q, 2H), 4.42 (broad d, J=9.9 Hz, 4H), 3.89 (broad s, 2H), 3.77 (dd, J=10.9 Hz, 2H), 3.74-3.49 (m, 54H), 3.42 (Broad s, 4H), 3.21 (m, J=14.5, 12.4 Hz, 10H), 2.95 (s, 6H), 2.83 (s, 6H), 2.41 (broad t, 4H), 2.21 (broad t, 2H), 2.05 (m, 2H), 1.97 (s, 6H), 1.73 (m, 6H), 1.67-1.36 (m, 12H), 1.36-0.96 (m, 20H), 0.80 (d, J=38.2 Hz, 1 OH). MS: Calculated for $C_{96}H_{170}N_8O_{38}$=2043.0; Found ES-Negative m/z=1066.8 ((M+formic acid−1)/2).

Example 12: Compound 22

Compound 22:

Prepared in an analogous manner from compound 12 and azetidine.

22

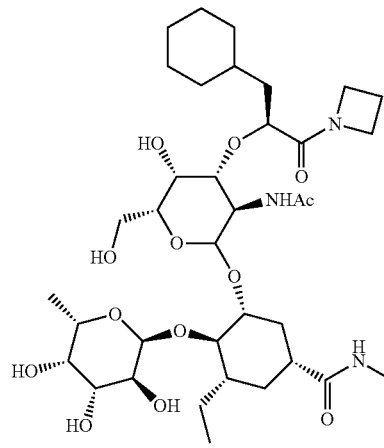
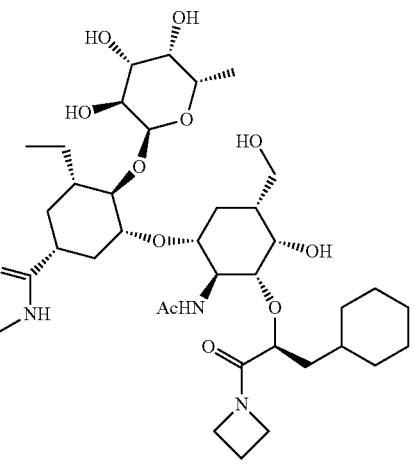

$^1$H NMR (400 MHz, Deuterium Oxide) δ 8.33 (s, 2H), 4.92 (d, J=4.0 Hz, 2H), 4.79 (q, J=6.6 Hz, 2H), 4.42 (Broad d, J=8.6 Hz, 2H), 4.24 (q, J=8.7 Hz, 2H), 4.15 (q, J=8.6 Hz, 2H), 3.96 (m, J=25.2, 9.1 Hz, 4H), 3.86 (broad s, 2H), 3.77 (dd, J=10.6, 3.1 Hz, 2H), 3.73-3.47 (m, 114H), 3.42 (m, J=7.8, 4.6 Hz, 4H), 3.20 (m, J=22.8, 8.6 Hz, 10H), 2.41 (t, J=6.1 Hz, 4H), 2.35-2.13 (m, 6H), 2.04 (m, J=10.8 Hz, 2H), 1.95 (s, 6H), 1.75 (broad d, J=12.7 Hz, 4H), 1.68-1.35 (m, 16H), 1.35-0.94 (m, 20H), 0.94-0.67 (m, 10H). MS: Calculated for $C_{128}H_{230}N_8O_{53}$=2727.5; Found ES-Negative m/z=1409.3 ((M+formic acid−1)/2).

Example 13: Compound 23

Compound 23:
Prepared in an analogous manner from compound 17 and azetidine.

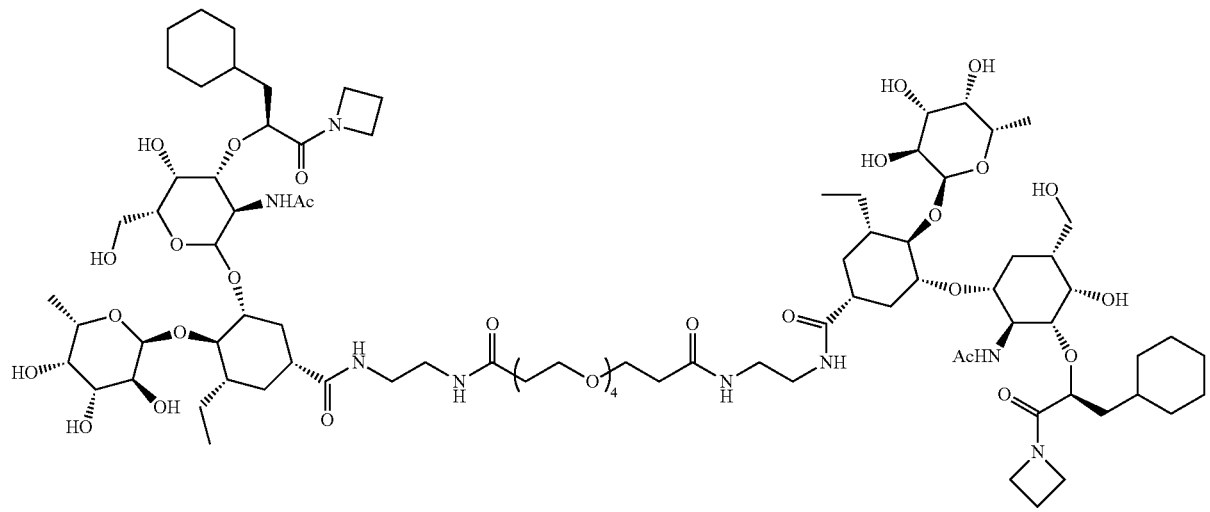

23

$^1$H NMR (400 MHz, Deuterium Oxide) δ 8.28 (broad s, 2H), 8.23 (broad d, 2H), 4.91 (d, J=4.0 Hz, 2H), 4.78 (q, J=7.4, 6.9 Hz, 2H), 4.41 (broad d, J=8.5 Hz, 2H), 4.23 (q, J=8.7 Hz, 2H), 4.14 (q, J=8.8 Hz, 2H), 4.04-3.80 ((m, 8H), 3.76 (dd, J=10.6, 3.2 Hz, 2H), 3.72-3.58 (m, 16H), 3.55 (d, J=3.0 Hz, 12H), 3.41 (m, J=7.7, 4.4 Hz, 4H), 3.30-3.10 (m, 10H), 2.40 (t, J=6.1 Hz, 4H), 2.34-2.12 (m, 6H), 2.03 (m, J=7.1 Hz, 2H), 1.94 (s, 6H), 1.74 (broad d, J=12.7 Hz, 4H), 1.67-1.33 (m, 14H), 1.33-1.16 (m, 8H), 1.16-0.95 (m, 14H), 0.95-0.64 (m, 10H). MS: Calculated for $C_{86}H_{146}N_8O_{32}$=1803.0; Found ES-Positive m/z=1826.8 (M+Na$^+$).

Example 14: Compound 24

Compound 24:
Prepared in an analogous manner from compound 16 and azetidine.

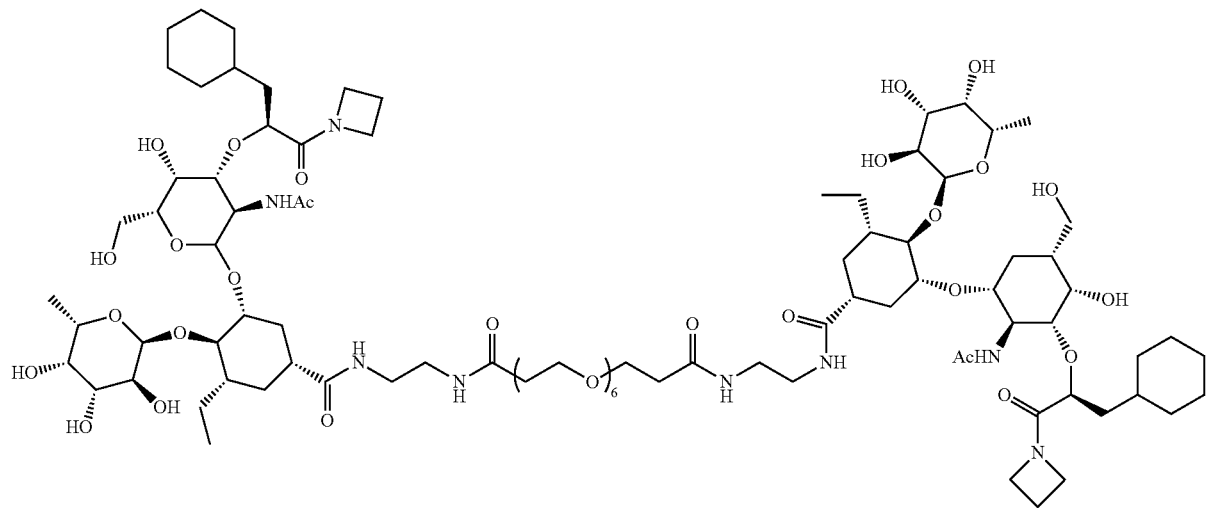

$^1$H NMR (400 MHz, Deuterium Oxide) δ 4.92 (d, J=4.0 Hz, 2H), 4.79 (q, J=6.6 Hz, 2H), 4.42 (m, 2H), 4.24 (q, J=8.7 Hz, 2H), 4.14 (q, J=8.4 Hz, 2H), 3.96 (m, J=24.9, 8.9 Hz, 8H), 3.80-3.48 (m, 36H), 3.42 (m, J=7.7, 4.4 Hz, 4H), 3.19 (m, J=23.4, 8.5 Hz, 10H), 2.40 (t, J=6.1 Hz, 4H), 2.32-2.10 (m, 8H), 2.02 (m, 2H), 1.94 (s, 61H), 1.74 (broad d, J=12.5 Hz, 4H), 1.67-1.34 (m, 14H), 1.24 (m, J=11.2 Hz, 8H), 1.16-0.94 (m, 14H), 0.94-0.64 (m, 10H). MS: Calculated for $C_{90}H_{154}N_8O_{34}$=1891.0; Found ES-Negative m/z=1935.9 (M+formic acid−1).

Example 15: Compound 25

Compound 25:
Prepared in an analogous manner from compound 18 and azetidine.

$^1$H NMR (400 MHz, Deuterium Oxide) δ 8.23 (d, J=9.6 Hz, 2H), 4.91 (d, J=4.0 Hz, 2H), 4.78 (q, J=6.7 Hz, 2H), 4.41 (broad d, J=8.5 Hz, 2H), 4.23 (q, J=8.6 Hz, 2H), 4.14 (q, J=8.7 Hz, 2H), 3.95 (m, J=24.6, 8.8 Hz, 8H), 3.76 (dd, J=10.6, 3.2 Hz, 2H), 3.72-3.55 (m, 14H), 3.53 (s, 4H), 3.41 (m, J=7.7, 4.4 Hz, 4H), 3.19 (m, J=13.5, 10.9 Hz, 12H), 2.39 (t, J=6.1 Hz, 4H), 2.21 (m, J=16.1, 8.8 Hz, 6H), 2.02 (m, 2H), 1.94 (s, 6f), 1.74 (broad d, J=12.4 Hz, 4H), 1.67-1.33 (m, 14H), 1.33-0.93 (m, 22H), 0.93-0.62 (m, 10H). MS: Calculated for $C_{82}H_{138}N_8O_{30}$=1714.9; Found ES-Positive m/z=1737.8 (M+Na$^+$).

Example 16: Compound 27

Compound 27:
To a mixture of compound 2 (72 mg, 91 μmole) and compound 26 (azido-PEG3-azide) (9.3 mg, 38 μmole) in deionized water (2 mL) was added a solution of CuSO$_4$-

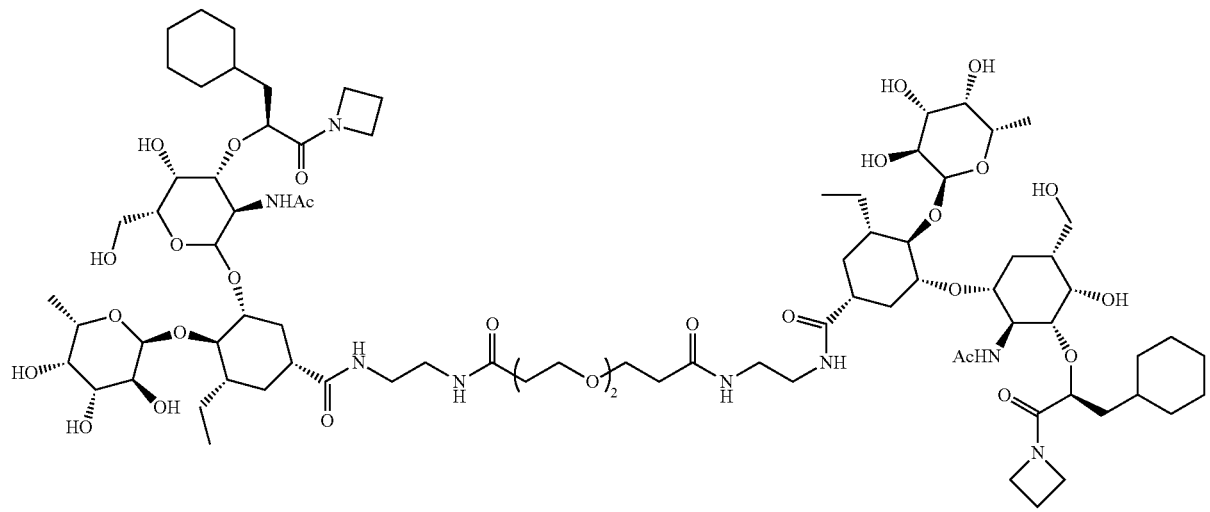

THPTA (0.04M) (0.5 mL) and sodium ascorbate (38 mg, 0.19 mmole) successively. The reaction mixture was stirred overnight at room temperature. The reaction mixture was concentrated under high vacuum and the residue was purified by HPLC. The product was lyophilized overnight to give compound 27 as a white solid (3.0 mg, 4%).

(m, 4H), 3.50 (m, 6H), 3.46-3.32 (m, 8H), 3.32-3.23 (m, 2H), 3.23-3.09 (m, 2H), 2.17 (broad t, J=12.8 Hz, 2H), 2.10-1.97 (m, 2H), 1.89 (s, 6H), 1.82-1.30 (m, 20H), 1.21 (d, J=12.1 Hz, 4H), 1.16-0.87 (m, 18H), 0.79 (dt, J=22.3, 10.7

27

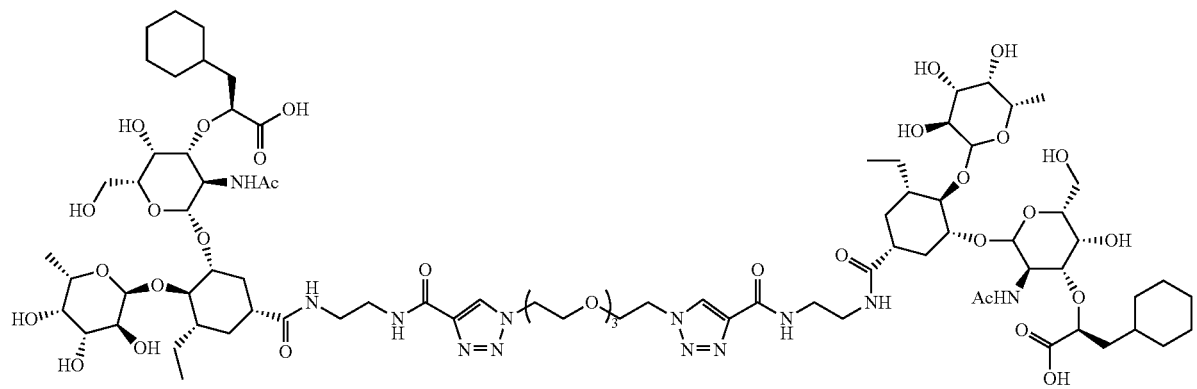

1H NMR (400 MHz, Deuterium Oxide) δ 8.27 (s, 2H), 8.22 (s, 2H), 4.88 (d, J=4.0 Hz, 2H), 4.78 (q, J=6.8 Hz, 2H), 4.53 (t, J=4.9 Hz, 4H), 4.39 (broad d, J=8.6 Hz, 2H), 3.94-3.80 (m, 8H), 3.80-3.72 (m, 4H), 3.72-3.64 (m, 4H), 3.60 (m, J=5.8 Hz, 4H), 3.54-3.31 (m, 18H), 3.31-3.09 (m, 4H), 2.16 (broad t, J=12.6 Hz, 2H), 2.01 (m, J=7.5 Hz, 2H), 1.90 (s, 6H), 1.80-1.30 (m, 20H), 1.22 (m, J=11.9 Hz, 2H), 1.16-0.87 (m, 18K), 0.78 (m, J=23.1, 10.9 Hz, 4H), 0.63 (t, J=7.3 Hz, 6H). MS: Calculated for C82H134N12O33=1814.9; Found ES-Negative m/z=1814.7 (M−1).

The following compounds were prepared in an analogous manner:

Example 17: Compound 28

Compound 28:
Prepared in an analogous manner from compound 2 and azido-PEG2-azide.

Hz, 4H), 0.62 (t, J=7.4 Hz, 6H). MS: Calculated for $C_{80}H_{130}N_{12}O_{32}$=1770.8; Found ES-Negative m/z=1769.7 (M−1).

Example 18: Compound 29

Compound 29:
To a solution of compound 7 (46 mg, 56 μmole) and compound 26 (azido-PEG3-azide) (5.6 mg, 23 μmole) in a solution of MeOH (3 mL) and distilled water (0.3 mL) was added a solution of CuSO4-THPTA (0.04M) (0.3 mL) and sodium ascorbate (23 mg, 0.12 mmole) successively. The resulting solution was stirred overnight at room temperature. To complete the reaction, another set of catalyst was added and the reaction was continued additional 6 hrs. After the reaction was completed, the solution was concentrated under high vacuum and the residue was purified by HPLC. The

28

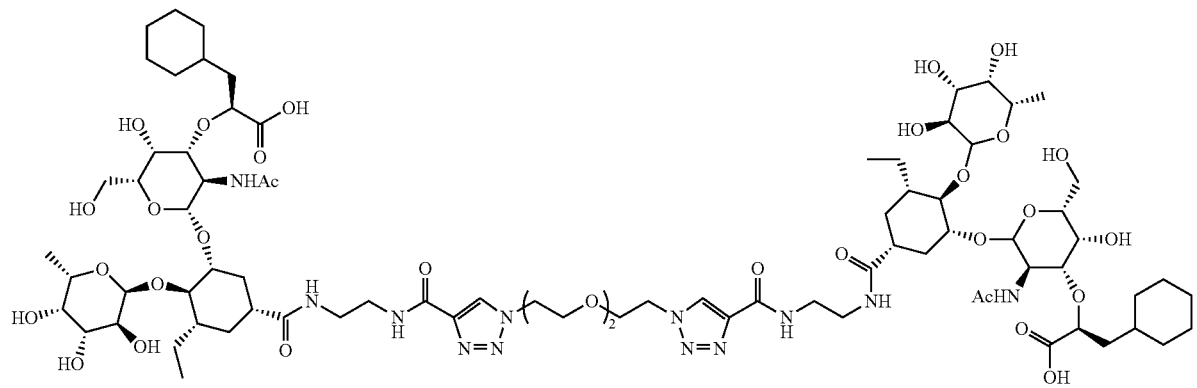

¹H NMR (400 MHz, Deuterium Oxide) δ 8.23 (s, 2H), 4.87 (d, J=4.0 Hz, 2H), 4.77 (q, J=6.9 Hz, 2H), 4.50 (t, J=4.9 Hz, 4H), 4.37 (broad d, J=8.6 Hz, 2H), 3.87 (broad d, J=5.9 Hz, 4H), 3.82-3.71 (m, 8H), 3.71-3.63 (m, 4H), 3.63-3.53 product portion was collected and evaporated, re-dissolved in minimum amount of distilled water then lyophilized overnight to give compound 29 as a white solid (25.2 mg, 13.3 μmole, 57%).

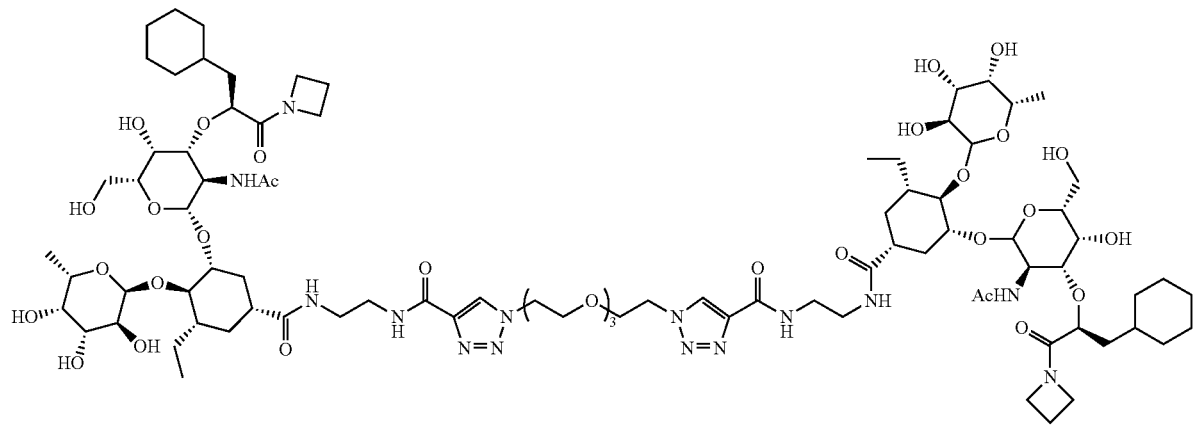

$^1$H NMR (400 MHz, Deuterium Oxide) δ 8.28 (s, 2H), 4.88 (d, J=4.0 Hz, 2H), 4.77 (q, J=6.8 Hz, 2H), 4.53 (t, J=4.8 Hz, 4H), 4.38 (broad d, 2H), 4.23 (q, J=7.7 Hz, 2H), 4.13 (q, J=8.4 Hz, 2H), 4.07-3.87 (m, 6H), 3.82 (t, J=4.9 Hz, 4H), 3.79-3.63 (m, 8H), 3.63-3.55 (m, 6H), 3.55-3.32 (m, 14H), 3.32-3.10 (m, 4H), 2.33-2.08 (m, 8H), 2.02 (m, 2H), 1.89 (s, 6H), 1.81-1.31 (m, 18H), 1.22 (m, J=11.6 Hz, 6H), 1.17-0.90 (m, 14H), 0.90-0.68 (m, 4H), 0.63 (t, J=7.3 Hz, 6H). MS: Calculated for $C_{88}H_{144}N_{14}O_{31}$=1893.0; Found ES-Positive m/z=969.5 (M/2+Na$^+$).

The following compounds were prepared in an analogous manner:

Example 19: Compound 30

Compound 30:

Prepared in an analogous manner from compound 7 and azido-PEG5-azide.

3.70 (broad d, J=3.0 Hz, 2H), 3.69-3.62 (m, 4H), 3.59 (m, J=7.7 Hz, 6H), 3.53 (m, J=5.6 Hz, 2H), 3.47 (m, J=11.4, 4.1 Hz, 12H), 3.43-3.31 (m, 6H), 3.31-3.22 (m, 2H), 3.17 (t, J=9.7 Hz, 2H), 2.20 (m, J=14.0 Hz, 8H), 2.01 (m, J=10.3 Hz, 2H), 1.90 (s, 6H), 1.75-1.31 (m, 18H), 1.22 (m, J=12.1 Hz, 6H), 1.16-0.91 (m, 14H), 0.91-0.69 (m, 4H), 0.63 (t, J=7.3 Hz, 6H). MS: Calculated for $C_{92}H_{152}N_{14}O_{33}$=1981.0; Found ES-Positive m/z=1013.6 (M/2+Na$^+$).

Example 20: Compound 31

Compound 31:

To a solution of compound 2 (30 mg, 38 µmole) and compound 9 (46 mg, 57 µmole) in distilled water (2 mL) was added a solution of CuSO$_4$-THPTA (0.04M) (0.2 mL) and sodium ascorbate (1.5 mg, 7.6 µmole) successively. The resulting solution was stirred for 4 hrs at room temperature.

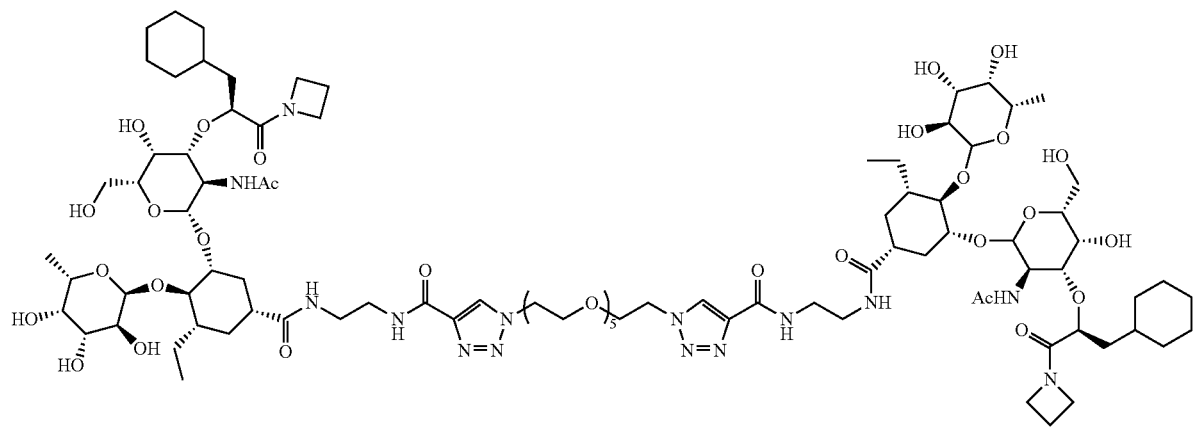

$^1$H NMR (400 MHz, Deuterium Oxide) δ 8.33 (s, 2H), 4.88 (d, J=3.9 Hz, 2H), 4.77 (q, J=6.8 Hz, 2H), 4.55 (t, J=5.0 Hz, 4H), 4.39 (m, 2H), 4.22 (q, J=8.2 Hz, 2H), 4.13 (q, J=8.7 Hz, 2H), 4.00 (broad d, J=9.9 Hz, 2H), 3.93 (q, J=7.7 Hz, 4H), 3.85 (t, J=5.0 Hz, 4H), 3.74 (dd, J=10.5, 3.2 Hz, 2H), The solution was concentrated under high vacuum and the residue was purified by HPLC. The product portion was collected and evaporated, re-dissolved in minimum amount of distilled water then lyophilized overnight to give compound 31 as a white solid (3.5 mg, 6%).

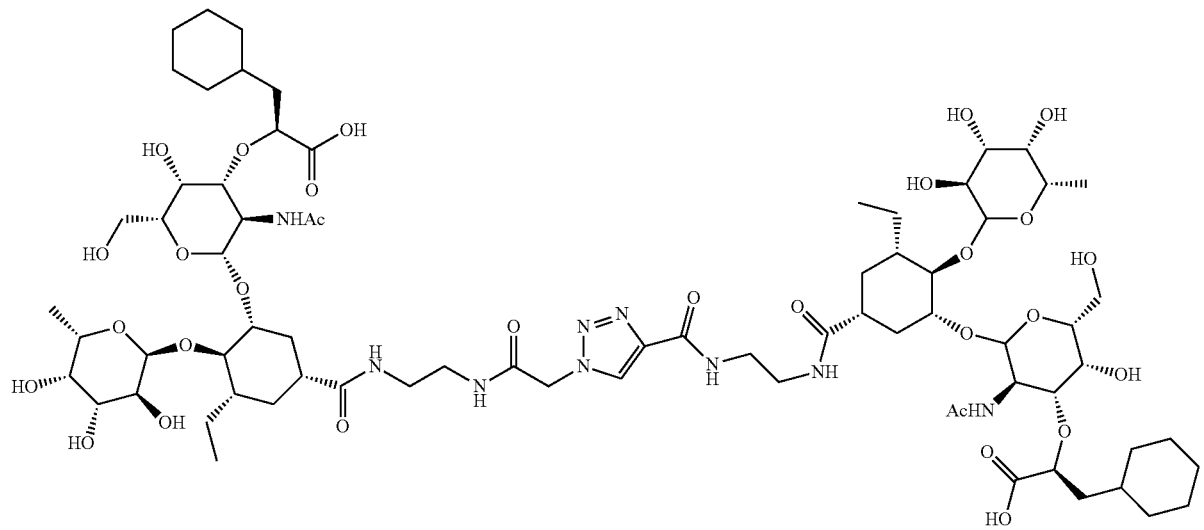

31

$^1$H NMR (400 MHz, Deuterium Oxide) δ 8.39 (s, 1H), 5.23 (s, 2H), 4.97 (t, J=4.5 Hz, 2H), 4.85 (m, 2H), 4.45 (broad t, 2H), 3.94 (m, 2H), 3.91-3.78 (m, 6H), 3.77-3.62 (m, 12H), 3.61-3.40 (m, 8H), 3.40-3.16 (m, 8H), 2.24 (m, J=12.0 Hz, 2H), 2.09 (m, 2H), 1.98 (two s, 6H), 1.89-1.37 (m, 20H), 1.36-1.24 (m, 4H), 1.23-0.94 (m, 18H), 0.93-0.77 (m, 4H), 0.71 (t, J=7.2 Hz, 6H). MS: Calculated for $C_{73}H_{119}N_9O_{30}$=1601.8; Found ES– Negative m/z=1600.5 (M–H).

Example 21: Compound 32

Compound 32:

To a solution of compound 1 (25 mg, 34 µmole) and carbonyldiimidazole (2.3 mg, 14 µmole) in anhydrous DMF (1 mL) was added DIPEA (20 µL). The resulting solution was stirred overnight at room temperature under an N$_2$ atmosphere. The reaction mixture was concentrated under high vacuum and the residue was purified by HPLC. The product portion was collected and evaporated, re-dissolved in minimum amount of distilled water then lyophilized overnight to give compound 32 as a white solid (1.6 mg, 8%).

Compound 32 (Alternative Synthesis):

To a solution of compound 1 (0.77 g, 1.04 mmole) in anhydrous DMSO (3 mL) was added bis(p-nitrophenyl) carbonate (0.15 g, 0.49 mole) (3 mL). The reaction mixture was stirred overnight at 40° C. The reaction mixture was lyophilized to dryness. The residue was purified by reverse phase C-18 column chromatography eluting with a solution of water/MeOH (gradient change from 9/1 to 1/9 v/v). The product portion was concentrated and lyophilized to give the desired product as a white solid (0.47 g, 0.31 mmole, 48%).

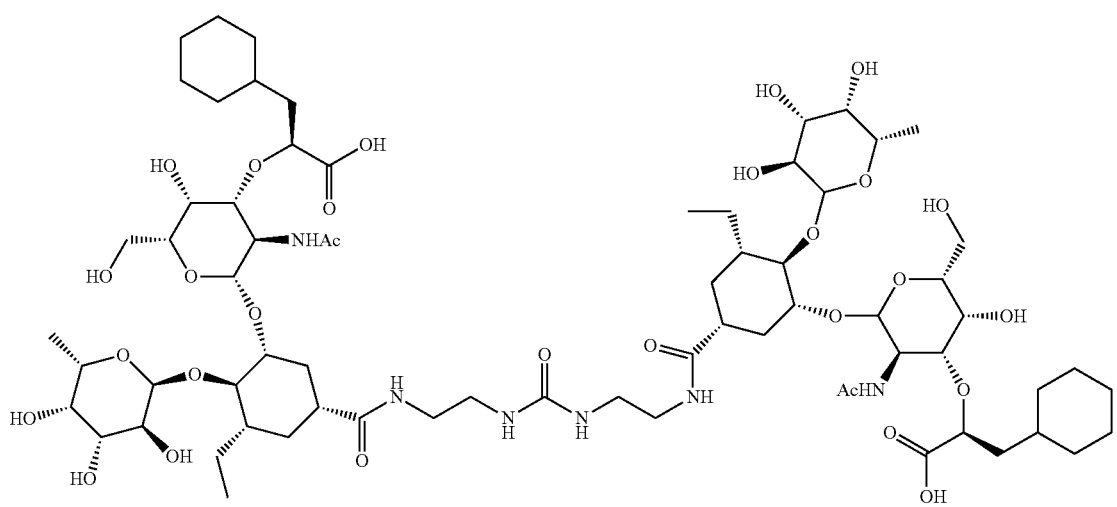

32

¹H NMR (400 MHz, Deuterium Oxide) δ 4.92 (d, J=4.0 Hz, 2H), 4.81 (q, J=6.7 Hz, 2H), 4.42 (broad d, J=8.5 Hz, 2H), 3.88 (m, 2H), 3.84-3.74 (m, 6H), 3.73-3.56 (m, 12H), 3.45 (t, J=5.9 Hz, 2H), 3.36 (broad d, J=10.1 Hz, 2H), 3.29-3.00 (m, 12H), 2.23 (broad t, J=12.7 Hz, 2H), 2.05 (m, 2H), 1.95 (s, 6H), 1.75 (broad d, J=12.5 Hz, 4H), 1.69-1.35 (m, 18H), 1.35-1.16 (m, 6H), 1.15-0.92 (m, 16H), 0.91-0.62 (m, 12H); MS: Calculated for $C_{69}H_{116}N_6O_{29}$=1492.7; Found ES-Negative m/z=1491.5 (M-H).

Example 22: Intermediate 35

Compound 35:
A solution of L-Lysine (OBn ester) (0.15 g, 0.49 mmole) in anhydrous DMF (3 mL) was cooled to 0° C. and DIPEA (0.35 mL, 2.0 mmole) was added. The solution was stirred for 10 min. This solution was added to a solution of $N_3$-PEG1-NHS ester (compound 34) (0.30 g, 1.16 mmole) over a 5 minute period followed by a catalytic amount of DMAP (20 mg). The resulting solution was stirred overnight while temperature was gradually increased to room temperature. The solution was concentrated and the residue was dried under high vacuum for 30 min to dryness, then directly purified by Combi-flash (EtOAc/MeOH. EtOAc only -2/1, v/v). The product portion was collected and evaporated, then dried under high vacuum to give compound 35 as a light yellow gel (0.25 g, 0.48 mmole, 98%). MS: Calculated (C23H34N8O6, 518.2), ES- positive (519.2, M+1, 541.2 M+Na).

35

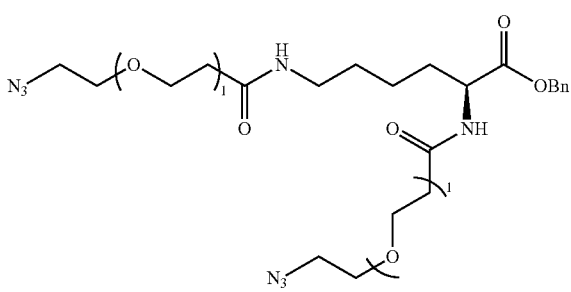

¹H NMR (400 MHz, Methanol-$d_4$) δ 7.47-7.22 (m, 5H), 5.31-5.03 (dd, 2H), 4.45 (dd, J=8.7, 5.2 Hz, 1H), 3.86-3.66 (m, 4H), 3.63 (q, J=4.9 Hz, 4H), 3.45-3.24 (m, 7H), 3.17 (td, J=6.9, 4.9 Hz, 2H), 2.63-2.48 (m, 2H), 2.45 (t, J=6.1 Hz, 2H), 1.86 (dtd, J=13.3, 8.0, 5.2 Hz, 1H), 1.80-1.63 (m, 1H), 1.63-1.45 (m, 2H), 1.39 (m, 2H).

Example 23: Intermediate 36

Compound 36:
Prepared in an analogous manner from compound 33 and azido-PEG5-NHS ester in 58% yield.

36

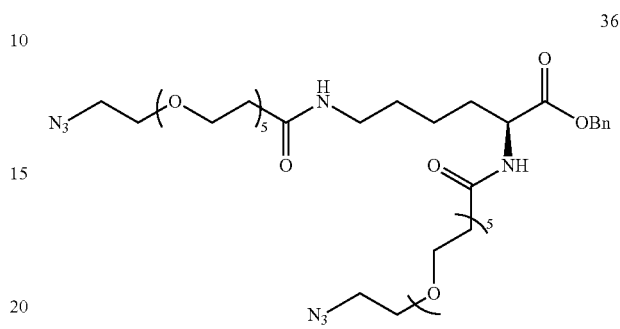

¹H NMR (400 MHz, Methanol-$d_4$) δ 7.48-7.26 (m, 5H), 5.29-5.09 (dd, 2H), 4.45 (dd, J=8.8, 5.2 Hz, 1H), 3.81-3.55 (m, 41H), 3.43-3.36 (m, 5H), 3.33 (p, J=1.7 Hz, 12H), 3.17 (t, J=7.0 Hz, 2H), 2.61-2.49 (m, 2H), 2.44 (t, J=6.1 Hz, 2H), 1.95-1.80 (m, 1H), 1.80-1.66 (m, 1H), 1.61-1.46 (m, 2H), 1.46-1.31 (m, 3H).

Example 24: Compound 37

Compound 37:
To a solution of compound 35 (24 mg, 46 µmole) and compound 2 (94 mg, 0.12 mmole) in of MeOH (1 mL) and water (1 mL) was added a solution of $CuSO_4$-THPTA (0.04M, 0.23 mL, 20 µmole) and sodium ascorbate (2.7 mg, 14 µmole) successively. The resulting solution was stirred for 3 days at room temperature. The solution was concentrated under reduced pressure and the mixture of mono- and di-coupled products was separated by C-18 column (water/MeOH, water only -¼ v/v). To complete the reaction, this mixture was re-subjected to the reaction conditions as described above overnight at 40° C. The reaction solution was then dialyzed against water with dialysis tube MWCO 1000 while distilled water was changed every 6 hours. The aqueous solution in the tube was collected and lyophilized to give compound 37 as a white solid (53 mg, 55% yield).

37

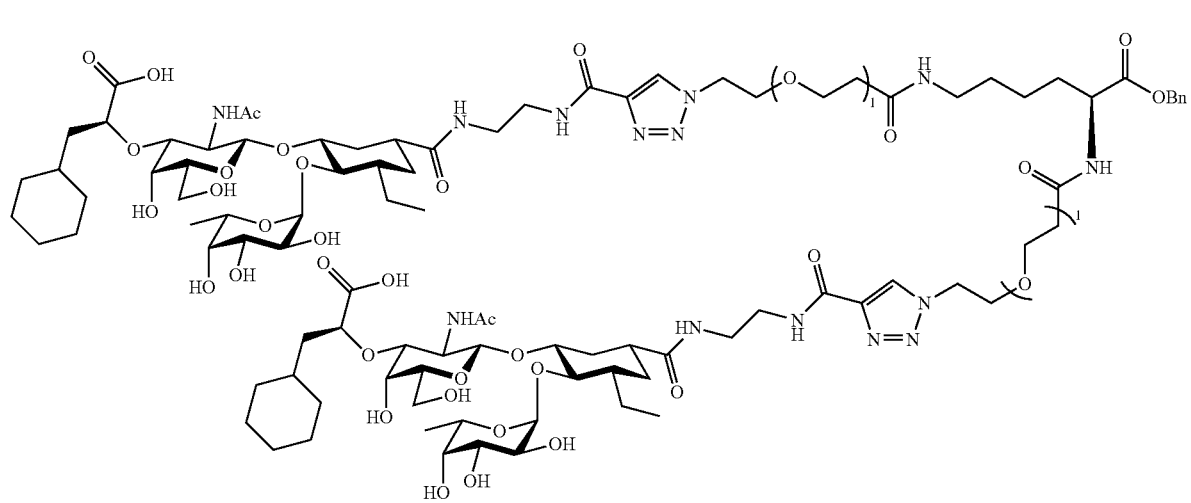

$^1$H NMR (400 MHz, Deuterium Oxide) δ 8.27 (broad two s, 2H), 7.27 (m, 5H), 5.05 (broad s, 2H), 4.92 (broad s, 2H), 4.81 (m, 2H), 4.62-4.28 (m, 6H), 4.20 (m, 1H), 4.09-3.55 (m, 26H), 3.55-3.10 (m, 13H), 2.93 (broad t, 2H), 2.42 (broad t, 2H), 2.31 (broad t, 2H), 2.20 (m. J=12.6 Hz, 2H), 2.06 (m, 4H), 1.95 (m, 10H), 1.84-1.36 (m, 12H), 1.35-0.91 (m, 12H), 0.91-0.72 (m, 10), 0.71-0.60 (broad t, 8H) MS: Calculated ($C_{97}H_{152}N_{14}O_{36}$, 2089.0), ES-Negative (2088.6, M−1, 1042.9 M/2−1).

Example 25: Compound 38

Compound 38:

A solution of compound 37 (13 mg, 6.2 μmole) in anhydrous MeOH (2 mL) was hydrogenated in the presence of Pd(OH)$_2$ (10 mg) for 2 hrs at room temperature. The solution was filtered through a Celite pad and the filtrate was concentrated. The crude product was purified by HPLC. The product portion was collected, evaporated, then lyophilized overnight to give compound 38 as a white solid (4.5 mg, 36% yield).

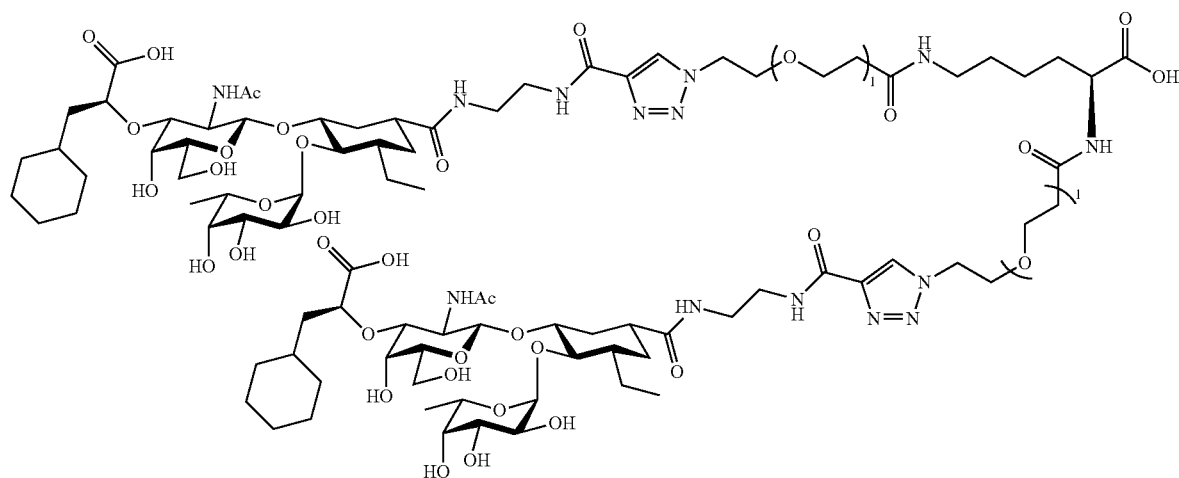

38

$^1$H NMR (400 MHz, Deuterium Oxide) δ 8.28 (two s, 2H), 4.89 (d, J=4.0 Hz, 2H), 4.79 (q, J=6.7 Hz, 2H), 4.54 (q, J=4.6 Hz, 5H), 4.40 (d, J=8.6 Hz, 2H), 3.98 (dd, J=8.5, 4.7 Hz, 1H), 3.95-3.79 (m, 6H), 3.78-3.74 (m, 5H), 3.73-3.67 (m, 6H), 3.66-3.55 (m, 13H), 3.54-3.32 (m, 11H), 3.31-3.24 (m, 2H), 3.18 (t, J=9.7 Hz, 2H), 2.92 (t, J=6.9 Hz, 2H), 2.49-2.33 (m, 2H), 2.30 (t, J=5.8 Hz, 2H), 2.19 (broad t, J=12.6 Hz, 2H), 2.11-1.98 (m, 2H), 1.92 (d, J=3.1 Hz, 6H), 1.79-1.33 (m, 24H), 1.23 (m, 3H), 1.18-0.89 (m, 20H), 0.88-0.69 (m, 5H), 0.64 (t, J=7.4 Hz, 6H) MS: Calculated ($C_{90}H_{146}N_{14}O_{36}$, 1999.0), ES-Negative (1219.2 M/2−1).

Example 26: Compound 39

Compound 39:

Compound 39 was prepared in 52% yield using an analogous procedure starting from compound 2 and compound 36.

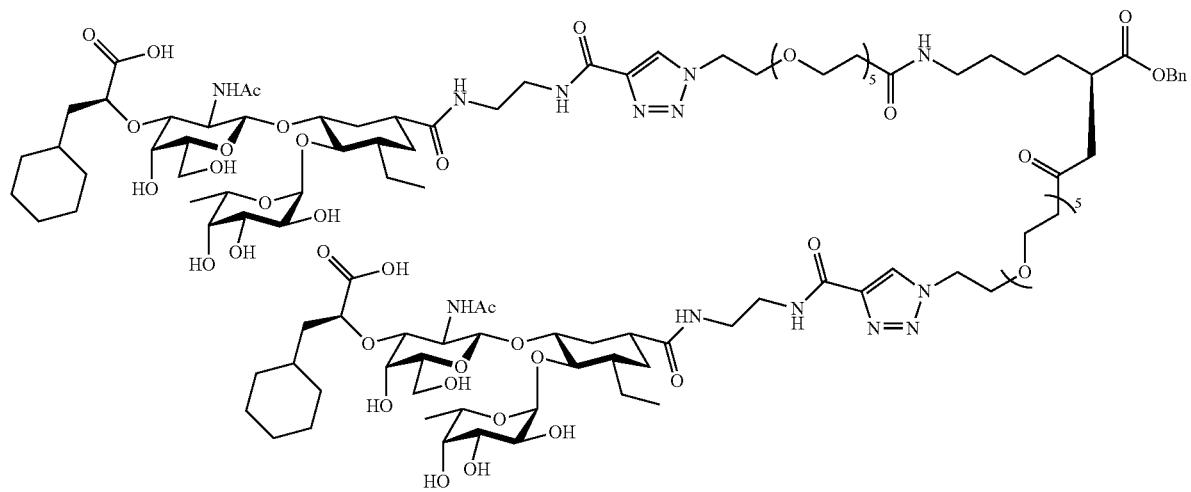

¹H NMR (400 MHz, Deuterium Oxide) δ 8.35 (s, 2H), 7.41-7.20 (m, 5H), 5.21-5.01 (dd, 2H), 4.92 (d, J=4.0 Hz, 2H), 4.81 (m, J=6.8 Hz, 2H), 4.58 (t, J=4.9 Hz, 4H), 4.42 (d, J=8.6 Hz, 2H), 4.35-4.21 (m, 1H), 3.88 (m, J=5.0 Hz, 6H), 3.84-3.75 (m, 5H), 3.74-3.70 (m, 4H), 3.69-3.59 (m, 11H), 3.58-3.44 (m, 36H), 3.43-3.34 (m, 6H), 3.33-3.24 (m, 3H), 3.20 (t, J=9.7 Hz, 2H), 3.03 (t, J=6.8 Hz, 2H), 2.46 (t, J=6.1 Hz, 2H), 2.37 (t, J=6.0 Hz, 2H), 2.20 (broad t, J=12.3 Hz, 2H), 2.05 (m, 2H), 1.93 (s, 6H), 1.82-1.33 (m, 24H), 1.32-1.18 (7H), 1.17-0.91 (m, 17H), 0.90-0.72 (m, 5H), 0.67 (t, J=7.3 Hz, 6H) MS: Calculated ($C_{113}H_{184}N_{14}O_{44}$, 2441.2), ES-Negative (1219.2 M/2−1).

Example 27: Compound 40

Compound 40:

Compound 40 was prepared in 26% yield using an analogous procedure starting from compound 39.

¹H NMR (400 MHz, Deuterium Oxide) δ 8.36 (two s, 2H), 4.90 (d, J=3.9 Hz, 2H), 4.80 (q, J=6.7 Hz, 2H), 4.58 (t, J=4.9 Hz, 5H), 4.41 (d, J=8.6 Hz, 2H), 4.05 (dd, J=8.5, 4.7 Hz, 1H), 3.98-3.82 (m, 5H), 3.81-3.72 (m, 5H), 3.72-3.59 (m, 11H), 3.59-3.32 (m, 34H), 3.32-3.11 (m, 5H), 3.06 (t, J=6.9 Hz, 2H), 2.57-2.42 (m, 2H), 2.38 (t, J=6.1 Hz, 2H), 2.20 (broad t, J=12.2 Hz, 2H), 2.04 (m, 2H), 1.92 (s, 61H), 1.78-1.32 (m, 20H), 1.32-0.88 (m, 24H), 0.89-0.70 (m, 5H), 0.66 (t, J=7.3 Hz, 6H) MS Calculated ($C_{106}H_{178}N_{14}O_{44}$, 2351.2), ES− negative (1173.9 M/2−1, 782.3, M/3−1).

Example 28: Compound 42

Compound 42:

A solution of compound 41 (described in JACS, 2002, 124(47), 14085) (22 mg, 49 μmole) and DIPEA (28 μL, 163 μmole) in anhydrous DMF (0.3 mL) was cooled to 0° C. and HATU (62 mg, 163 μmole) was added. The solution was stirred for 30 minutes. This solution was added to a solution of compound 1 (0.12 g, 163 μmole) over a 5 min. period. The resulting solution was stirred overnight. The reaction solution was dialyzed against water with dialysis tube MWCO

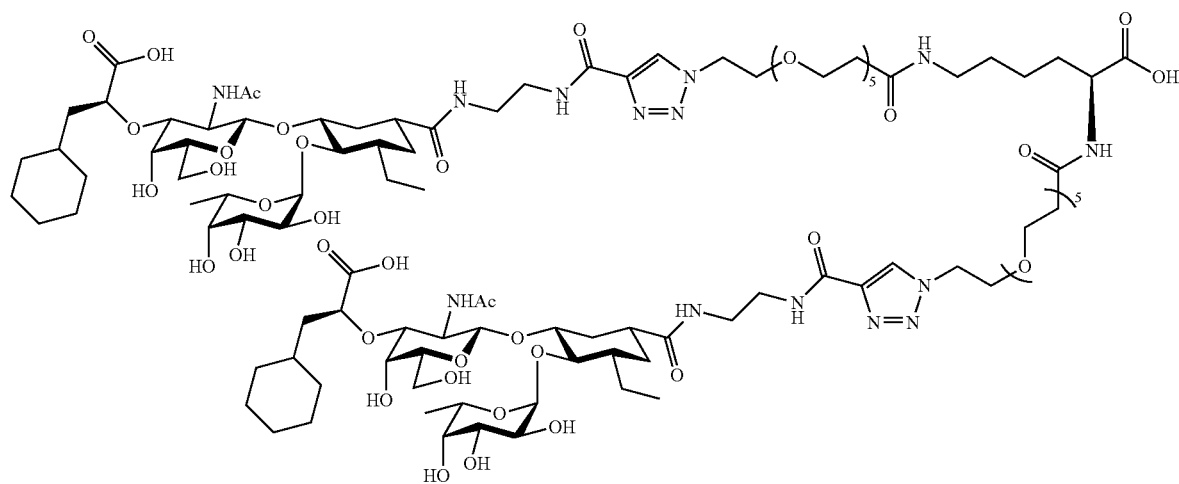

1000 while distilled water was changed every 6 hours. The aqueous solution in the tube was collected and lyophilized overnight to give compound 42 as a white solid (69 mg, 54%).

¹H NMR (400 MHz, Deuterium Oxide) δ 4.92 (d, J=4.0 Hz, 4H), 4.81 (d, J=6.8 Hz, 4H), 4.42 (d, J=7.8 Hz, 4H), 3.96 (s, 8H), 3.78 (m, 12H), 3.74-3.50 (m, 188H), 3.42-3.34 (m,

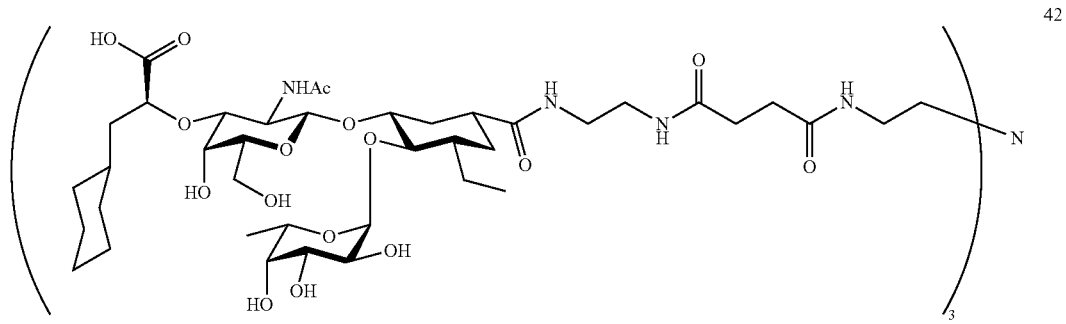

42

¹H NMR (400 MHz. Methanol-d₄) δ 4.85 (m, 6H), 4.52 (broad s, 3H), 3.75 (M, J=11.1 Hz, 15H), 3.69-3.52 (m, 12H), 3.38 (broad t, J=1.7 Hz, 3H), 3.37-3.06 (m, 45H, partially hidden by MeOH), 2.67 (m, 6H), 2.52-2.34 (m, 15H), 2.15 (broad t, 3H), 2.08-1.96 (m, 3H), 1.88 (m, 12H), 1.73 (m, 3H), 1.70-1.37 (m, 12H), 1.36-0.98 (m, 36H), 0.93-0.71 (m, J=7.3 Hz, 15H). MS: Calculated for $C_{120}H_{201}N_{13}O_{48}$=2592.3; Found ES– Negative m/z=1295.6 (M/2–H).

12H), 3.33-3.16 (m, 8H), 3.10 (q, J=7.4 Hz, 4H), 2.37-2.14 (m, 4H), 2.05 (m, 4H), 1.96 (s, 12H), 1.75 (m, 8H), 1.70-1.33 (m, 8H).

Example 29: Compound 44

Compound 44:

A solution of tetravalent PEG-active ester (Average MW=20176, 0.5 g, 0.24 mmole) in DMSO (5 mL) was added a solution of compound 1 (1.4 g, 1.93 mmole) and DIPEA (0.5 mL) in distilled water (10 mL) over 1 hr period at room temperature. The resulting solution was stirred for 3 days under the same condition. The reaction solution was dialyzed against water with dialysis tube MWCO 1000 while distilled water was changed every 6 hours. The aqueous solution in the tube was collected and lyophilized overnight to give compound 44 (average chain length (n)=110) as a white solid (0.67 g, 0.15 mmole, 63%).

Example 30: Compound 45

Compound 45:

A solution of compound 32 (300 mg, 0.2 mmole) and DIPEA (0.2 mL, 1.0 mmole) in anhydrous DMF (15 mL) was cooled to 0° C. TBTU (200 mg, 0.6 mmole) was added. The resulting solution was stirred for 3 hrs at room temperature. Azetidine (4.0 mL, 60.0 mmol) was added. The solution was transferred to a sealed tube and stirred overnight at 55° C. The reaction mixture was cooled to room temperature and concentrated in vacuo. The residue was partially purified by chromatography using the Combi-flash system and eluting with EtOAc/MeOH/water (5/5/1, v/v/v). The crude product was de-salted using a C-18 column (water/MeOH, 9/1-1/9, v/v). The pure product was lyophilized to afford a white solid (0.37 g, 2.35 mmole, quantitative).

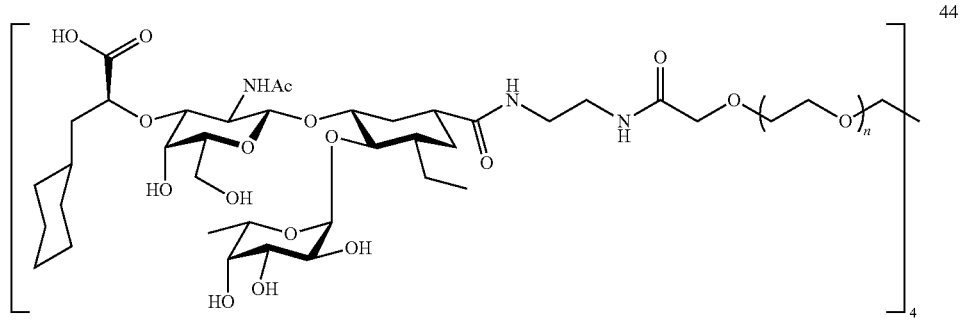

44

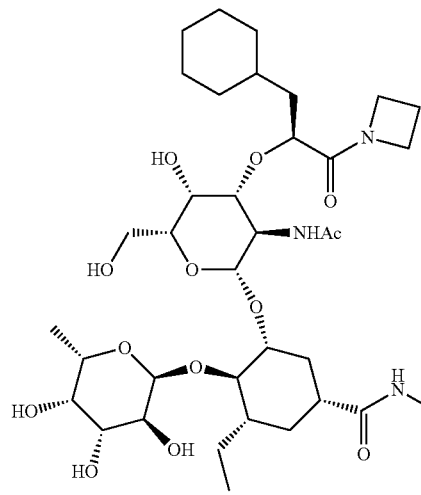
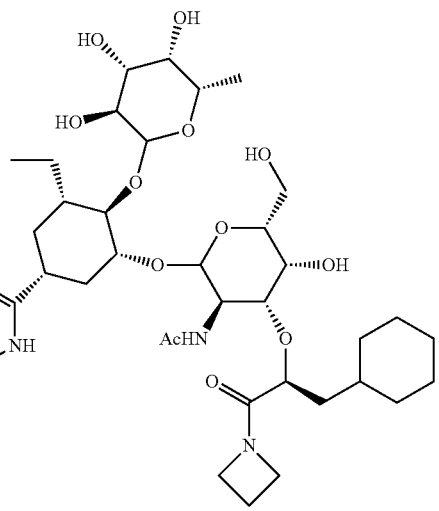

$^1$H NMR (400 MHz, Deuterium Oxide) δ 4.93 (broad s, 1H), 4.88-4.76 (m, 1H), 4.42 (broad s, 1H), 4.19 (m, 3H), 3.97 (m, 3H), 3.88-3.73 (m, 2H), 3.72-3.54 (m, 6H), 3.42 (m, 2H), 3.29-3.00 (m, 6H), 2.67-2.49 (m, 0.5H), 2.35-2.15 (m, 4H), 2.14-1.98 (m, 1H), 1.94 (s, 3H), 1.75 (broad d, J=12.8 Hz, 2H), 1.68-1.36 (m, 8H), 1.35-1.17 (m, J=11.3 Hz, 4H), 1.16-0.98 (dd, J=20.5, 9.1 Hz, 7H), 0.94-0.67 (m, J=32.9, 8.9 Hz, 5H) MS: Calculated (C75H126N8O27, 1570.8), ES-Positive (1594.5, M+Na; 808.5 (M/2+Na), ES–Negative (1569.6, M−1; 784.4. M/2−1).

Example 31

E-Selecting Activity—Analysis by SPR

Surface Plasmon Resonance (SPR) measurements were performed on a Biacore X100 instrument (GE Healthcare). A CM5 sensor chip (GE Healthcare) was used for the interaction between E-selectin and GMI compound. Anti-human IgG (Fc) antibody (GE Healthcare) was immobilized onto the chip by amine coupling according to the manufacturer's instructions. In brief, after a 7-min injection (flow rate of 5 µl/min) of 1:1 mixture of N-ethyl-N'-(3-dimethylaminopropyl) carbodiimide hydrochloride and N-hydroxysuccinimide, anti-human IgG (Fc) antibody (25 µg/ml in 10 mM sodium acetate buffer, pH 5.0) was injected using a 6-min injection at 5 µl min. Remaining activated groups were blocked by injecting 1 M ethanolamine/HCl, pH 8.5. The recombinant human E-selectin/CD63E Fc Chimera (50 µg/ml) (R & D systems) was injected into the experimental cell until 6000-7000 RU was captured onto the antibody surface. No recombinant human E-selectin/CD63E was injected into the control cell. Increasing concentrations of GMI compound samples were injected at 30 µl/min into both flow cells and all sensorgrams were recorded against the control. Regeneration of the anti-human IgG (Fc) surface was achieved by injecting 3M magnesium chloride, followed by 50 mM sodium hydroxide. Data were analyzed using Biacore X100 evaluation/BIA evaluation 4.1.1 software (GE Healthcare) and Graphad prism 6 software.

E-Selectin Antagonist Activity of Compounds

| Compound | KD (nM) |
| --- | --- |
| 11 | 8.5 |
| 12 | 3.7 |
| 13 | 4.7 |
| 14 | 6.6 |
| 15 | 6.0 |
| 16 | 6.0 |
| 17 | 5.1 |
| 18 | 3.5 |
| 19 | 10.2 |
| 20 | 0.8 |
| 21 | 18.3 |
| 22 | 2.3 |
| 23 | 2.8 |
| 24 | 2.4 |
| 25 | 3.0 |
| 27 | 8.6 |
| 28 | 3.2 |
| 29 | 3.2 |
| 30 | 2.0 |
| 31 | 3.3 |
| 32 | 8.8 |
| 37 | 3.9 |
| 38 | 6.4 |
| 39 | 5.1 |
| 40 | 5.5 |
| 42 | 1.5 |
| 44 | 8.0 |
| 45 | 2.1 |
| 3 (monomer —CO$_2$H) | 2260 |
| 4 (monomer azetidine) | 2600 |

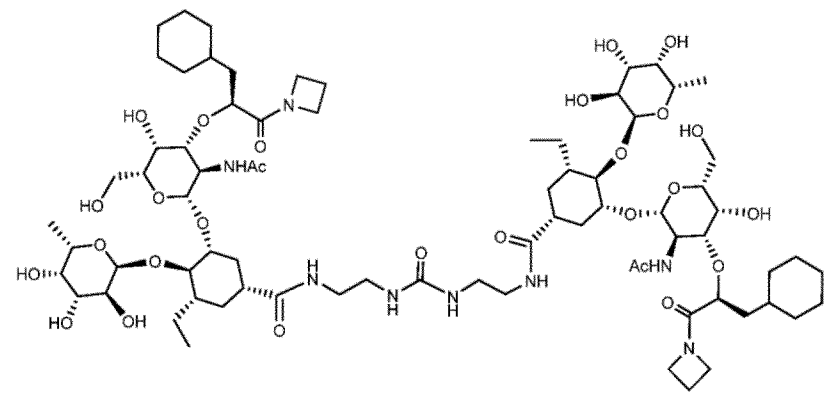

What is claimed is:

1. At least one compound chosen from glycomimetic E-selectin antagonists of Formula (I):

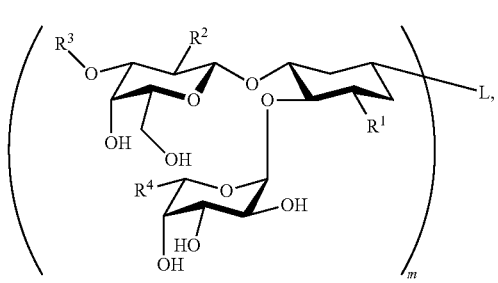

(I)

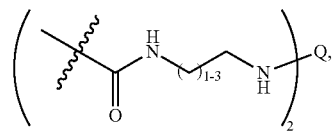

L is chosen from prodrugs of glycomimetic E-selectin antagonists of Formula (I), and pharmaceutically acceptable salts of any of the foregoing,
wherein
  each $R^1$, which may be identical or different, is independently chosen from H, $C_{1-12}$ alkyl, $C_{2-12}$ alkenyl, $C_{2-12}$ alkynyl, and $NHC(=O)R^5$ groups, wherein each $R^5$, which may be identical or different, is independently chosen from $C_{1-12}$ alkyl, $C_{2-12}$ alkenyl, $C_{2-12}$ alkynyl, $C_{6-18}$ aryl, and $C_{1-13}$ heteroaryl groups;
  each $R^2$, which may be identical or different, is independently chosen from halo, $-OY^1$, $-NY^1Y^2$, $-OC(=O)Y^1$, $-NHC(=O)Y^1$, and $-NHC(=O)NY^1Y^2$ groups, wherein each $Y^1$ and each $Y^2$, which may be identical or different, are independently chosen from H, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{6-18}$ aryl, and $C_{1-13}$ heteroaryl groups, wherein $Y^1$ and $Y^2$ may join together along with the nitrogen atom to which they are attached to form a ring;
  each $R^3$, which may be identical or different, is independently chosen from

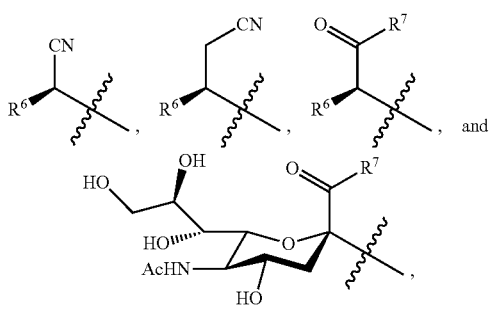

wherein each $R^6$, which may be identical or different, is independently chosen from H, $C_{1-12}$ alkyl and $C_{1-12}$ haloalkyl groups, and wherein each $R^7$, which may be identical or different, is independently chosen from $C_{1-8}$ alkyl, $C_{2-8}$ alkenyl, $C_{2-8}$ alkynyl, $-OY^3$, $-NHOH$, $-NHOCH_3$, $-NHCN$, and $-NY^3Y^4$ groups, wherein each $Y^3$ and each $Y^4$, which may be identical or different, are independently chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, wherein $Y^3$ and $Y^4$ may join together along with the nitrogen atom to which they are attached to form a ring;
  each $R^4$, which may be identical or different, is independently chosen from $-CN$, $C_{1-4}$ alkyl, and $C_{1-4}$ haloalkyl groups;
  m is 2; and

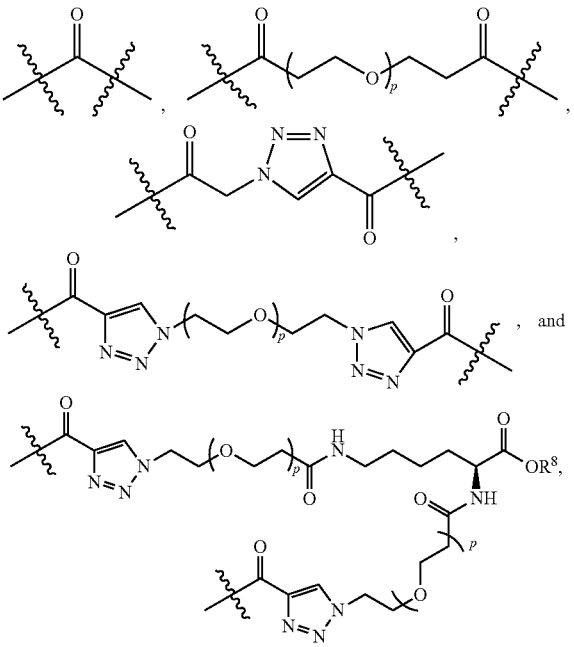

wherein Q is chosen from wherein $R^8$ is chosen from H and benzyl, and wherein p is chosen from integers ranging from 0 to 30.

2. The at least one compound according to claim 1, wherein p is chosen from integers ranging from 0 to 5.

3. The at least one compound according to claim 1, wherein at least one $R^1$ is H.

4. The at least one compound according to claim 1, wherein at least one $R^1$ is methyl.

5. The at least one compound according to claim 1, wherein at least one $R^1$ is ethyl.

6. The at least one compound according to claim 1, wherein at least one $R^1$ is chosen from $-NHC(=O)R^5$ groups.

7. The at least one compound according to claim 6, wherein at least one $R^5$ is chosen from

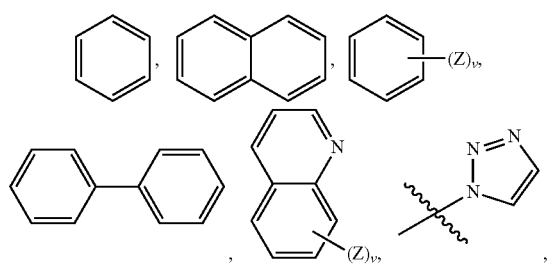

-continued

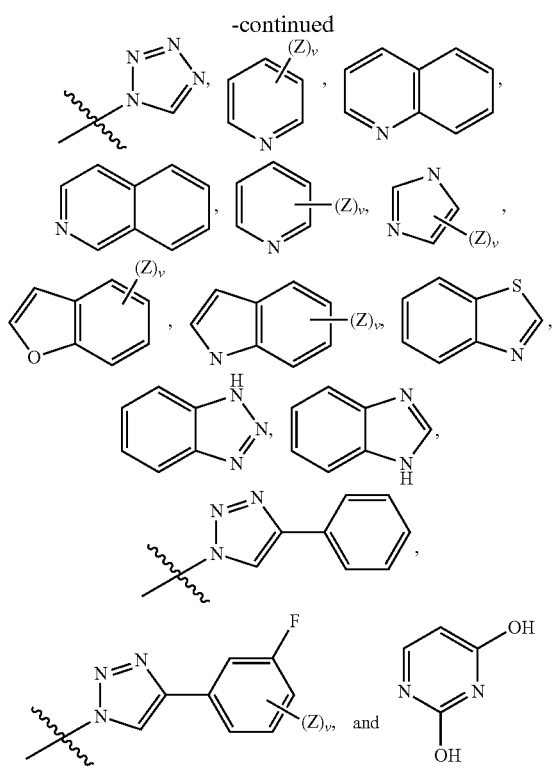

groups, wherein each Z, which may be identical or different, is independently chosen from H, —OH, Cl, F, $N_3$, —$NH_2$, $C_{1-8}$ alkyl, $C_{2-8}$ alkenyl, $C_{2-8}$ alkynyl, $C_{6-14}$ aryl, —$OC_{1-8}$ alkyl, —$OC_{2-8}$ alkenyl, —$OC_{2-8}$ alkynyl, and —$OC_{6-14}$ aryl groups, and wherein v is chosen from integers ranging from 0 to 3.

8. The at least one compound according to claim 1, wherein at least one $R^2$ is F.

9. The at least one compound according to claim 1, wherein at least one $R^2$ is Cl.

10. The at least one compound according to claim 1, wherein at least one $R^2$ is chosen from —$OY^1$ groups.

11. The at least one compound according to claim 1, wherein at least one $R^2$ is chosen from —OC(=O)$Y^1$ groups.

12. The at least one compound according to claim 1, wherein at least one $R^2$ is chosen from —$NY^1Y^2$ groups.

13. The at least one compound according to claim 1, wherein at least one $R^2$ is chosen from —NH(C=O)$Y^1$ groups.

14. The at least one compound according to claim 1, wherein at least one $R^2$ is chosen from —NH(C=O)$NY^1Y^2$ groups.

15. The at least one compound according to claim 1, wherein at least one $R^2$ is chosen from

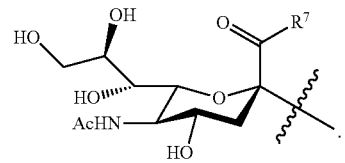

16. The at least one compound according to claim 1, wherein at least one $R^3$ is chosen from

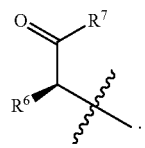

17. The at least one compound according to claim 1, wherein at least one $R^3$ is chosen from

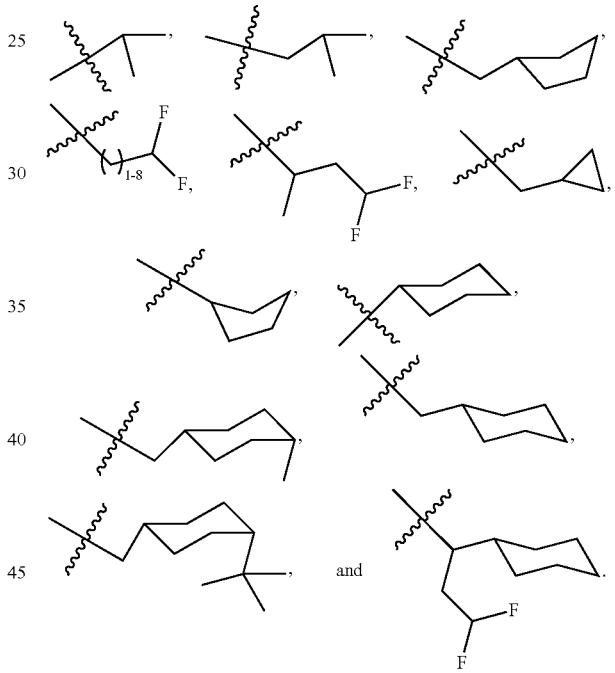

18. The at least one compound according to claim 1, wherein at least one $R^6$ is chosen from

19. The at least one compound according to claim 18, wherein at least one $R^6$ is chosen from

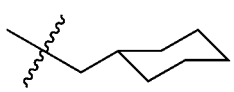

20. The at least one compound according to claim 18, wherein at least one $R^6$ is chosen from

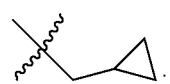 [SMILES: *CC1CC1]

21. The at least one compound according to claim 1, wherein at least one $R^7$ is —OH.

22. The at least one compound according to claim 1, wherein at least one $R^7$ is chosen from

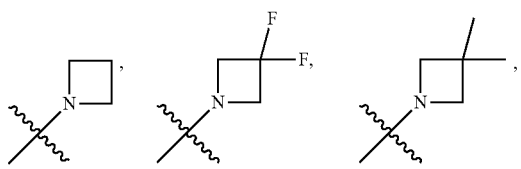

23. The at least one compound according to claim 22, wherein at least one $R^7$ is chosen from

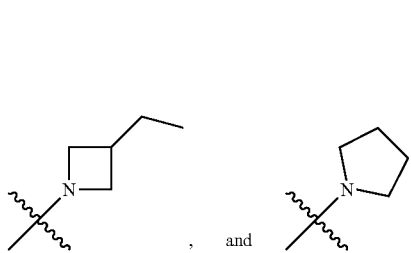

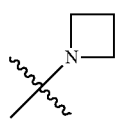

24. The at least one compound according to claim 1, wherein at least one $R^4$ is $CH_3$.

25. The at least one compound according to claim 1, wherein at least one $R^4$ is chosen from $CH_2F$, $CHF_2$, and $CF_3$.

26. The at least one compound according to claim 1, wherein at least one $R^4$ is $CF_3$.

27. The at least one compound according to claim 1, wherein the at least one compound is chosen from compounds having the following Formula:

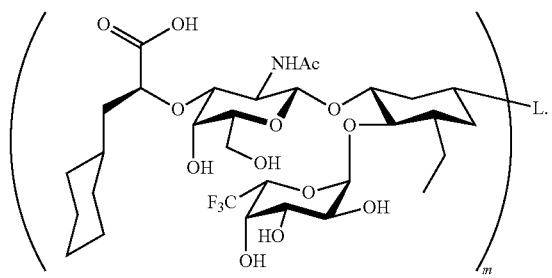

28. The at least one compound according to claim 1, wherein the at least one compound is chosen from compounds having the following Formula:

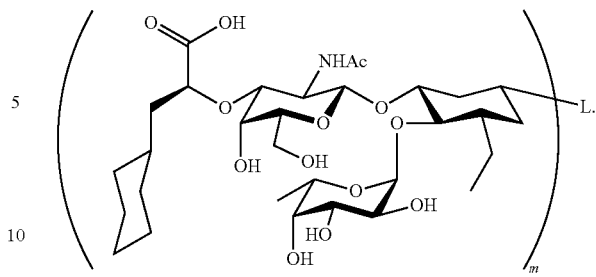

29. The at least one compound according to claim 1, wherein the at least one compound is chosen from compounds having the following Formula:

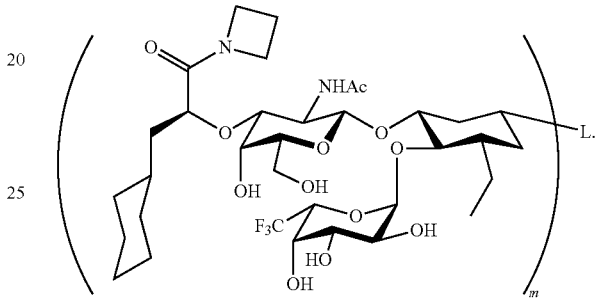

30. The at least one compound according to claim 1, wherein the at least one compound is chosen from compounds having the following Formula:

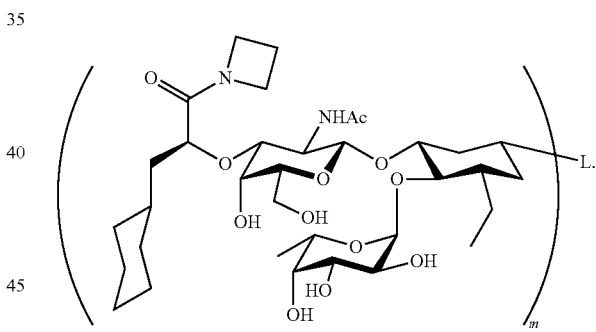

31. The at least one compound according to claim 1, 27, 28, 29, or 30, wherein the at least one compound is symmetrical.

32. A composition comprising at least one compound according to claim 1 and at least one additional pharmaceutically acceptable ingredient.

33. The at least one compound according to claim 1, wherein L is

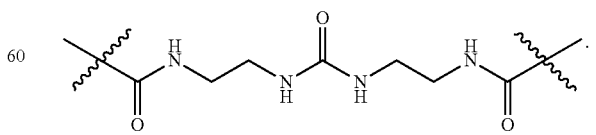

34. The at least one compound according to claim 1, wherein the at least one compound is chosen from compounds having the following Formulae:

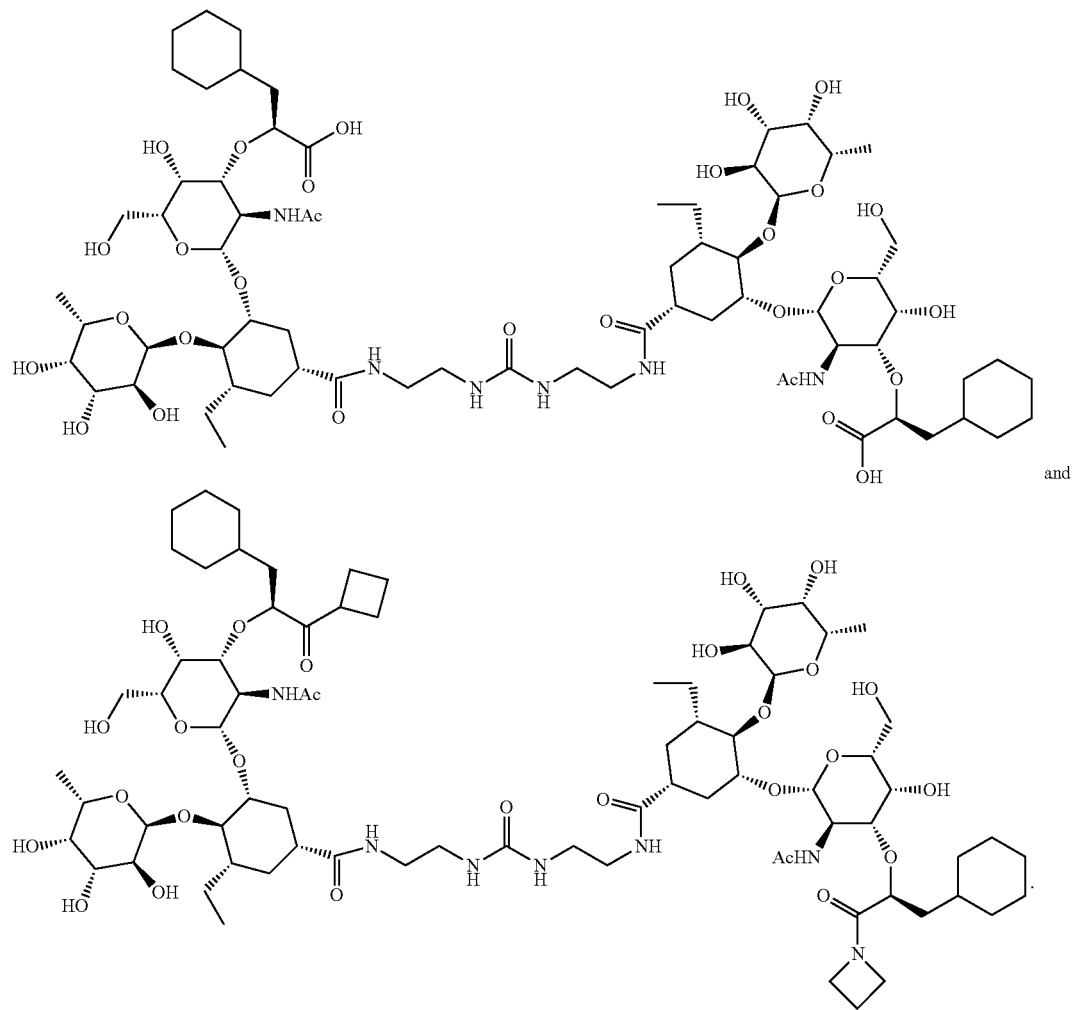
and
35. The at least one compound according to claim 1, wherein the at least one compound is
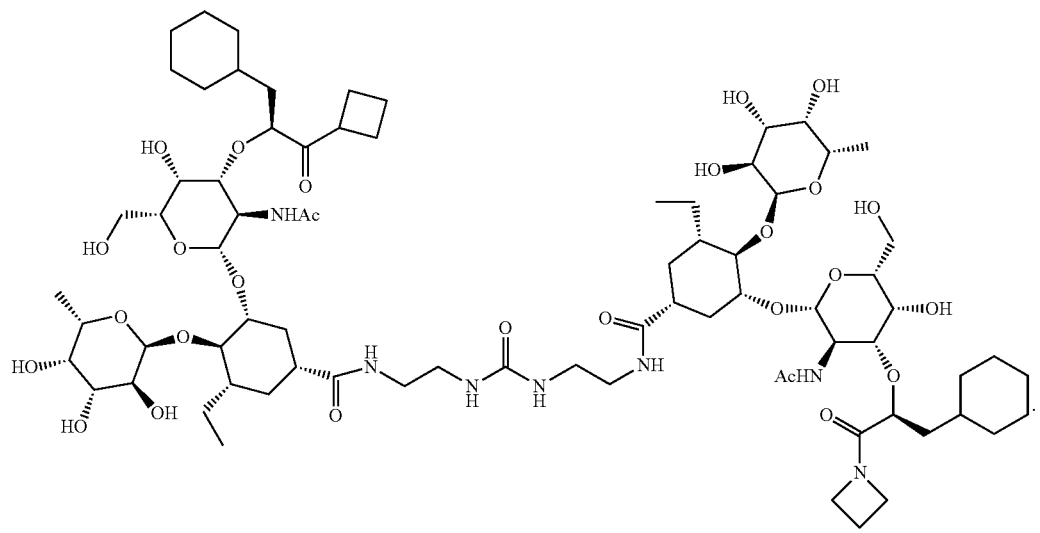 [SMILES: CC[C@H]1C[C@@H](C(=O)NCCNC(=O)NCCNC(=O)[C@@H]2C[C@H](CC)[C@@H](O[C@@H]3O[C@@H](C)[C@@H](O)[C@@H](O)[C@@H]3O)[C@H](O[C@@H]3O[C@H](CO)[C@H](O)[C@H](O[C@@H](CC4CCCCC4)C(=O)N4CCC4)[C@H]3NC(C)=O)C2)C[C@@H](O[C@@H]2O[C@H](CO)[C@H](O)[C@H](O[C@@H](CC3CCCCC3)C(=O)C3CCC3)[C@H]2NC(C)=O)[C@@H]1O[C@@H]1O[C@@H](C)[C@@H](O)[C@@H](O)[C@@H]1O]
* * * * *

UNITED STATES PATENT AND TRADEMARK OFFICE
CERTIFICATE OF CORRECTION

Page 1 of 2

PATENT NO. : 11,072,625 B2
APPLICATION NO. : 16/339646
DATED : July 27, 2021
INVENTOR(S) : John L. Magnani et al.

It is certified that error appears in the above-identified patent and that said Letters Patent is hereby corrected as shown below:

In the Claims

Claim 34, Columns 121 and 122, Lines 20-40:

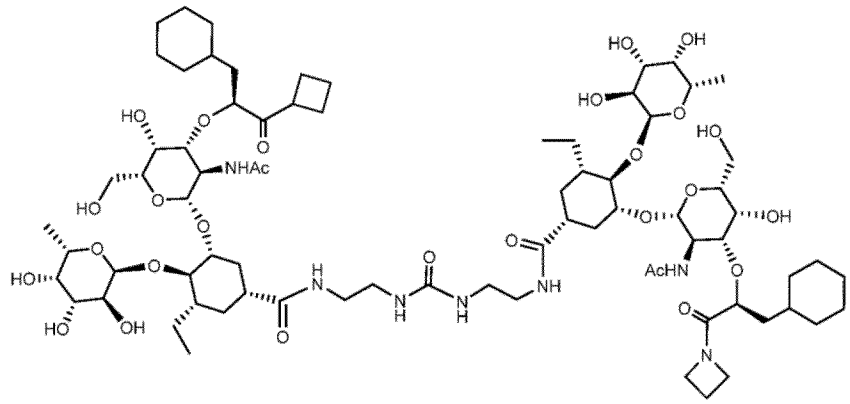

Should read:

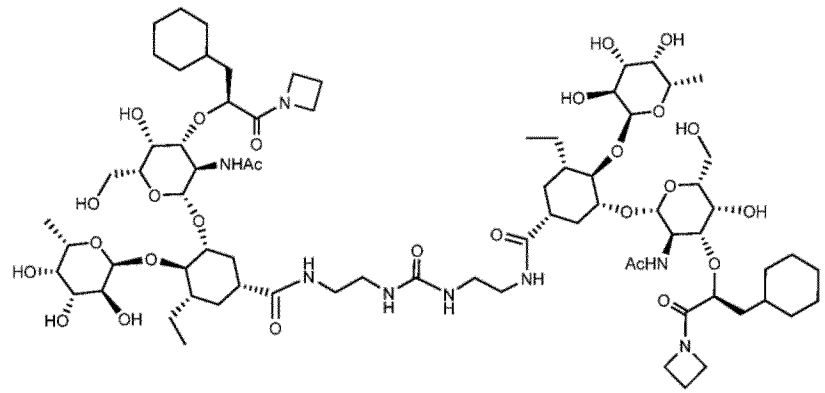

Signed and Sealed this
Second Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,072,625 B2

Claim 35, Columns 121 and 122, Lines 45-65:

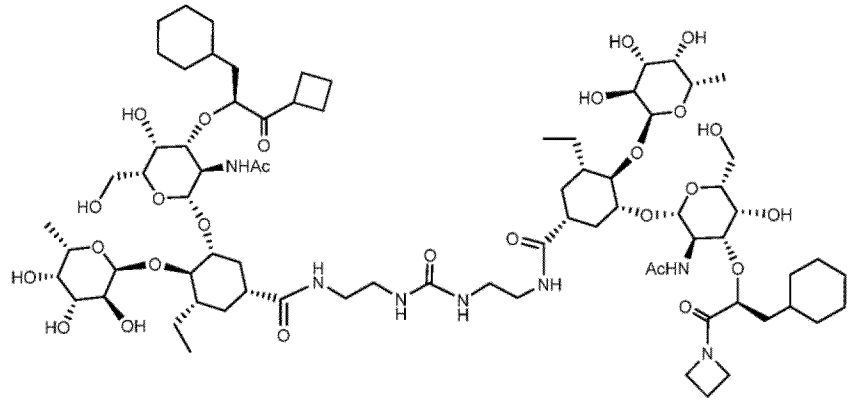

Should read: